United States Patent
Fukushima et al.

(10) Patent No.: US 10,591,819 B2
(45) Date of Patent: Mar. 17, 2020

(54) MONOMER, POLYMER, RESIST COMPOSITION, AND PATTERNING PROCESS

(71) Applicant: Shin-Etsu Chemical Co., Ltd., Tokyo (JP)

(72) Inventors: Masahiro Fukushima, Joetsu (JP); Masayoshi Sagehashi, Joetsu (JP); Koji Hasegawa, Joetsu (JP); Jun Hatakeyama, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/380,093

(22) Filed: Apr. 10, 2019

(65) Prior Publication Data

US 2019/0235381 A1   Aug. 1, 2019

Related U.S. Application Data

(62) Division of application No. 15/346,981, filed on Nov. 9, 2016.

(30) Foreign Application Priority Data

Nov. 10, 2015   (JP) .................. 2015-220175

(51) Int. Cl.
*G03F 7/038* (2006.01)
*C08F 220/28* (2006.01)
(Continued)

(52) U.S. Cl.
CPC .......... *G03F 7/0382* (2013.01); *C07C 69/653* (2013.01); *C07D 307/93* (2013.01);
(Continued)

(58) Field of Classification Search
CPC .. C07C 69/653; C07D 307/93; C07D 493/08; C07D 493/18; C08F 220/28;
(Continued)

(56) References Cited

U.S. PATENT DOCUMENTS 6,800,423 B2   10/2004   Yokoyama et al.
8,227,183 B2   7/2012   Tsubaki et al.
(Continued)

FOREIGN PATENT DOCUMENTS

JP   2003-195502 A   7/2003
JP   2004-302189 A   10/2004
(Continued)

OTHER PUBLICATIONS

Sooriyakumaran et al., 193-nm Negative Resist Based on Acid-Catalyzed Elimination of Polar Molecules, SPIE vol. 5376 (2004) (8 pages).
(Continued)

*Primary Examiner* — Cynthia Hamilton
(74) *Attorney, Agent, or Firm* — Westerman, Hattori, Daniels & Adrian, LLP

(57) ABSTRACT

A monomer of formula (1a) or (1b) is provided wherein A is a polymerizable group, $R^1$-$R^6$ are monovalent hydrocarbon groups, $X^1$ is a divalent hydrocarbon, group, $Z^1$ is an aliphatic group, $Z^2$ forms an alicyclic group, k=0 or 1, m=1 or 2, n=1 to 4. A useful polymer is obtained by polymerizing the monomer. A resist composition comprising the polymer has improved development properties and is processed to form a negative pattern having high contrast, high resolution and etch resistance which is insoluble in alkaline developer.

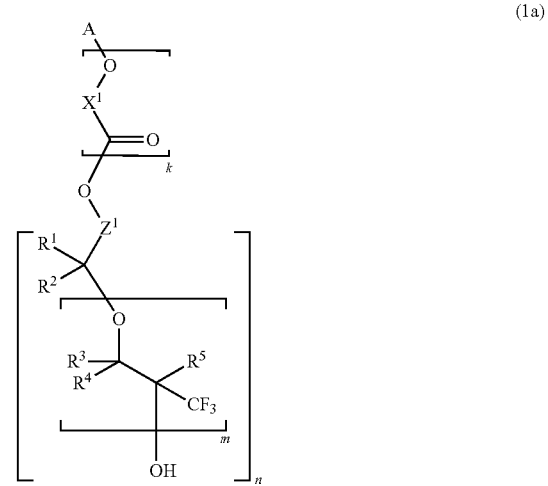

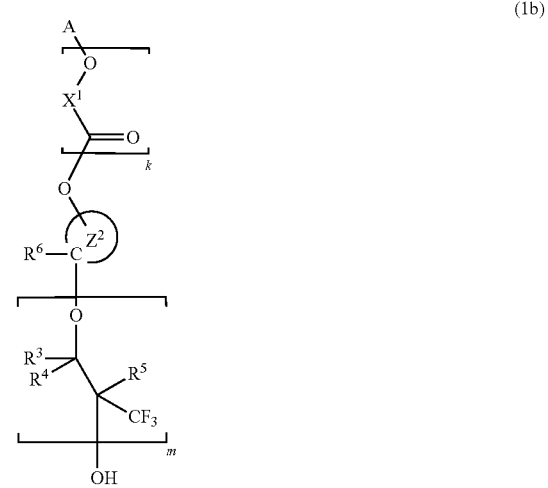

8 Claims, No Drawings

(51) Int. Cl.

| | | |
|---|---|---|
| *C09D 133/16* | (2006.01) | |
| *C07D 307/93* | (2006.01) | |
| *C07D 493/08* | (2006.01) | |
| *C07D 493/18* | (2006.01) | |
| *G03F 7/004* | (2006.01) | |
| *G03F 7/32* | (2006.01) | |
| *C07C 69/653* | (2006.01) | |
| *C08F 220/68* | (2006.01) | |
| *G03F 7/16* | (2006.01) | |
| *G03F 7/20* | (2006.01) | |

(52) U.S. Cl.
CPC ......... *C07D 493/08* (2013.01); *C07D 493/18* (2013.01); *C08F 220/28* (2013.01); *C08F 220/68* (2013.01); *C09D 133/16* (2013.01); *G03F 7/0045* (2013.01); *G03F 7/0046* (2013.01); *G03F 7/162* (2013.01); *G03F 7/2006* (2013.01); *G03F 7/322* (2013.01); *G03F 7/327* (2013.01); *C07C 2601/14* (2017.05); *C07C 2602/42* (2017.05); *C07C 2603/74* (2017.05)

(58) Field of Classification Search
CPC .... C08F 220/68; G03F 7/0045; G03F 7/0046; G03F 7/162; G03F 7/2006; G03F 7/322; G03F 7/0382; G03F 7/327
See application file for complete search history.

(56) References Cited

U.S. PATENT DOCUMENTS

| | | |
|---|---|---|
| 2007/0026339 A1 | 2/2007 | Allen et al. |
| 2007/0207413 A1 | 9/2007 | Crawford et al. |
| 2007/0218402 A1 | 9/2007 | Kinsho et al. |
| 2008/0233517 A1 | 9/2008 | Allen et al. |
| 2010/0203445 A1 | 8/2010 | Hoshino et al. |
| 2013/0181199 A1 | 7/2013 | Apanius et al. |
| 2013/0189620 A1 | 7/2013 | Suka et al. |
| 2016/0342086 A1 | 11/2016 | Sagehashi et al. |

FOREIGN PATENT DOCUMENTS

| | | |
|---|---|---|
| JP | 2005-3862 A | 1/2005 |
| JP | 2005-3863 A | 1/2005 |
| JP | 2005-91428 A | 4/2005 |
| JP | 2006-145775 A | 6/2006 |
| JP | 2006-215067 A | 8/2006 |
| JP | 2006-317803 A | 11/2006 |
| JP | 4554665 B2 | 9/2010 |
| WO | 03/040827 A1 | 5/2003 |
| WO | 2004/074936 A1 | 9/2004 |

OTHER PUBLICATIONS

"Hydrocarbons" obtained from online goldbook, source PAC, 1995, 67, 1307 (Glossary of class names of organic compounds and reactivity intermediates based on structure ( IUPAC Recommendations 1995)) on p. 1341.

Non-Final Office Action dated Jun. 14, 2019, issued in U.S. Appl. No. 15/346,981. (7 pages).

MONOMER, POLYMER, RESIST COMPOSITION, AND PATTERNING PROCESS

CROSS-REFERENCE TO RELATED APPLICATIONS

This application is a Divisional of U.S. application Ser. No. 15/346,981, filed on Nov. 9, 2016, and wherein U.S. application Ser. No. 15/346,981 is a non-provisional application which claims priority under 35 U.S.C. § 119(a) to Patent Application No. 2015-220175 filed in Japan on Nov. 10, 2015, the entire contents of which are hereby incorporated by reference.

This invention relates to a monomer useful as a starting reactant for functional, pharmaceutical and agricultural chemicals, a polymer comprising recurring units derived from the monomer, a resist composition comprising the polymer, and a pattern forming process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, the self-aligned double patterning (SADP) process of adding film to opposite sidewalls of lines of a resist pattern resulting from ArF lithography for thereby forming two patterns with half line width from one pattern is successful in manufacturing microelectronic devices at the 20-nm node in a mass scale. As the miniaturization technology for microelectronic devices of the next generation 10-nm node, the self-aligned quadruple patterning (SAQP) which is double repetition of SADP is a candidate. It is pointed out that this process is quite expensive because formation of sidewall film by CVD and processing by dry etching are repeated several times. Extreme ultraviolet (EUV) lithography of wavelength 13.5 nm is capable of forming a pattern with a size of the order of 10 nm via single exposure, but suffers from the problems of still low laser power and low productivity. As the miniaturization technology comes to the deadlock, the development of three-dimensional devices such as vertically stacked flash memories typically BiCS is started, but expected to be a high cost process.

Recently, a highlight is put on the organic solvent development again. A positive resist composition featuring a high resolution is subjected to organic solvent development to form a negative pattern. As the ArF resist composition for negative tone development with organic solvent, positive ArF resist compositions of the prior art design may be used. Such a pattern forming process is described in Patent Document 1.

In the process of forming a negative tone pattern via organic solvent development, a film from which a robust protective group such as cyclic structure having dry etch resistance has been eliminated is left as the negative pattern. Thus the film is short of dry etch resistance. This serious problem must be overcome before the negative pattern formation via organic solvent development can be implemented.

On the other hand, studies have also been made on the negative pattern formation via development in alkaline aqueous solution. Known resist compositions used in this process include a negative resist composition of polarity switch type comprising a base resin comprising recurring units having γ-hydroxycarboxylic acid which forms lactone ring by PEB (see Patent Document 2), a negative resist composition comprising a copolymer comprising alcoholic hydroxyl-containing (meth)acrylate units and fluoroalcohol-containing units and a crosslinker (see Patent Document 3), and negative resist compositions of crosslinking type comprising a crosslinker and a combination of α-hydroxyacrylate and lactone units (see Patent Document 4), α-hydroxyacrylate and fluoroalcohol units (see Patent Documents 5 to 7), and mono(meth)acryloyloxypinacol and fluoroalcohol units (see Patent Document 8).

Of these, Patent Document 2 describes a negative resist composition of polarity switch type, not resorting to crosslinking reaction, in which γ-hydroxycarboxylic acid units incur swell of the pattern after development. Patent Documents 3 to 7 relate to negative resist compositions of crosslinking type. Although the negative pattern formation by cooperation of alcoholic hydroxyl group and crosslinker has the problems of bridging between pattern features and pattern collapse due to swell, it is observed that the incorporation of fluoroalcohol units has a swell-reducing effect. Moreover, as recent examples of negative pattern formation by polarity switch, there are proposed base resins having polar units such as tertiary hydroxyl group, tertiary ether bond, tertiary ester bond or acetal bond as the polarity switch group. Of these, a polymer using a polar unit having one tertiary hydroxyl group is unlikely to swell after development. However, the difference of dissolution rate in developer between unexposed and exposed regions is insufficient, which raises the problem that a footing occurs at the bottom of a line-and-space pattern, that is, pattern features take a tapered shape. See Patent Documents 9 and 10 and Non-Patent Document 1.

All the negative pattern forming processes mentioned above are effective to some extent in forming pattern features with a size of the order of 100 nm. However, their performance is insufficient in forming pattern features with a size of finer than 100 nm, because pattern bridging and collapse due to swell, and footing at the pattern bottom inevitably occur. Although active efforts have recently been devoted on the negative pattern forming process via organic solvent development, the organic solvent used as the developer is more expensive than conventional alkaline developers. From the standpoint of etch resistance improvement, it is desired to have a negative resist composition which is amenable to conventional alkaline development at a high resolution and allows a robust backbone structure to be left in the film after development.

CITATION LIST

Patent Document 1: JP 4554665 (U.S. Pat. No. 8,227,183)
Patent Document 2: JP-A 2003-195502
Patent Document 3: WO 2004/074936
Patent Document 4: JP-A 2005-003862
Patent Document 5: JP-A 2005-003863
Patent Document 6: JP-A 2006-145775
Patent Document 7: JP-A 2006-317803
Patent Document 8: JP-A 2006-215067
Patent Document 9: U.S. Pat. No. 7,300,739
Patent Document 10: U.S. Pat. No. 7,563,558
Non-Patent Document 1: Proc. SPIE vol. 5376, p 71 (2004)

DISCLOSURE OF INVENTION

The requirements for further miniaturization continue severer in these years. In the negative pattern forming process via organic solvent development, on which active efforts have been devoted, the negative pattern defined in the resist film has a reduced carbon density as compared with that prior to exposure. It is then desired to improve the resistance to etching of the resist film and the retention of pattern shape after etching.

An object of the invention is to provide a polymerizable monomer having a substituent group capable of polarity switch under the action of acid, a polymer derived from the monomer, a resist composition comprising the polymer, and a pattern forming process using the composition.

The inventors have found that a monomer having the formula (1a) or (1b) defined below is readily prepared, and that a resist composition comprising a polymer derived from the monomer as base resin forms at a high contrast and resolution a negative pattern insoluble in alkaline developer and having high etch resistance.

Aside from the polarity switch due to dehydration reaction of tertiary alcohol in the prior art, the invention introduces a 1,1,1,3,3,3-hexafluoro-2-propanol unit (featuring high solubility in alkaline developer) into a polymerizable monomer as the acid labile group via a tertiary ether bond. A polymer comprising the monomer has a high affinity to and a very high dissolution rate in alkaline developer. Since this unit undergoes elimination reaction with the aid of an acid generated by an acid generator upon exposure, the polymer is advantageous in forming at a high contrast a negative pattern insoluble in alkaline developer.

In one aspect, the invention provides a monomer having the formula (1a) or (1b).

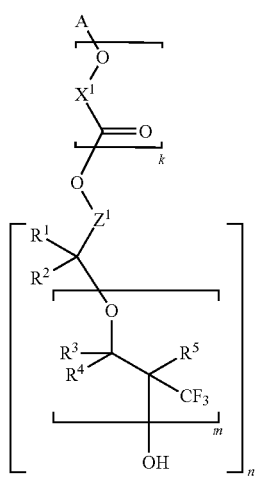

(1a)

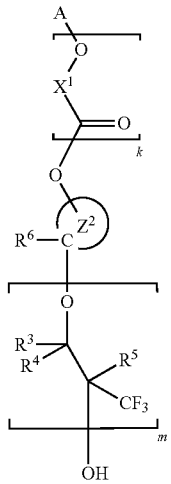

(1b)

Herein A is a polymerizable group; $R^1$ to $R^6$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$, $R^3$ and $R^4$, $R^3$ and $R^5$, or $R^4$ and $R^5$ may bond together to form an alicyclic group with the carbon atom to which they are attached; $X^1$ is a straight; branched or cyclic $C_1$-$C_{15}$ divalent hydrocarbon group in which any constituent —$CH_2$— moiety may be replaced by —O— or —C(=O)—; $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, k is 0 or 1, m is 1 or 2, n is an integer of 1 to 4; $Z^2$ is an atomic group necessary to form a $C_3$-$C_{10}$ alicyclic group with the carbon atom to which it is attached, in which any constituent —$CH_2$— moiety may be replaced by —O— or —C(=O)—; with the proviso that when the oxygen atom attached to $Z^1$ or $Z^2$ forms a bond with the polymerizable group A or the linker —[O—$X^1$—C(=O)]—, a tertiary ester bond is not formed.

One embodiment is a monomer having the formula (1aa) or (1bb).

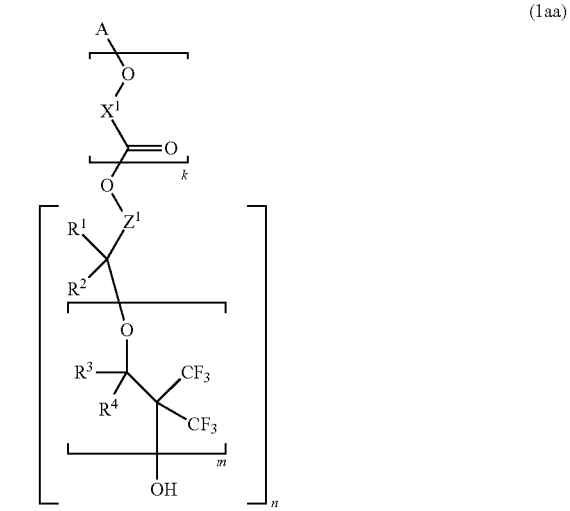

(1aa)

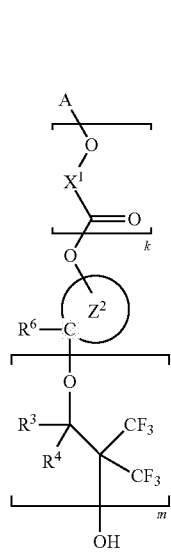

(1bb)

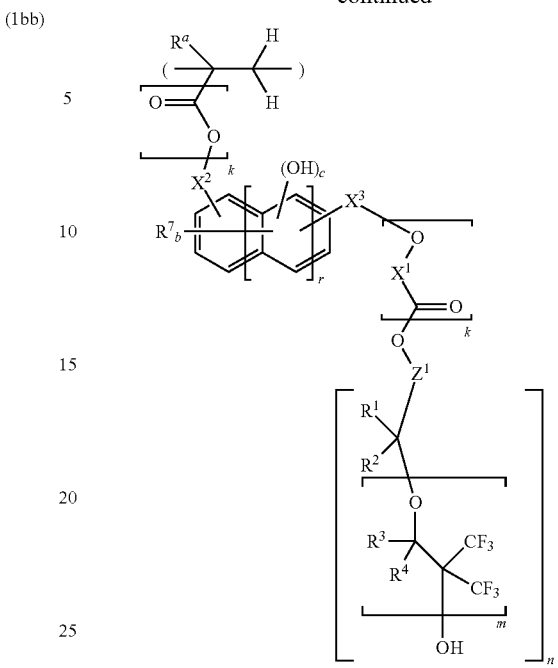

(2b)

Herein A, $R^1$ to $R^4$, $R^6$, $X^1$, $Z^1$, $Z^2$, k, m and n are as defined above. When the oxygen atom attached to $Z^1$ or $Z^2$ forms a bond with the polymerizable group A or the linker —[O—$X^1$—C(=O)]—, a tertiary ester bond is not formed.

In another aspect, the invention provides a polymer comprising recurring units derived from the monomer defined herein.

In a preferred embodiment, the recurring units have any one of the formulae (2a) to (2d).

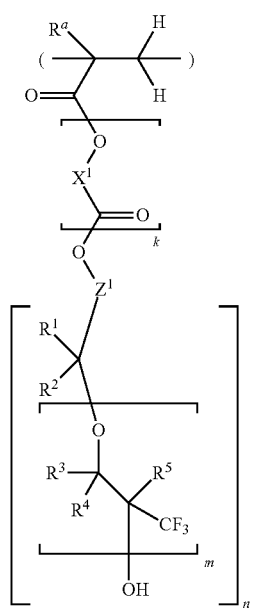

(2a)

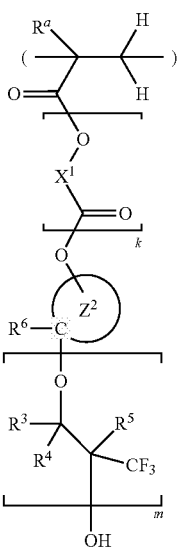

(2c)

-continued (2d)

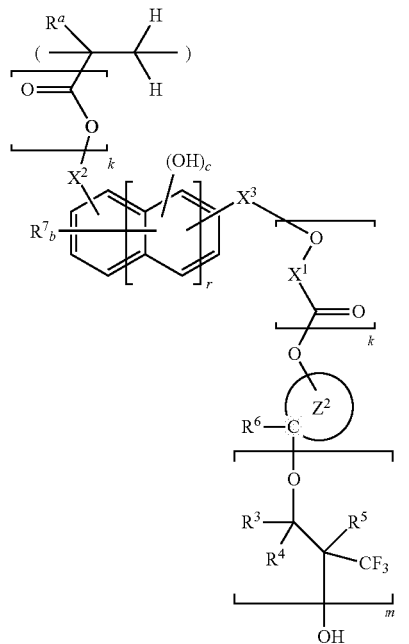

Herein $R^a$ is hydrogen, methyl or trifluoromethyl; $R^1$ to $R^7$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$, $R^3$ and $R^4$, $R^3$ and $R^5$, or $R^4$ and $R^5$ may bond together to form an alicyclic group with the carbon atom to which they are attached; $X^1$ is a straight, branched or cyclic $C_1$-$C_{15}$ divalent hydrocarbon group in which any constituent —$CH_2$— moiety may be replaced by —O— or —C(=O)—; $X^2$ and $X^3$ are each independently a single bond or a straight, branched or cyclic $C_1$-$C_{15}$ divalent hydrocarbon group in which any constituent —$CH_2$-moiety may be replaced by —O— or —C(=O)—; $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, b is an integer meeting b≤5+2r−c, c is an integer of 1 to 3, k is 0 or 1, m is 1 or 2, n is an integer of 1 to 4, r is an integer of 0 to 2; $Z^2$ is an atomic group necessary to form a $C_3$-$C_{10}$ alicyclic group with the carbon atom to which it is attached, in which any constituent —$CH_2$— moiety may be replaced by —O— or —C(=O)—; with the proviso that when the oxygen atom attached to $Z^1$ or $Z^2$ forms a bond with the carbonyl carbon bonded to a polymerizable group or the linker —[O—$X^1$—C(=O)]—, a tertiary ester bond is not formed.

In a more preferred embodiment, the recurring units have any one of the formulae (2aa) to (2dd).

(2aa)

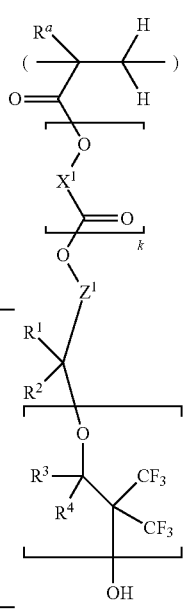

(2bb)

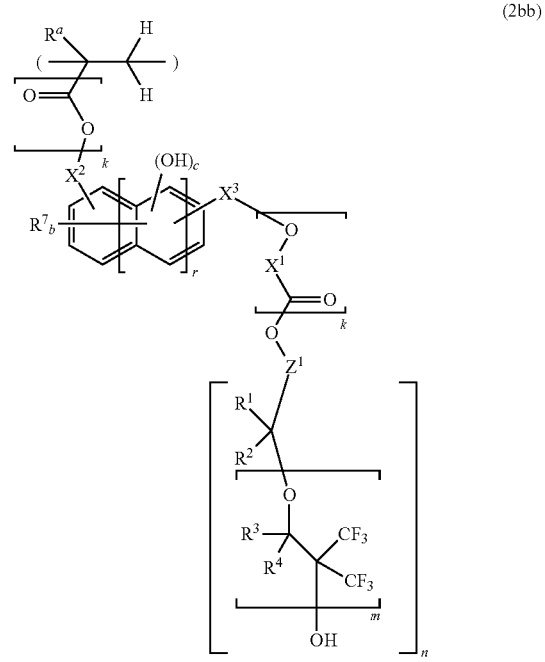

-continued (2cc)

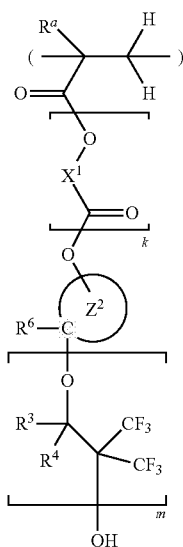

(2dd)

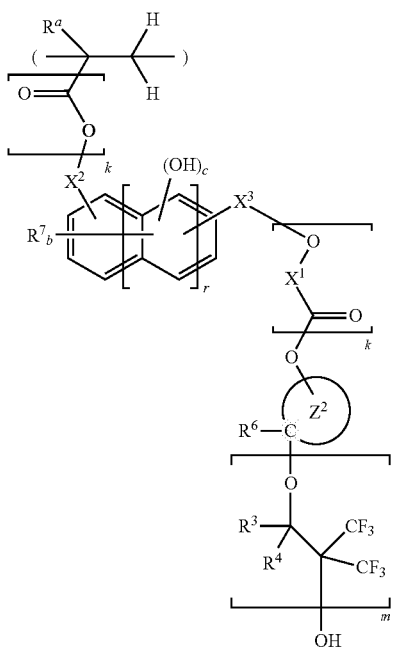

Herein $R^a$, $R^1$ to $R^4$, $R^6$, $R^7$, $X^1$, $X^2$, $X^3$, $Z^1$, $Z^2$, b, c, k, m, n, and r are as defined above.

The polymer may further comprise recurring units of at least one type selected from recurring units having the formulae (A) to (D).

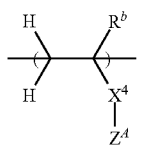 (A)

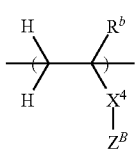 (B)

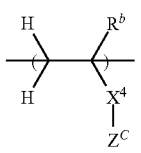 (C)

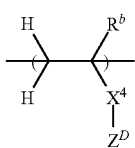 (D)

Herein $R^b$ is hydrogen, methyl or trifluoromethyl, $Z^A$ is a $C_1$-$C_{20}$ fluoroalcohol-containing group, $Z^B$ is a $C_1$-$C_{20}$ phenolic hydroxyl-containing group, $Z^C$ is a $C_5$-$C_{20}$ carboxyl-containing group, $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety, $X^4$ is a single bond, methylene, ethylene, phenylene, fluorinated phenylene, naphthylene, —O—$R^c$, or —C(=O)—$Z^E$—$R^c$, $Z^E$ is oxygen or NH, and $R^c$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety.

The polymer may further comprise recurring units of at least one type selected from recurring units having the formulae (3a) to (3d).

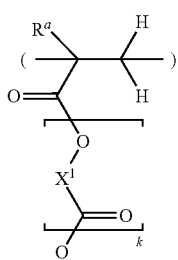 (3a)

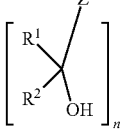

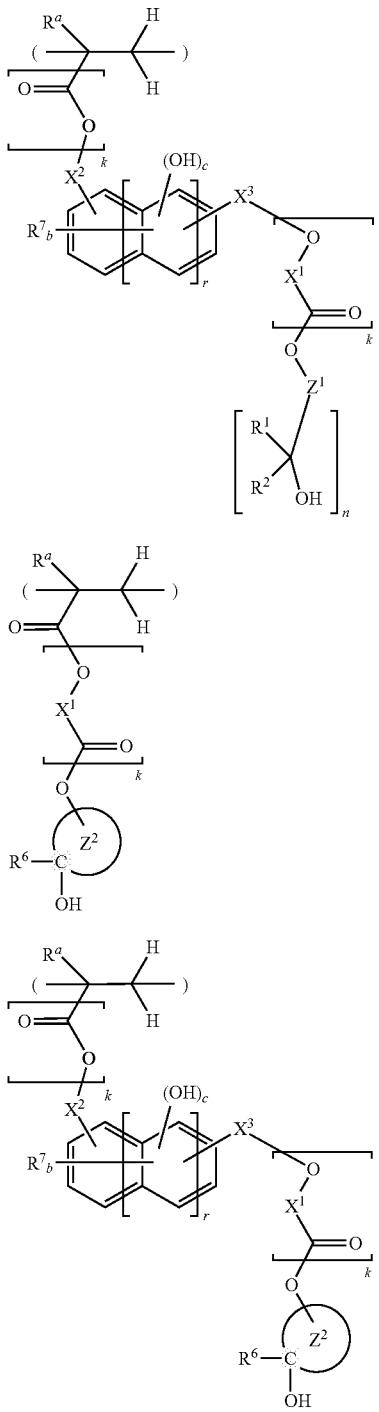

(3b)

(3c)

(3d)

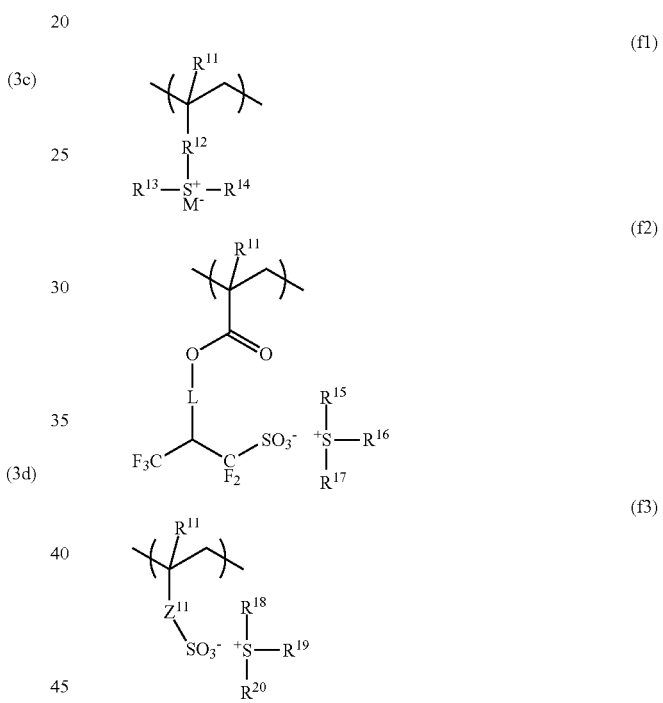

(f1)

(f2)

(f3)

constituent —CH$_2$— moiety may be replaced by —O— or —C($\alpha$O)—; Z$^1$ is a straight C$_1$-C$_{20}$ or branched or cyclic C$_3$-C$_{20}$, (n+1)-valent aliphatic hydrocarbon group in which any constituent —CH$_2$— moiety may be replaced by —O— or —C(=O)—, b is an integer meeting b≤5+2r–c, c is an integer of 1 to 3, k is 0 or 1, n is an integer of 1 to 4, r is an integer of 0 to 2; Z$^2$ is an atomic group necessary to form a C$_3$-C$_{10}$ alicyclic group with the carbon atom to which it is attached, in which any constituent —CH$_2$— moiety may be replaced by —O— or —C(=O)—; with the proviso that when the oxygen atom attached to Z$^1$ or Z$^2$ forms a bond with the carbonyl carbon bonded to a polymerizable group or the linker —[O—X$^1$—C(=O)]—, a tertiary ester bond is not formed.

The polymer may further comprise recurring units of at least one type selected from recurring units having the formulae (f1) to (f3).

Herein R$^a$ is hydrogen, methyl or trifluoromethyl; R$^1$ and R$^2$ are each independently a straight C$_1$-C$_{10}$ or branched or cyclic C$_3$-C$_{10}$ monovalent hydrocarbon group in which any constituent —CH$_2$— moiety may be replaced by —O— or —C(=O)—, a pair of R$^1$ and R$^2$ may bond together to form an alicyclic group with the carbon atom to which they are attached; X$^1$ is a straight, branched or cyclic C$_1$-C$_{15}$ divalent hydrocarbon group in which any constituent —CH$_2$— moiety may be replaced by —O— or —C(=O)—; X$^2$ and X$^3$ are each independently a single bond or a straight, branched or cyclic C$_1$-C$_{15}$ divalent hydrocarbon group in which any Herein R$^{11}$ is each independently hydrogen or methyl, R$^{12}$ is a single bond, phenylene, —O—R$^{21}$—, or —C(=O)—Z$^{22}$—R$^{21}$—, Z$^{22}$ is oxygen or NH, R$^{21}$ is a straight, branched or cyclic C$_1$-C$_6$ alkylene group, straight, branched or cyclic C$_2$-C$_6$ alkenylene group or phenylene group, which may contain a carbonyl (—C—), ester (—COO—), ether (—O—) or hydroxyl moiety, L is a single bond or —Z$^{33}$—C(=O)—O—, Z$^{33}$ is a straight, branched or cyclic C$_1$-C$_{20}$ divalent hydrocarbon group which may be substituted with a heteroatom, Z$^{11}$ is a single bond, methylene, ethylene, phenylene, fluorinated phenylene, —O—R$^{22}$—, or —C(=O)—Z$^{44}$—R$^{22}$—, Z$^{44}$ s oxygen or NH, R$^{22}$ is a straight, branched or cyclic C$_1$-C$_6$ alkylene group, straight, branched or cyclic C$_2$-C$_6$ alkenylene group or phenylene group, which may contain a carbonyl, ester, ether or hydroxyl moiety, R$^{13}$ to R$^{20}$ are each independently a straight, branched or cyclic C$_1$-C$_{20}$ monovalent hydrocarbon group in which at least one hydrogen atom may be substituted by a heteroatom, and M$^-$ is a non-nucleophilic counter ion.

In a further aspect, the invention provides a resist composition comprising a base resin, an acid generator, and an organic solvent, the base resin comprising the polymer defined above.

In a still further aspect, the invention provides a pattern forming process comprising the steps of applying the resist composition onto a substrate, baking to form a resist film, exposing the resist film to high-energy radiation to define exposed and unexposed regions, baking, and developing the exposed resist film in a developer to form a pattern.

In a preferred embodiment, the developing step uses an alkaline developer in which the unexposed region of resist film is dissolved and the exposed region of resist film is not dissolved, for forming a negative tone pattern.

Advantageous Effects of Invention

Using a polymer comprising recurring units derived from the inventive monomer as base resin, a resist composition having high transparency to radiation of wavelength 500 nm or less, especially 300 nm or less, e.g., KrF, ArF or $F_2$ laser radiation is formulated. From the resist composition having improved development properties, a negative pattern insoluble in alkaline developer and having a high contrast, high resolution and etch resistance can be formed.

DESCRIPTION OF EMBODIMENTS

In the disclosure, the singular forms "a," "an" and "the" include plural referents unless the context clearly dictates otherwise. The notation (Cn-Cm) means a group. containing from n to m carbon atoms per group. In the chemical formulae, the broken line denotes a valence bond. Me stands for methyl, and Ph for phenyl.

The abbreviations and acronyms have the following meaning.

EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake
LWR: line width roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

Monomer

The invention provides a polymerizable monomer having the formula (1a) or (1b).

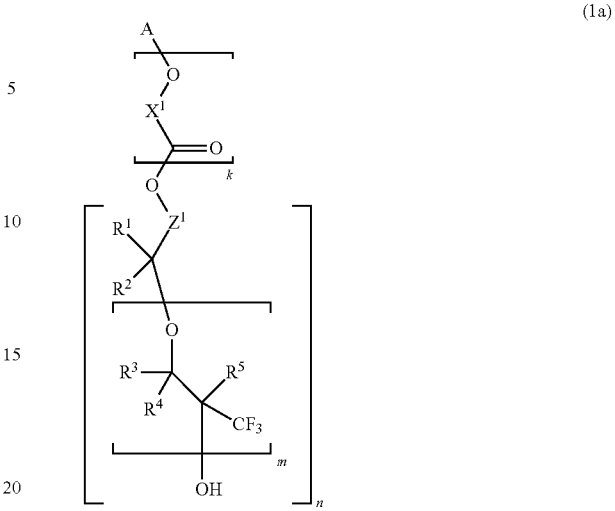

(1a)

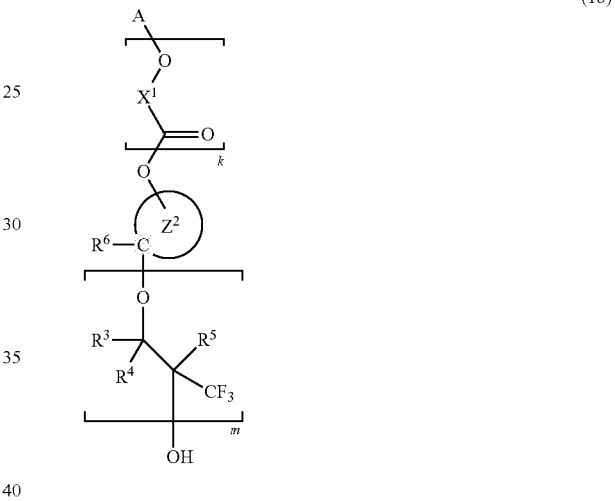

(1b)

Herein A is a polymerizable group. $R^1$ to $R^6$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$, $R^3$ and $R^4$, $R^3$ and $R^5$, or $R^4$ and $R^5$ may bond together to form an alicyclic group with the carbon atom to which they are attached. $X^1$ is a straight, branched or cyclic $C_1$-$C_{15}$ divalent, hydrocarbon group in which any constituent —$CH_2$— moiety may be replaced by —O— or —C(=O)—. $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, k is 0 or 1, m is 1 or 2, n is an integer of 1 to 4, $Z^2$ is an atomic group necessary to form a $C_3$-$C_{10}$ alicyclic group with the carbon atom to which it is attached, in which any constituent —$CH_2$— moiety may be replaced by —O— or —C(=O)—. In formulae (1a) and (1b), when the oxygen atom attached to $Z^1$ or atomic group $Z^2$ forms a bond with the polymerizable group A or the linker —[O—$X^1$—C(=O)]—, a tertiary ester bond is not formed, i.e., the bond is other than a tertiary ester bond.

Among the monomers, monomers having the formula (1aa) or (1bb) are preferred.

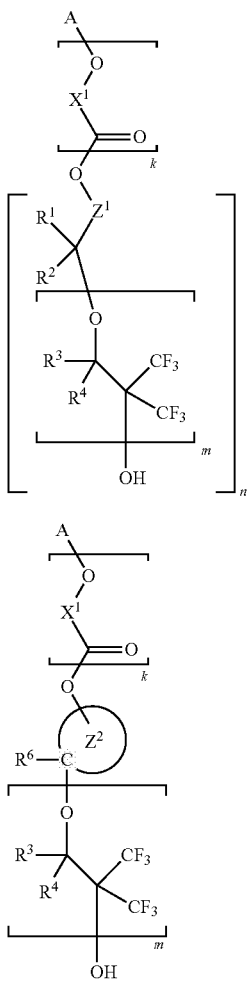

(1aa)

(1bb)

Herein A is a polymerizable group. $R^1$ to $R^4$ and $R^6$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$, or $R^3$ and $R^4$ may bond together to form an alicyclic group with the carbon atom to which they are attached. $X^1$ is a straight, branched or cyclic $C_1$-$C_{15}$ divalent hydrocarbon group in which any constituent —$CH_2$— moiety may be replaced by —O— or —C(=O)—. $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, k is 0 or 1, m is 1 or 2, n is an integer of 1 to 4. $Z^2$ is an atomic group necessary to form a $C_3$-$C_{10}$ alicyclic group with the carbon atom to which it is attached, in which any constituent —$CH_2$— moiety may be replaced by —O— or —C(=O)—. In formulae (1aa) and (1bb), when the oxygen atom attached to group $Z^1$ or atomic group $Z^2$ forms a bond with the polymerizable group A or the linker —[O—$X^1$—C(=O)]—, a tertiary ester bond is not formed.

Examples of the polymerizable group represented by A include acryloyl, methacryloyl, trifluoromethylmethacryloyl, vinyl, 4-vinylphenyl, 4-acryloylphenyl, 4-methacryloylphenyl, and 4-trifluoromethylxmethacryloylphenyl. From the standpoint of transparency or absorption of wavelength 193 nm in the ArF resist application, acryloyl, methacryloyl, and trifluoromethylmethacryloyl groups are preferred, with methacryloyl being most preferred.

Typical of the straight, branched or cyclic $C_1$-$C_{10}$ monovalent hydrocarbon group represented by $R^1$ to $R^6$ are alkyl groups including methyl, ethyl, propyl, isopropyl, n-butyl, s-butyl, t-butyl, cyclopentyl, cyclohexyl, 2-ethylhexyl, n-octyl, norbornyl, tricyclodecanyl, and adamantyl.

When a pair of $R^1$ and $R^2$, $R^3$ and $R^4$, $R^3$ and $R^5$, or $R^4$ and $R^5$ bond together to form an alicyclic group with the carbon atom to which they are attached, suitable alicyclic groups include cyclopropane, cyclobutane, cyclopentane and cyclohexane.

Examples of the straight, branched or cyclic $C_1$-$C_{15}$ divalent hydrocarbon group represented by $X^1$ are given below, but not limited thereto.

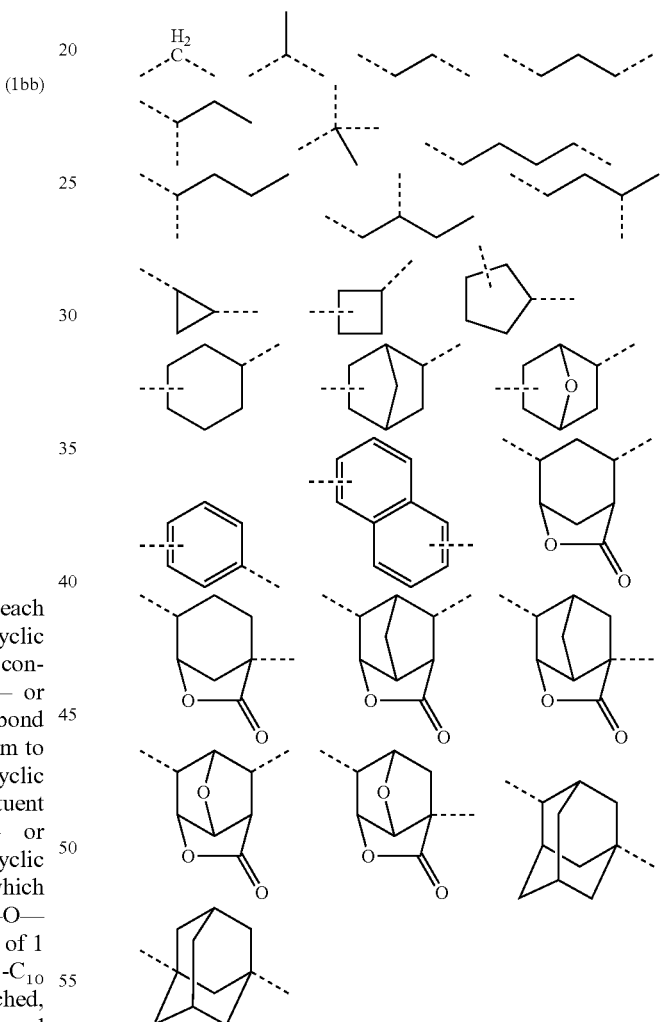

Examples of the straight $C_1$-$C_{20}$, or branched or cyclic $C_3$-$C_{20}$, (n+1)-valent aliphatic hydrocarbon group represented by $Z^1$ are given below, but not limited thereto.

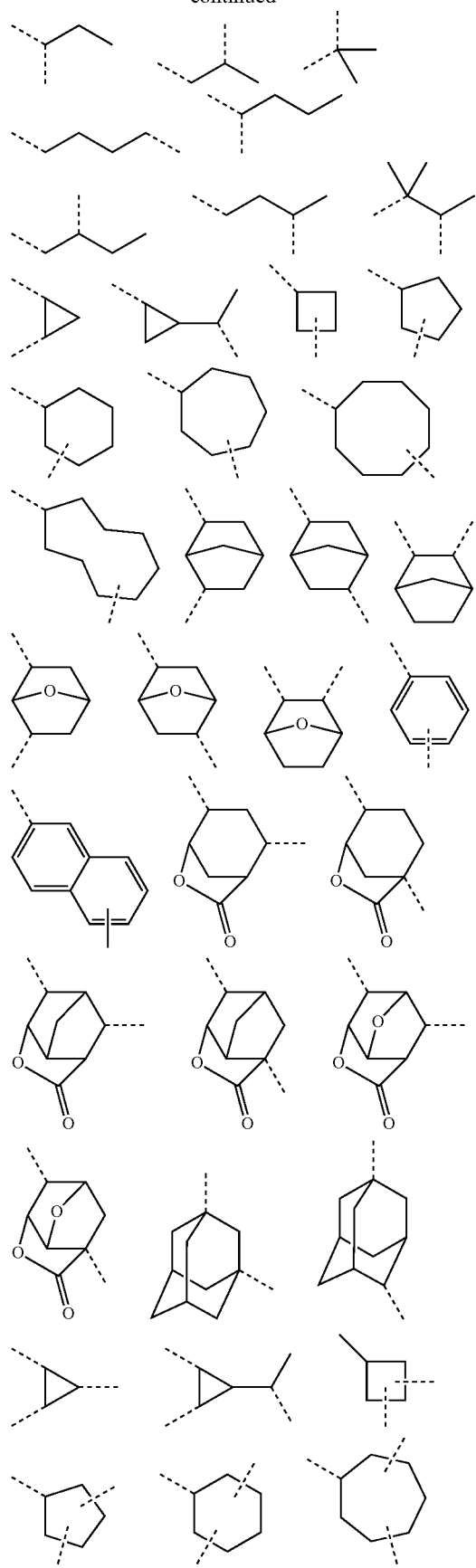
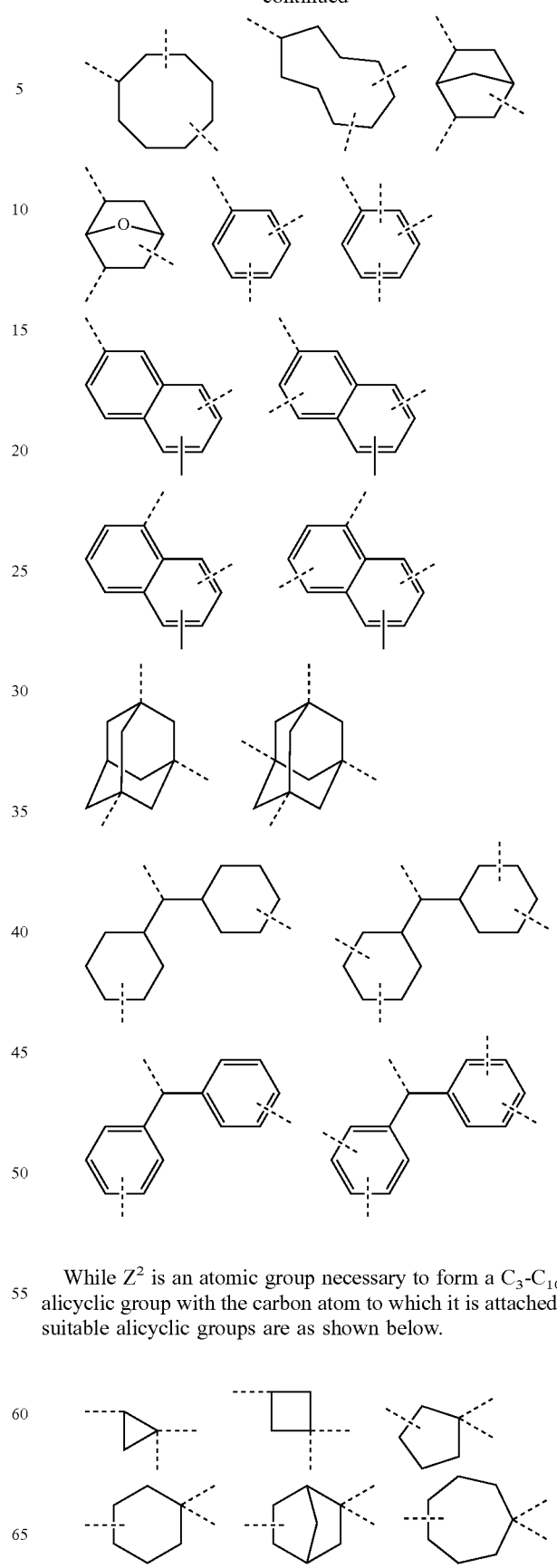
While $Z^2$ is an atomic group necessary to form a $C_3$-$C_{10}$ alicyclic group with the carbon atom to which it is attached, suitable alicyclic groups are as shown below.
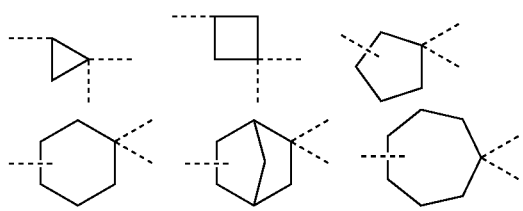

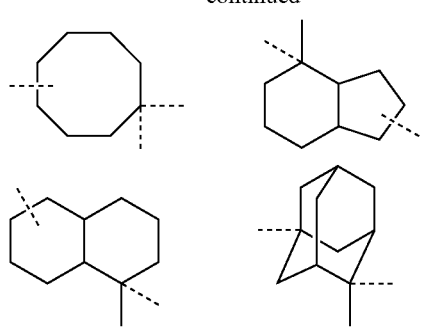
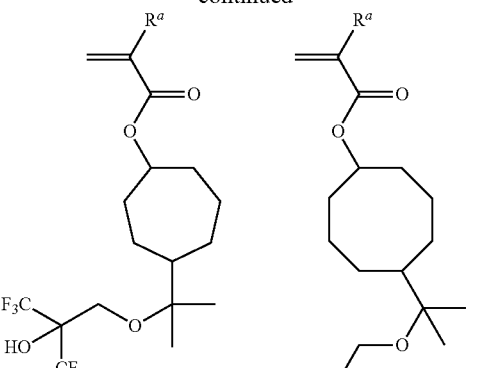
Examples of the monomers having formulae (1a), (1b), (1aa) and (1bb) are shown below.
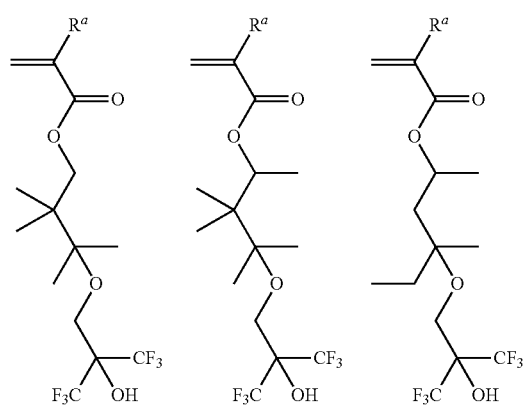
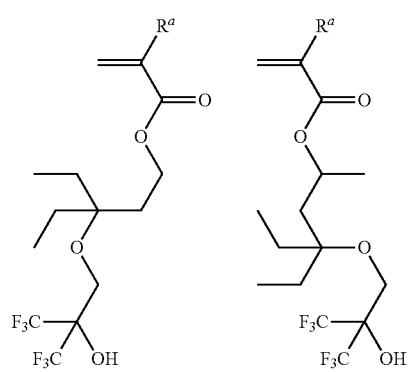
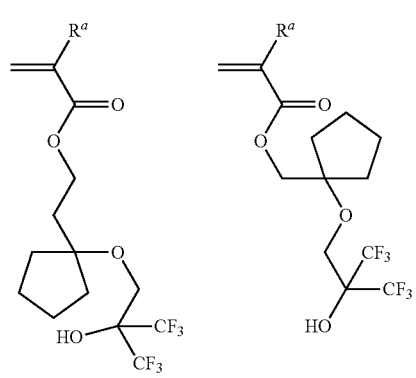

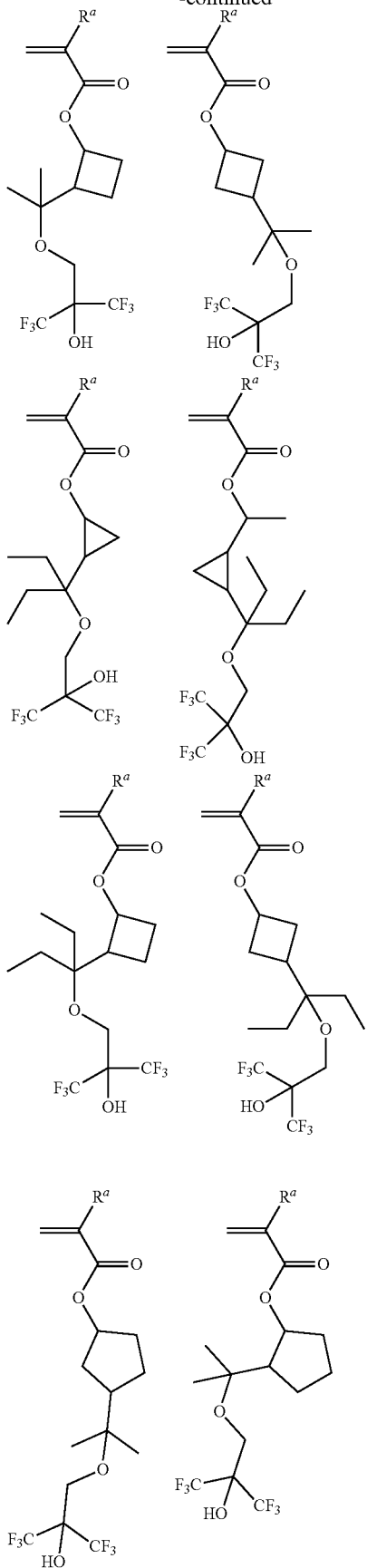
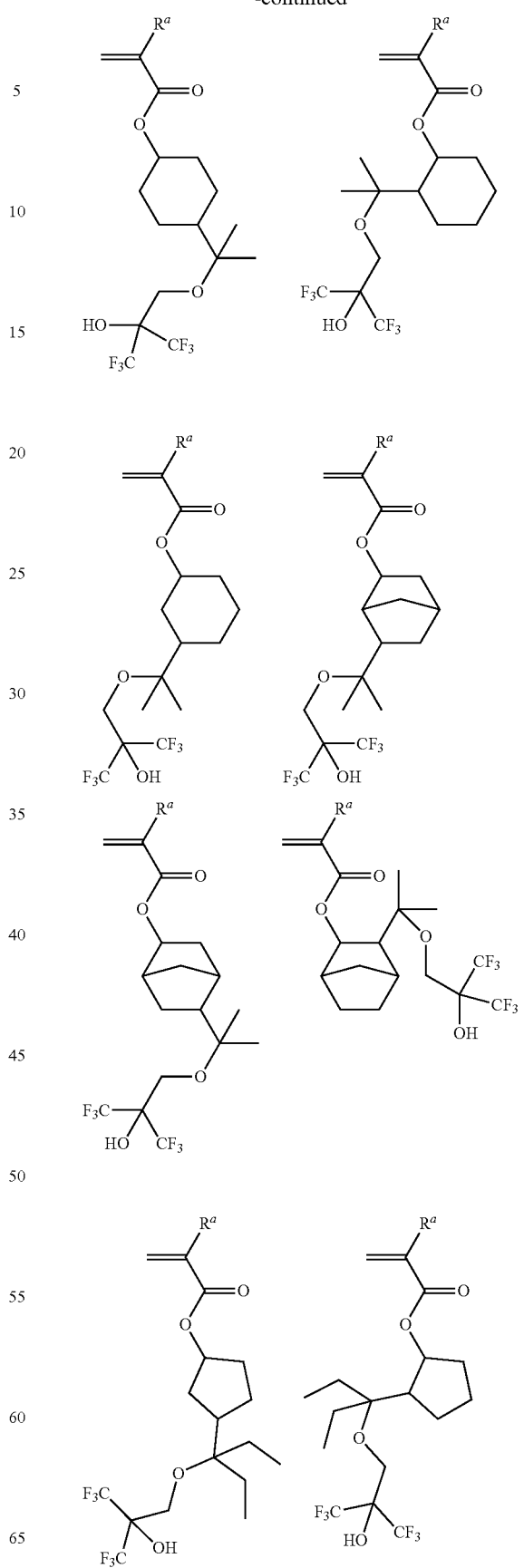

-continued
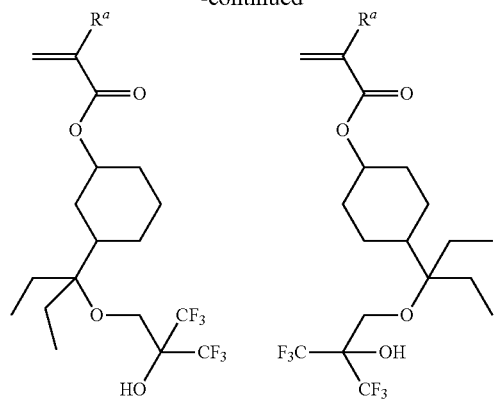
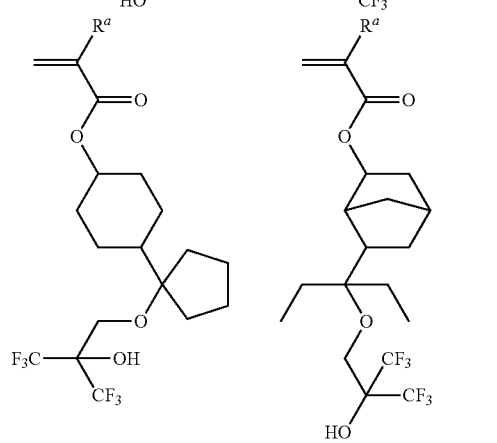
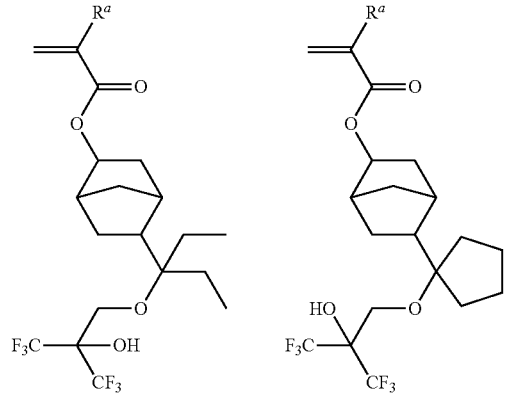
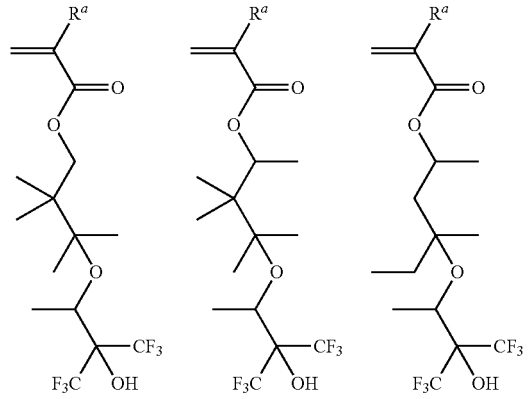
-continued
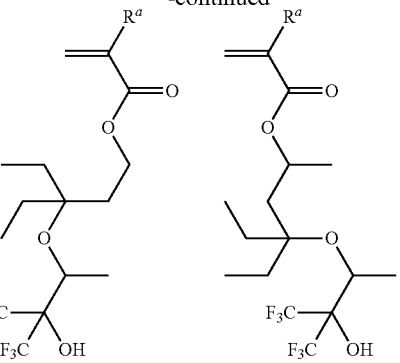
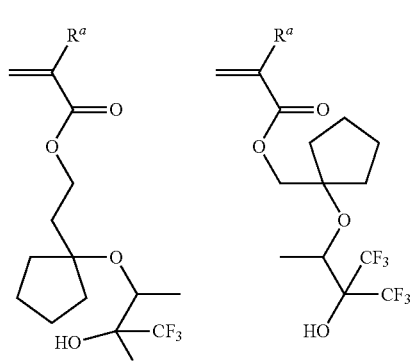
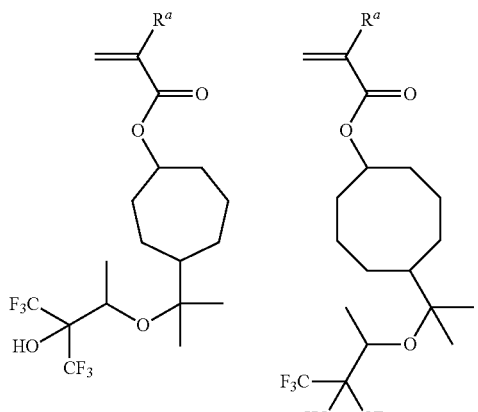
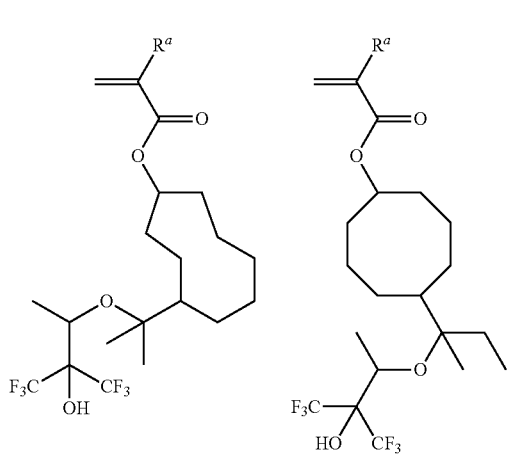

-continued
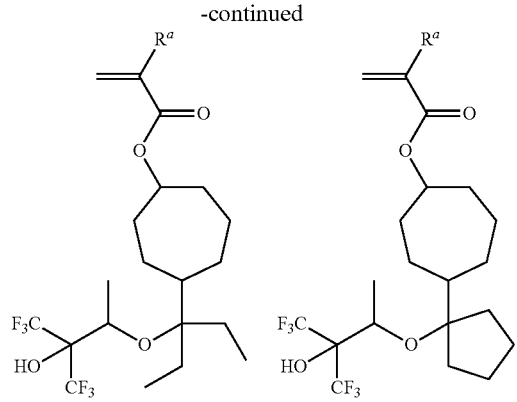
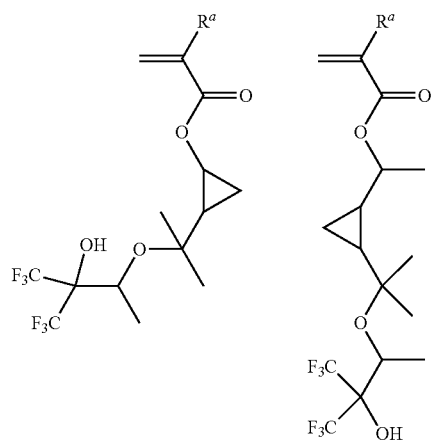
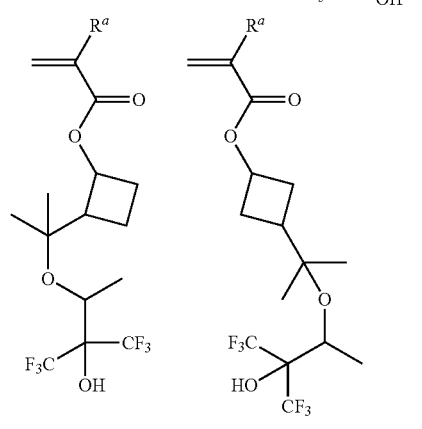
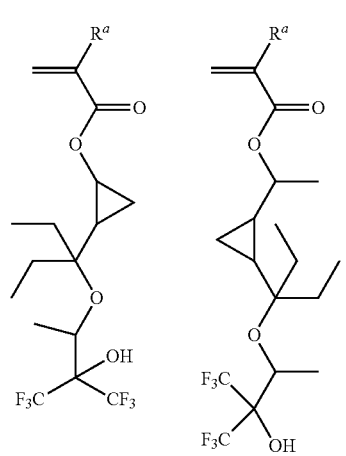
-continued
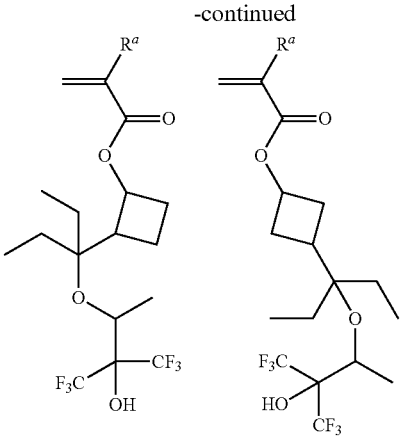
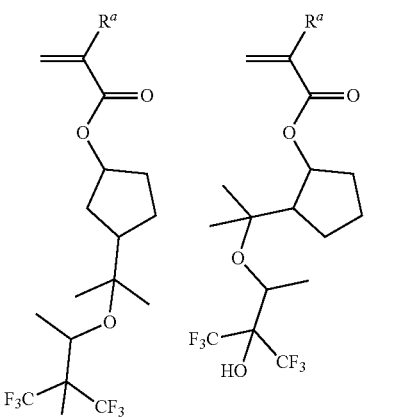
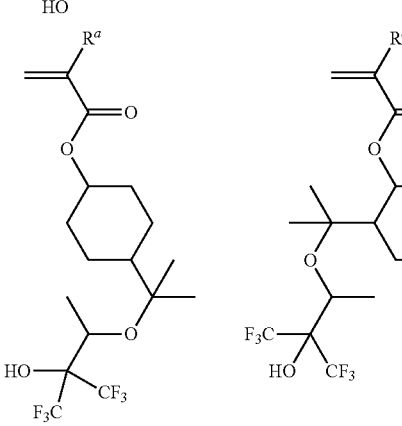
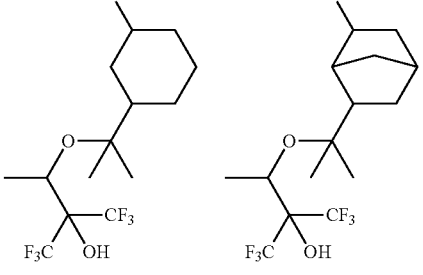

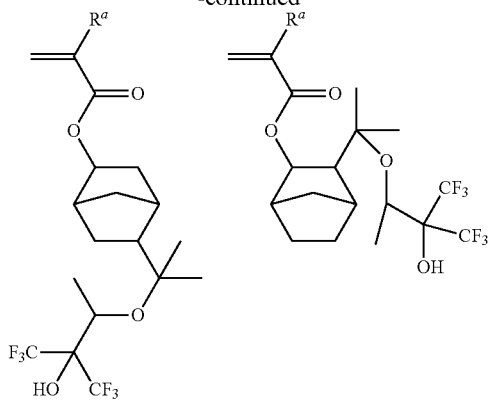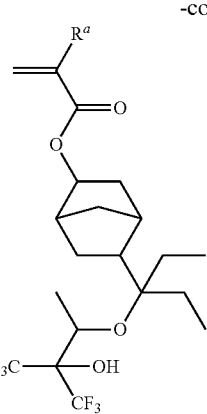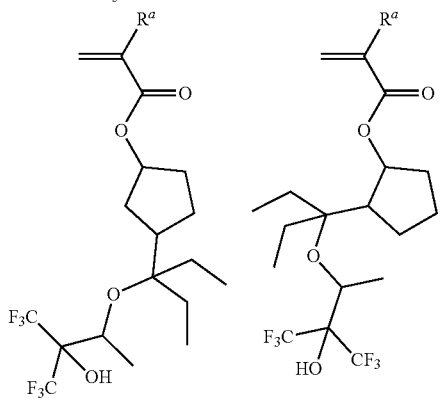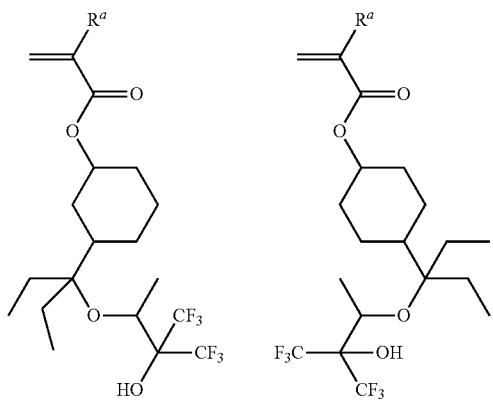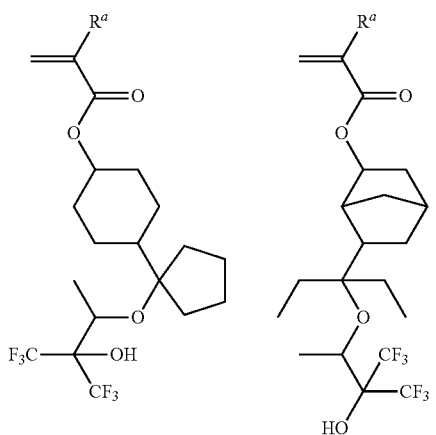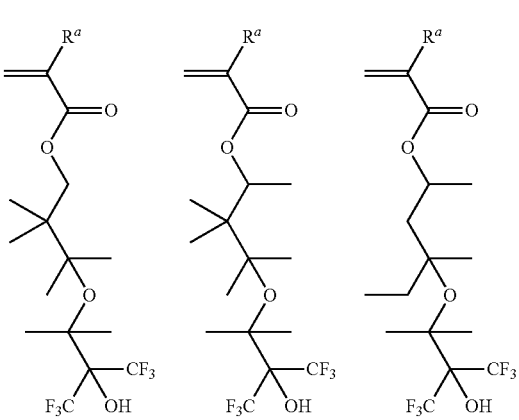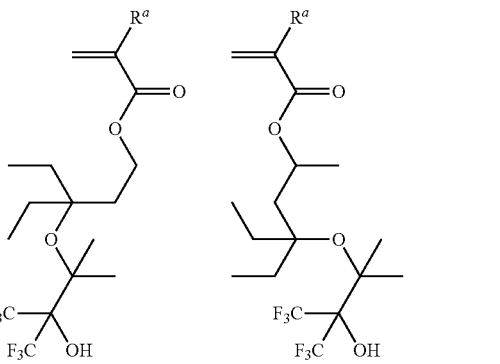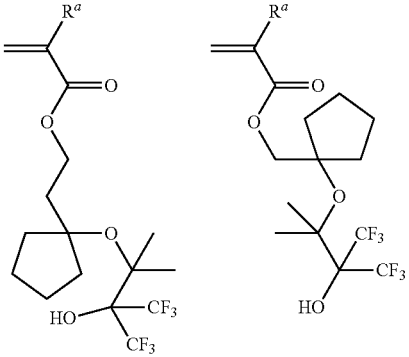

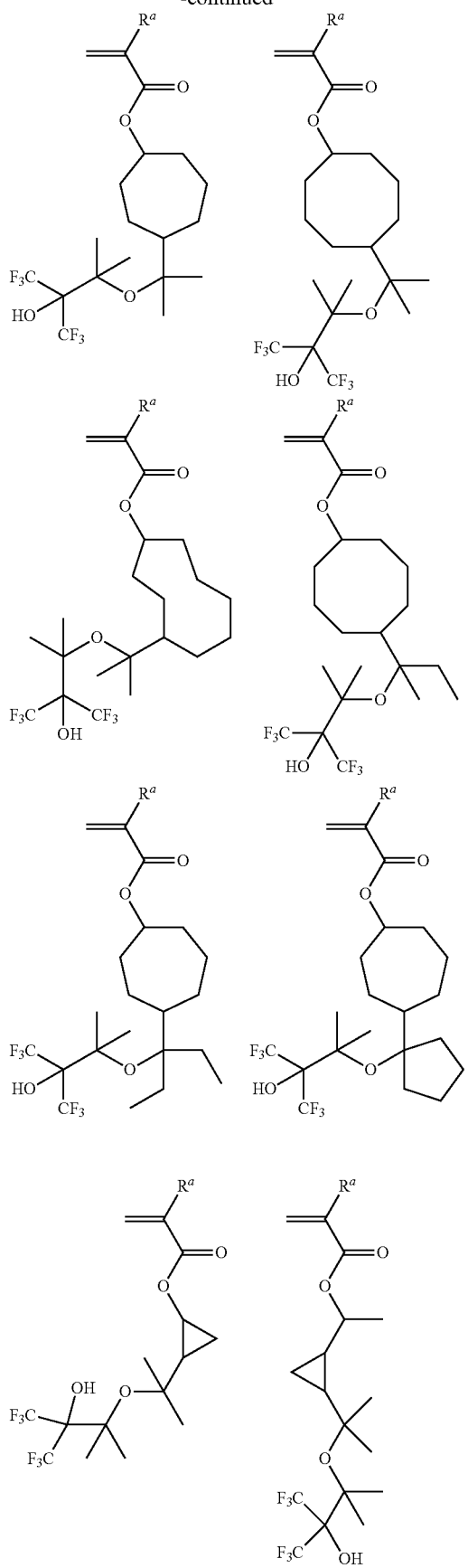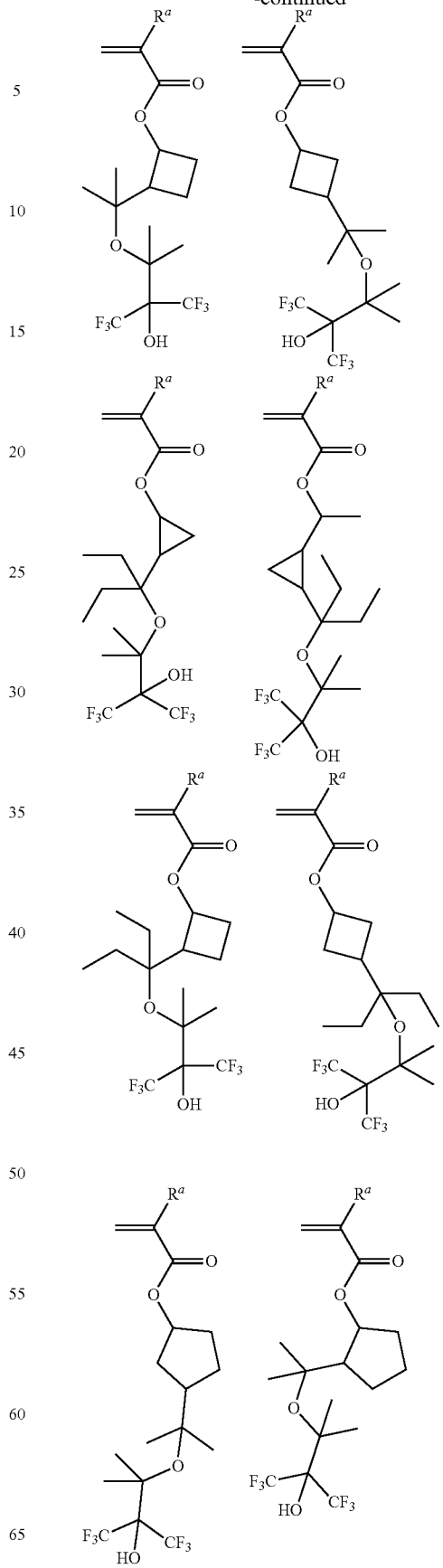

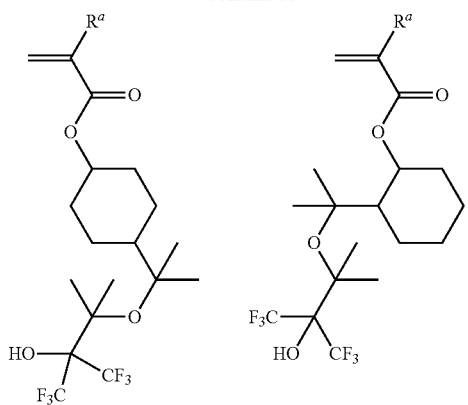
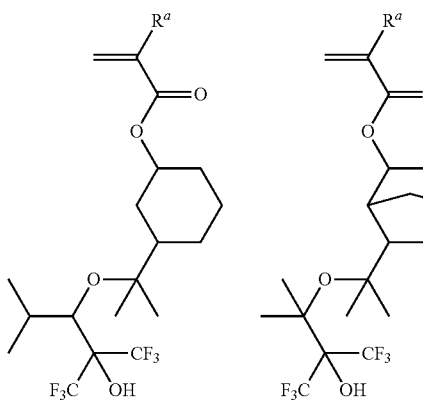
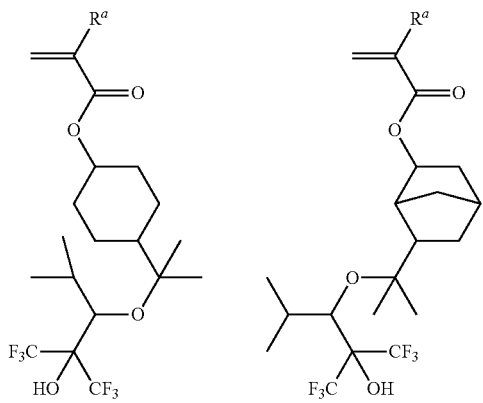
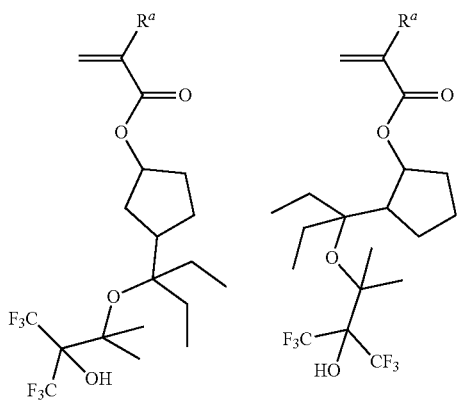
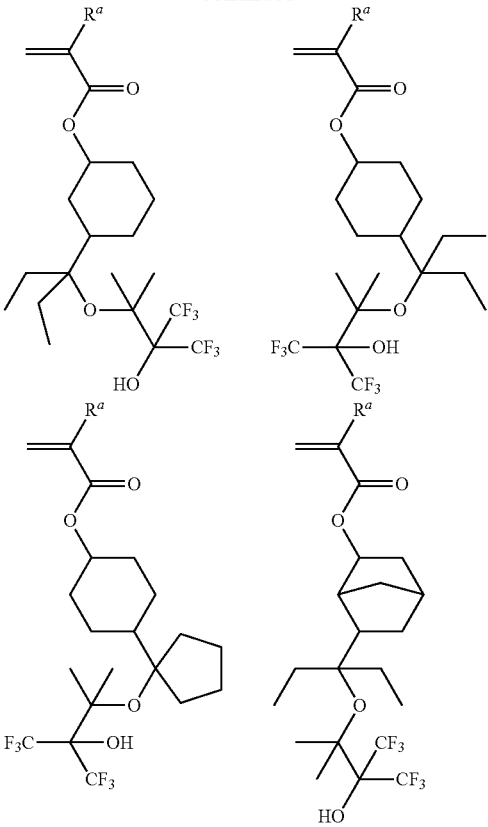
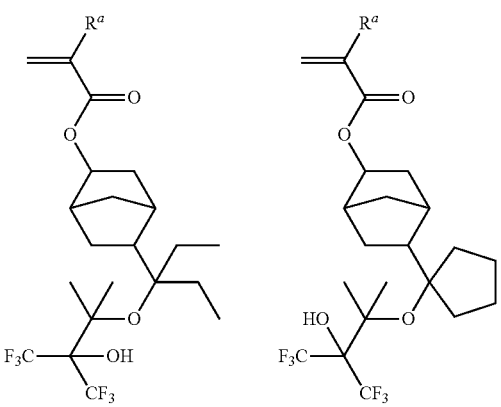
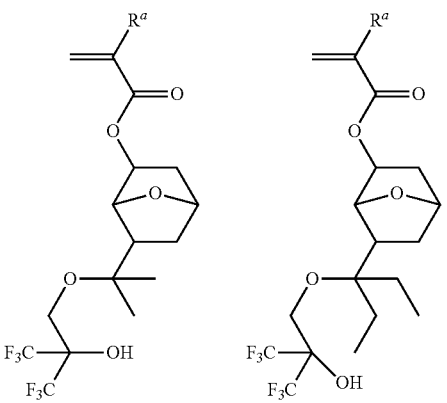

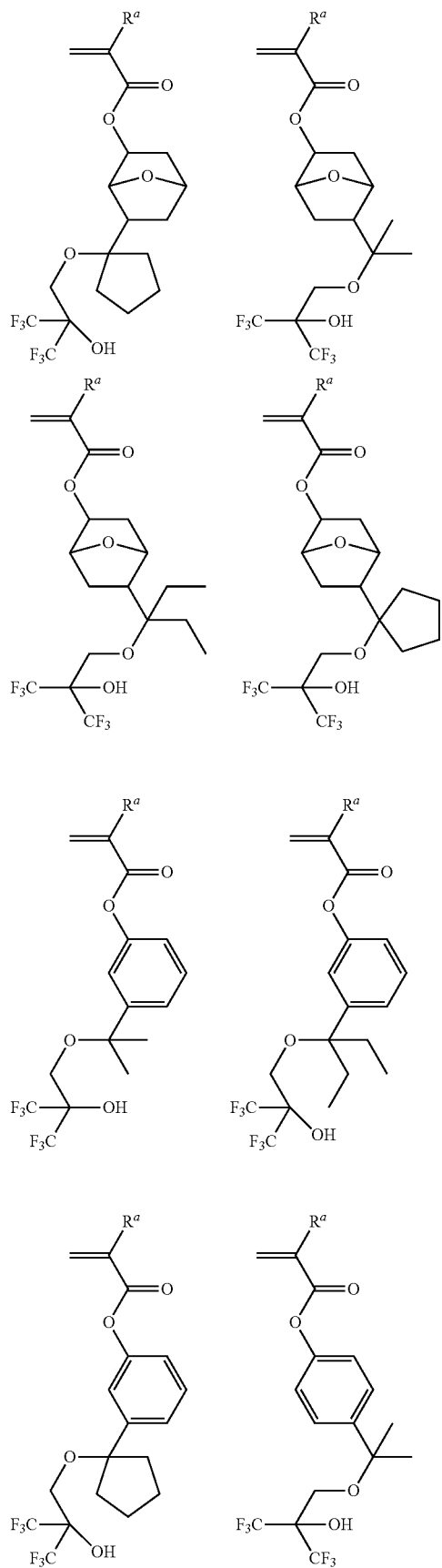
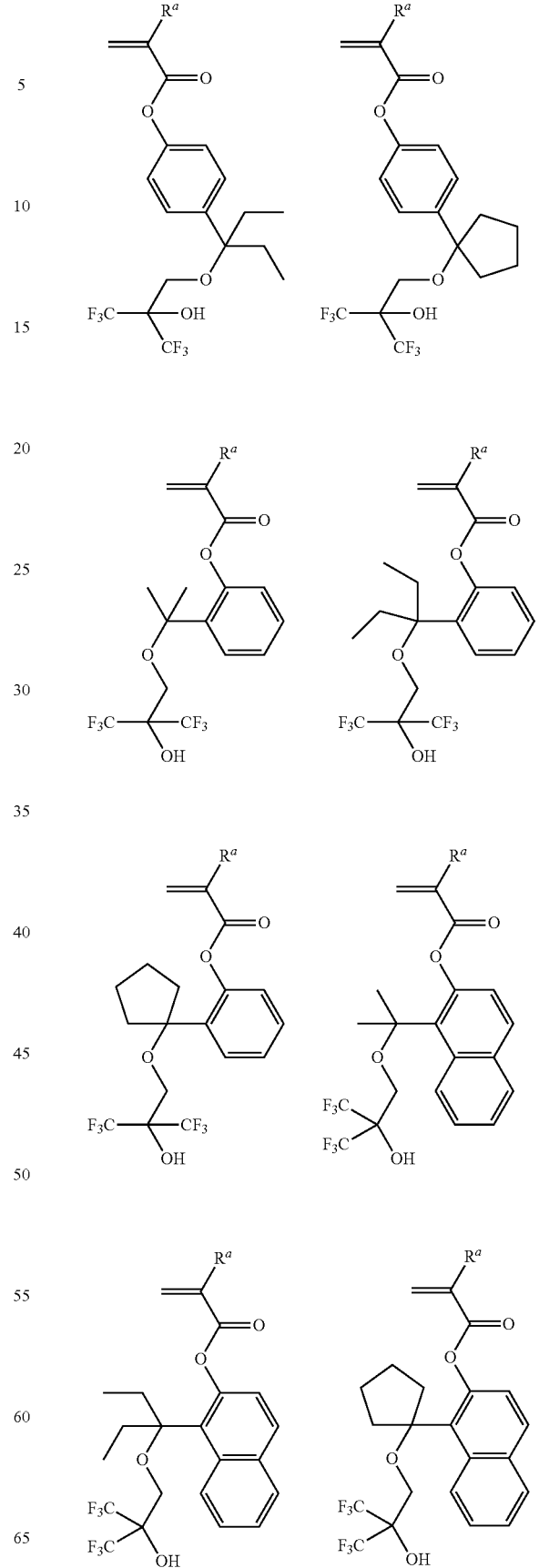

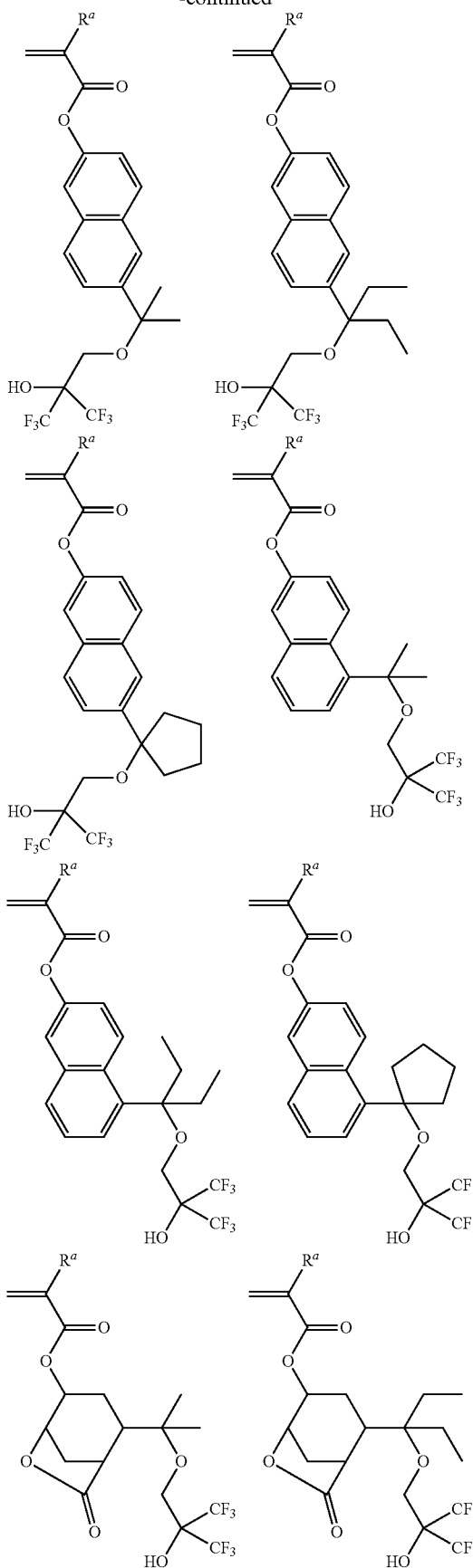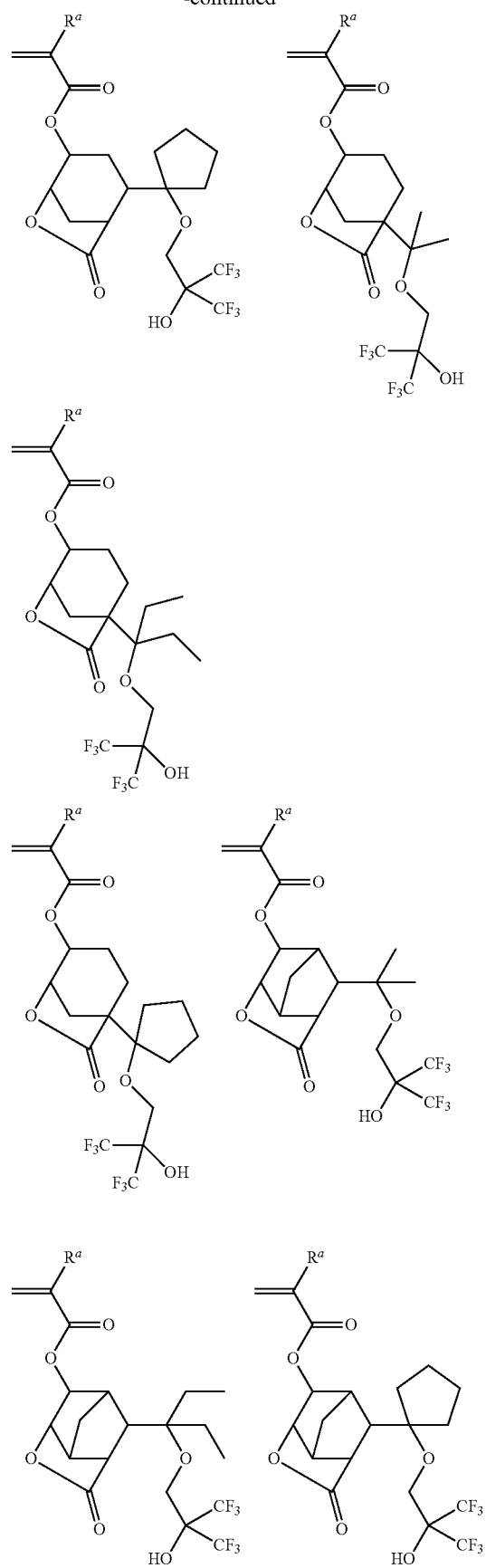

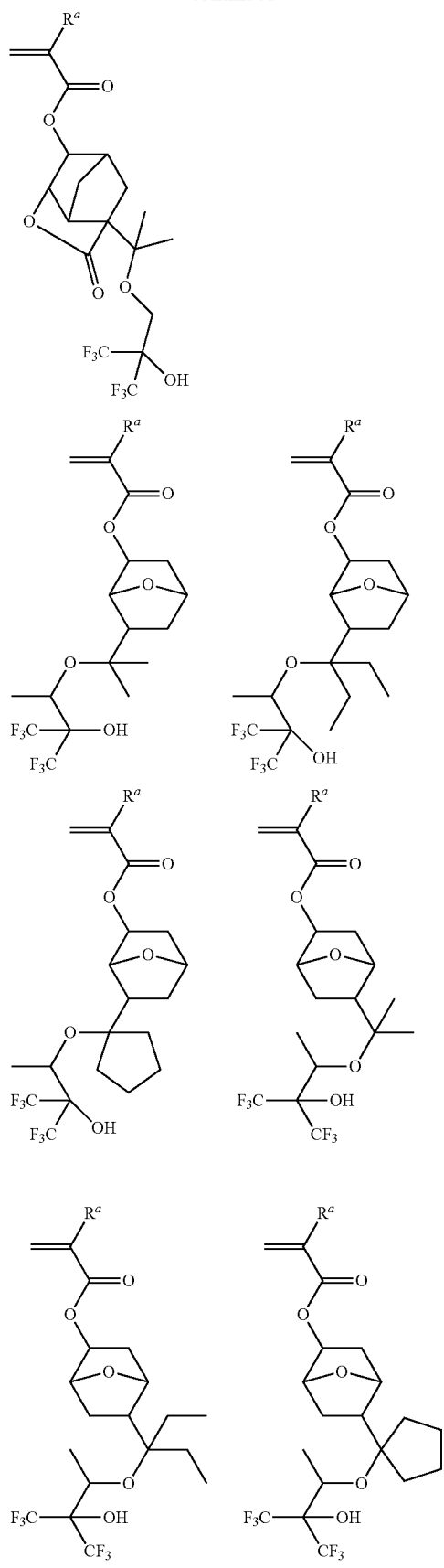
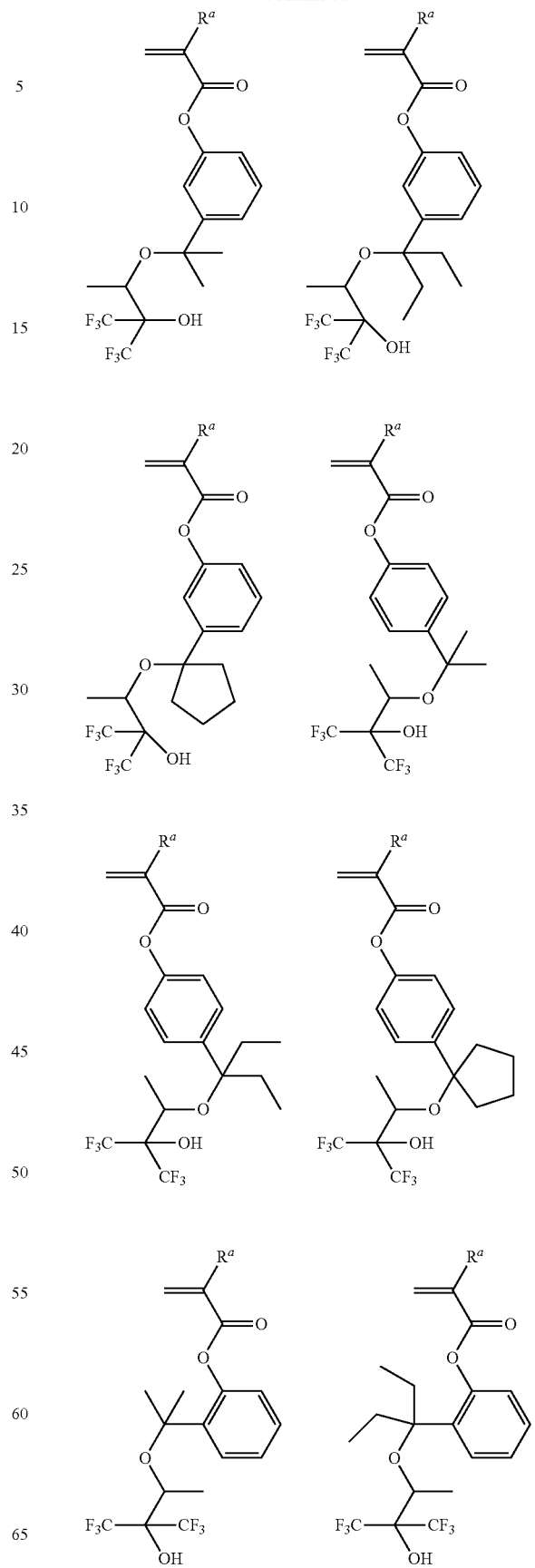

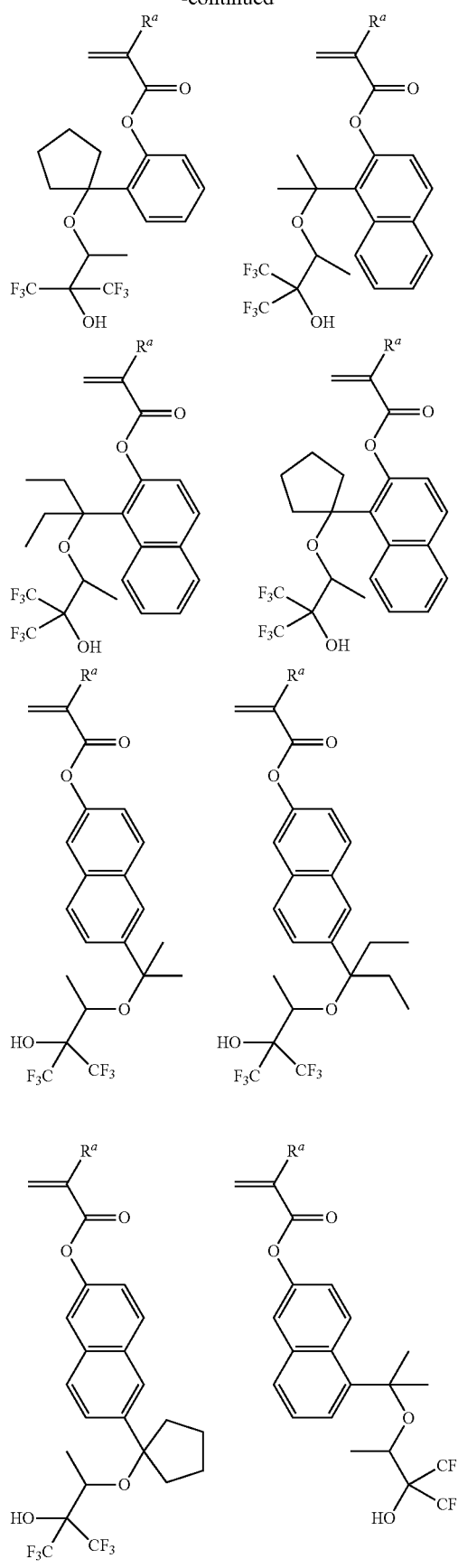
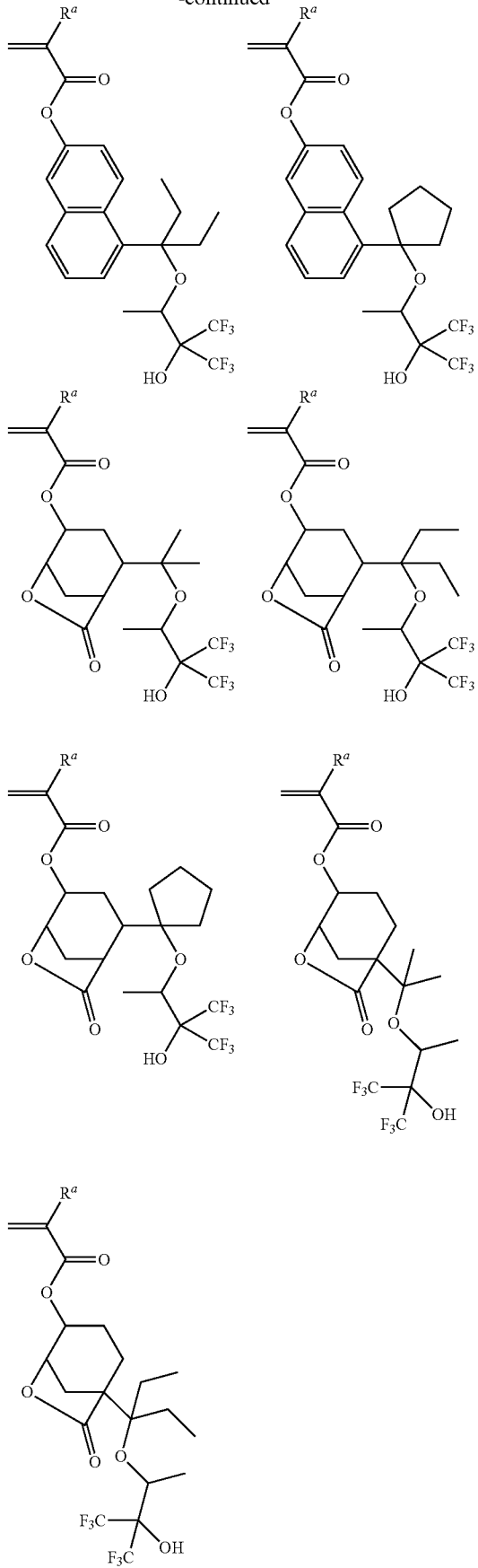

-continued
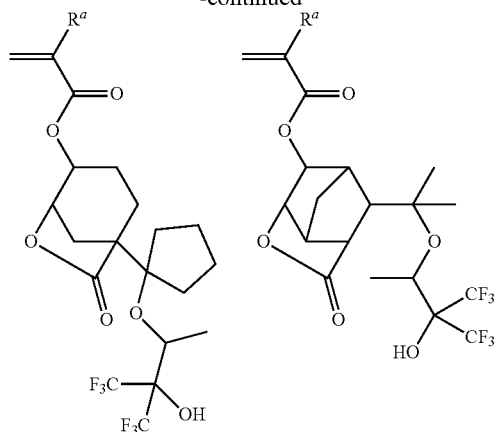
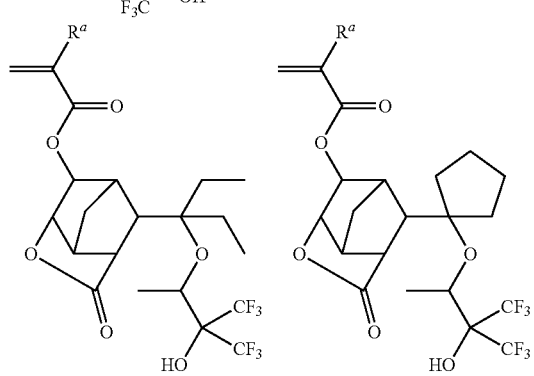
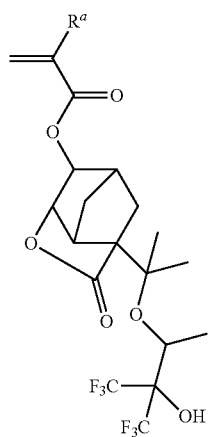
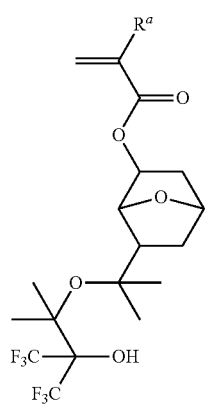
-continued
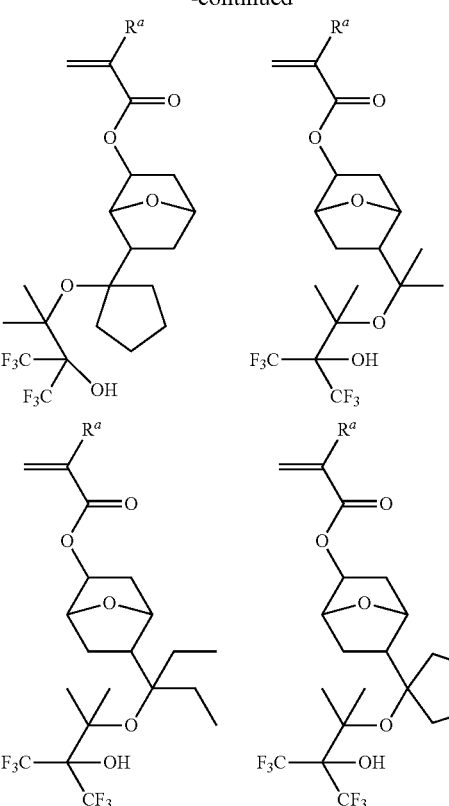
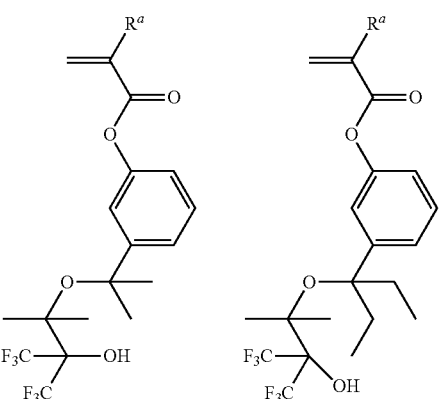
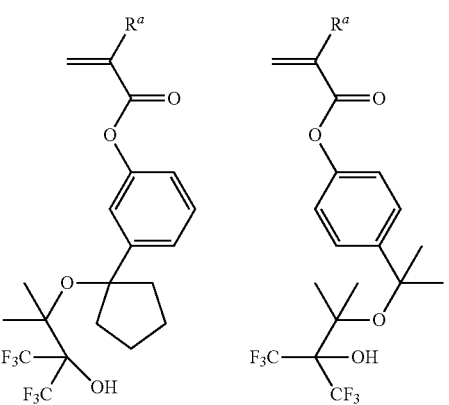

-continued
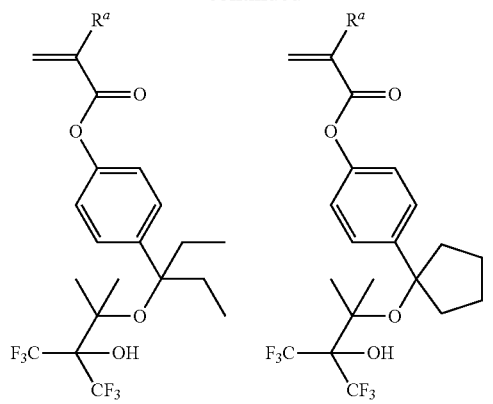
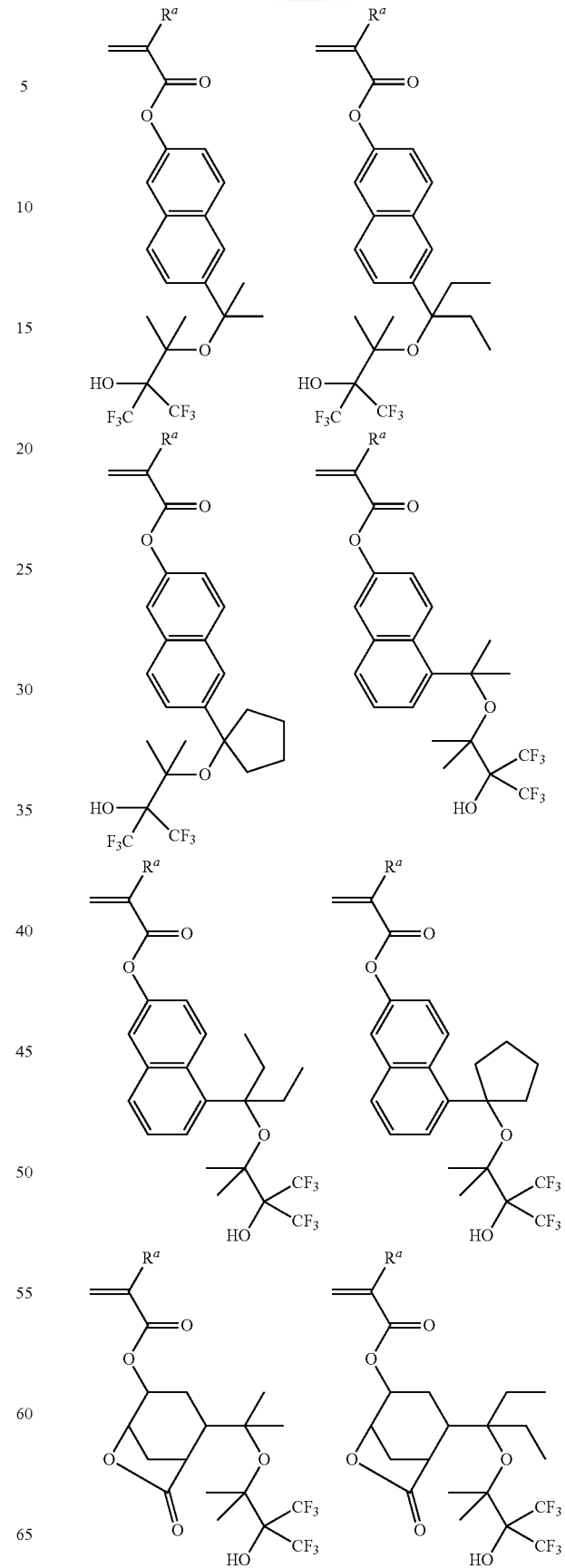

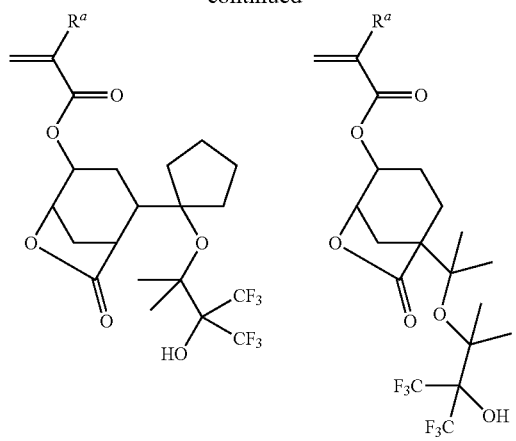
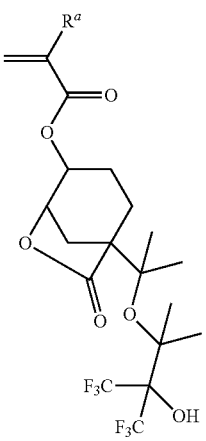
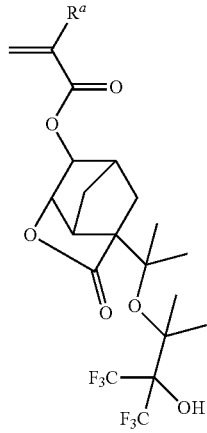
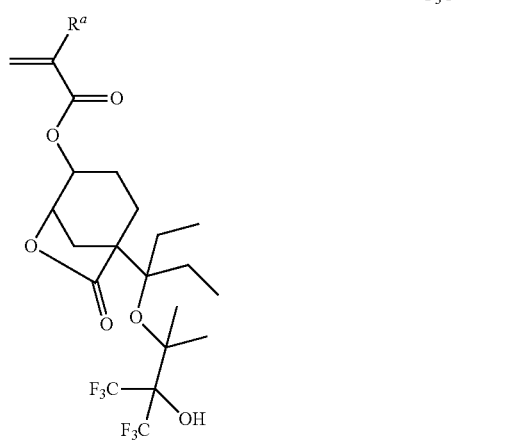
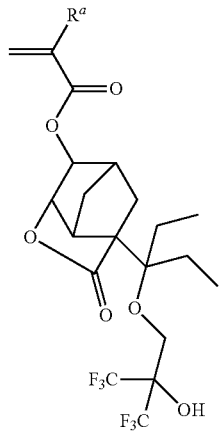
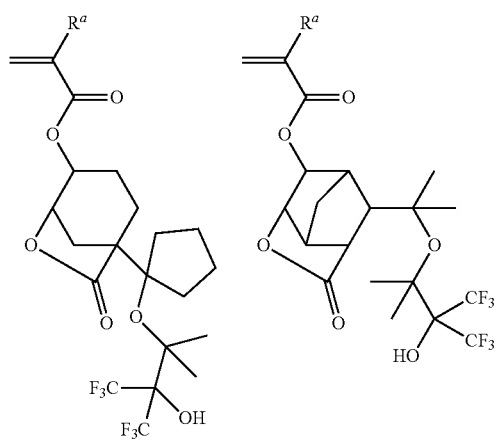
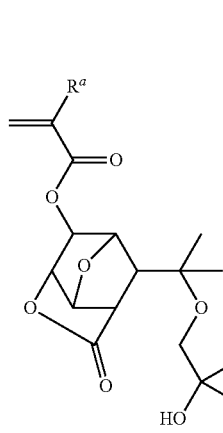
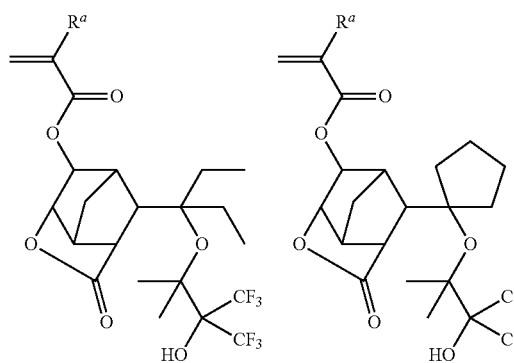
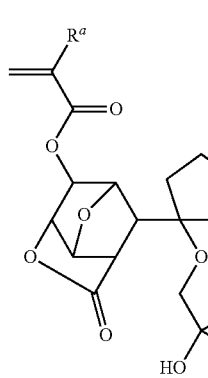

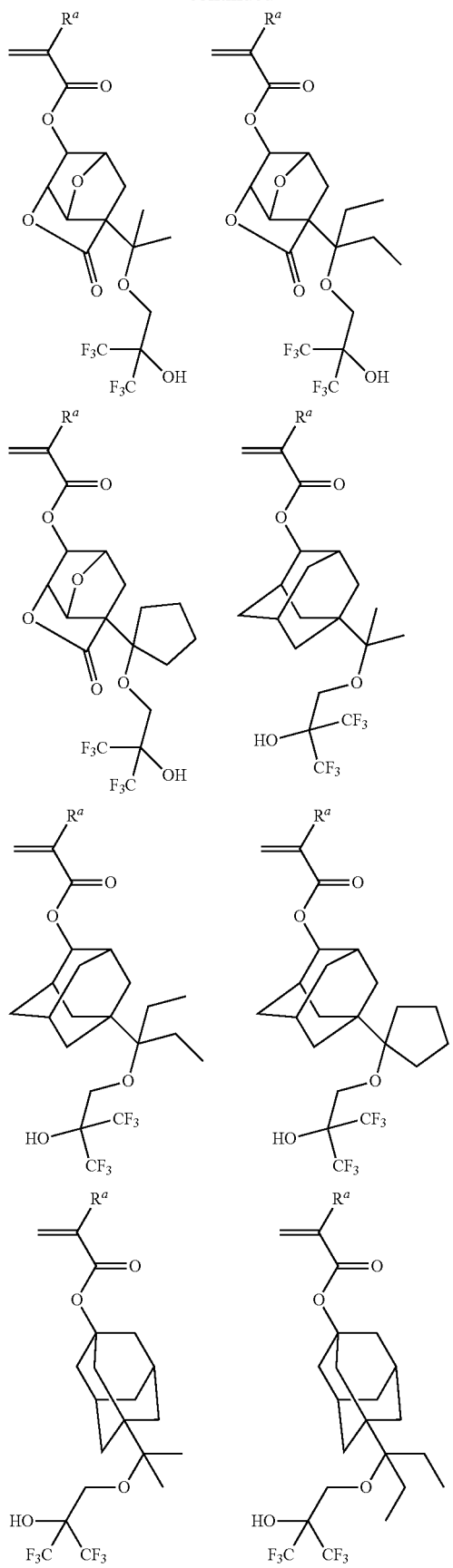
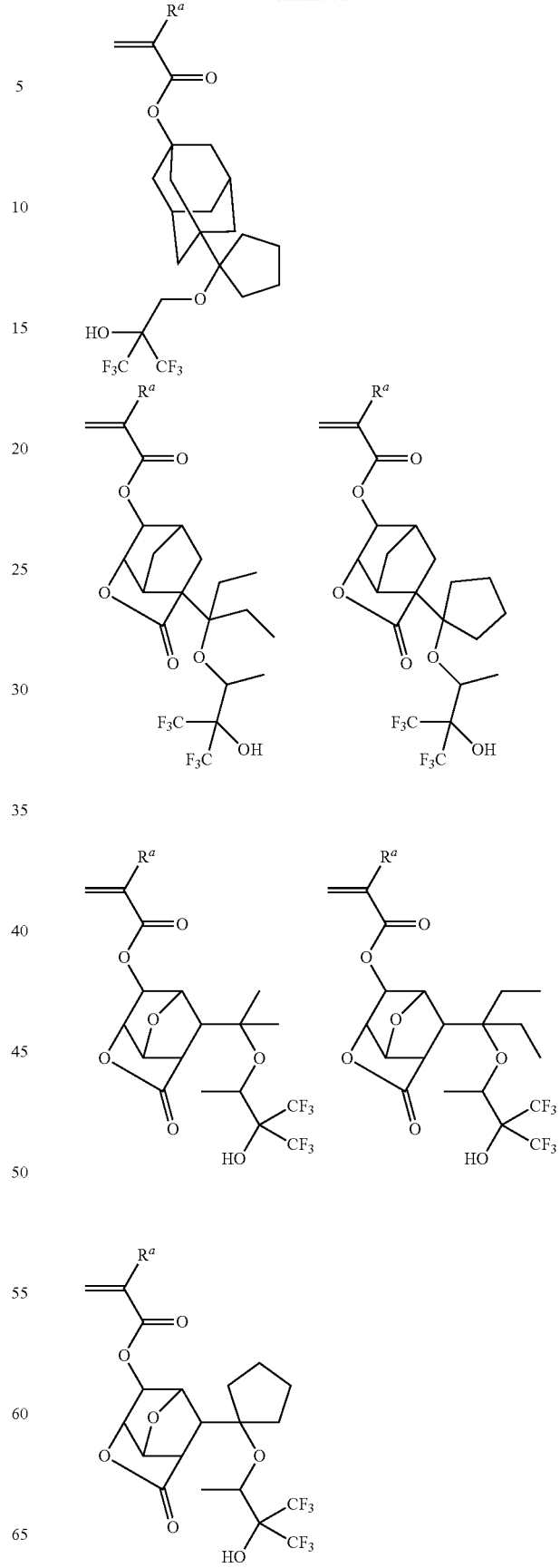

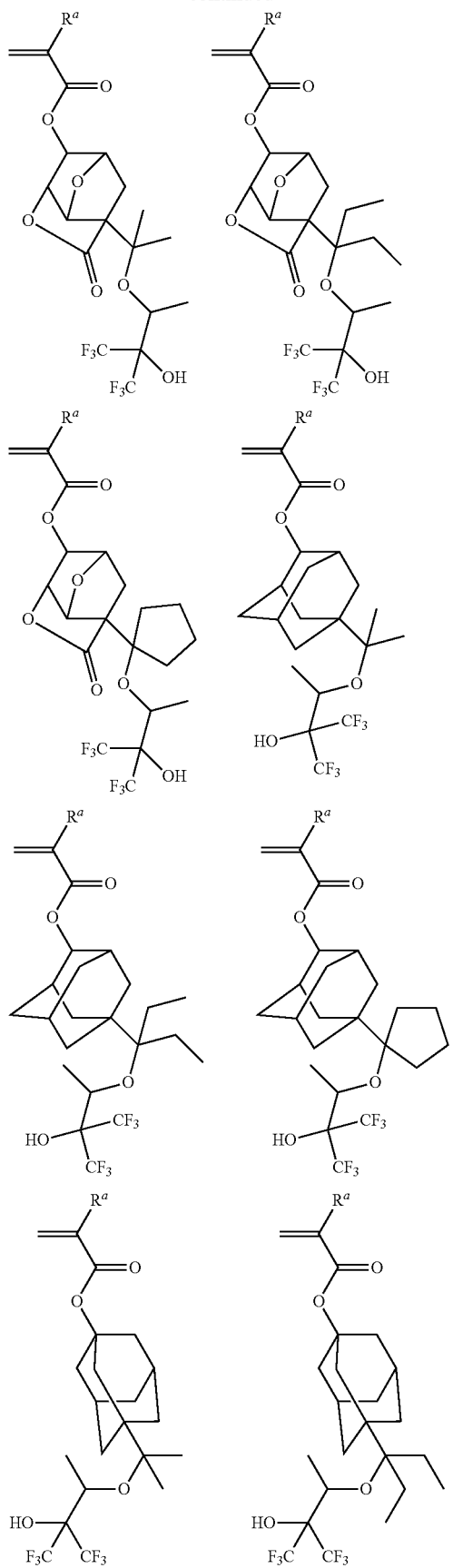
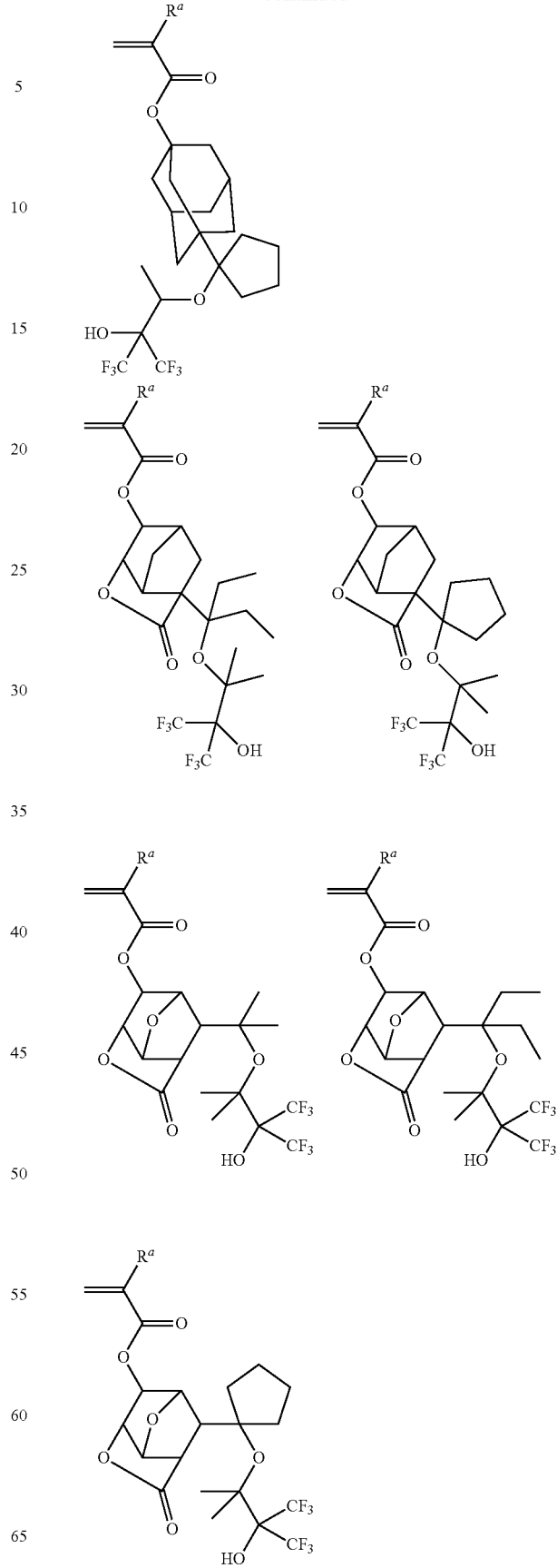

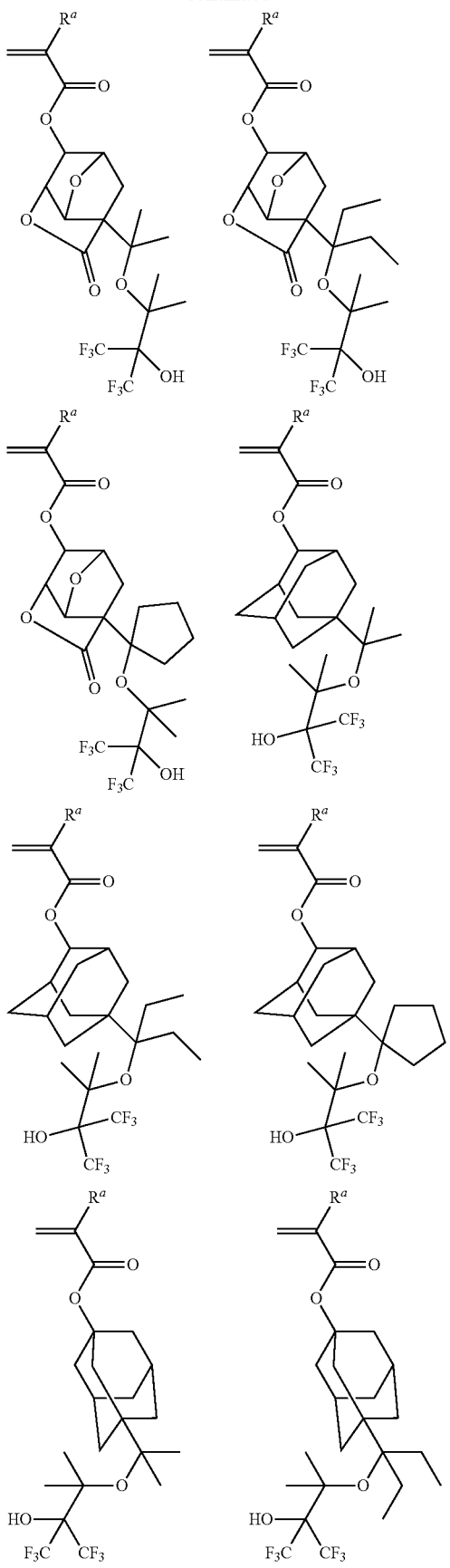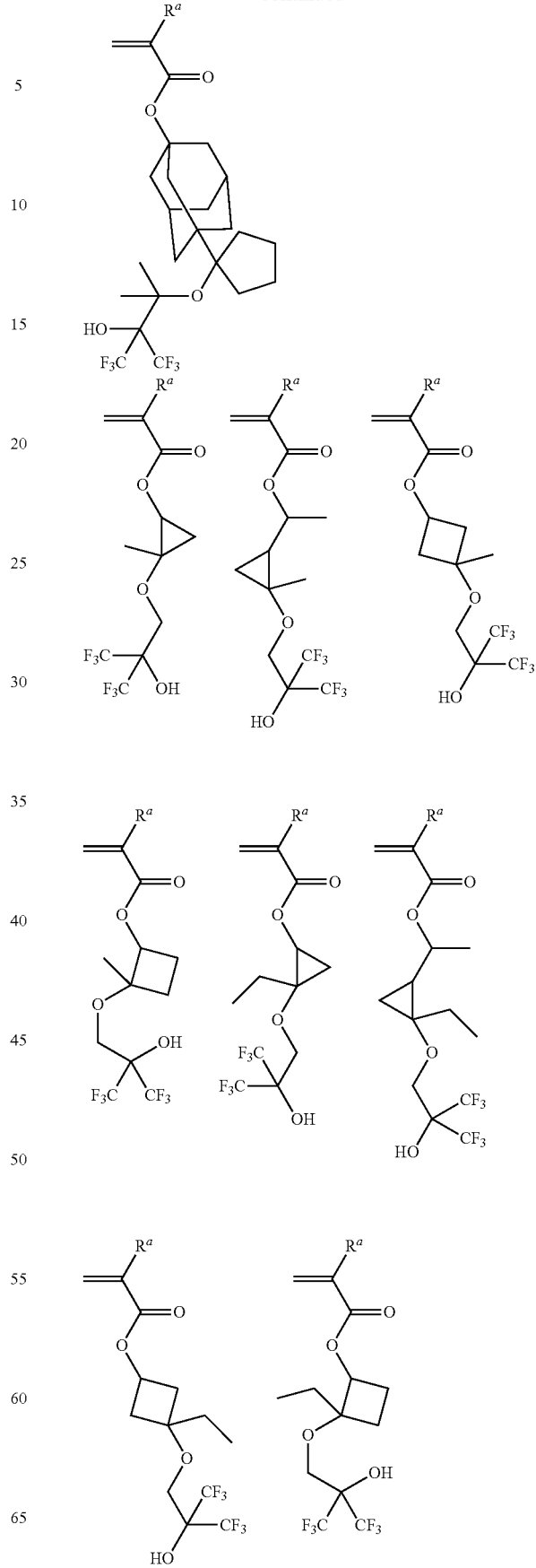

-continued
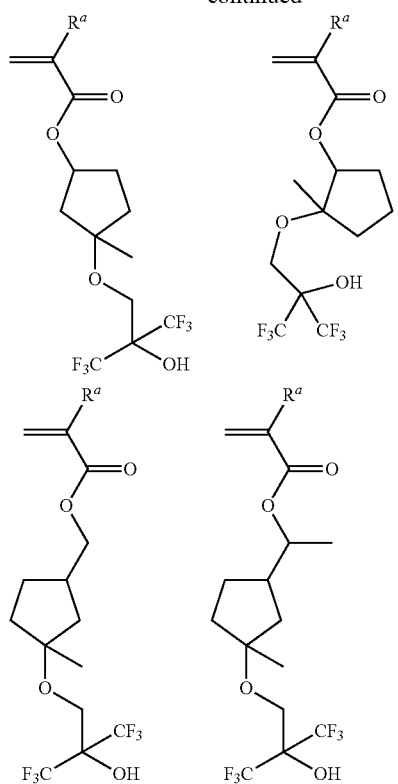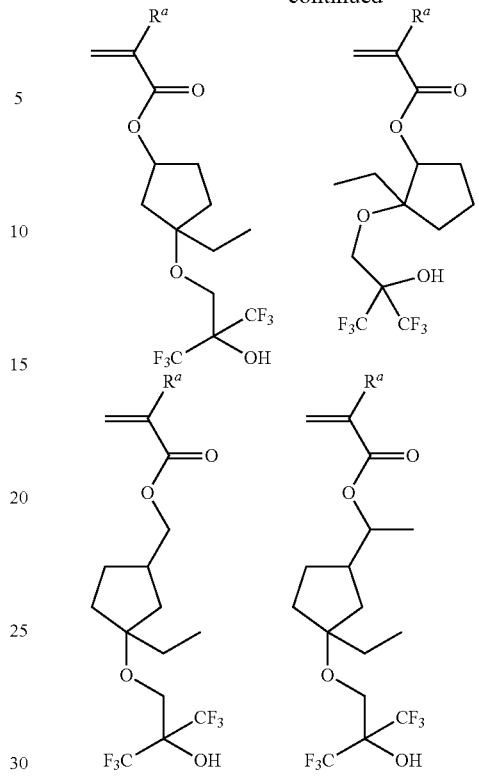
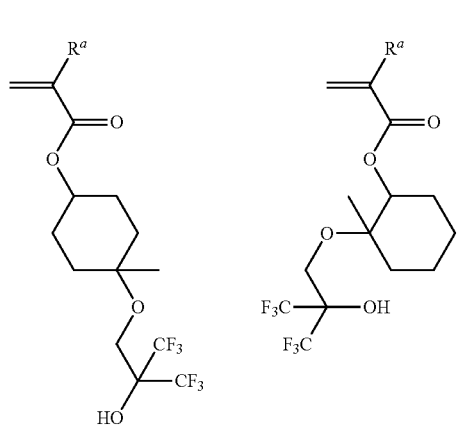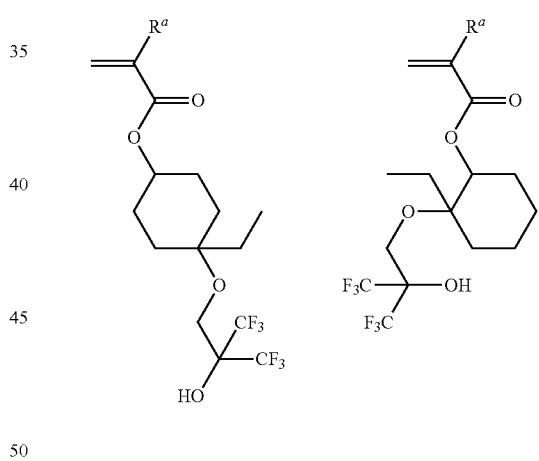
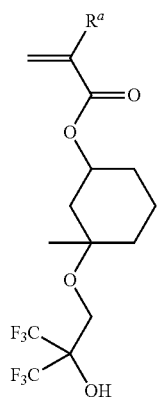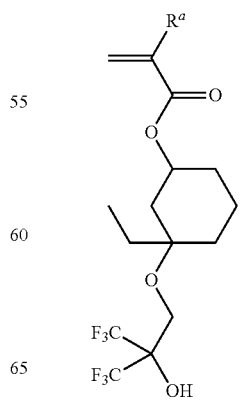

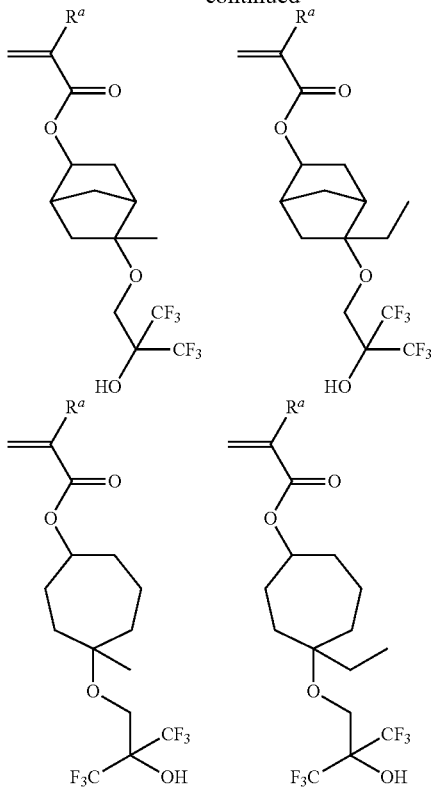
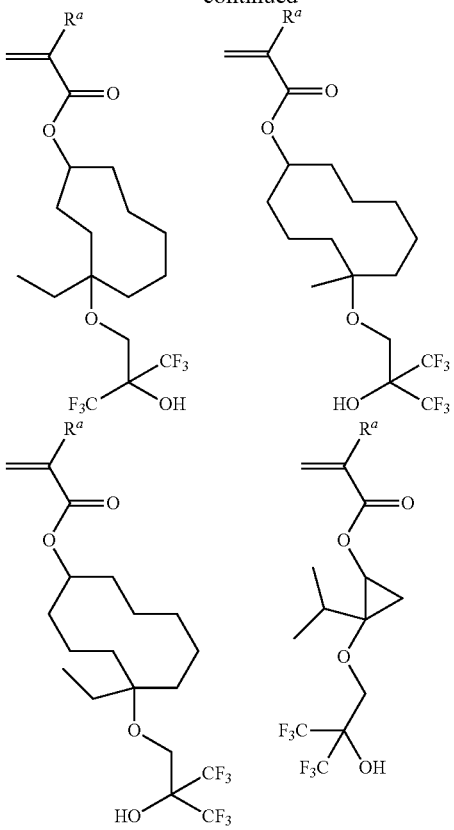

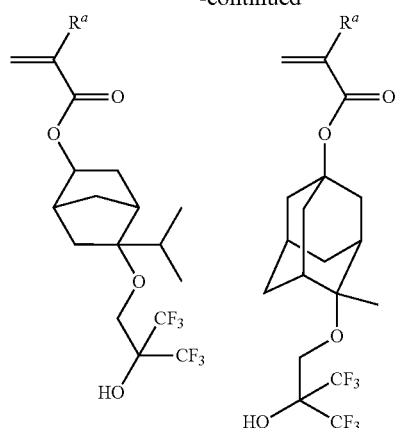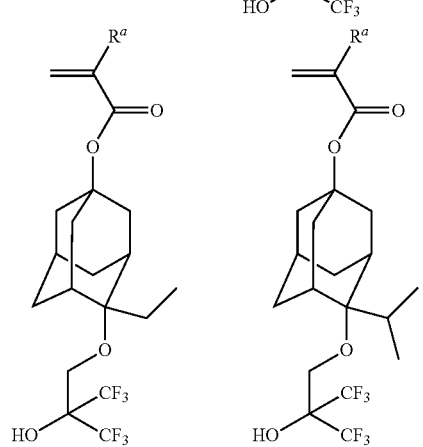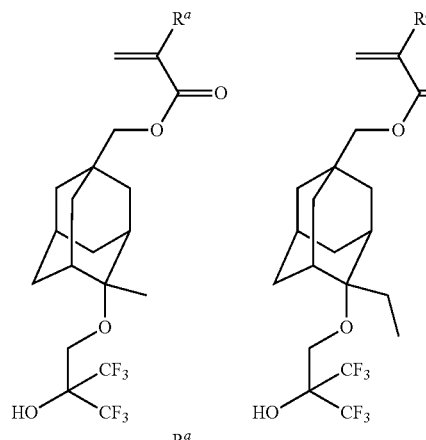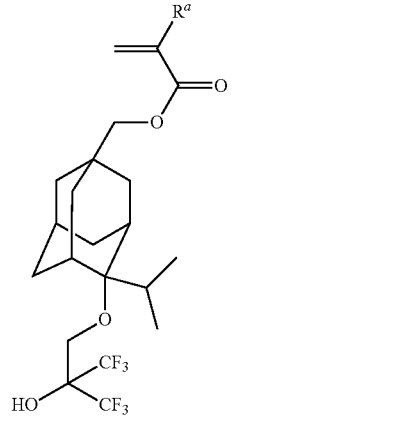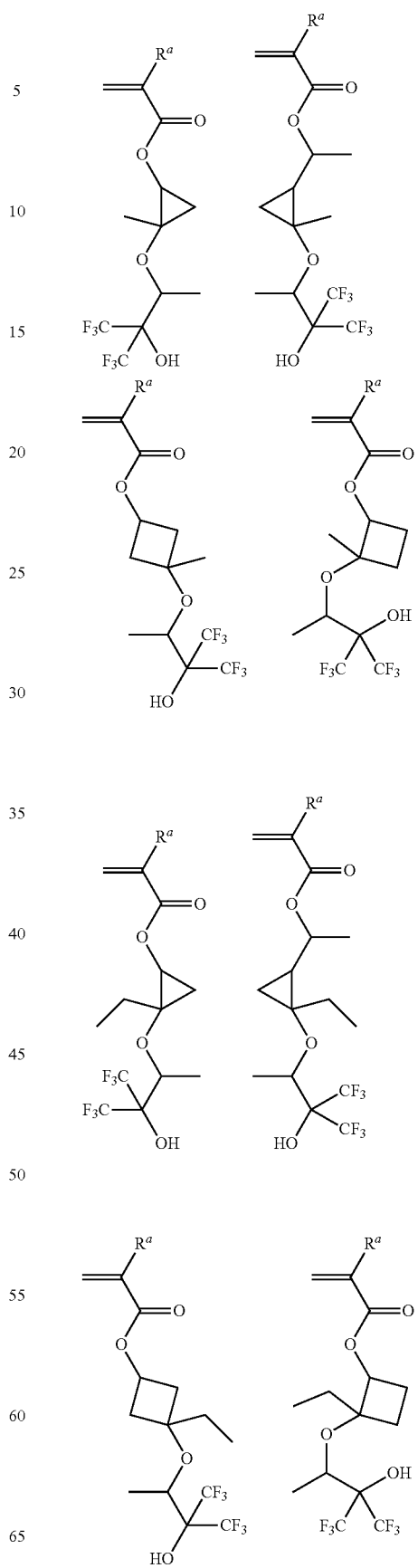

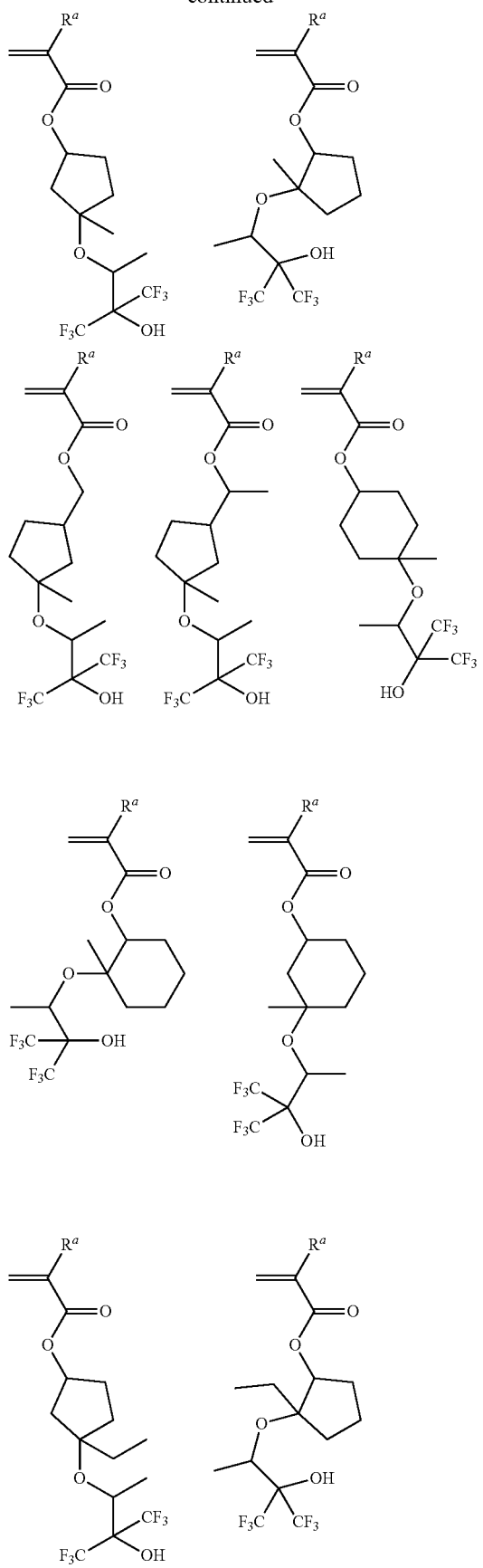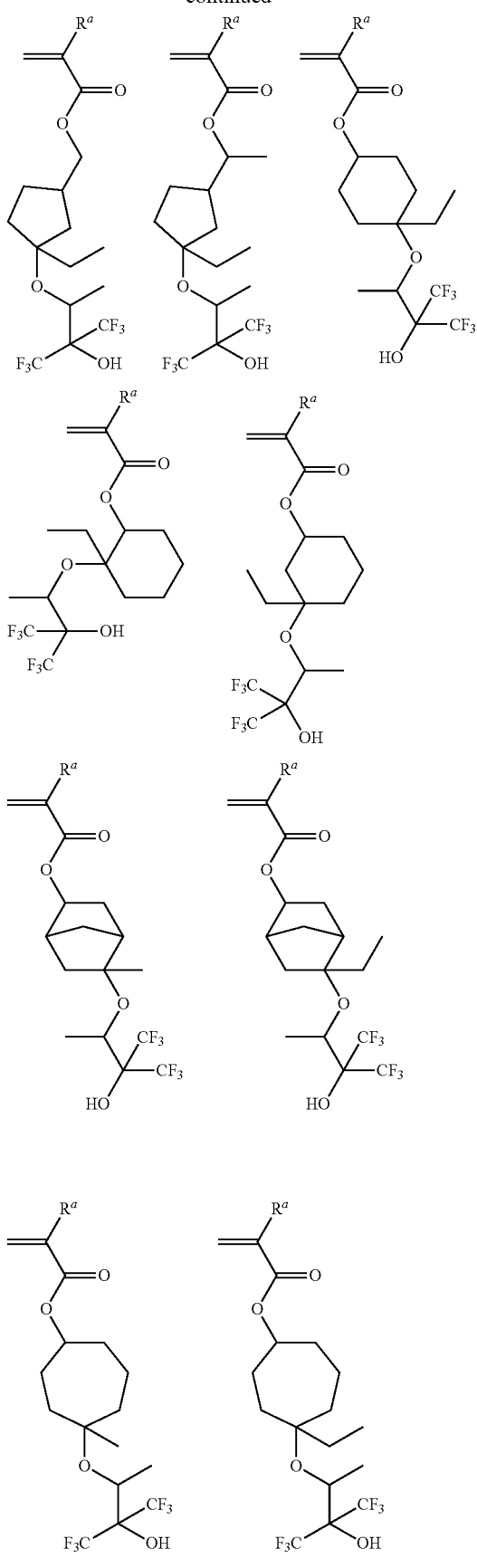

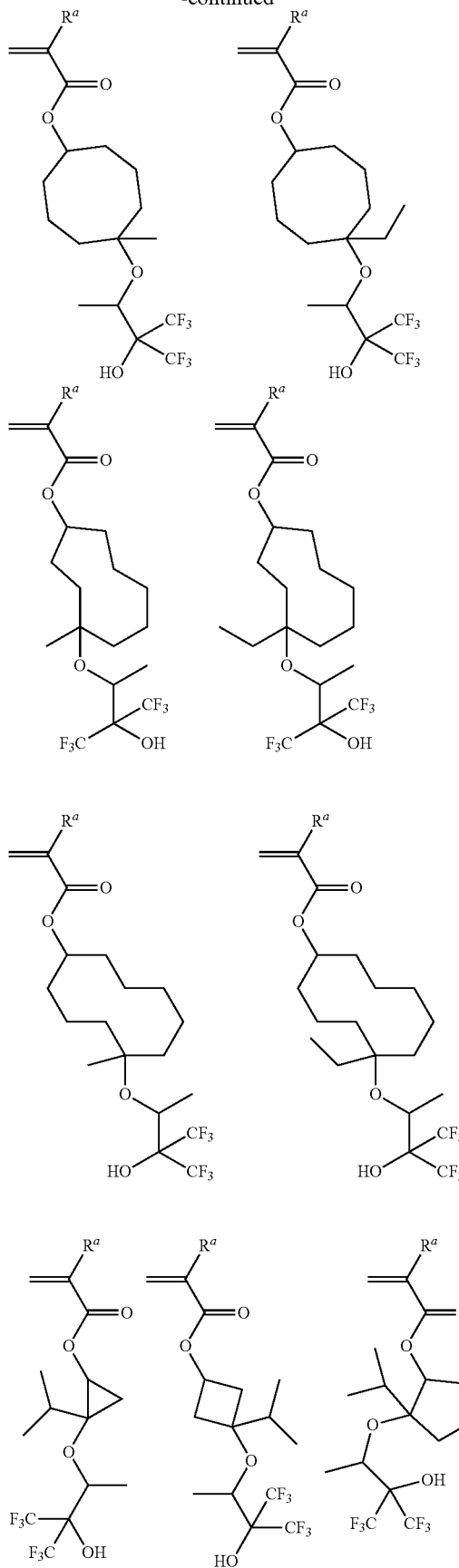
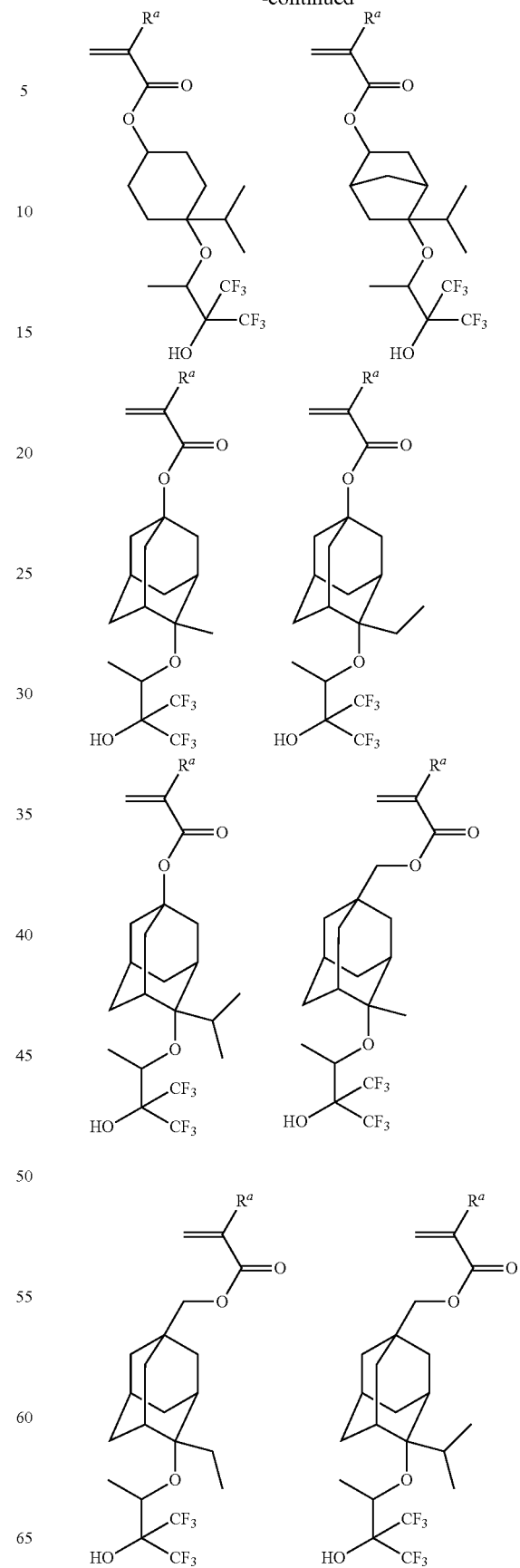

-continued
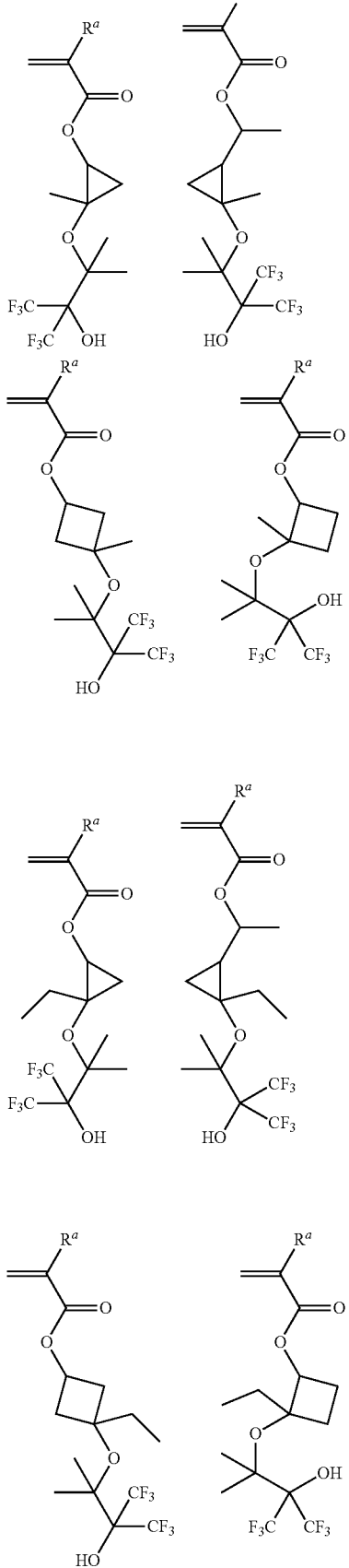
-continued
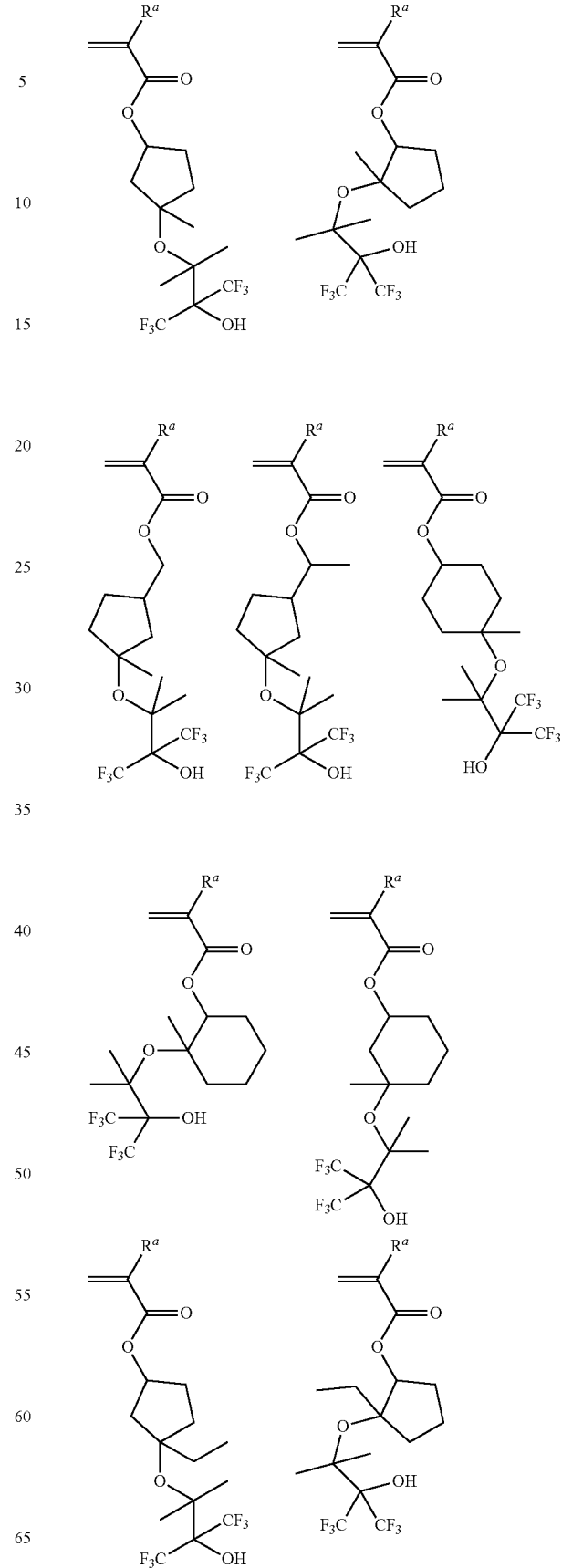

-continued
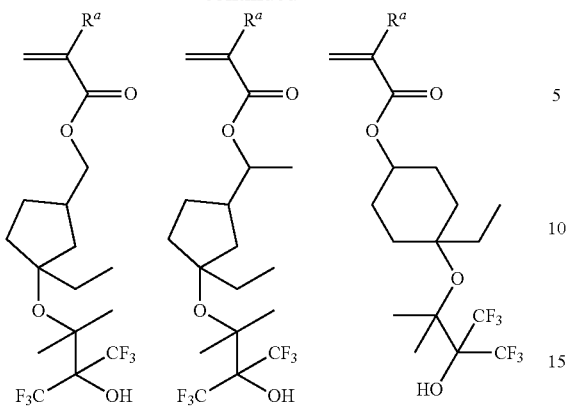
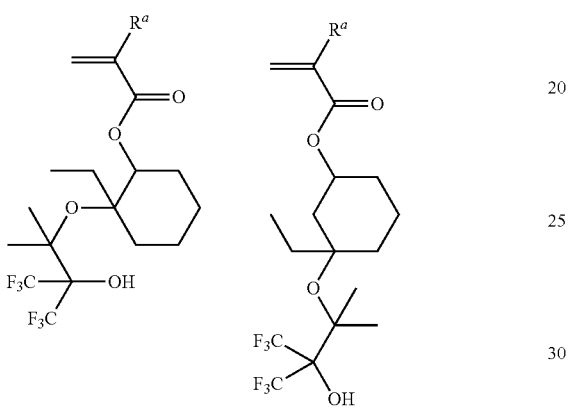
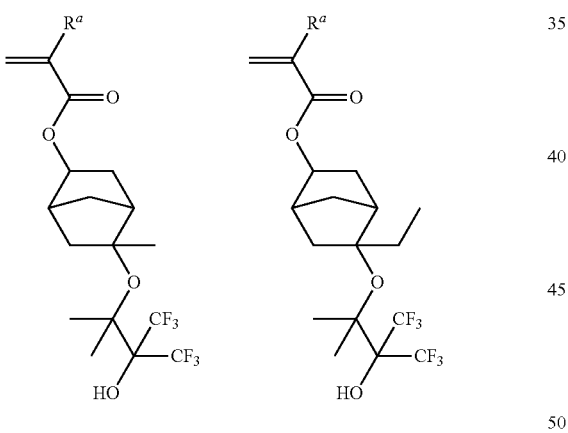
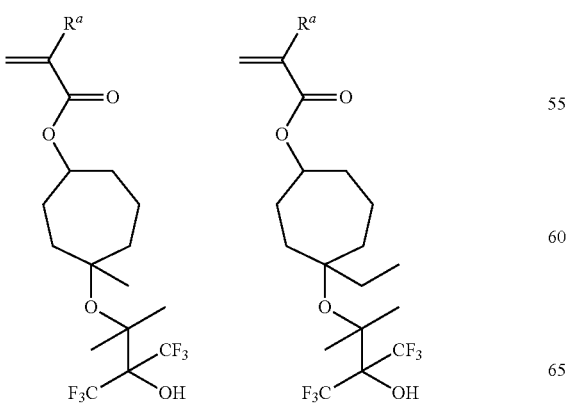
-continued
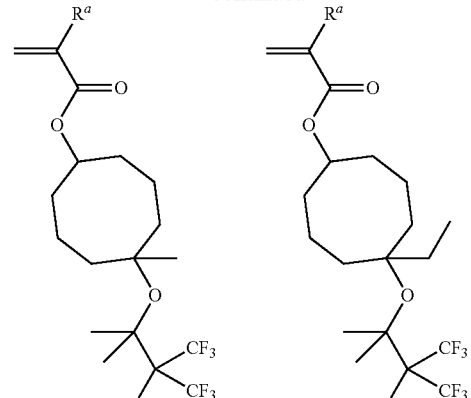
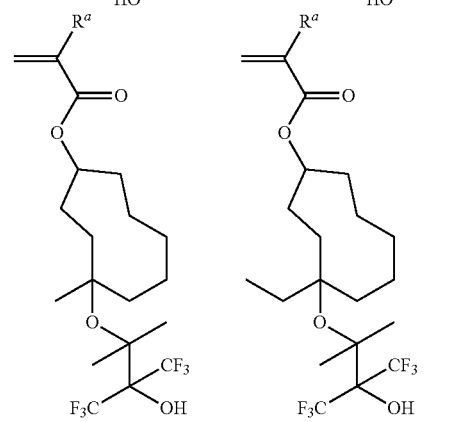
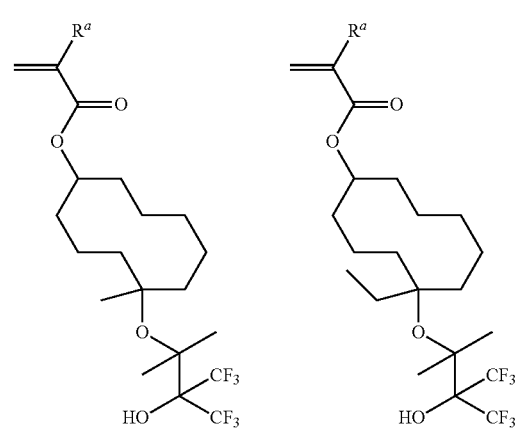
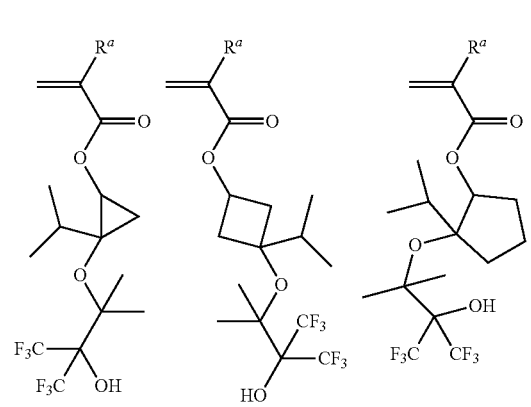

-continued
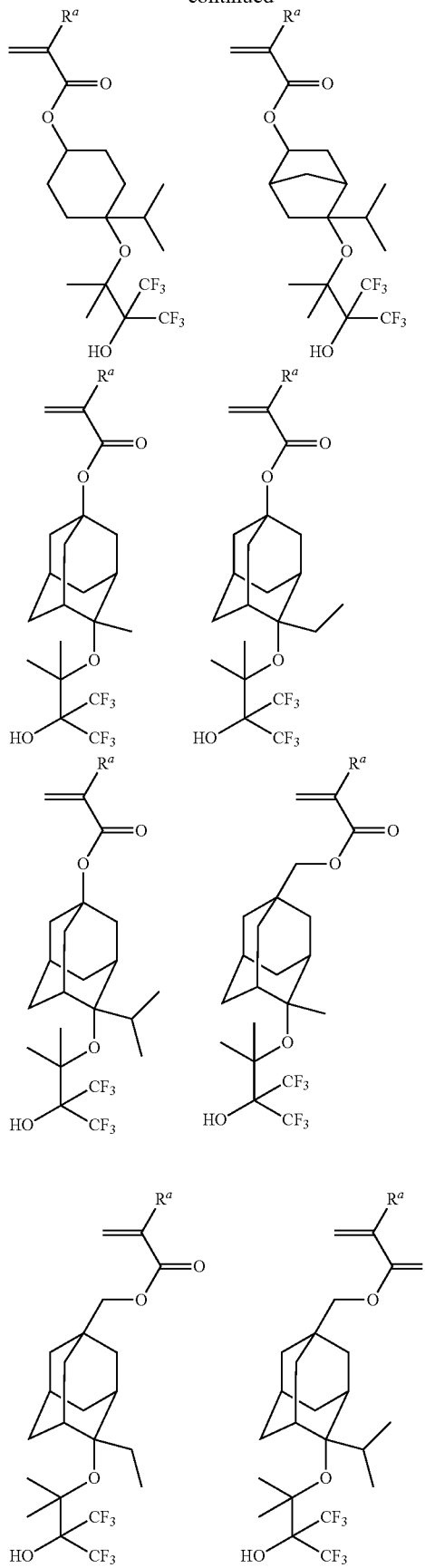
-continued
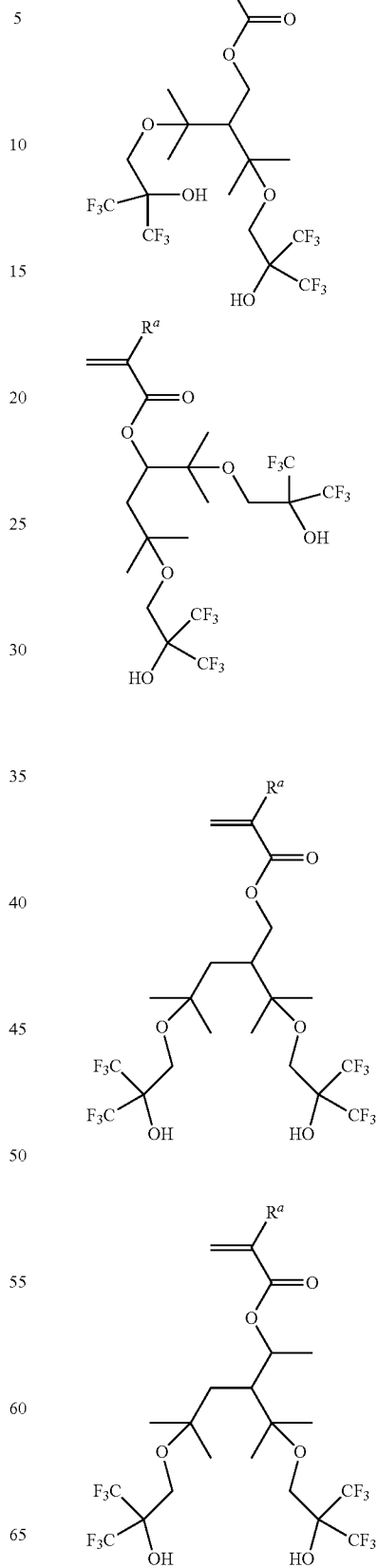

69
-continued
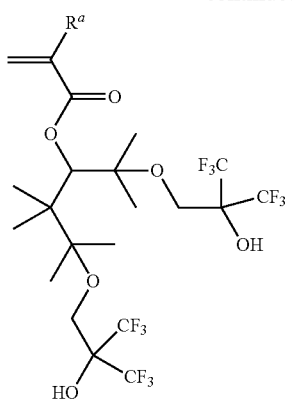
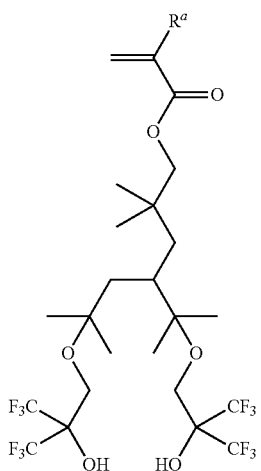
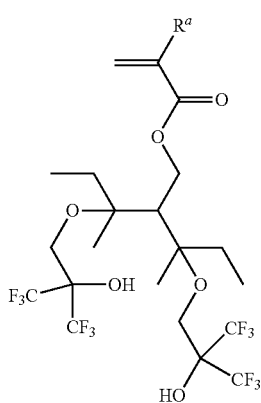
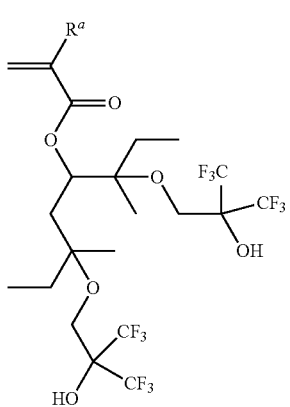
70
-continued
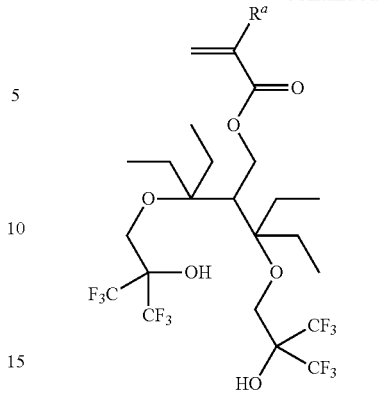
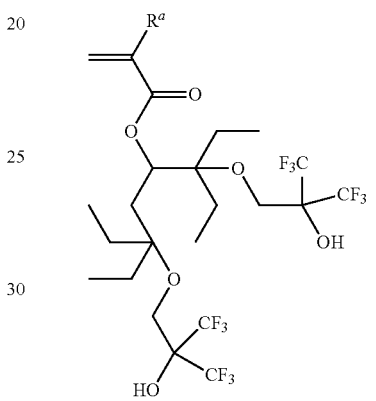
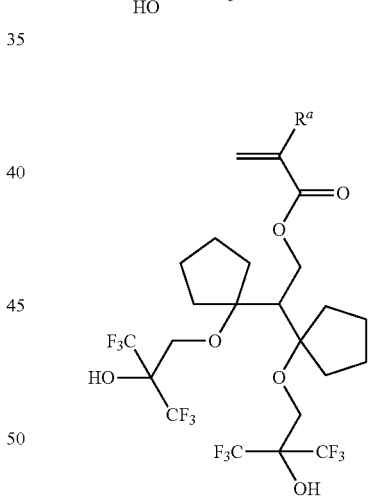
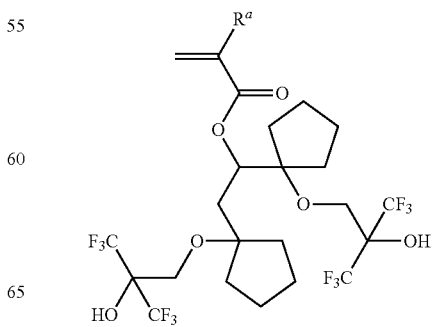

-continued
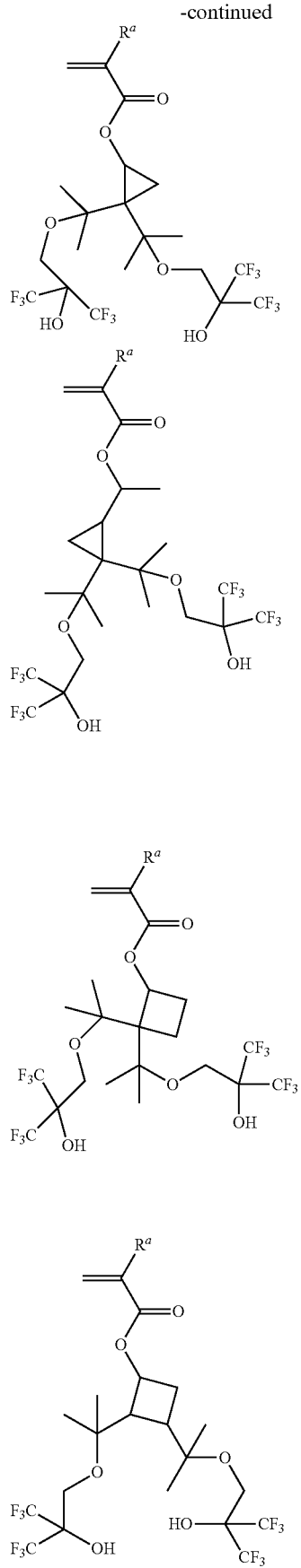
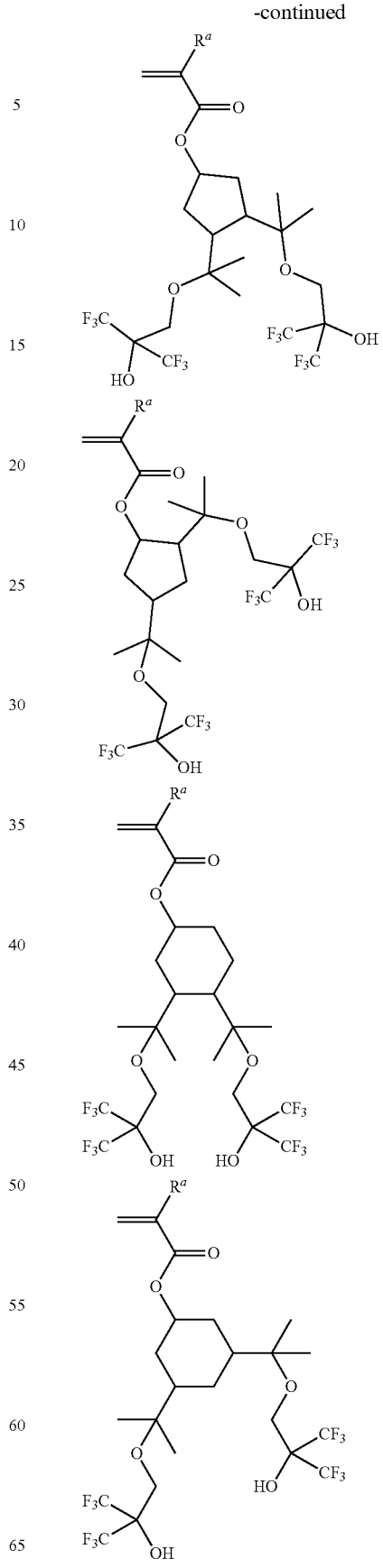

73
-continued
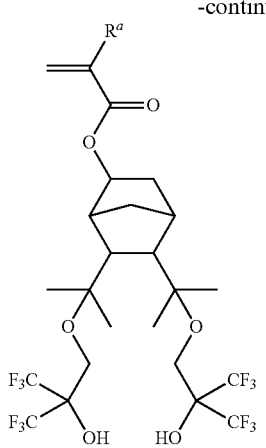
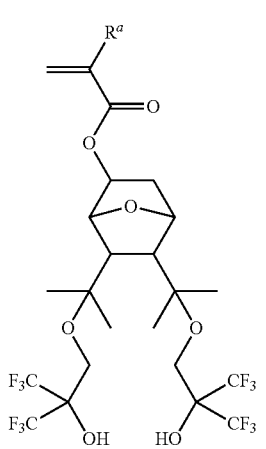
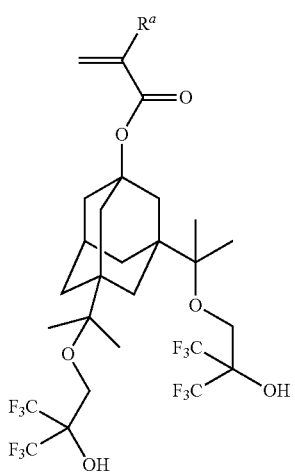
74
-continued
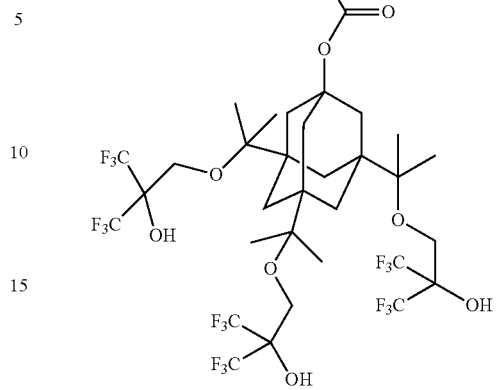
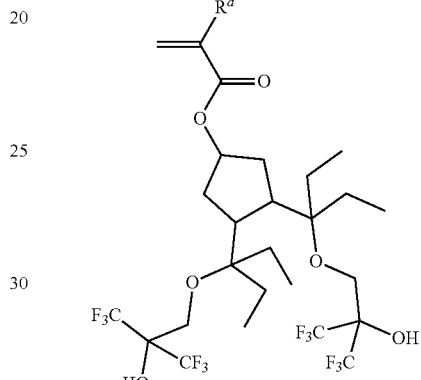
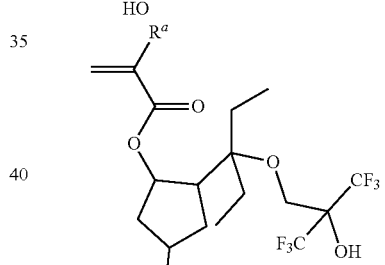
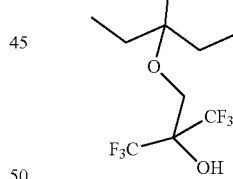
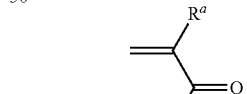
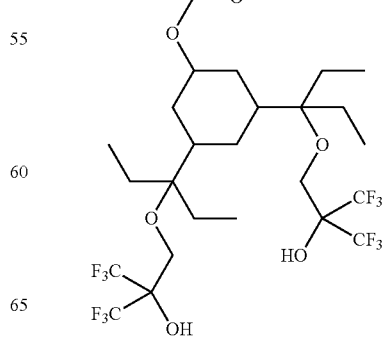

75
-continued
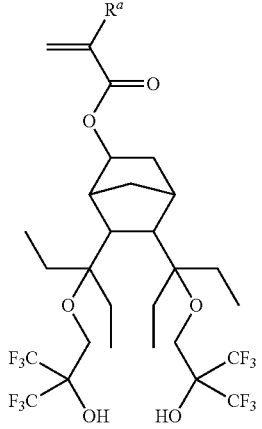
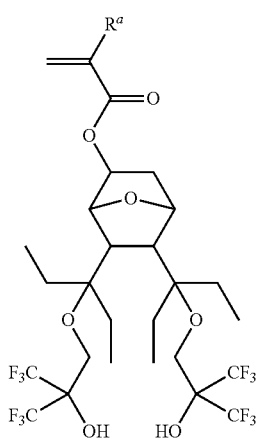
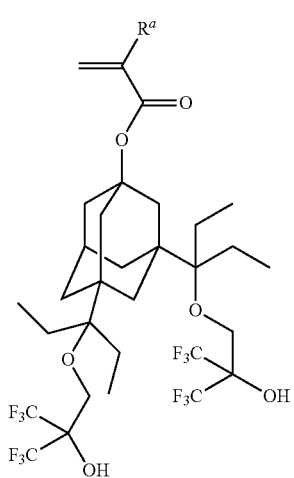
76
-continued
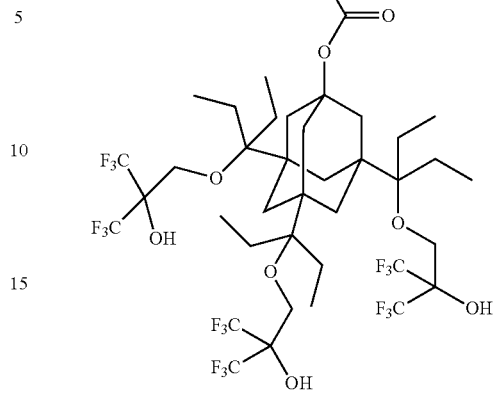
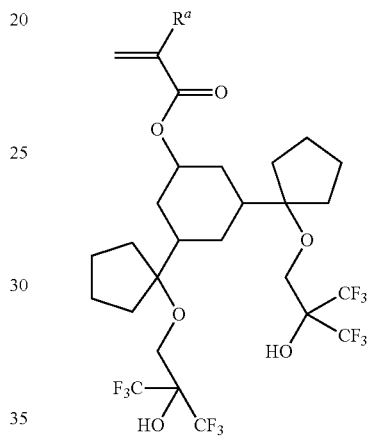
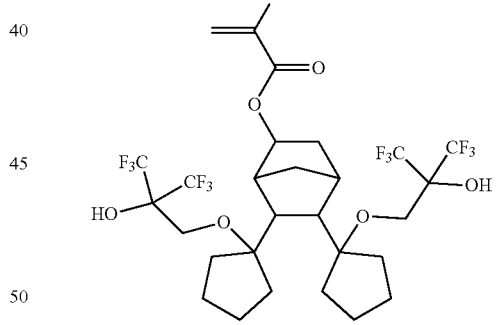
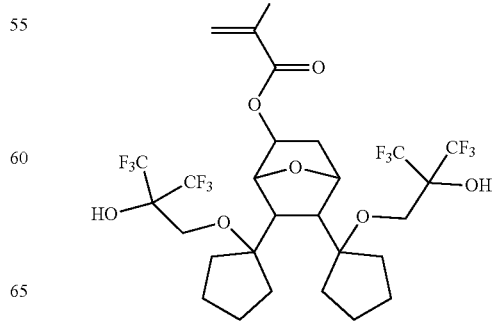

-continued
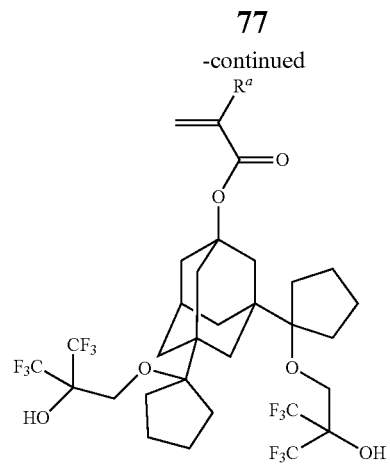
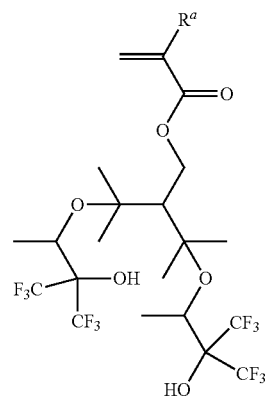
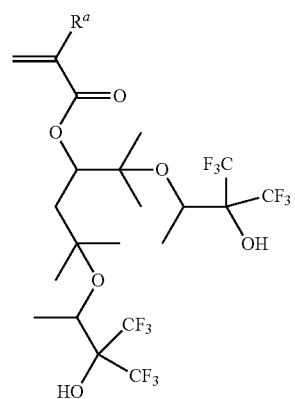
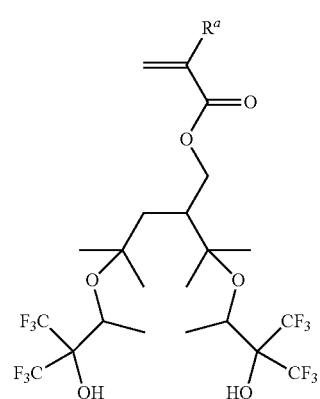
-continued
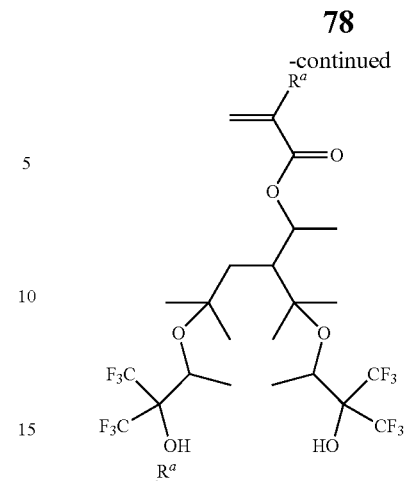
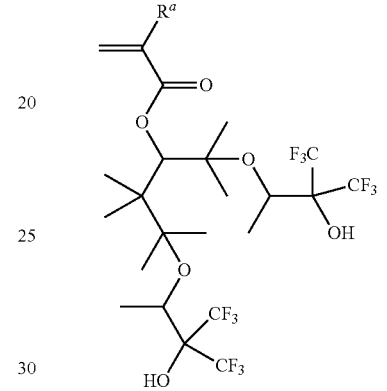
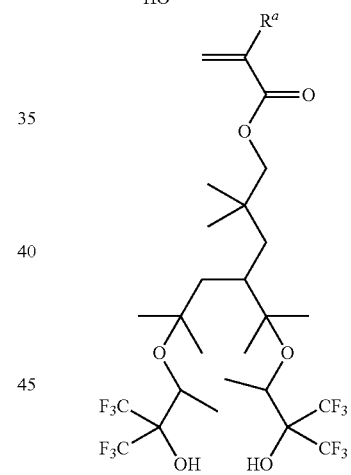
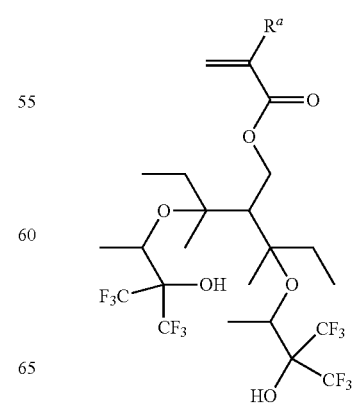

-continued
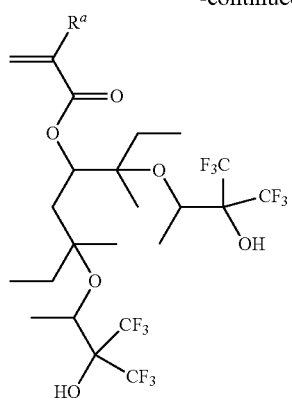
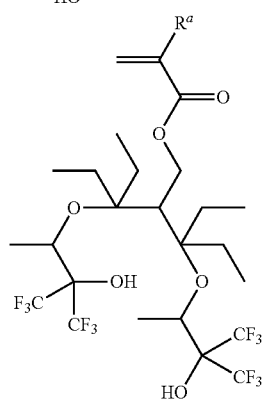
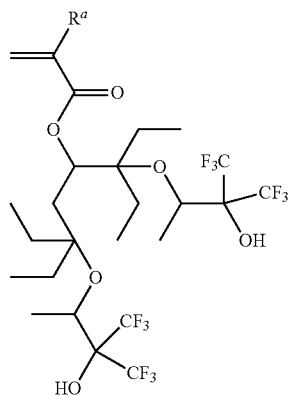
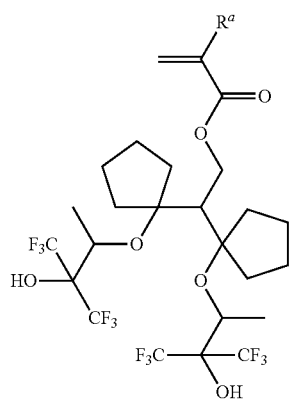
-continued
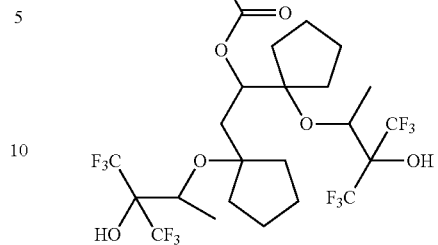
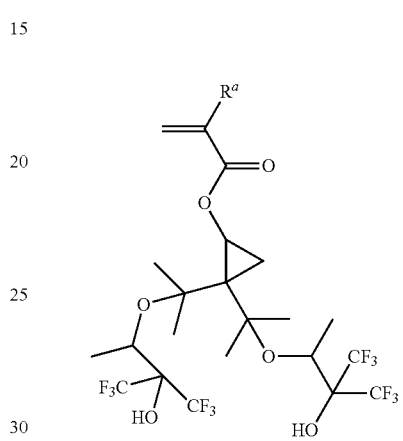
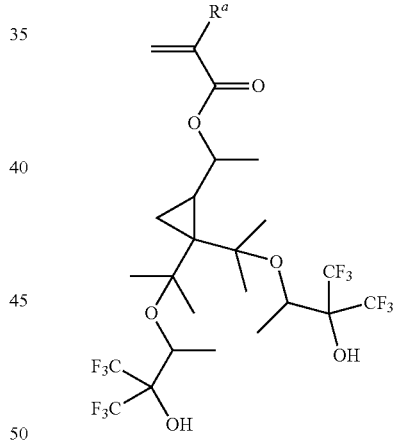
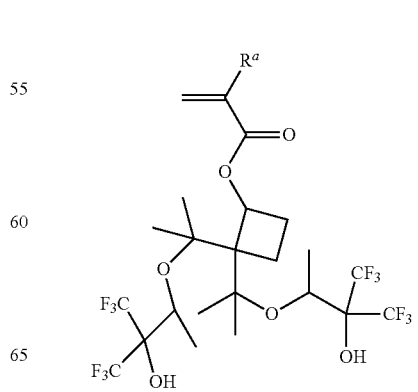

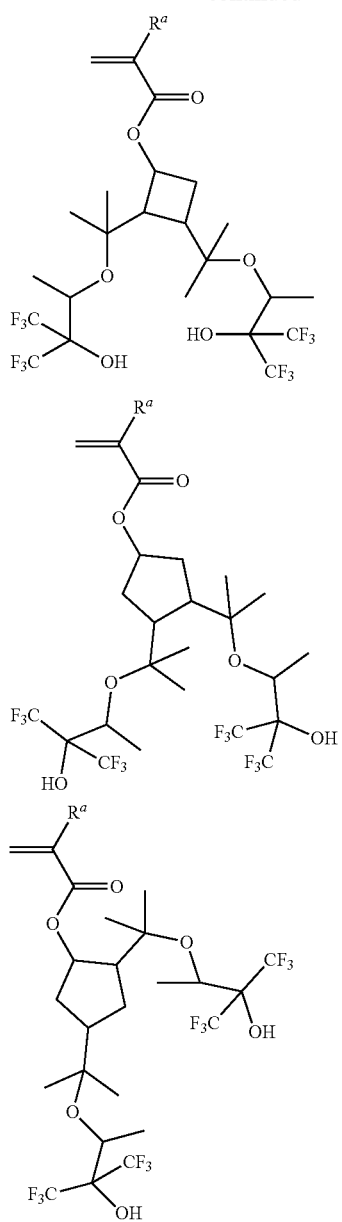
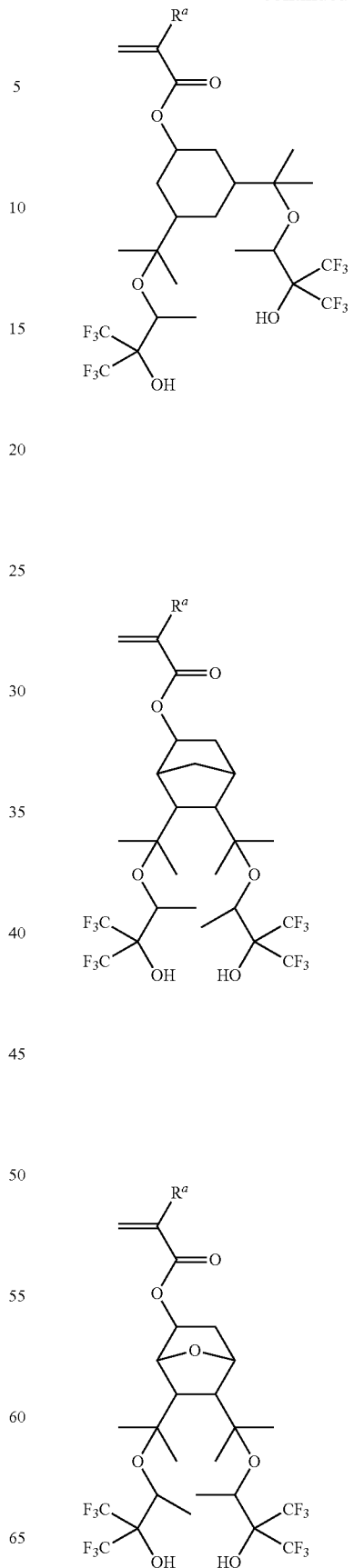

83
-continued
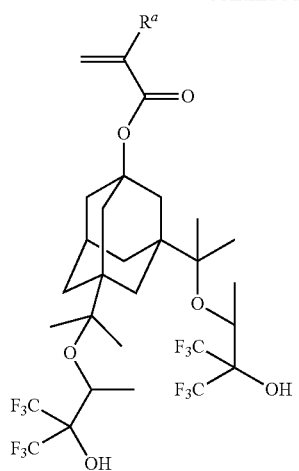
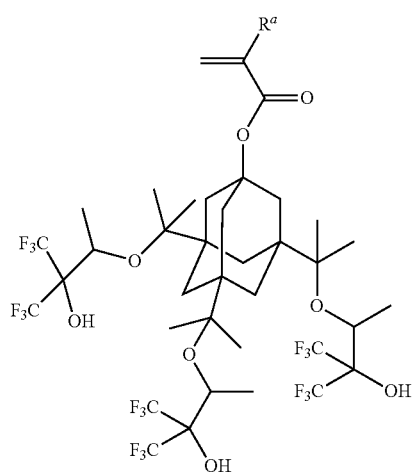
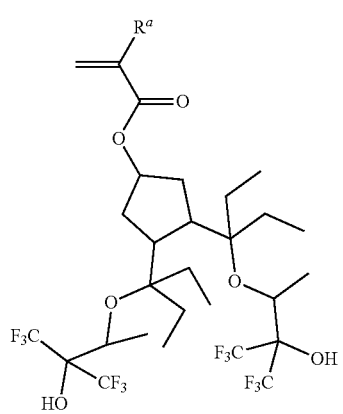
84
-continued
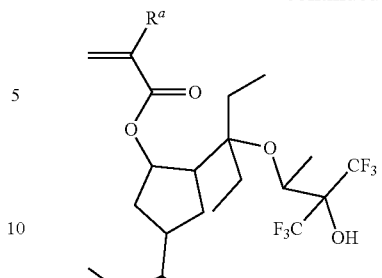
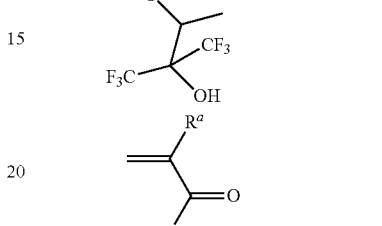
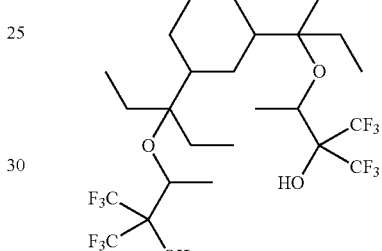
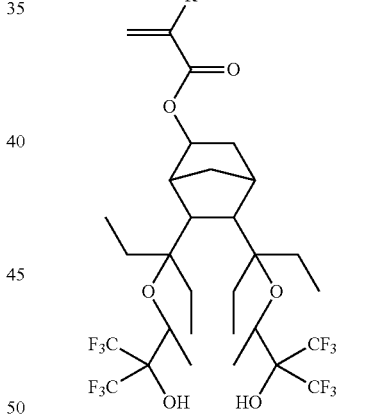
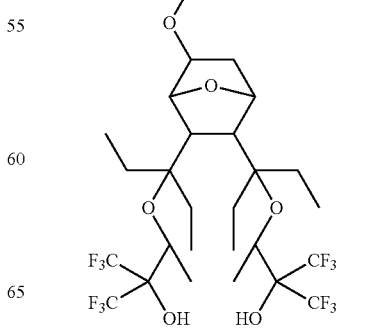

85
-continued
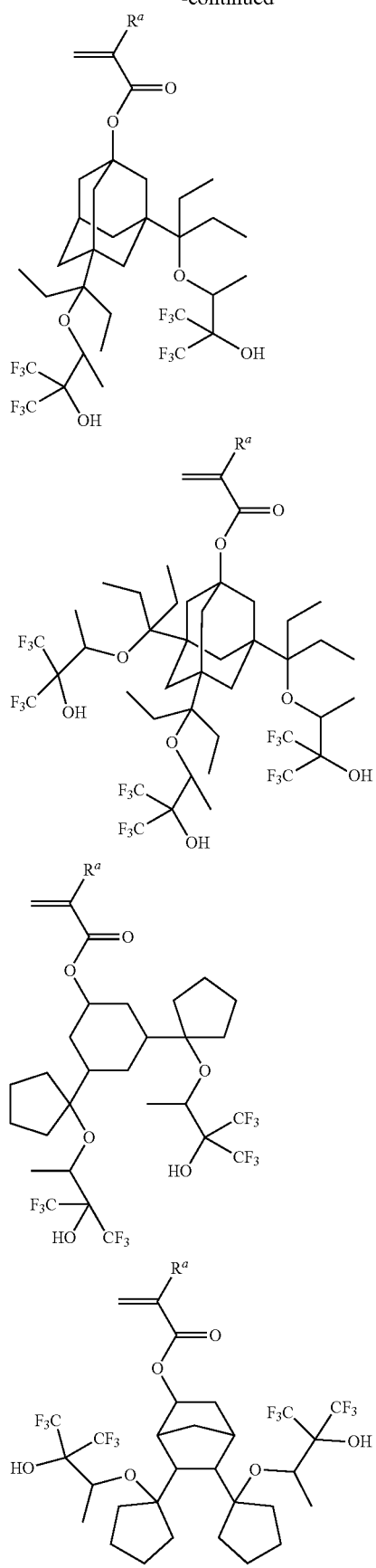
86
-continued
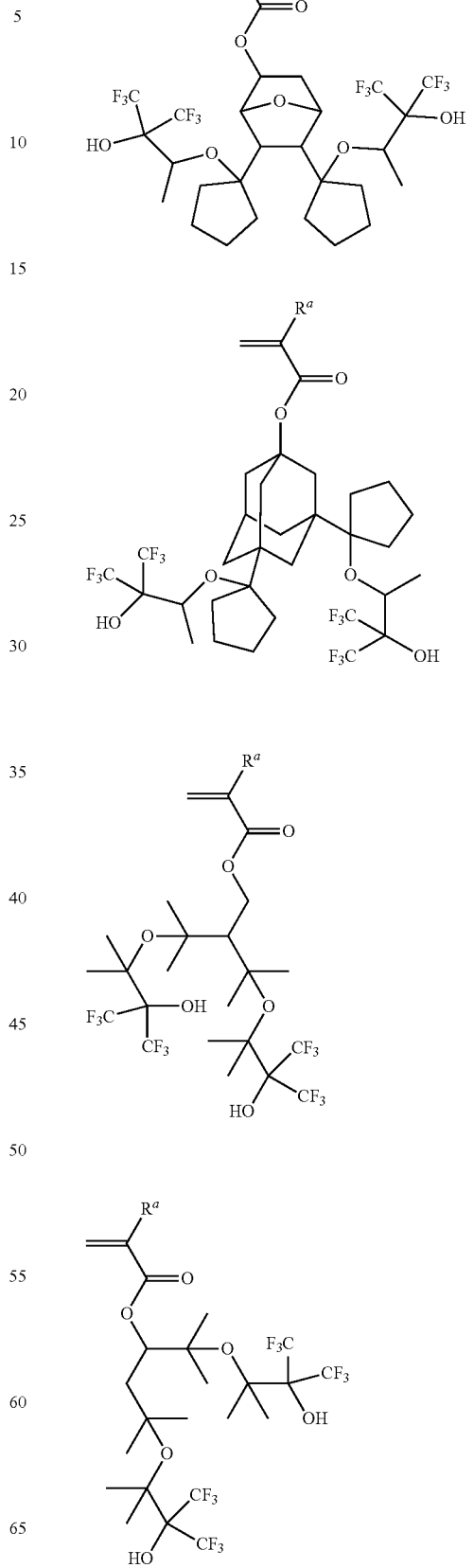

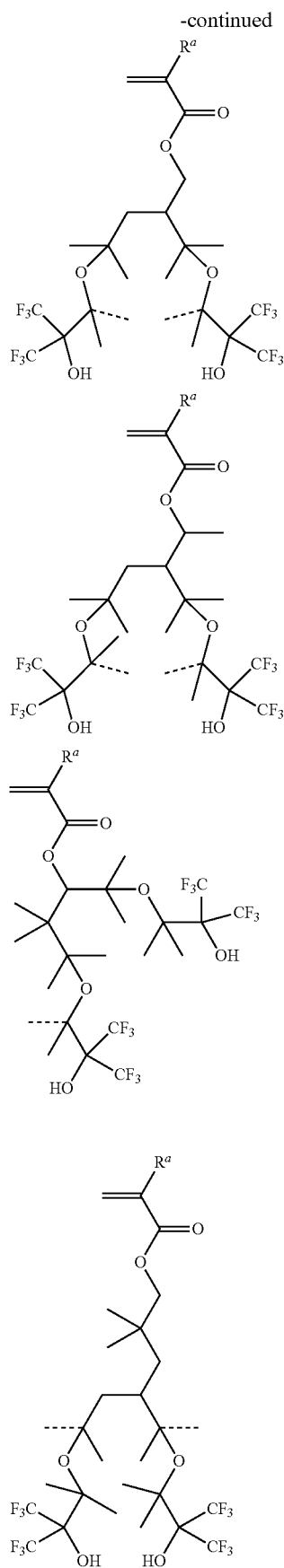
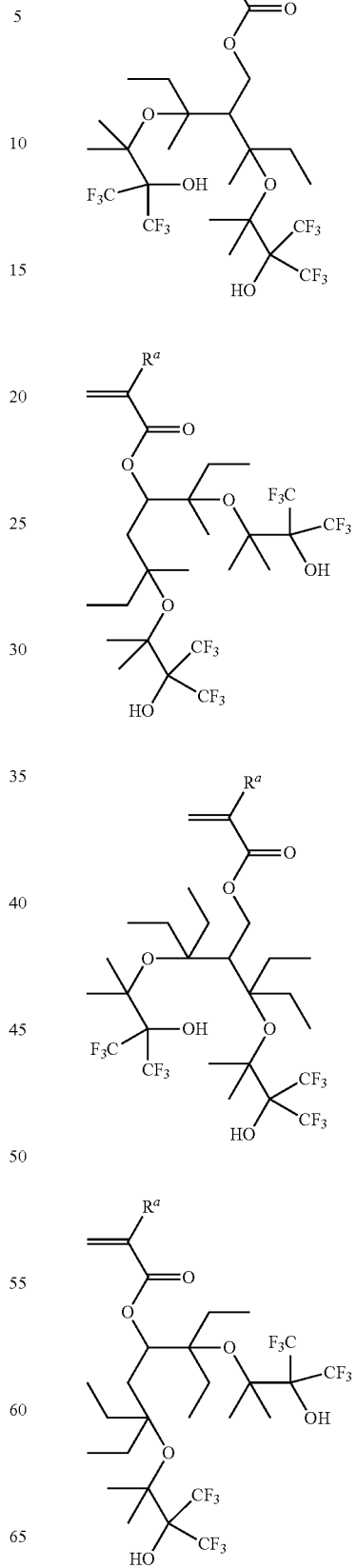

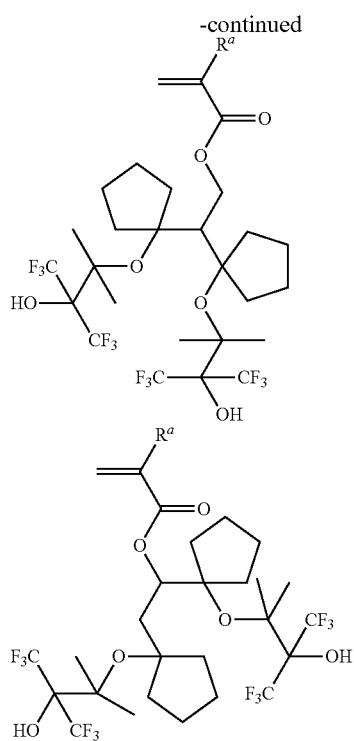
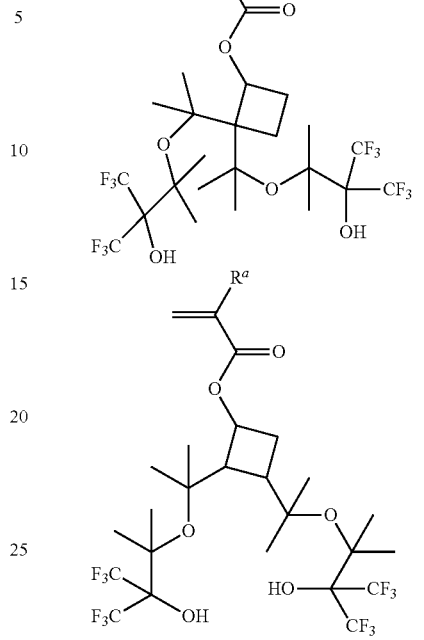
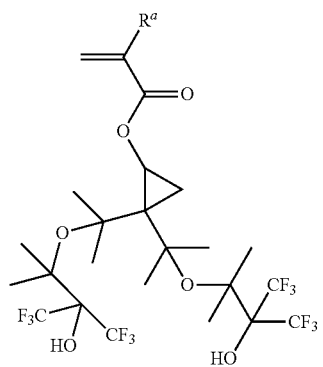
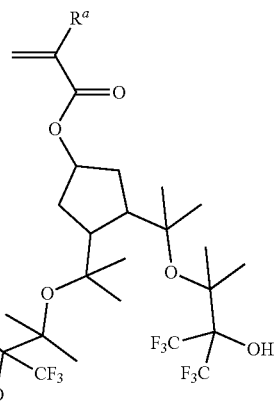
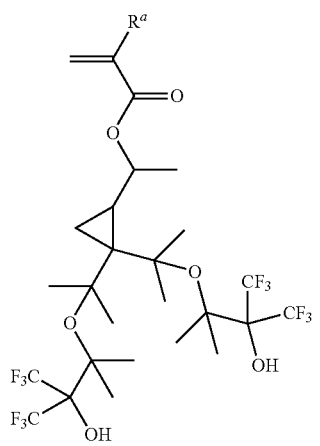

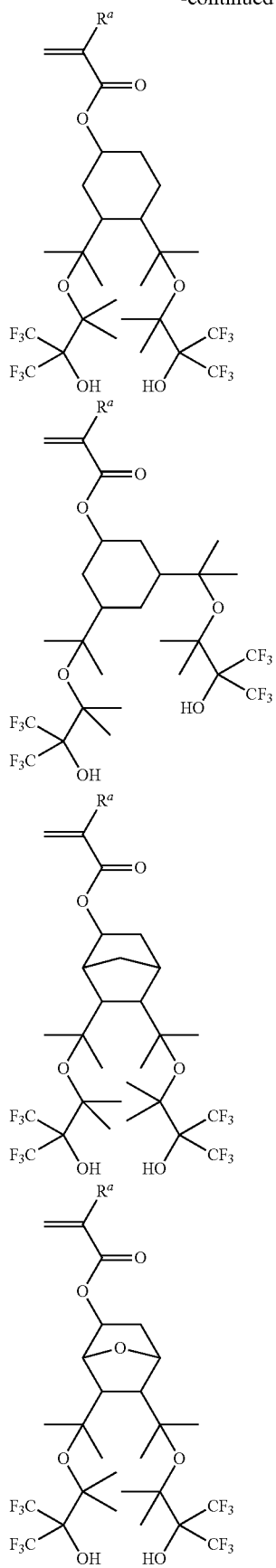
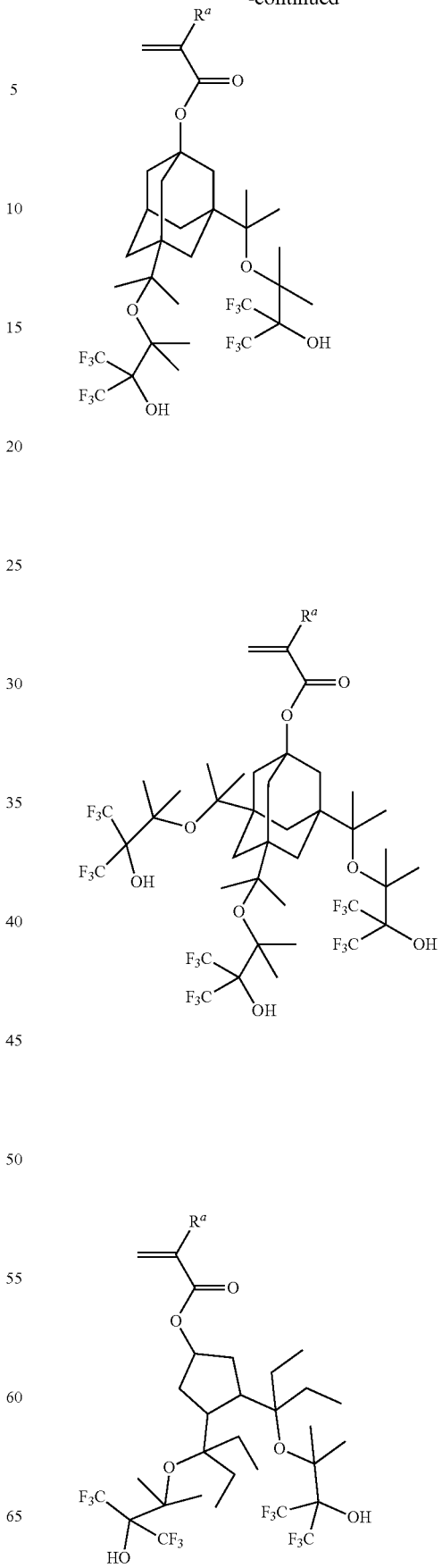

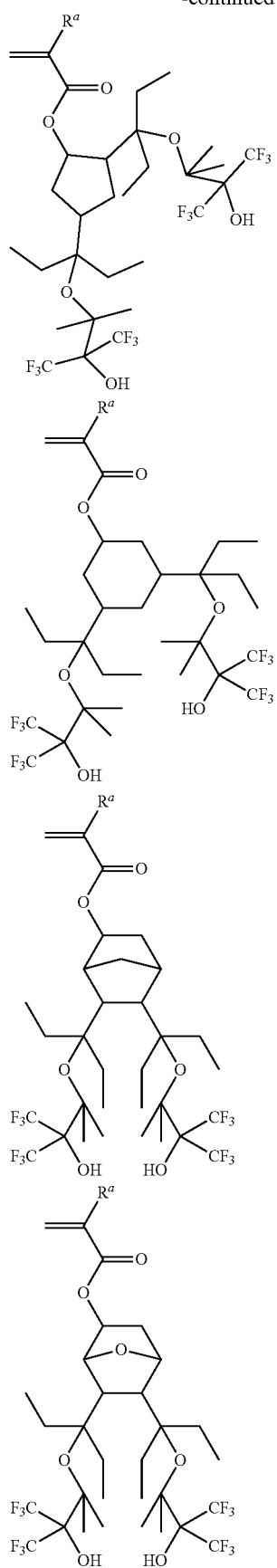
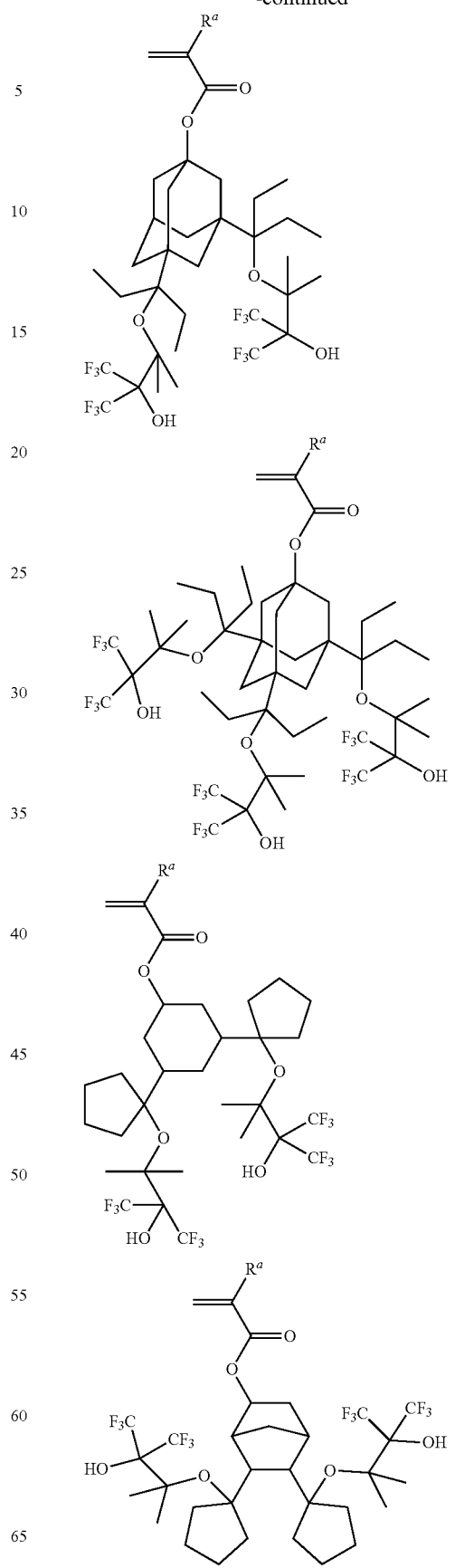

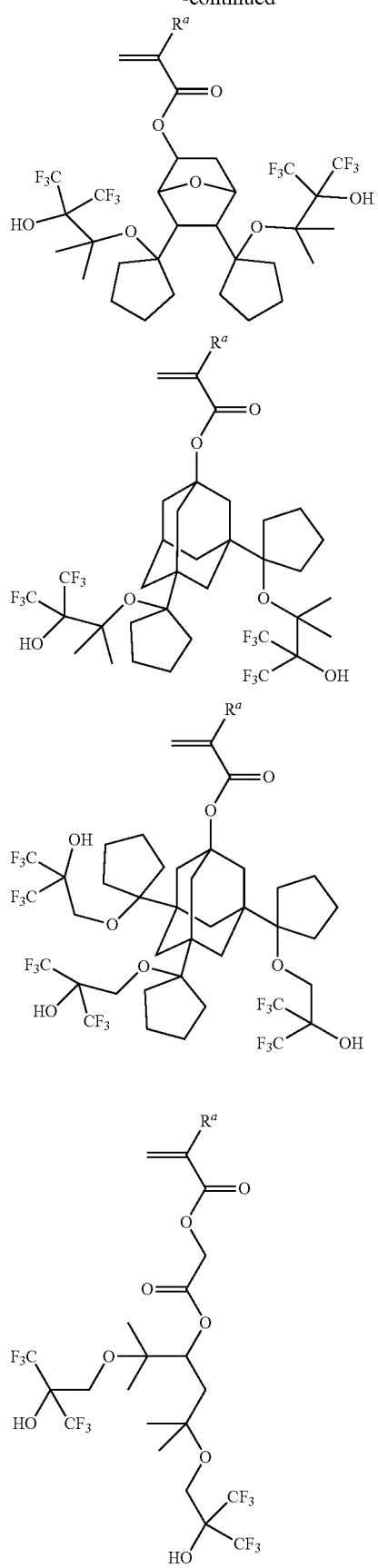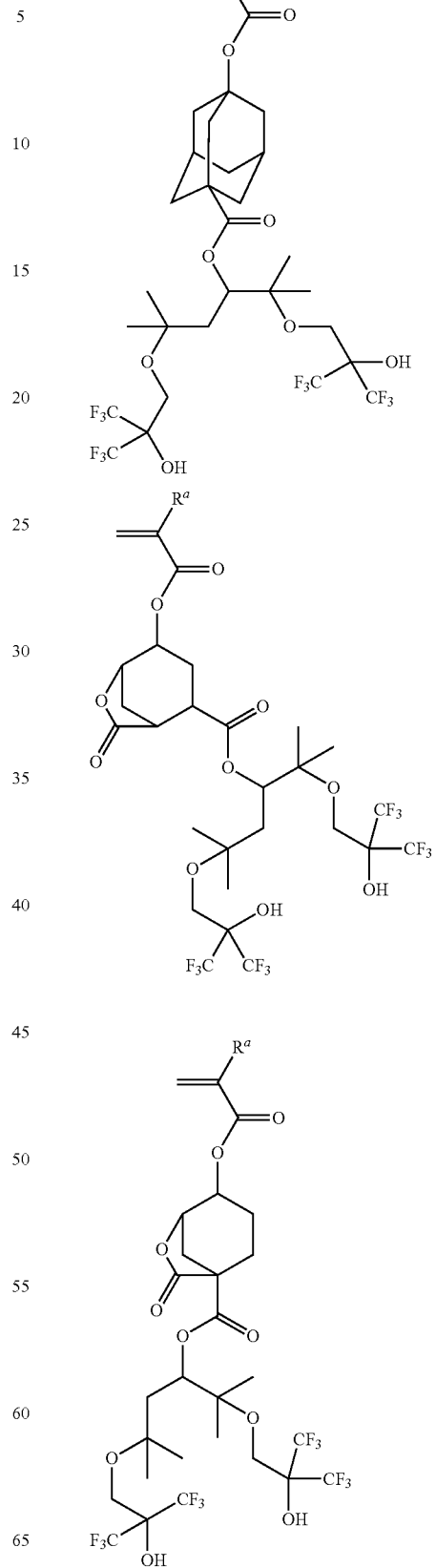

97
-continued
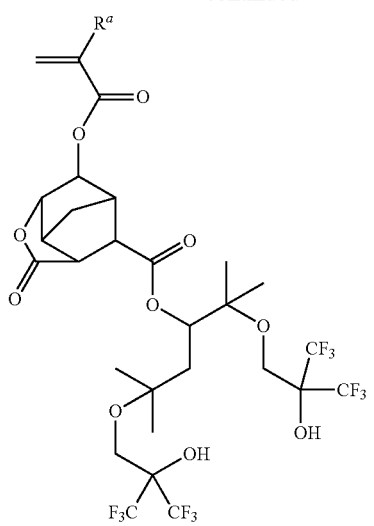
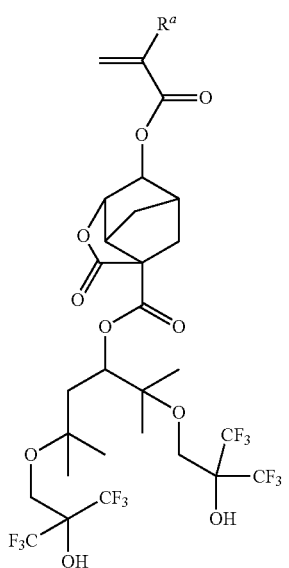
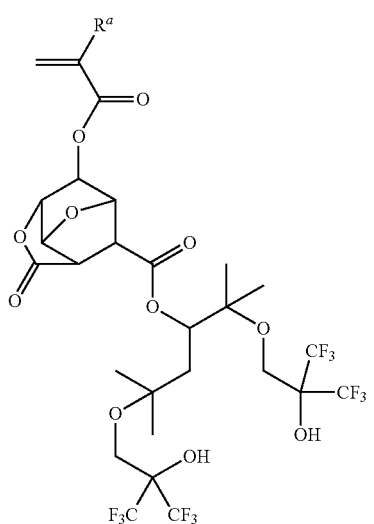
98
-continued
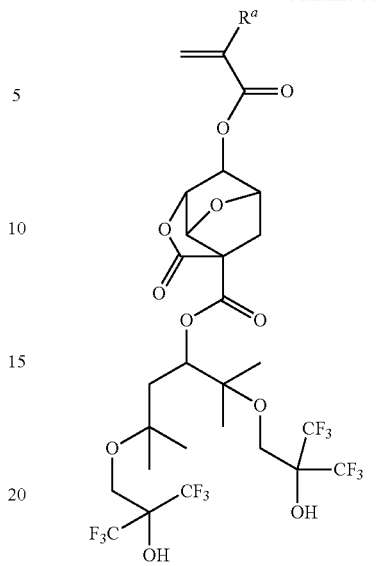
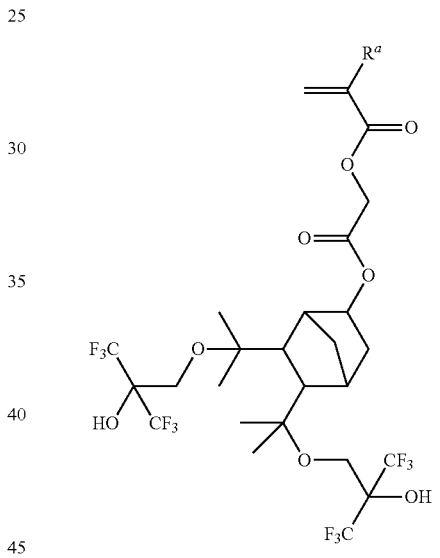
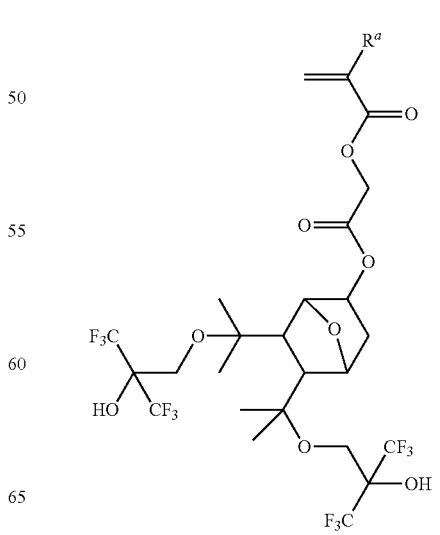

99
-continued
100
-continued
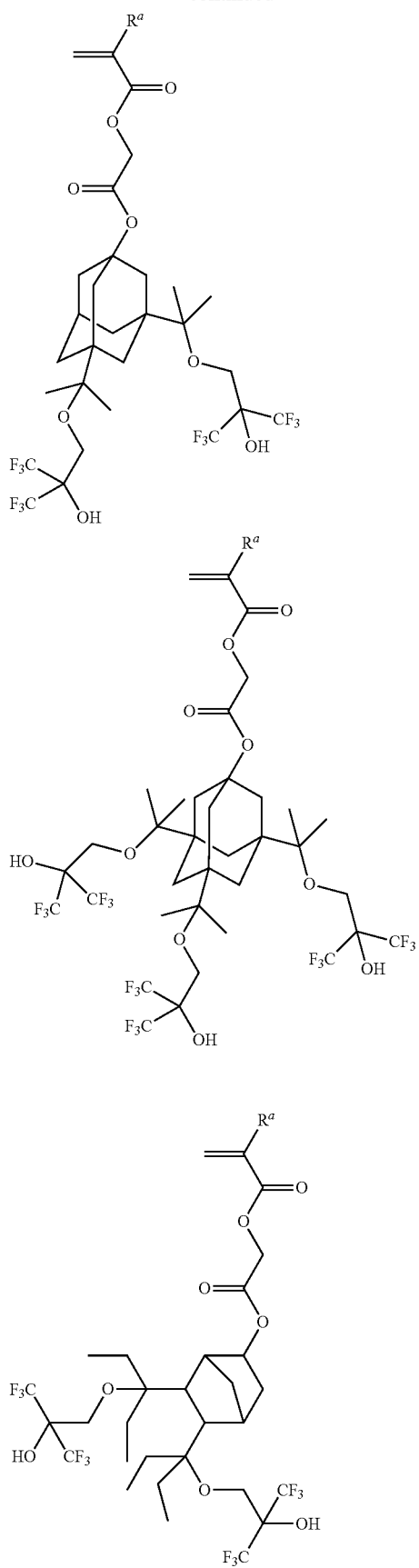
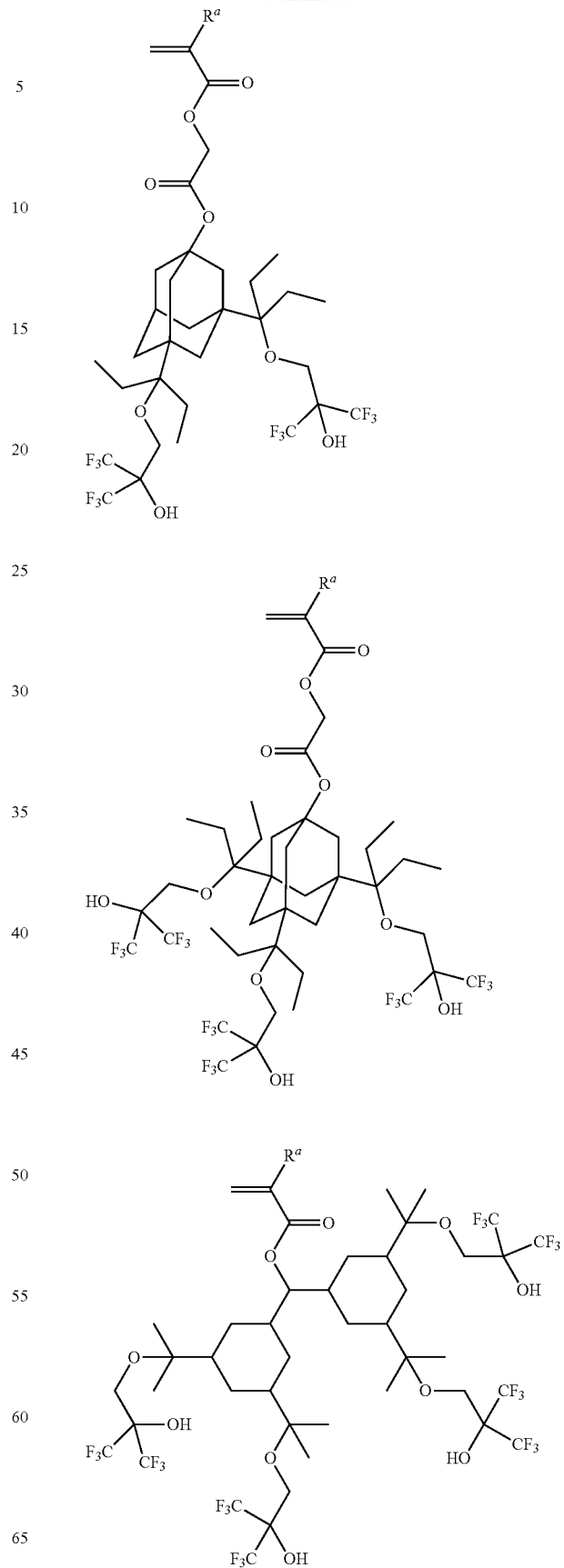

101
-continued
102
-continued
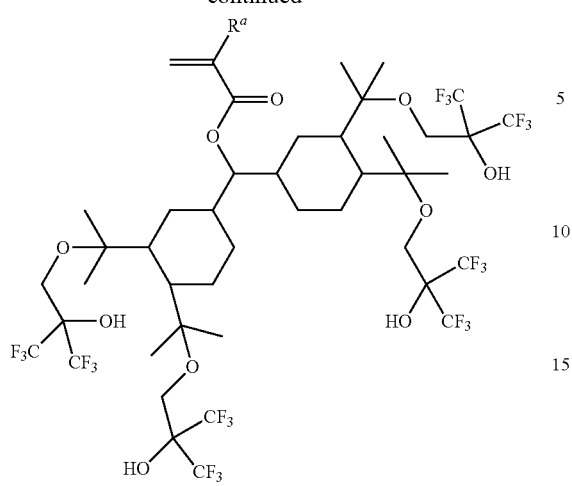
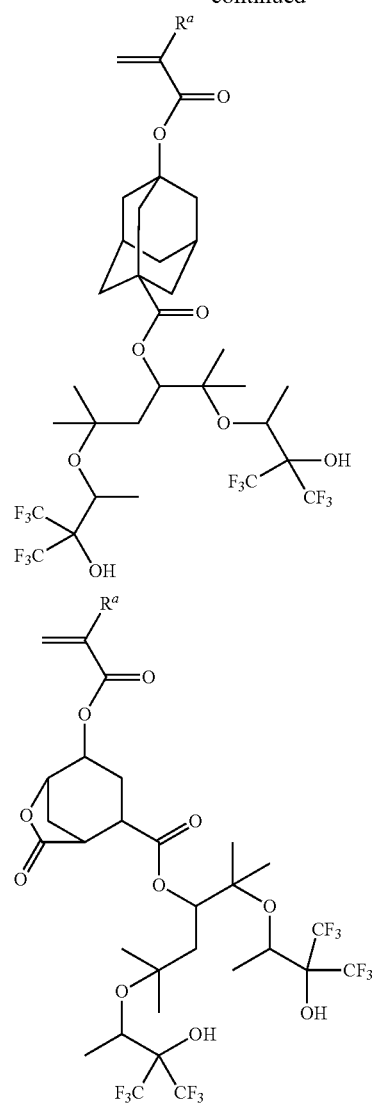
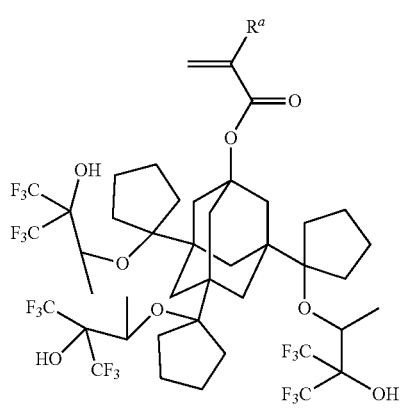
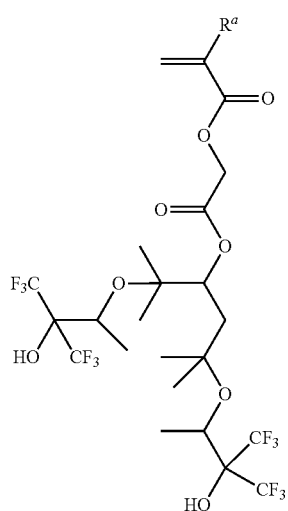
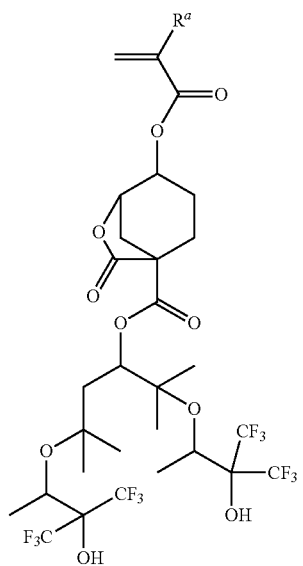

103
-continued
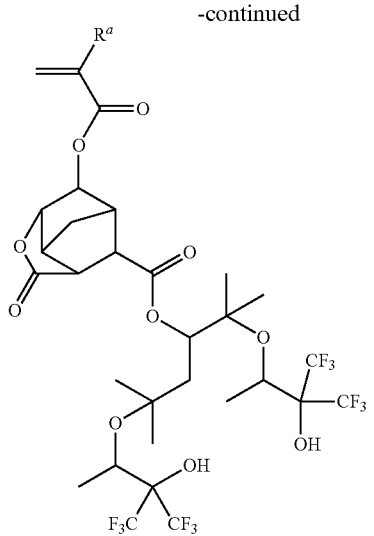
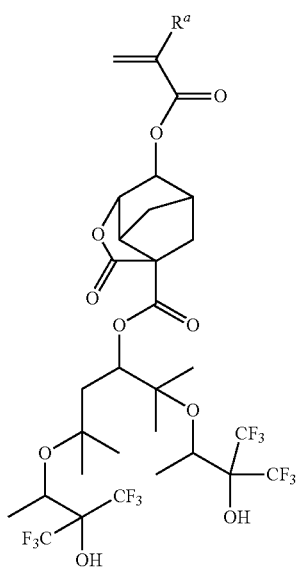
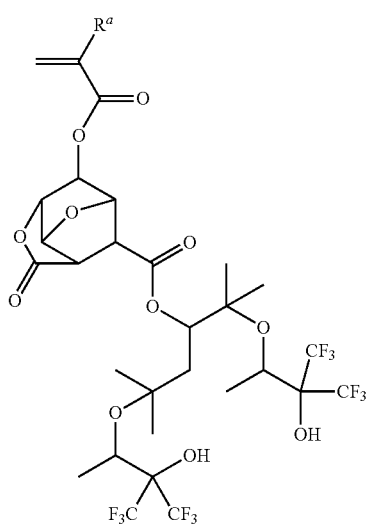
104
-continued
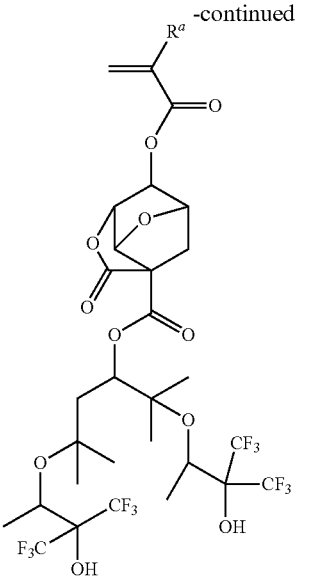
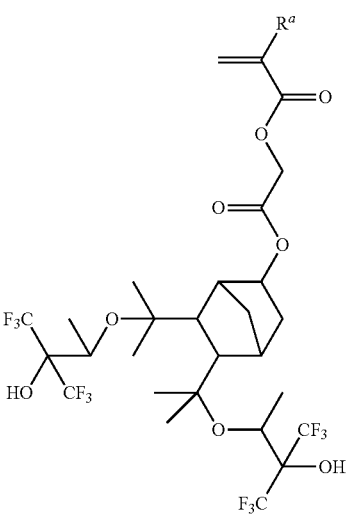
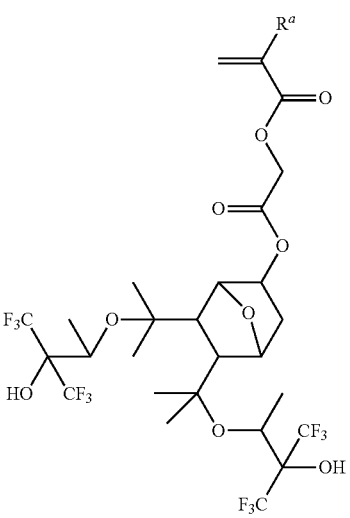

105
-continued
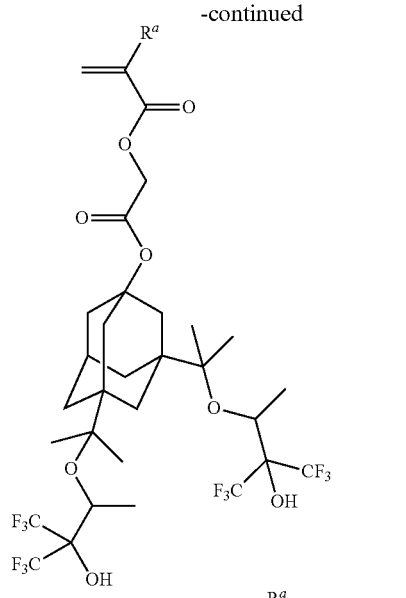
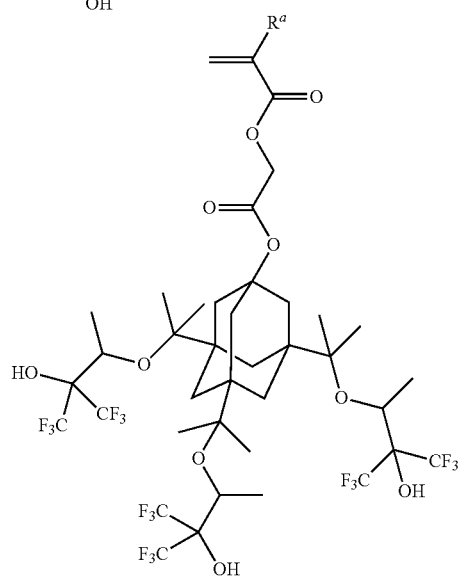
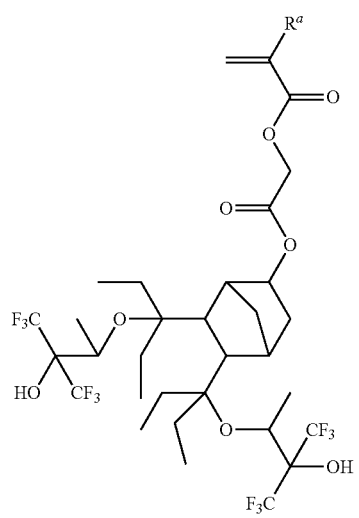
106
-continued
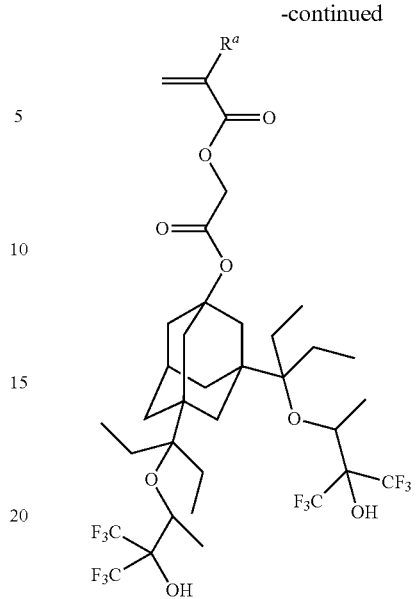
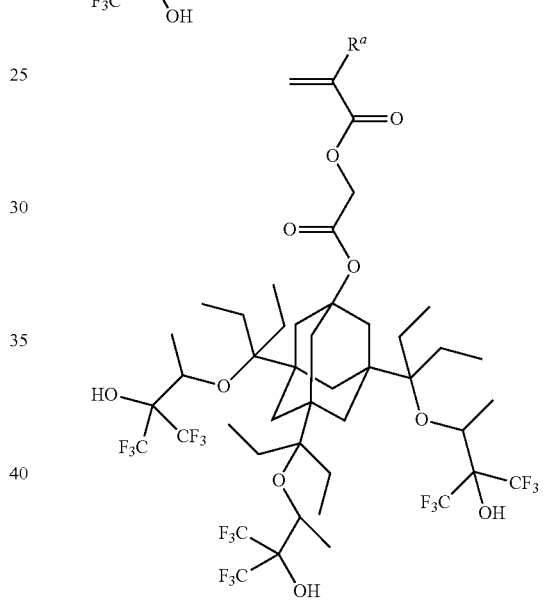
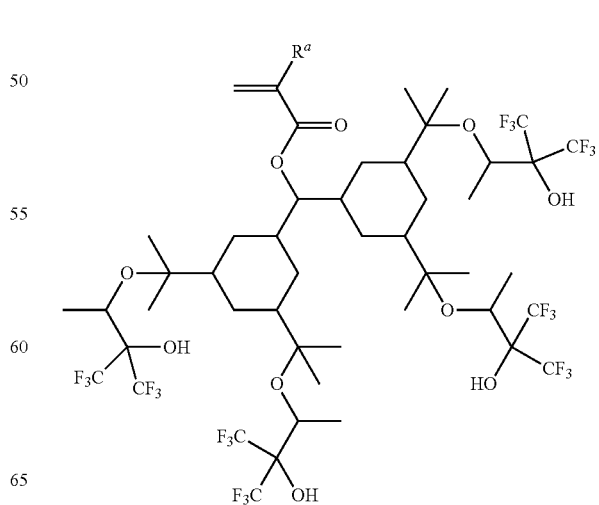

107
-continued
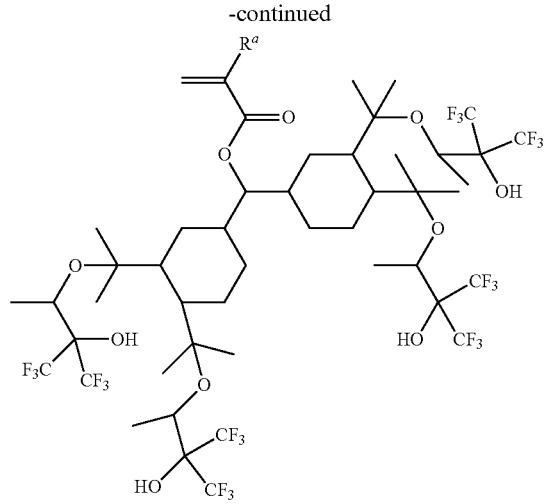
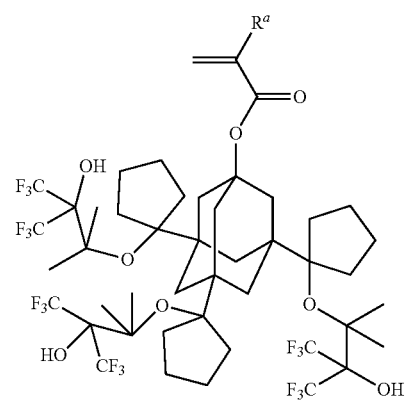
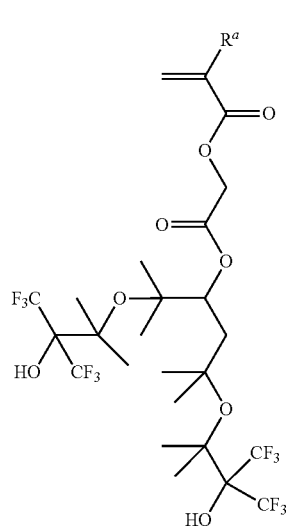
108
-continued
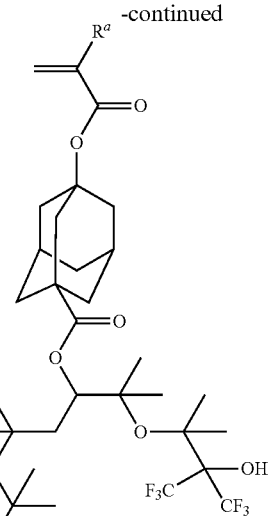
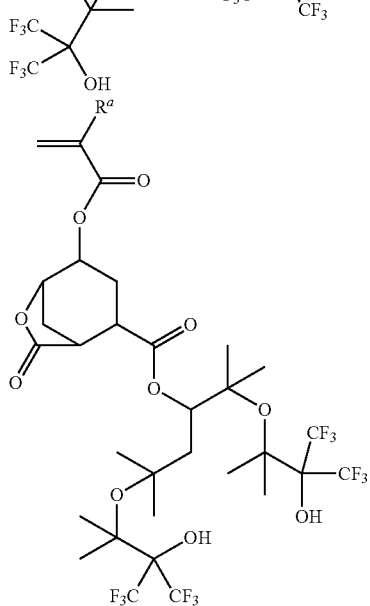
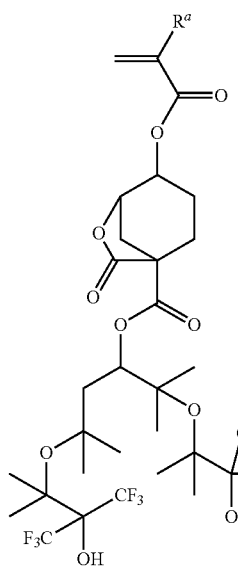

109
-continued
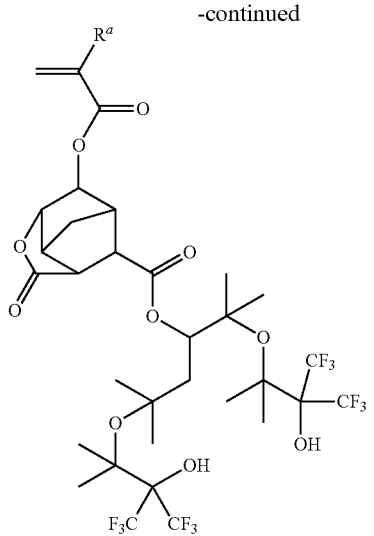
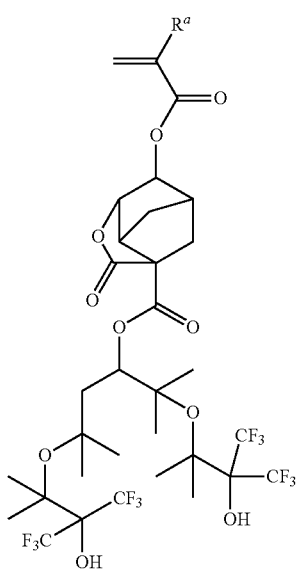
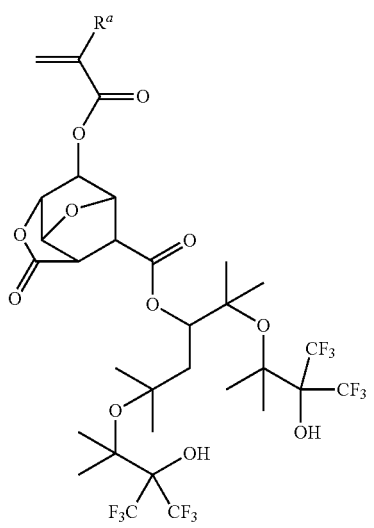
110
-continued
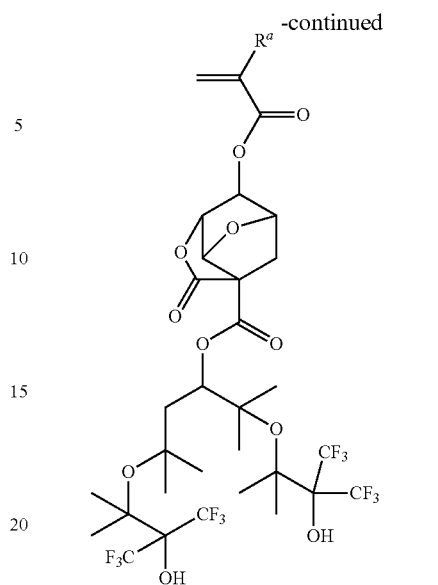
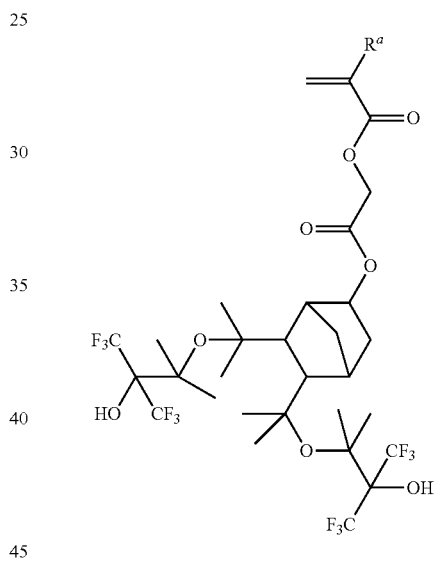
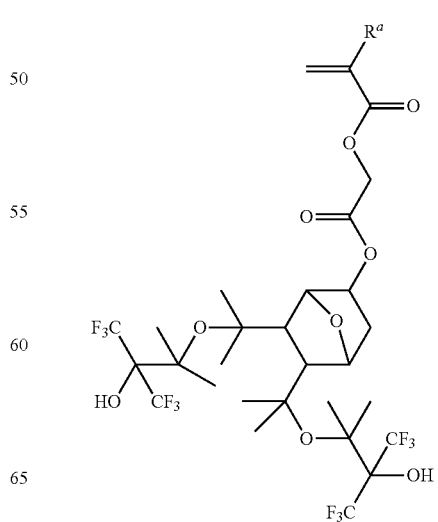

111
-continued
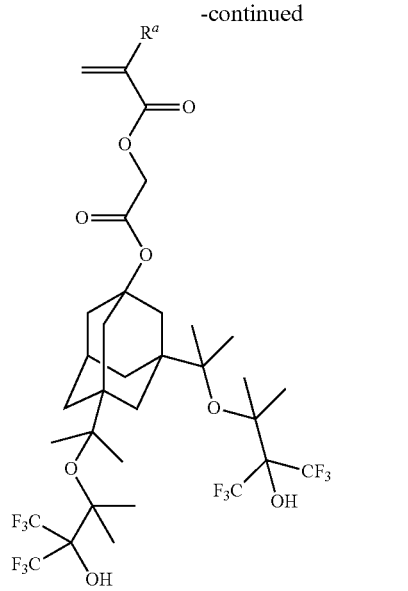
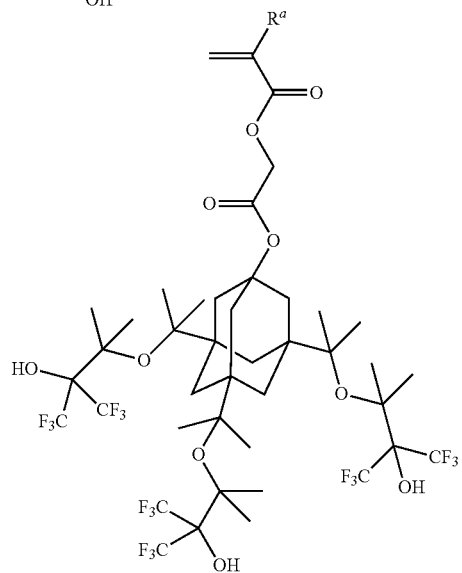
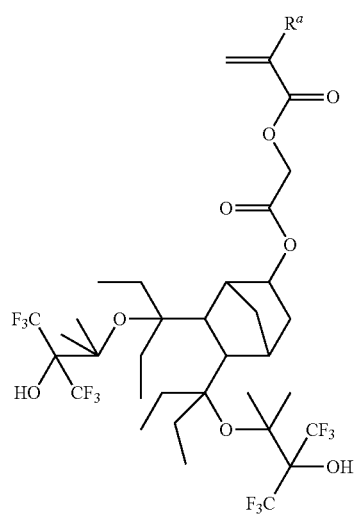
112
-continued
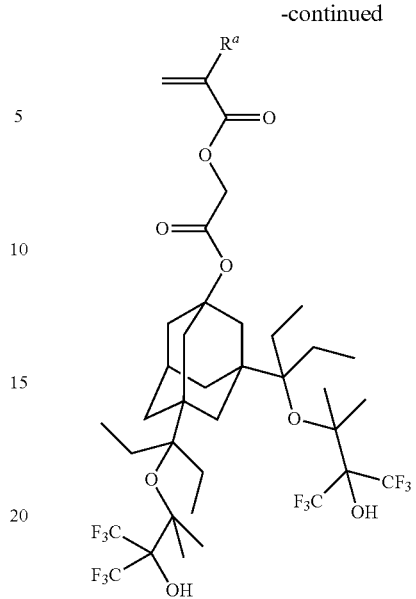
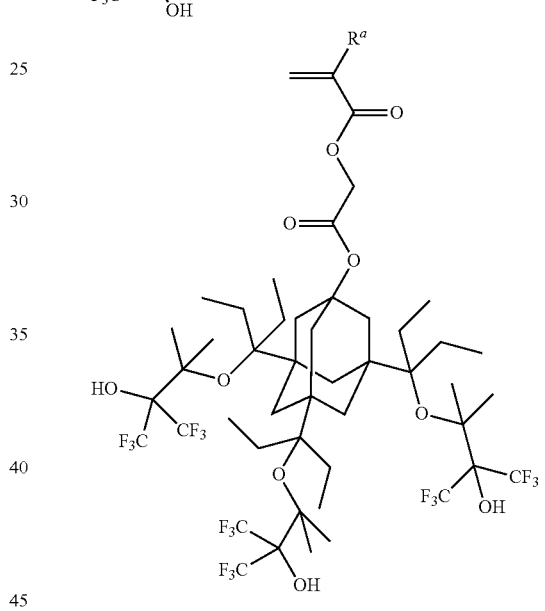
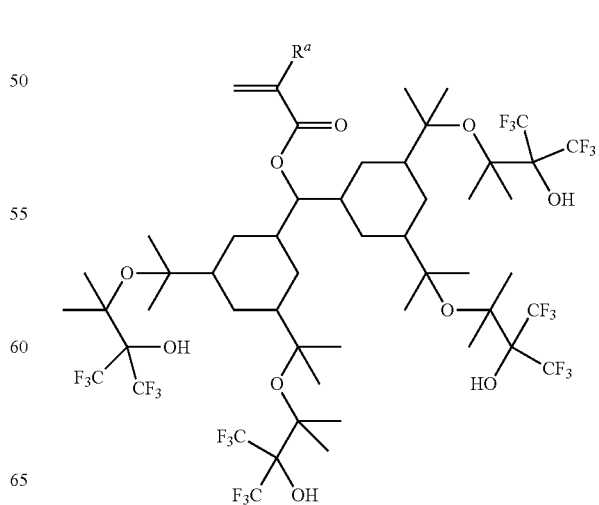

-continued
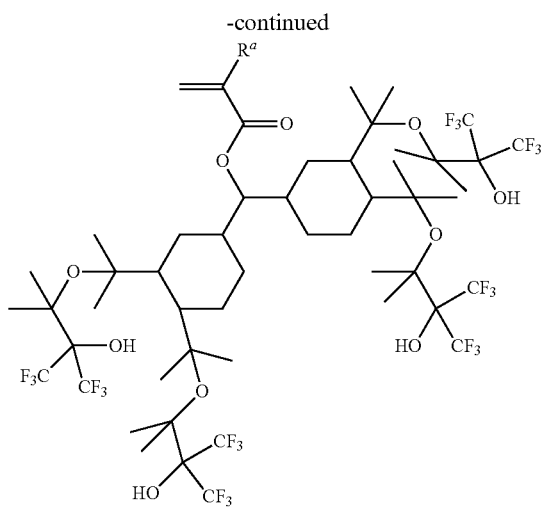
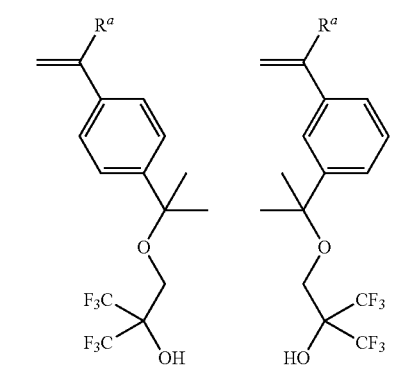
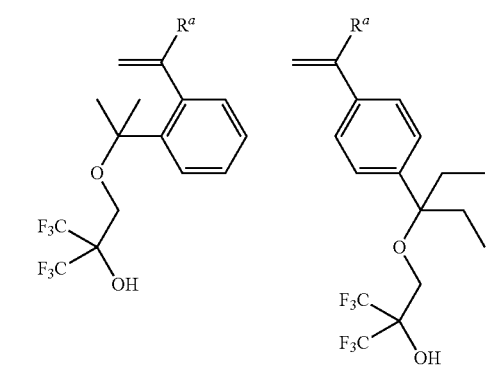
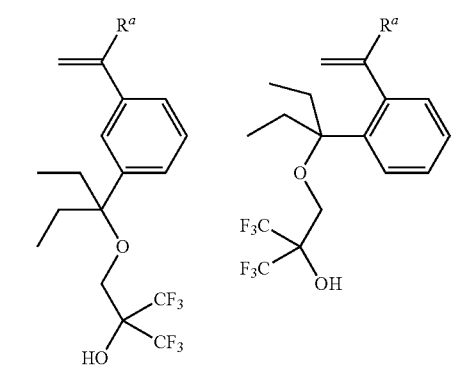
-continued
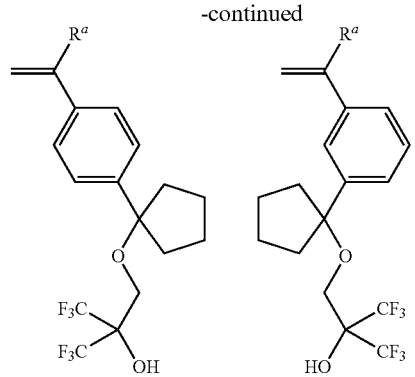
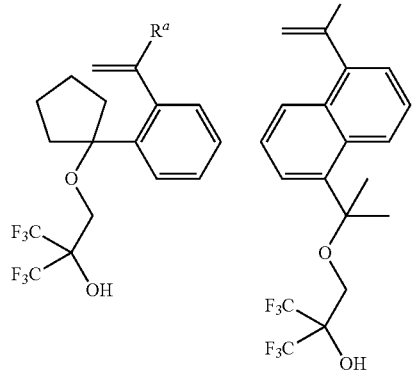
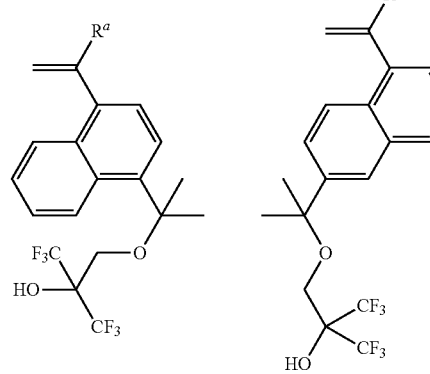
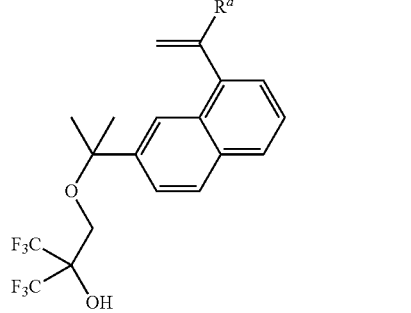
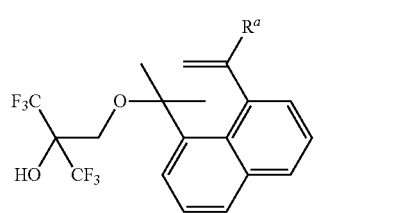

-continued
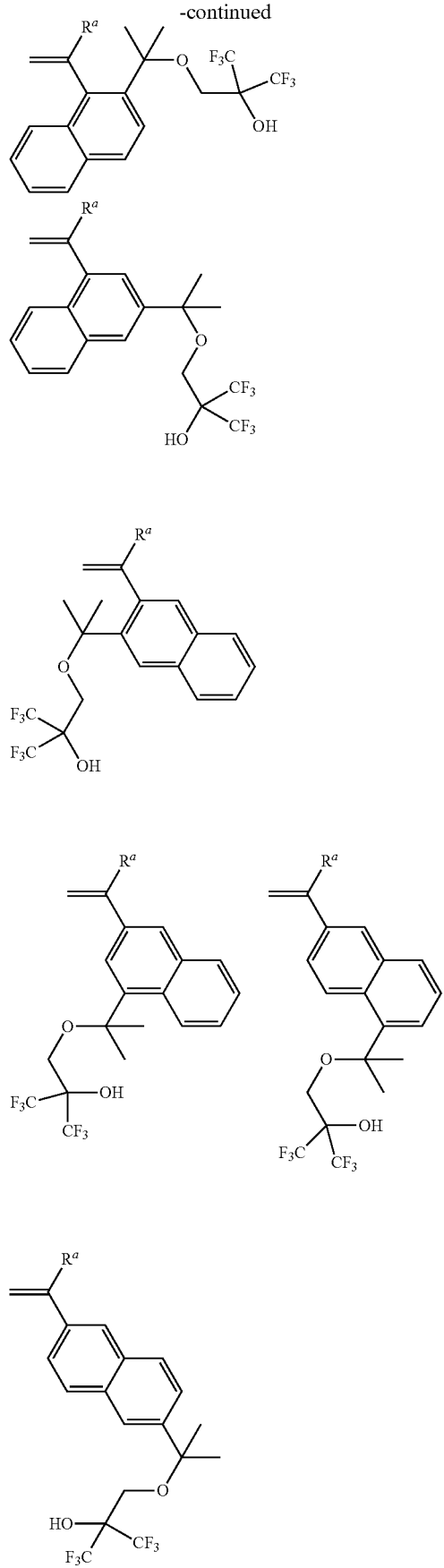
-continued
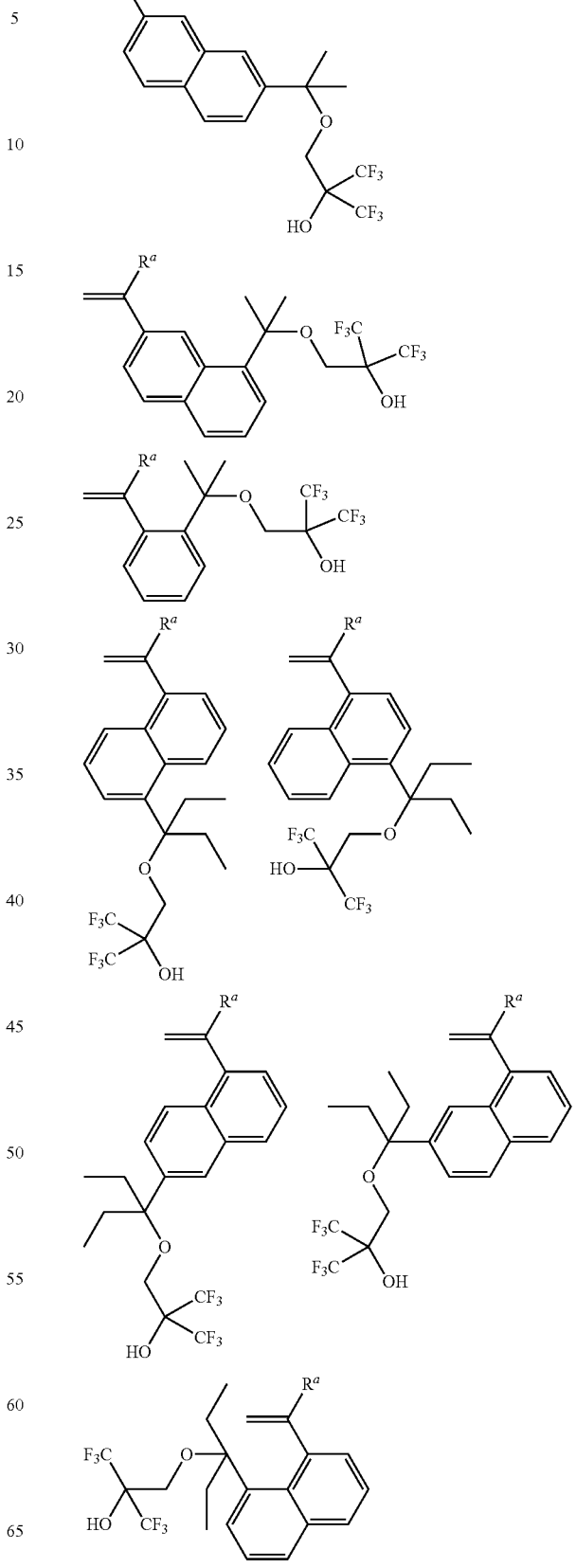

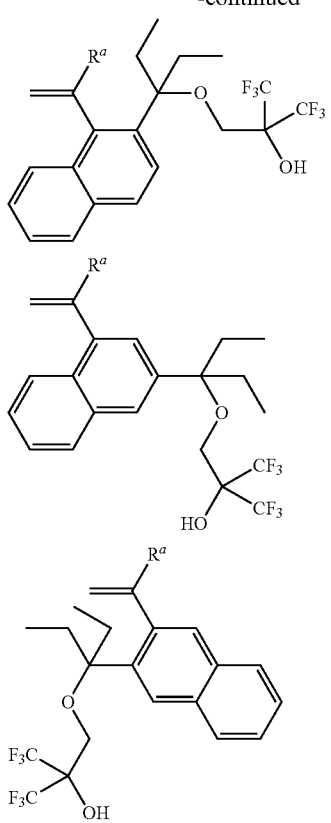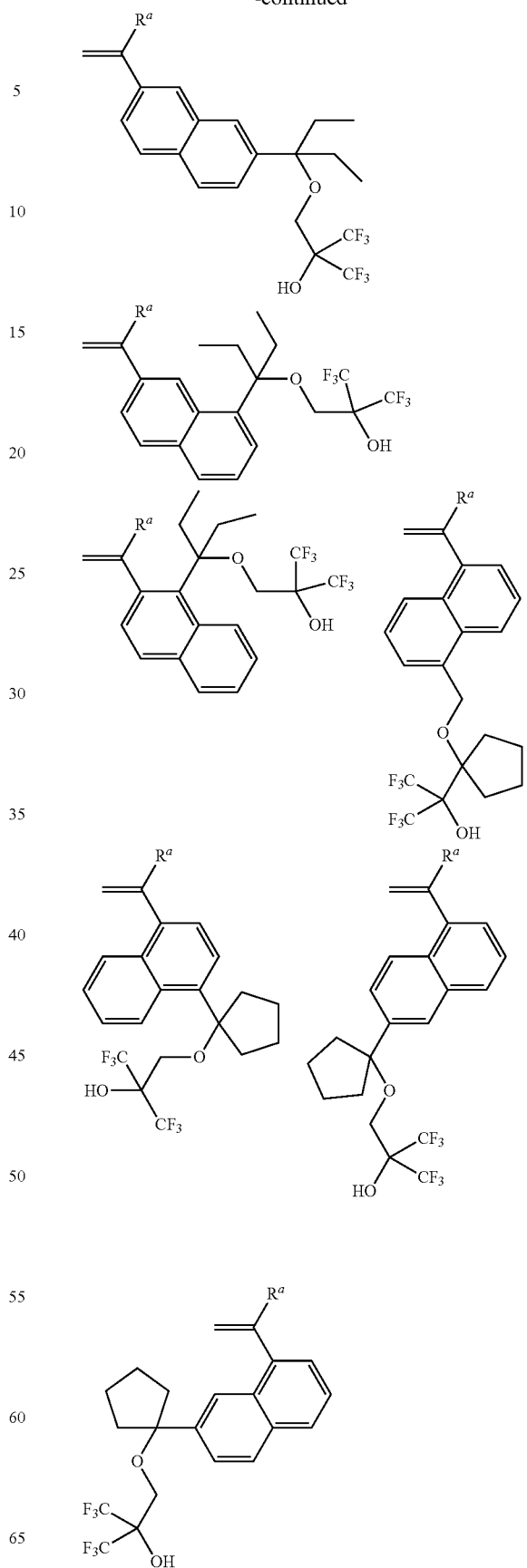

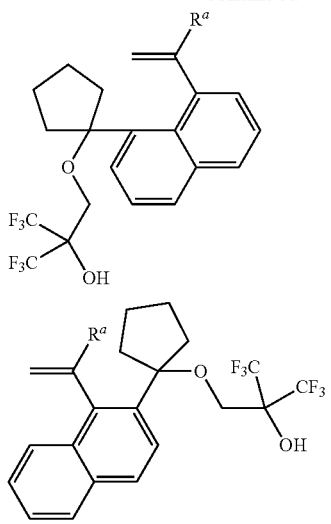
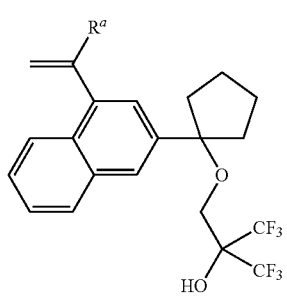
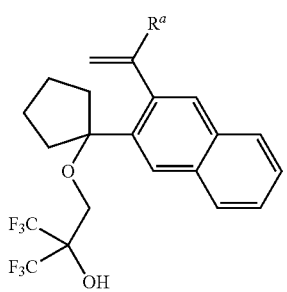
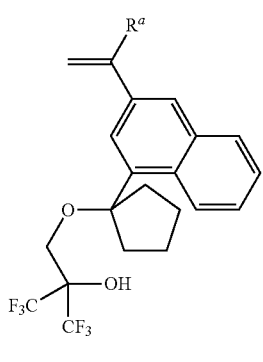
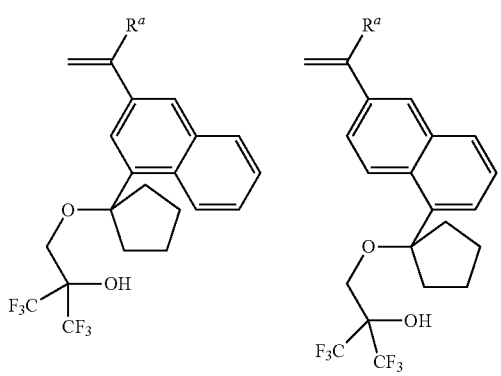
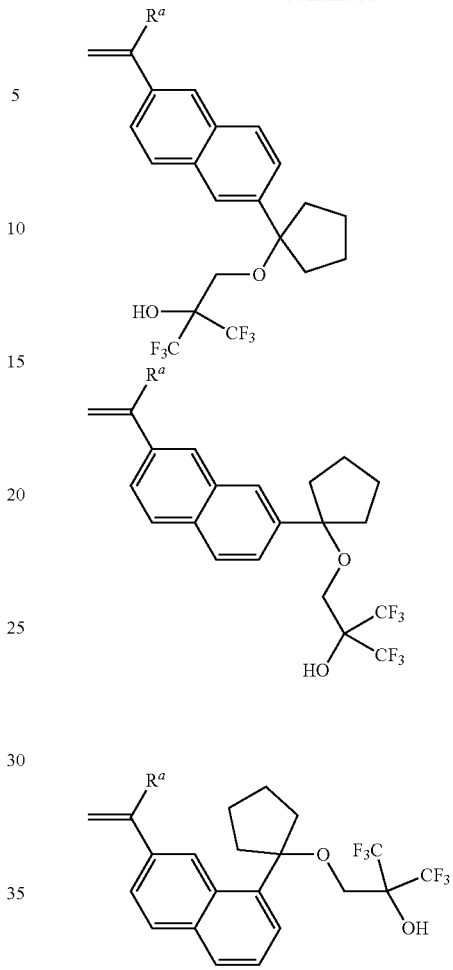
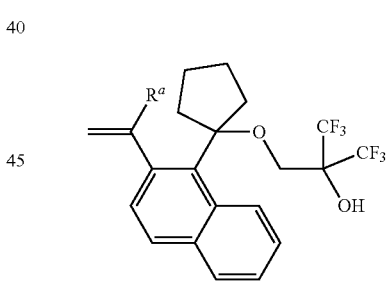
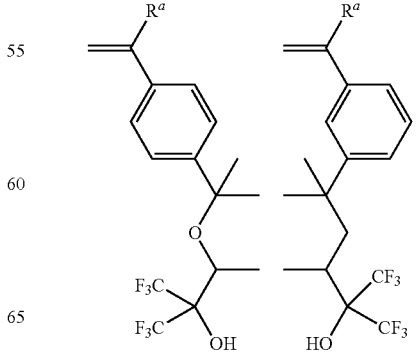

-continued
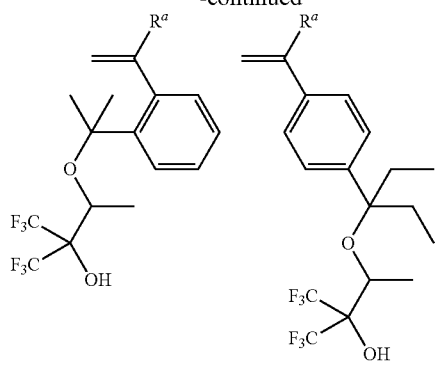
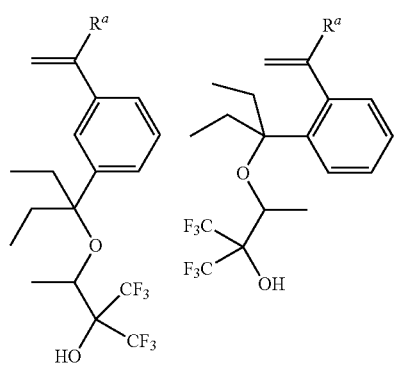
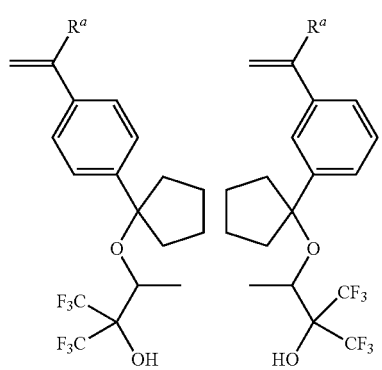
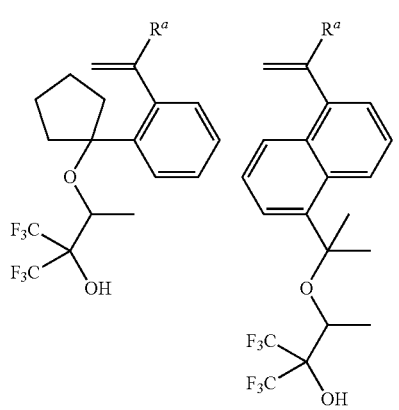
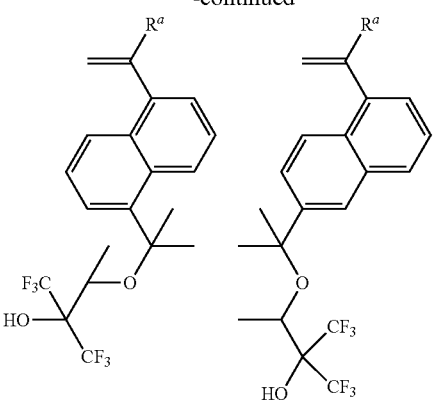
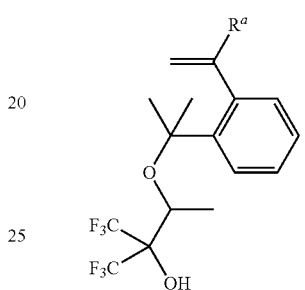
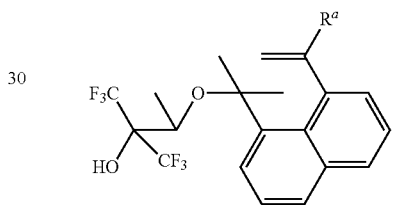
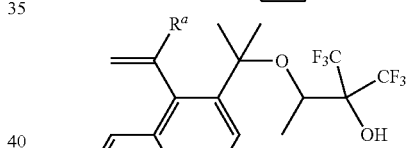
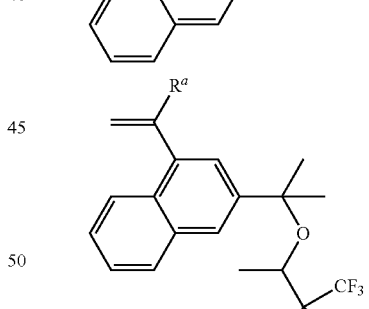
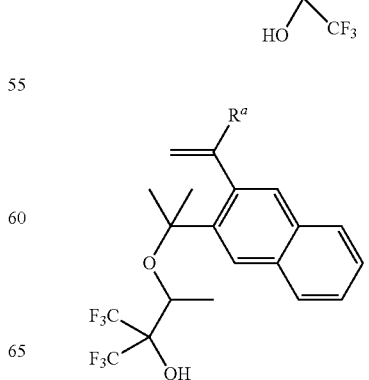

-continued
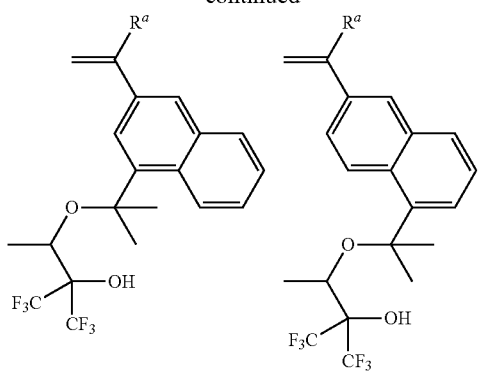
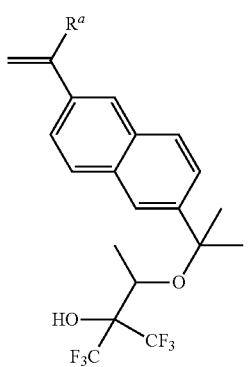
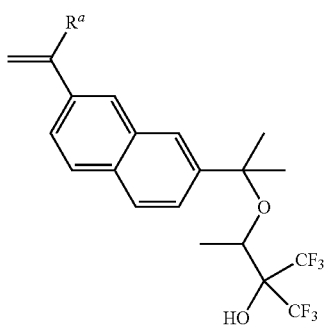
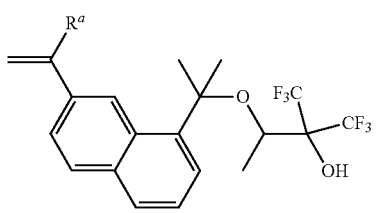
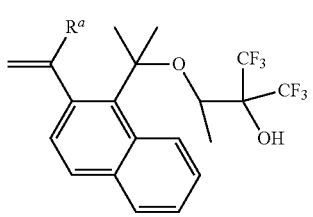
-continued
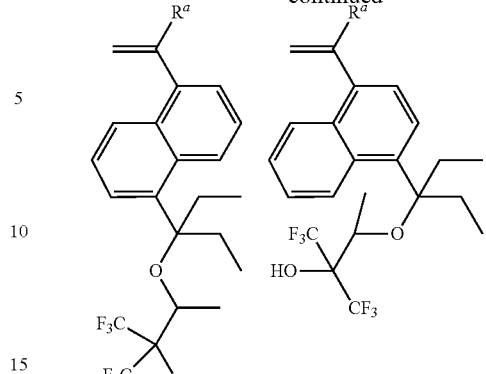
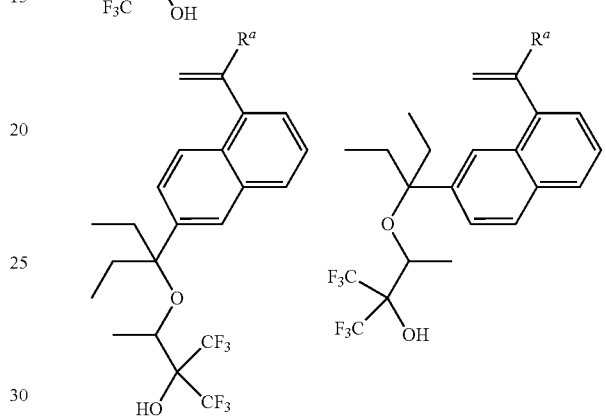
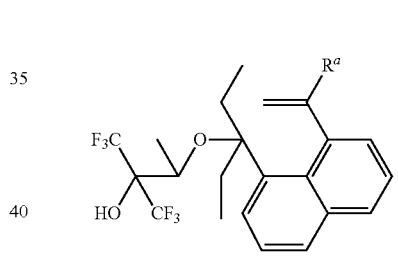
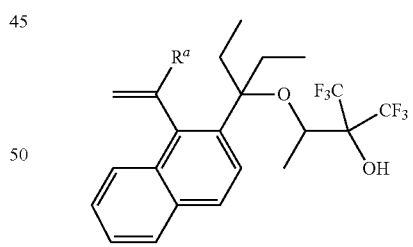
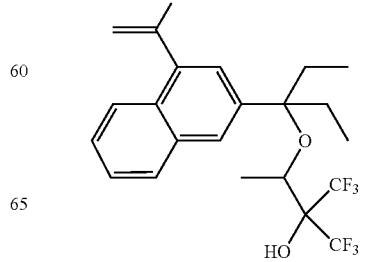

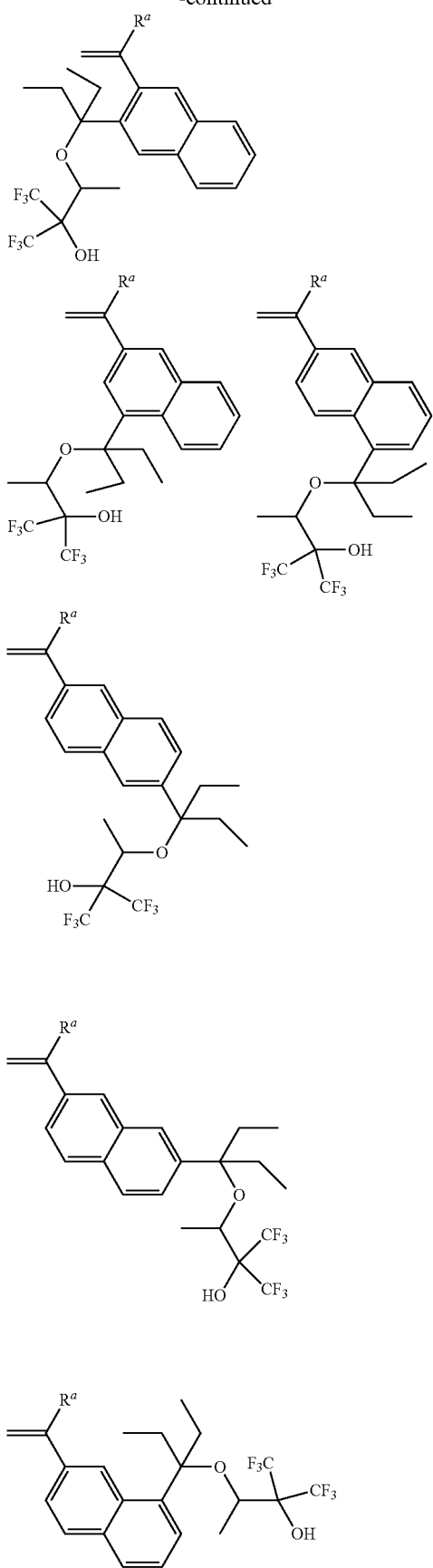
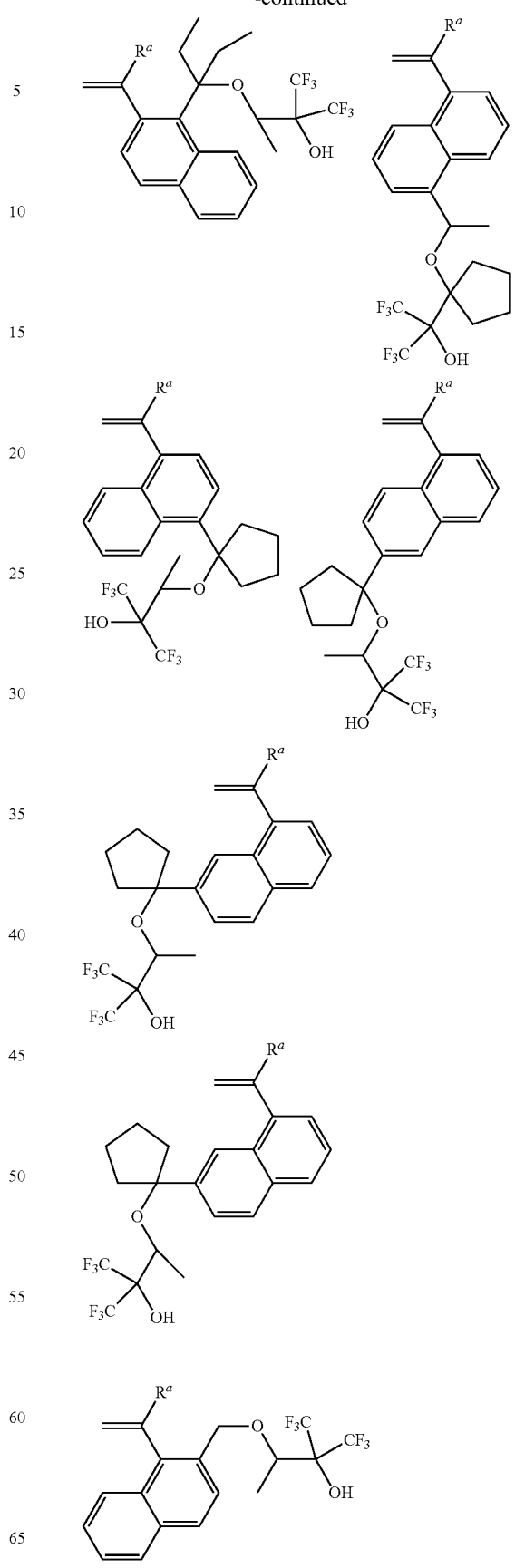

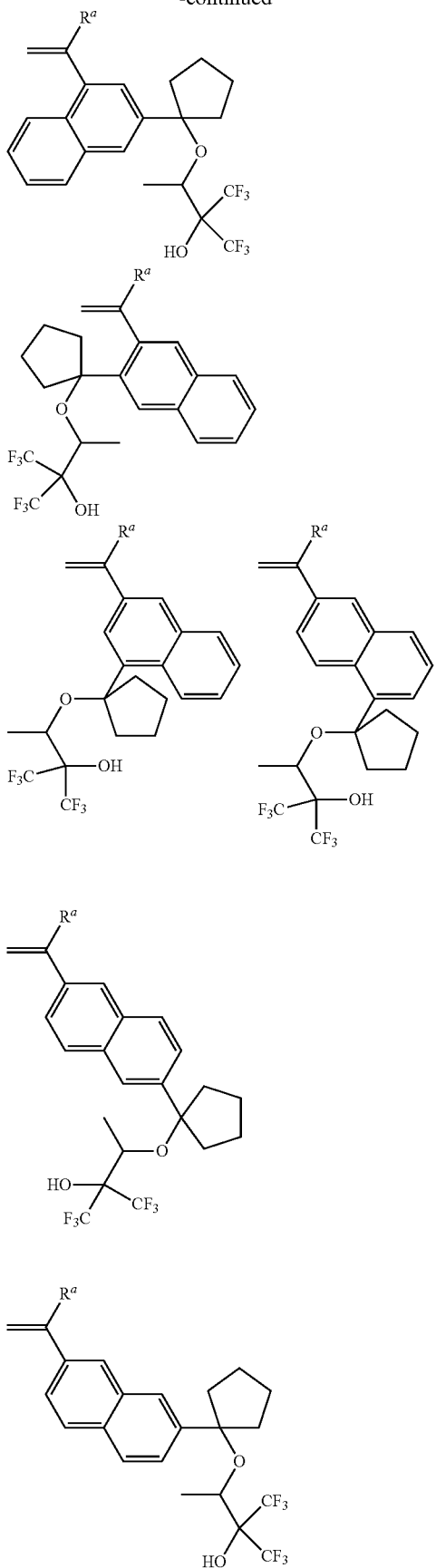
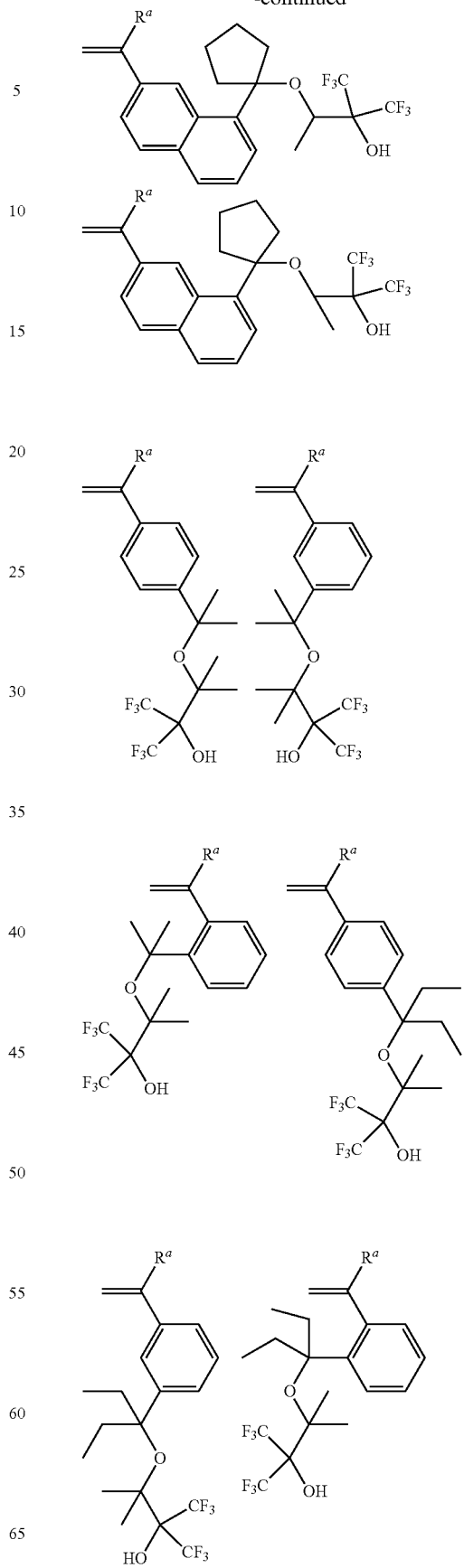

-continued
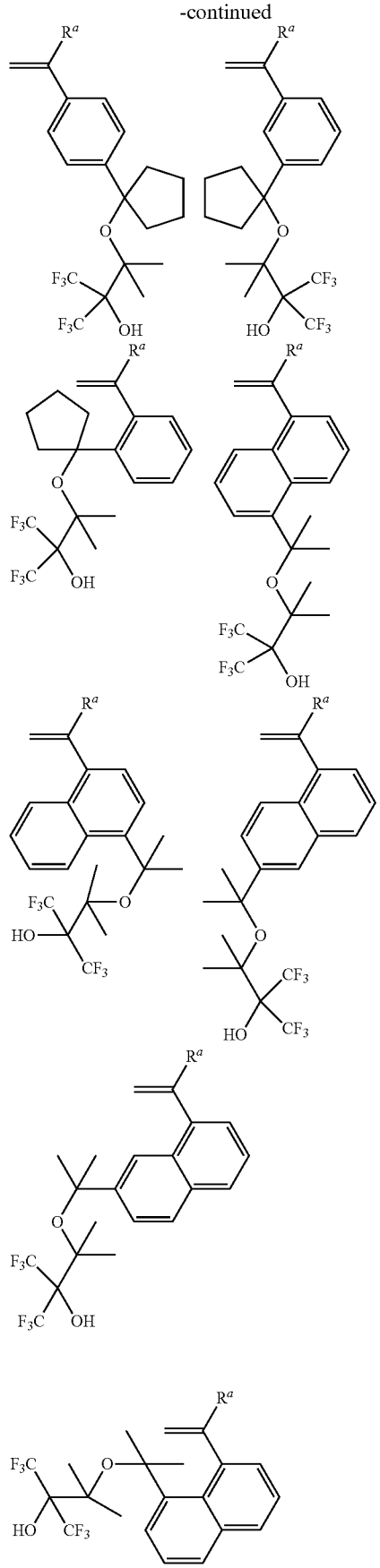
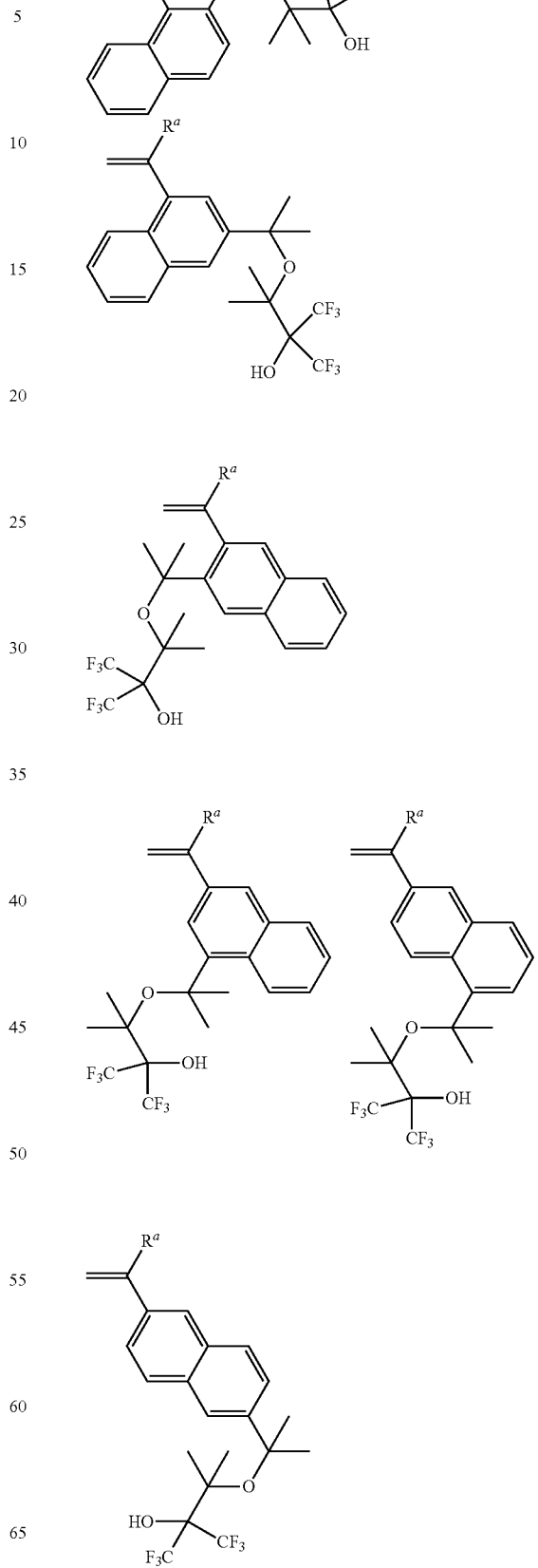

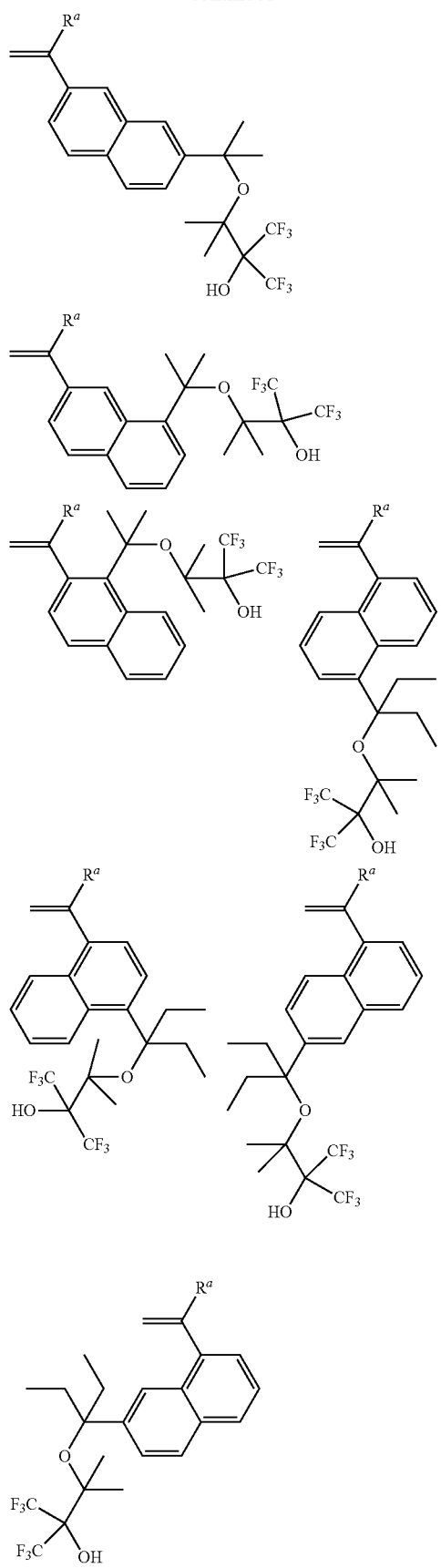
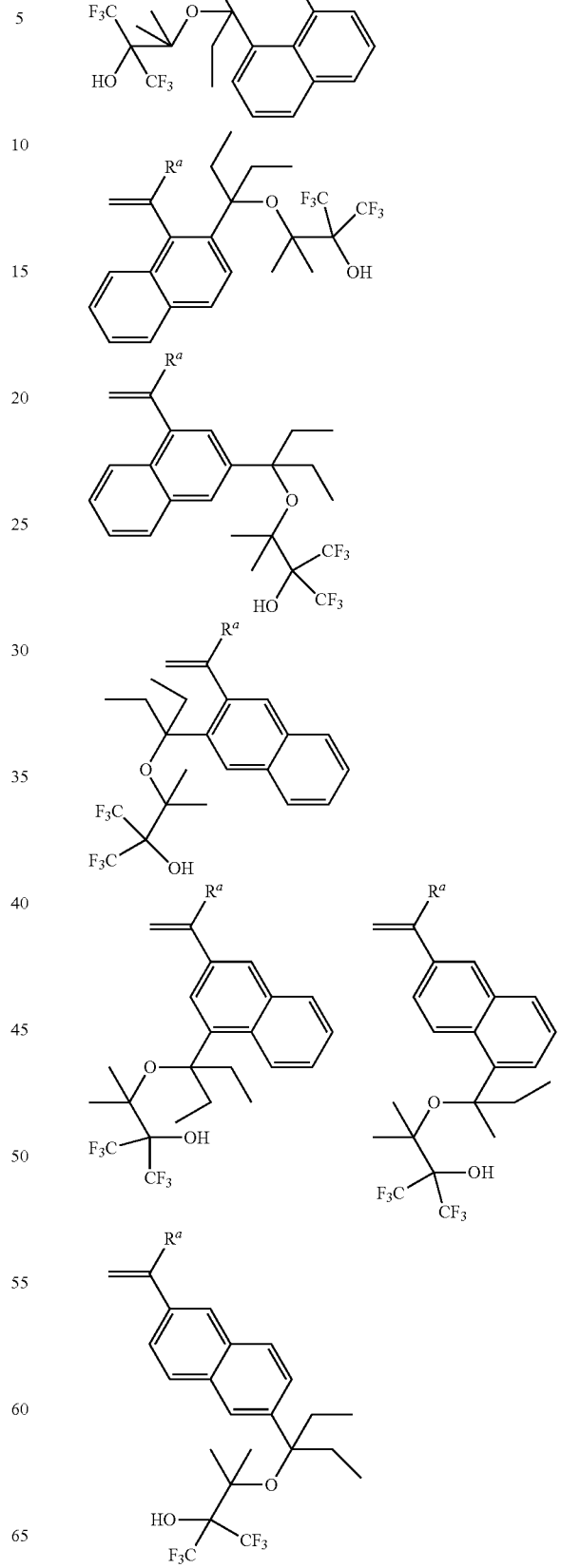

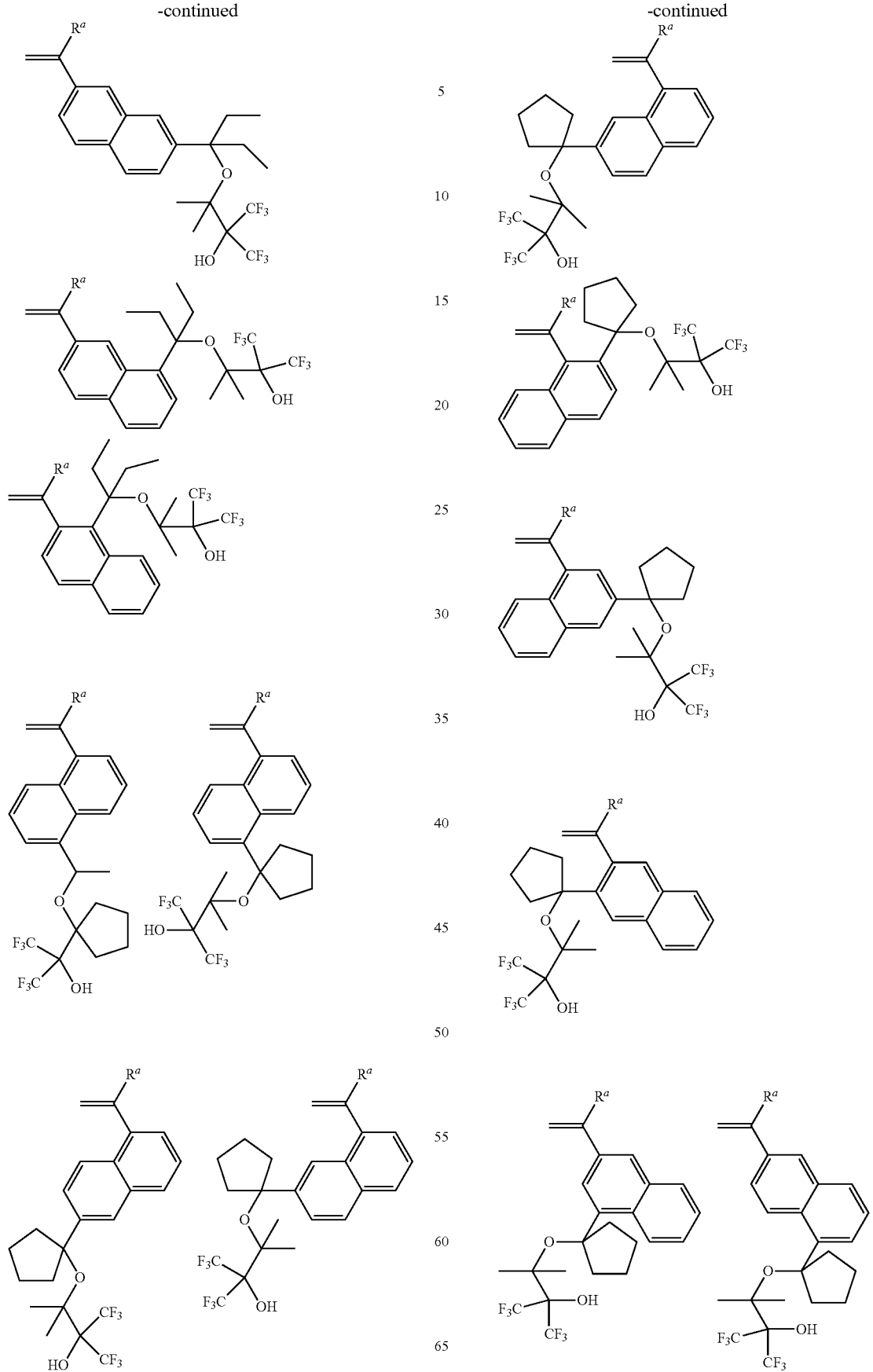

135
-continued
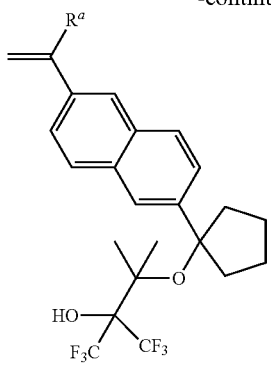
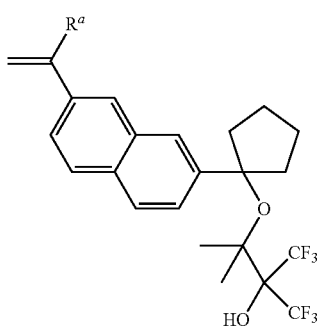
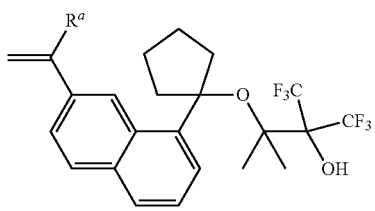
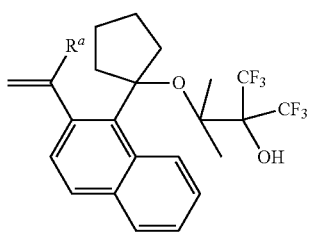
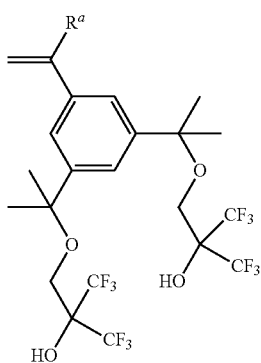
136
-continued
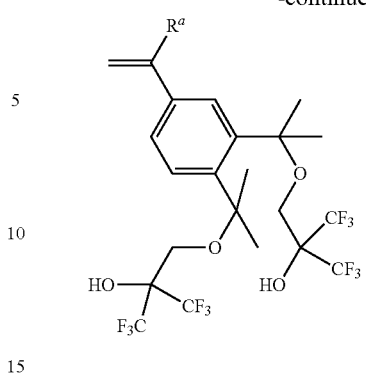
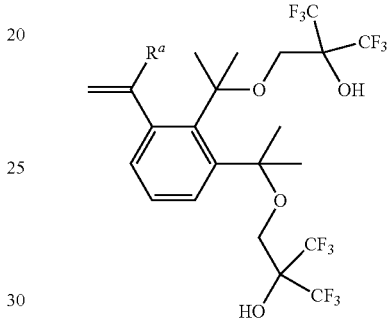
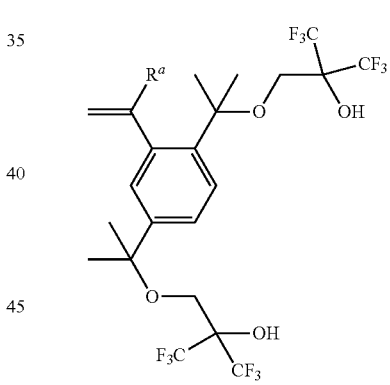
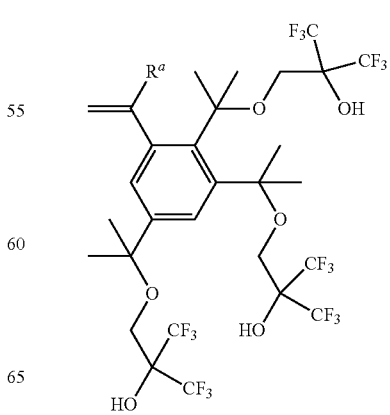

-continued
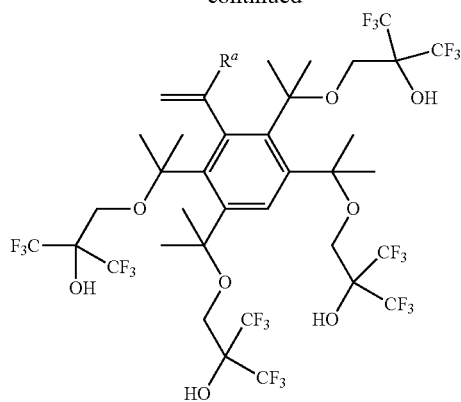
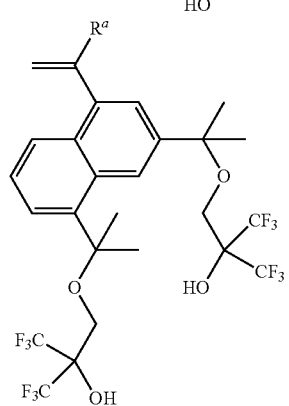
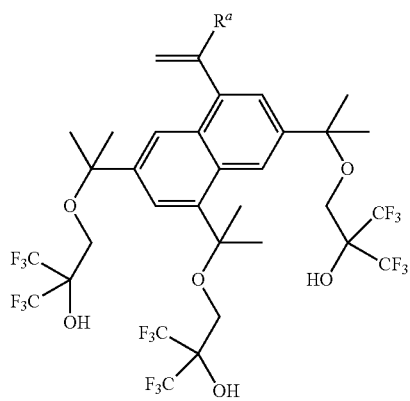
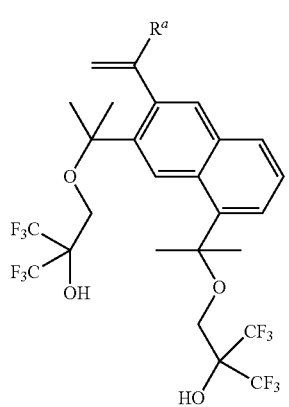
-continued
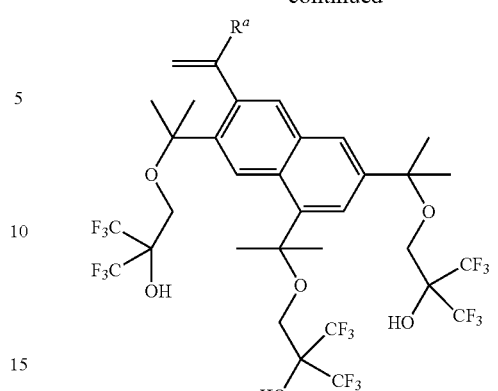
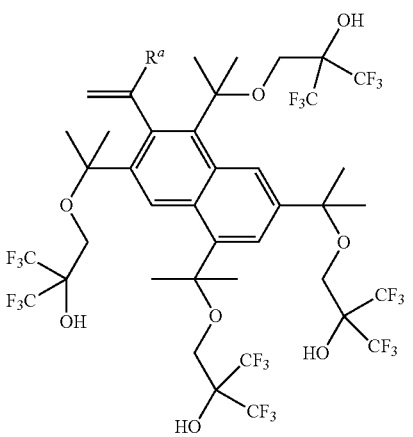
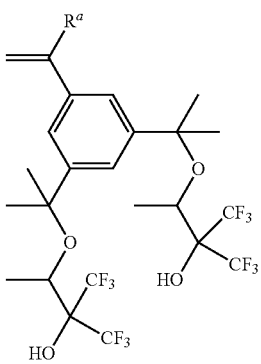
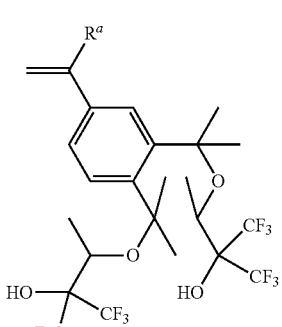

-continued
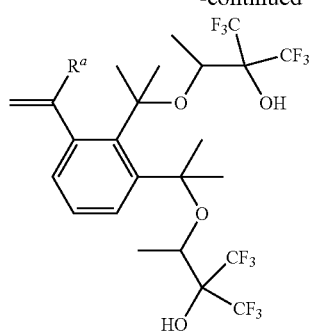
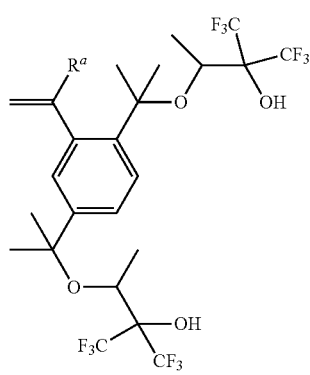
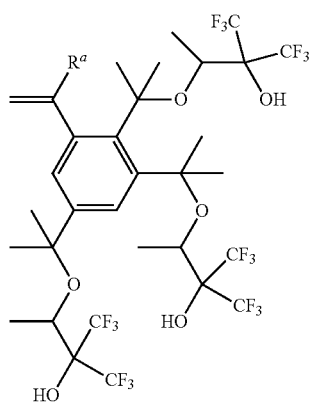
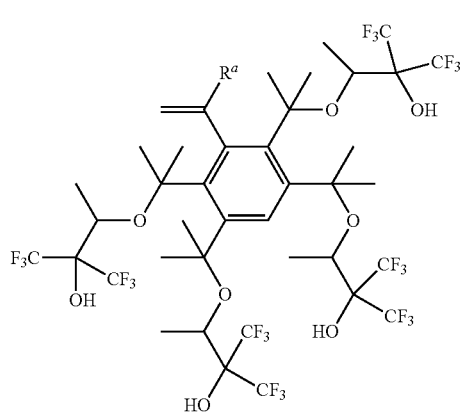
-continued
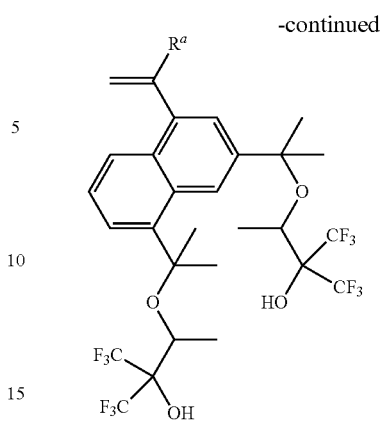
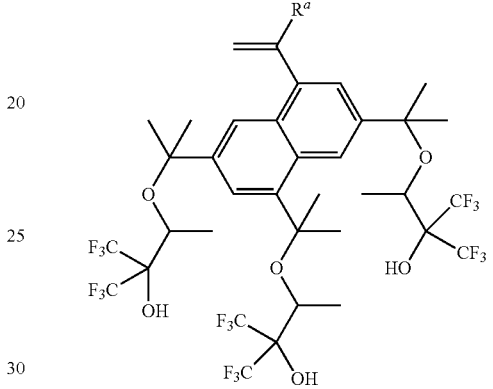
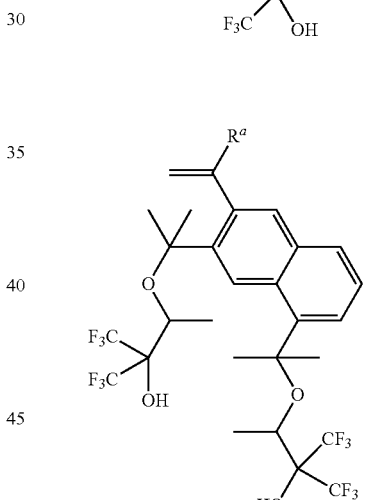
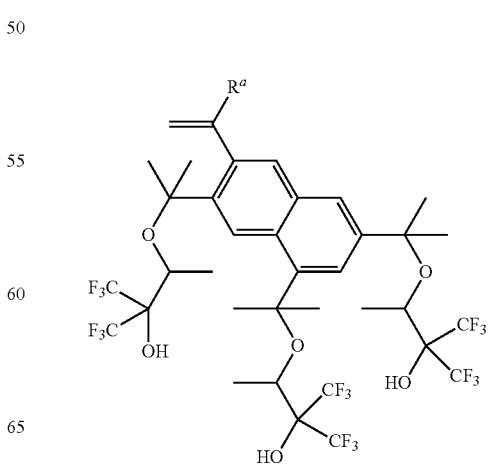

141
-continued
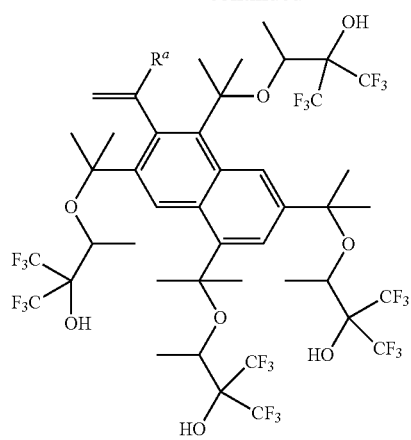
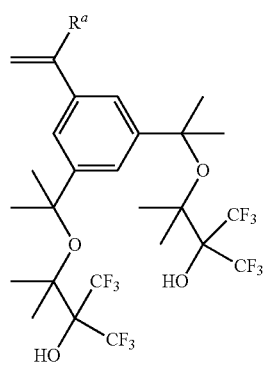
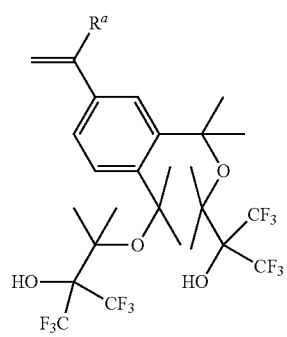
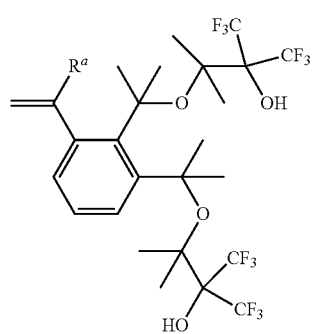
142
-continued
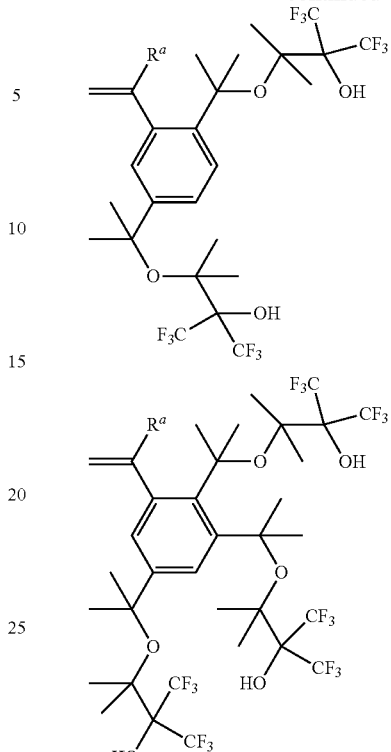
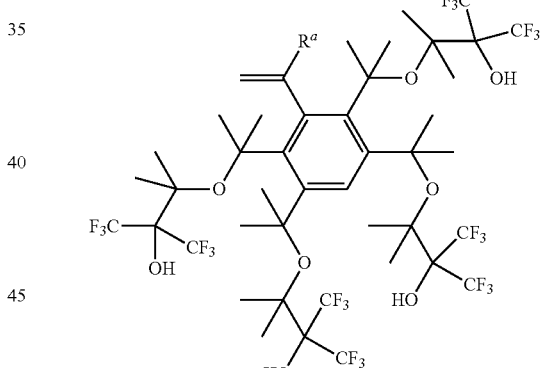

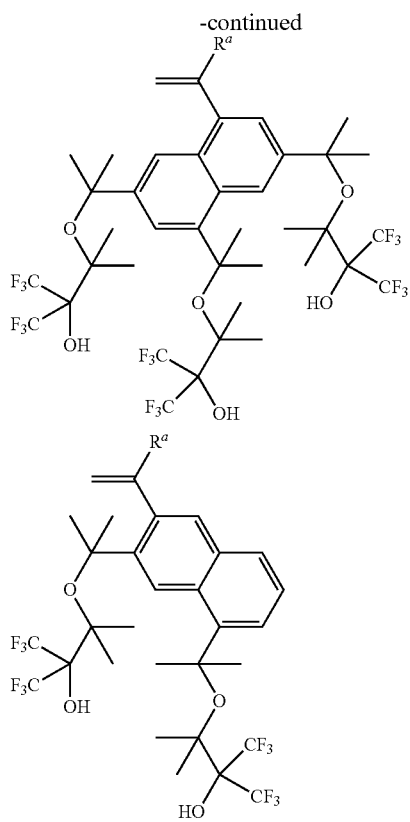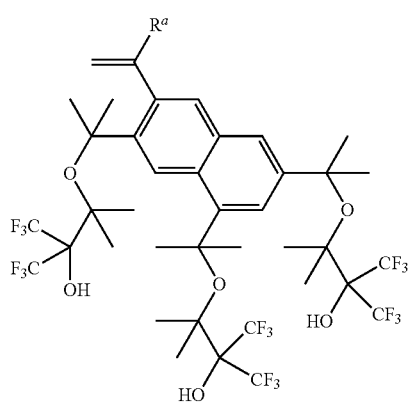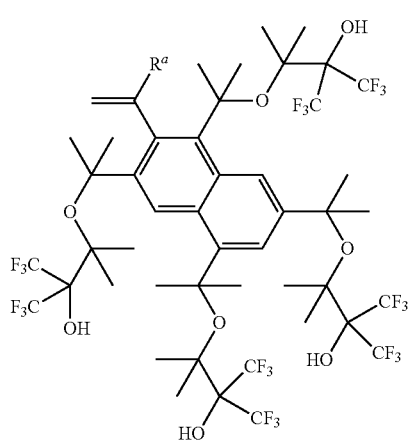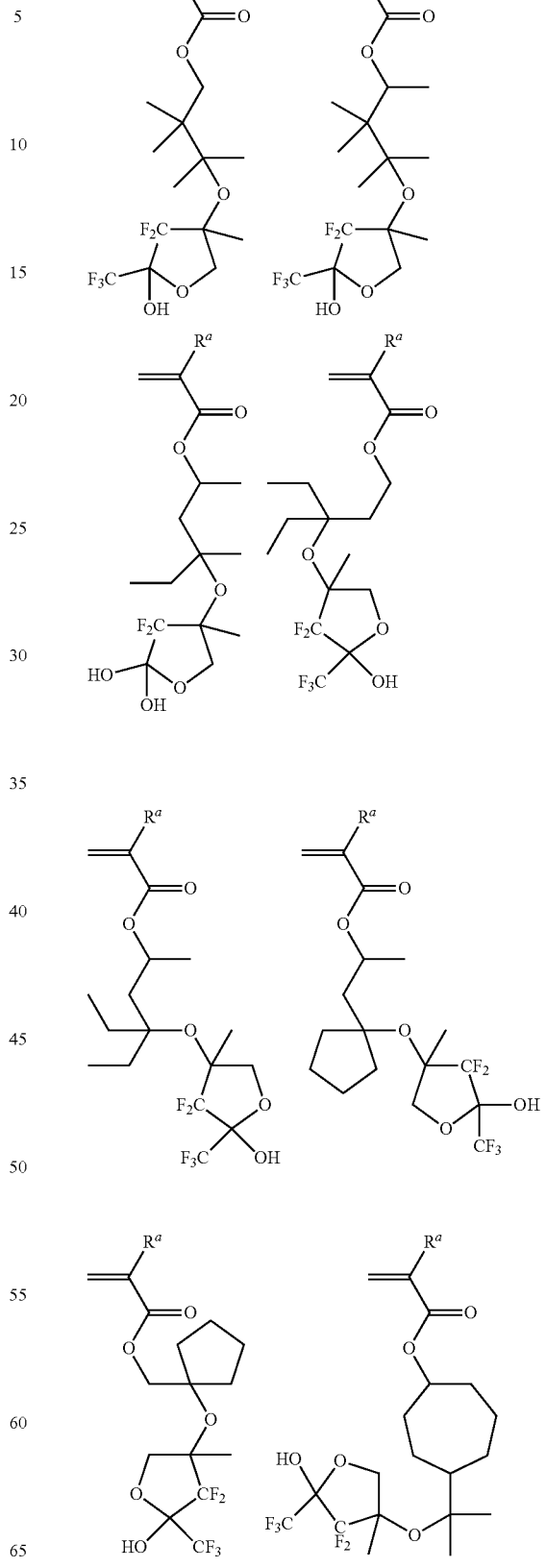

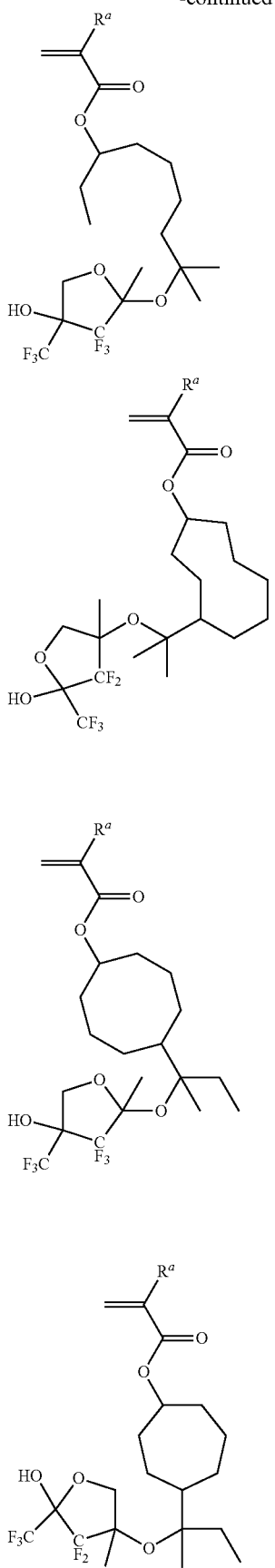
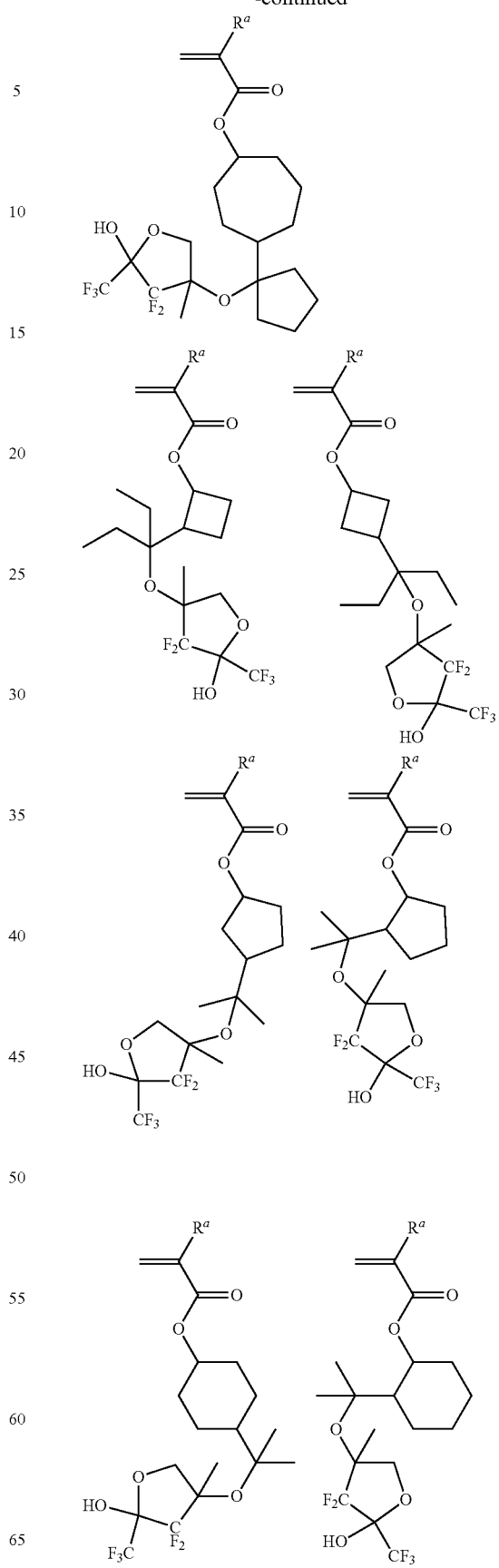

147
-continued
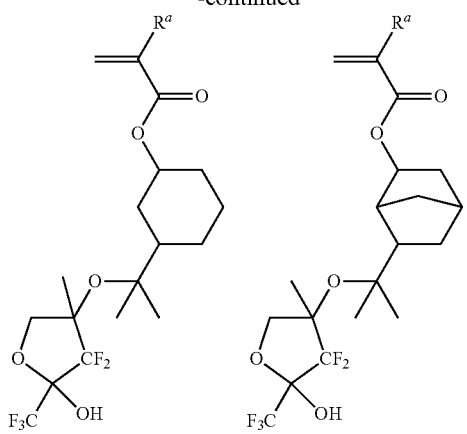
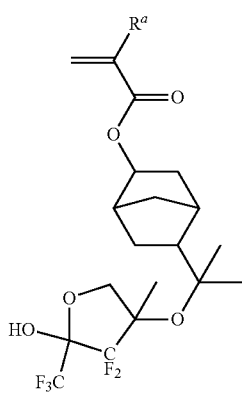
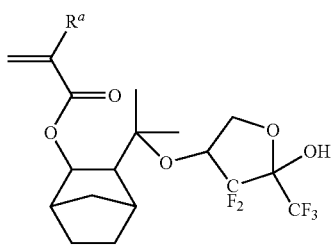
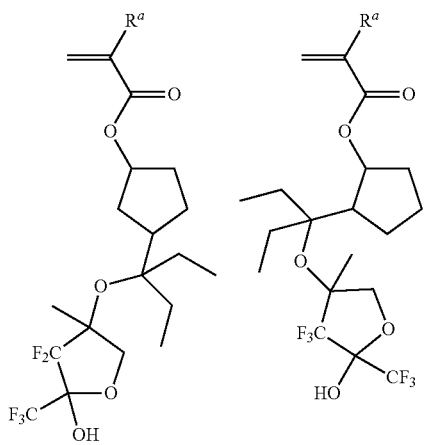
148
-continued
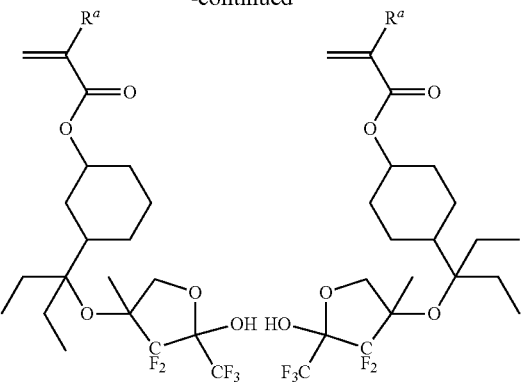
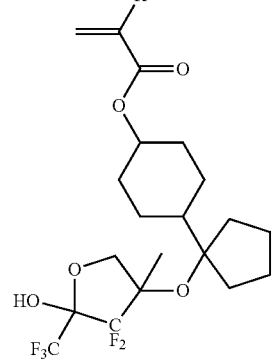
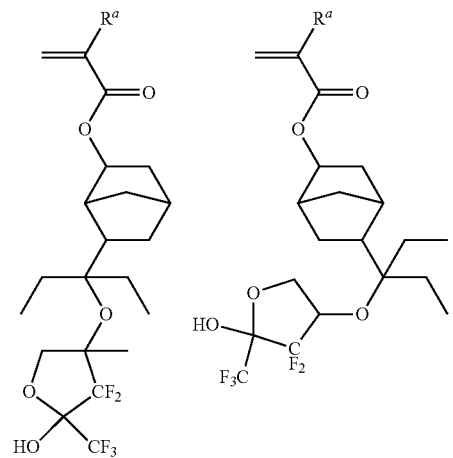
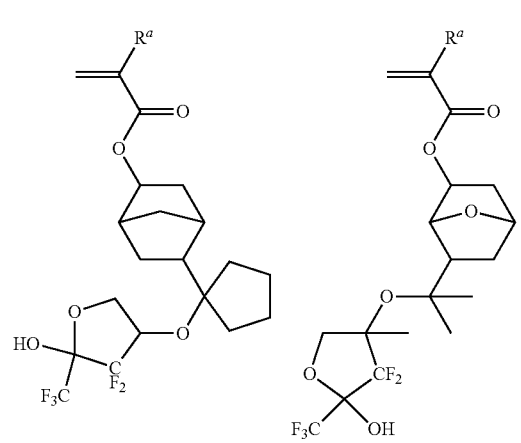

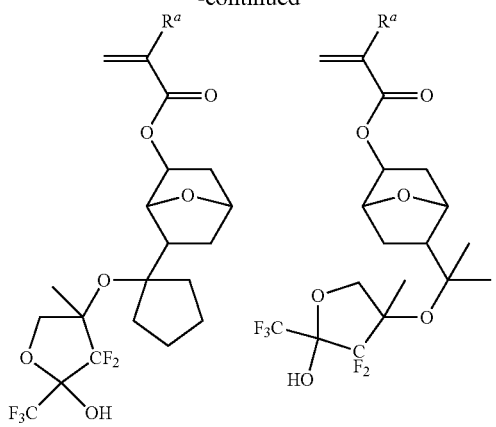
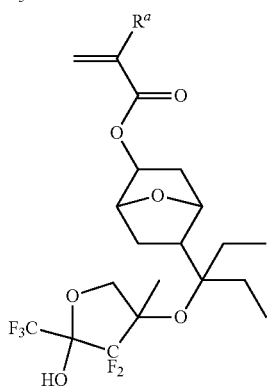
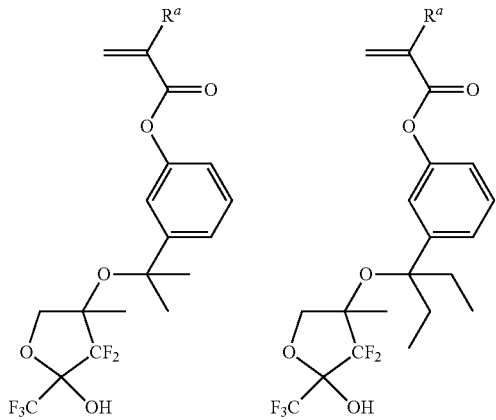
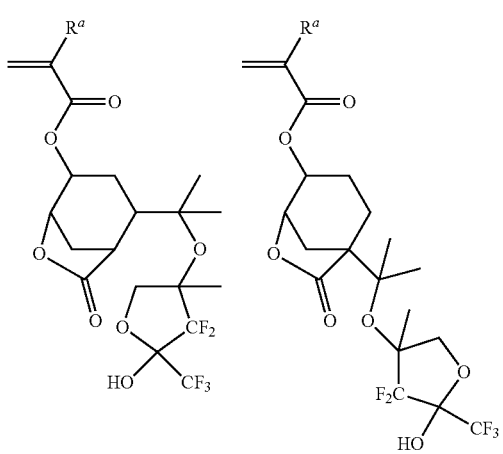
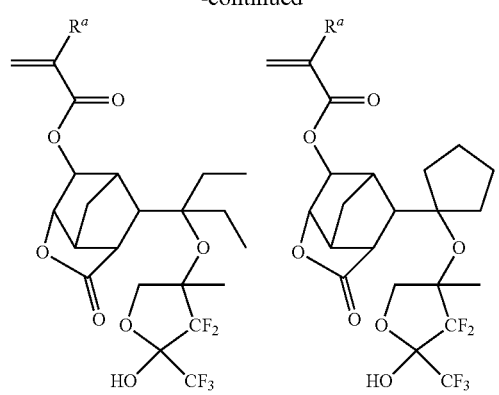
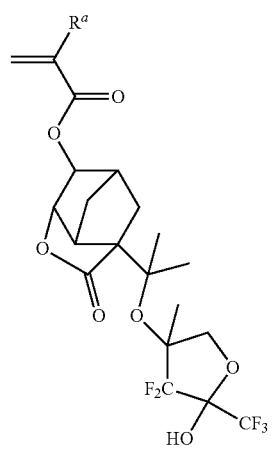
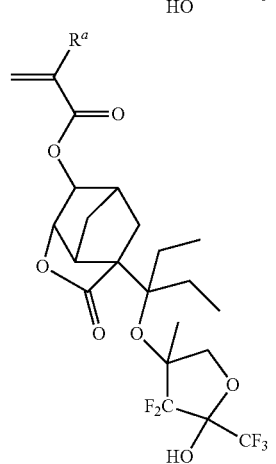
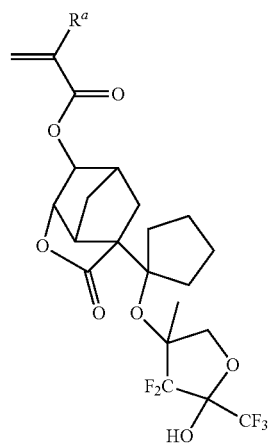

-continued
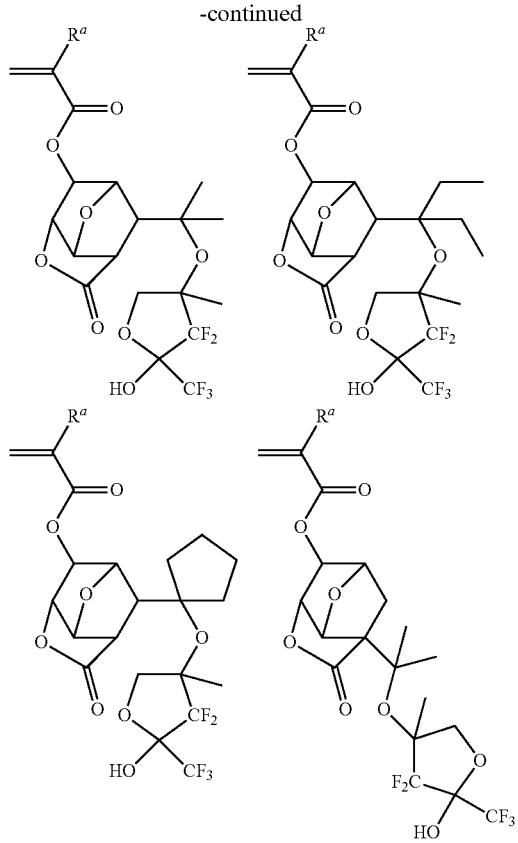
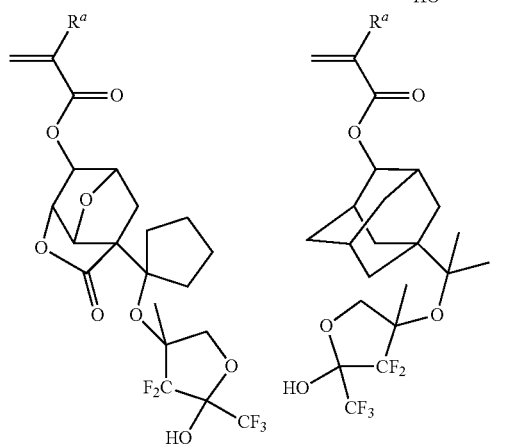
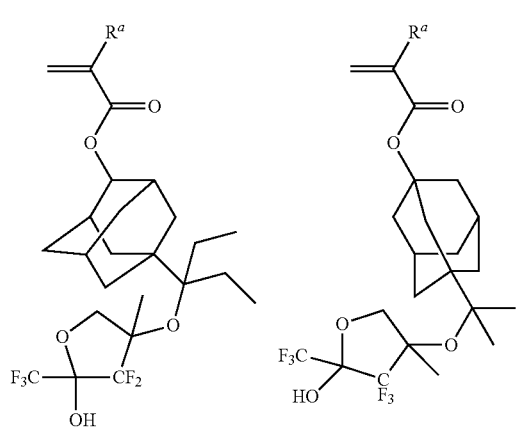
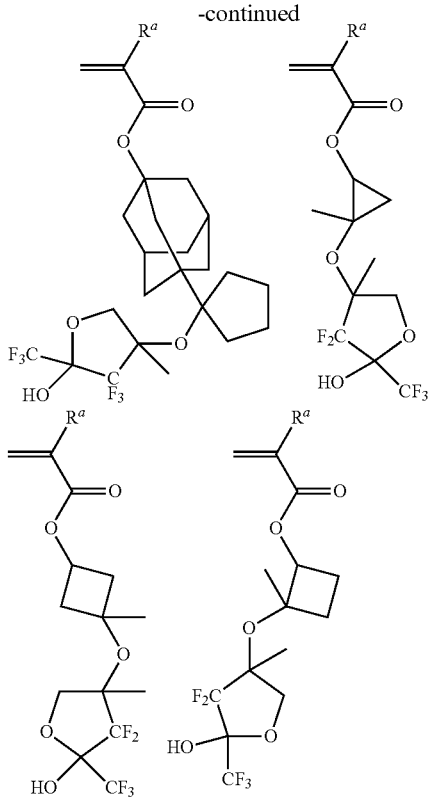
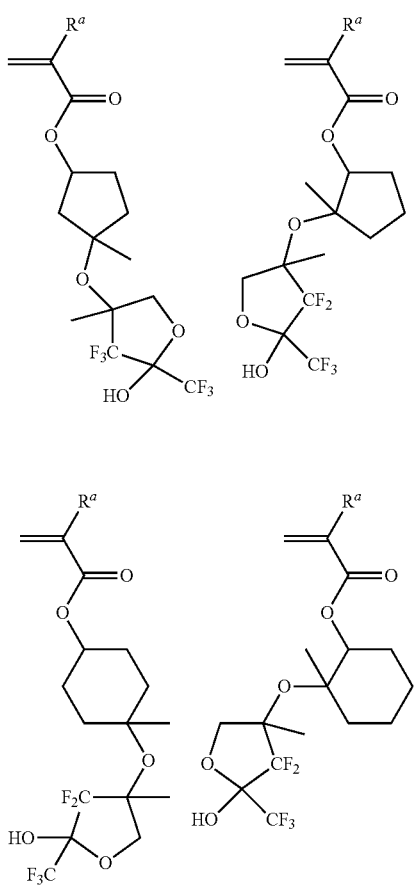

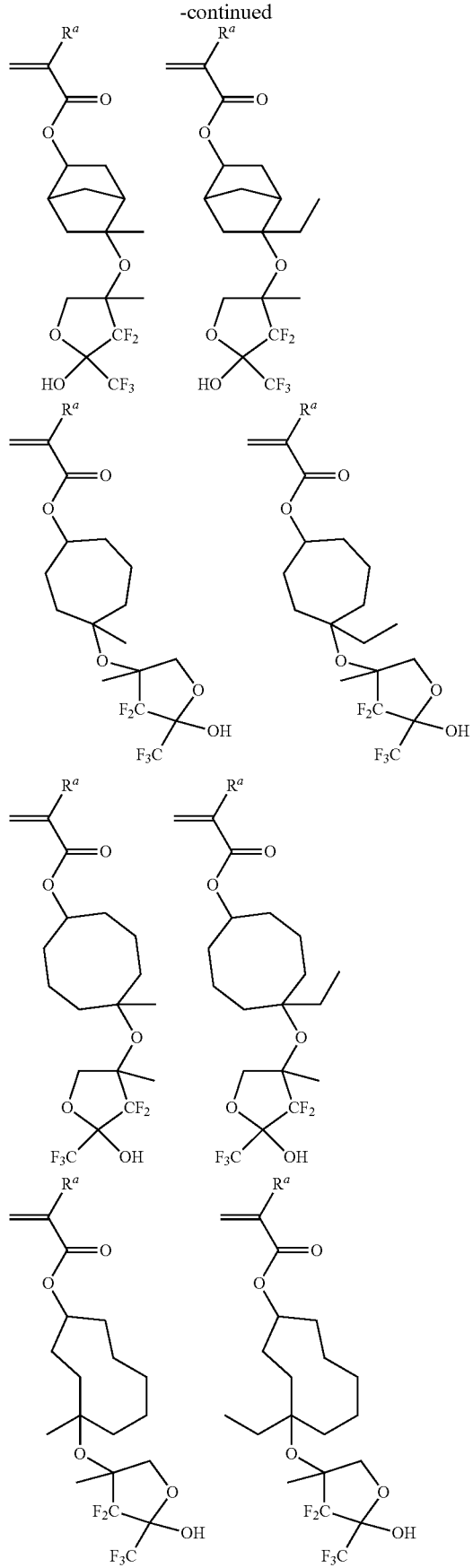
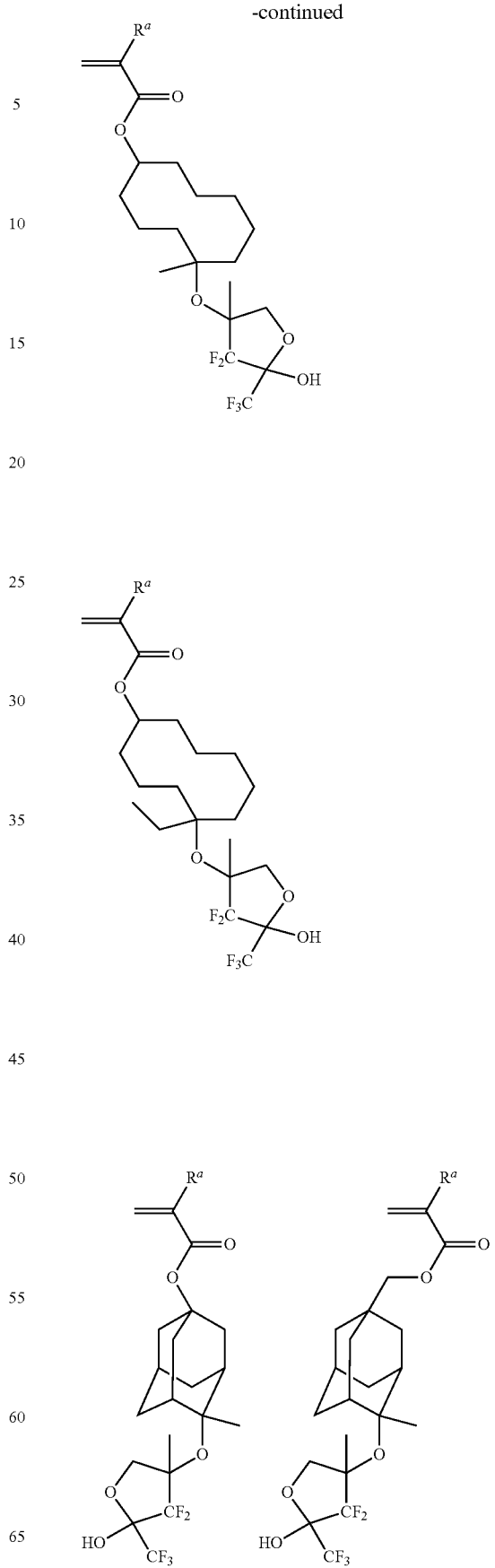

155
-continued
156
-continued
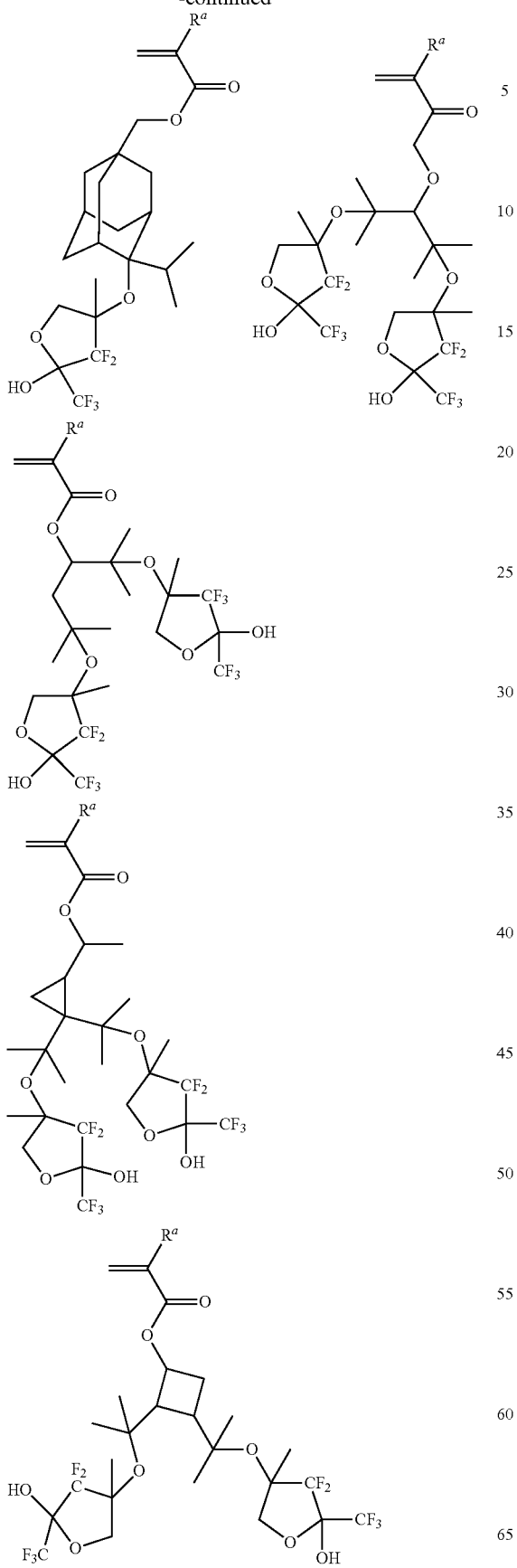
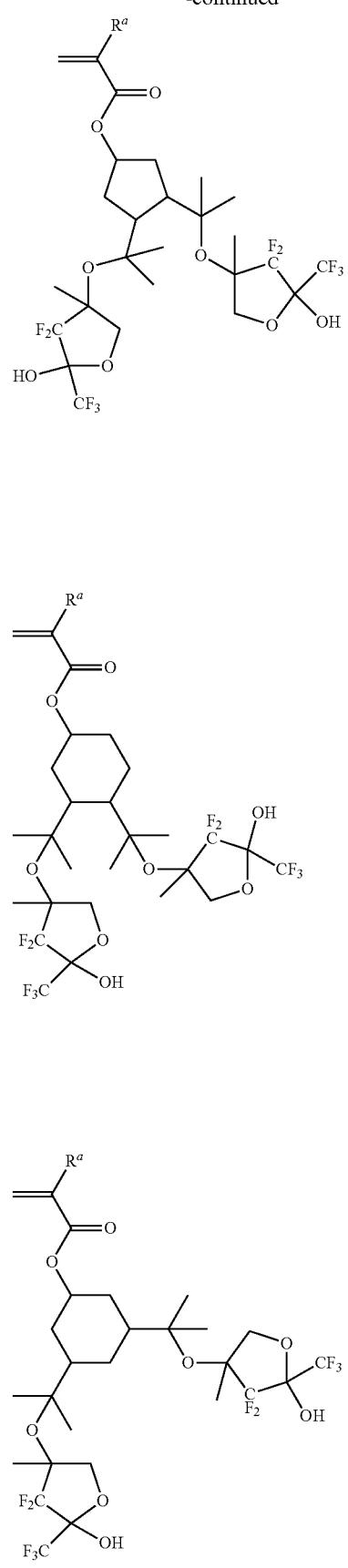

157
-continued
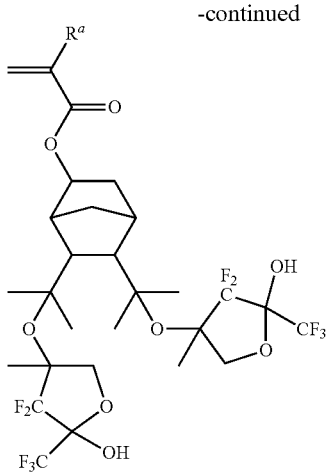
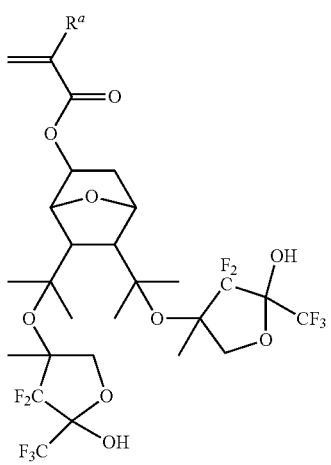
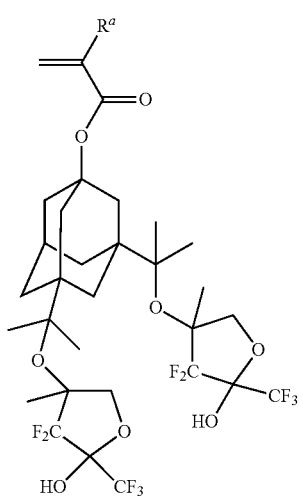
158
-continued
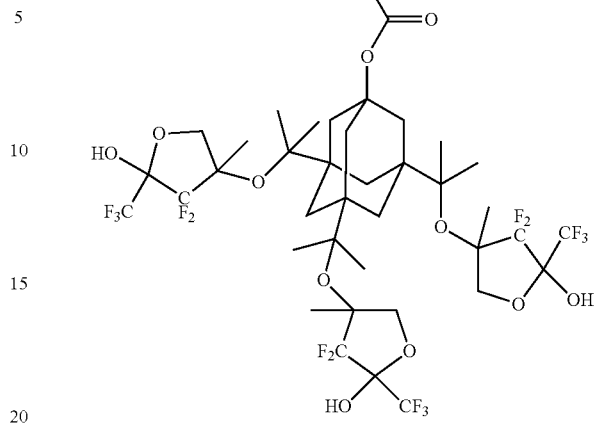
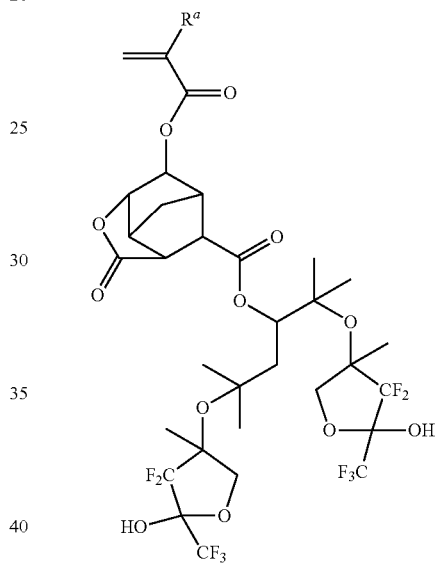
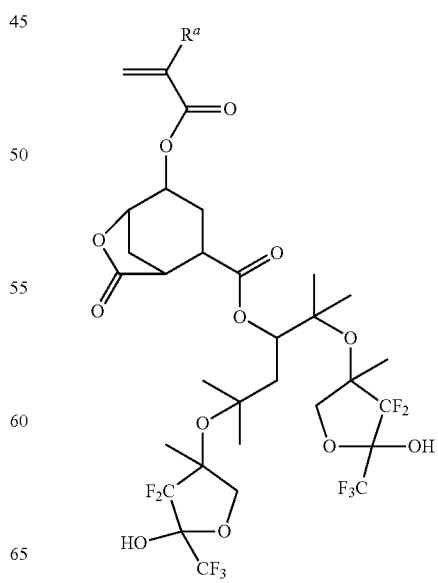

159
-continued
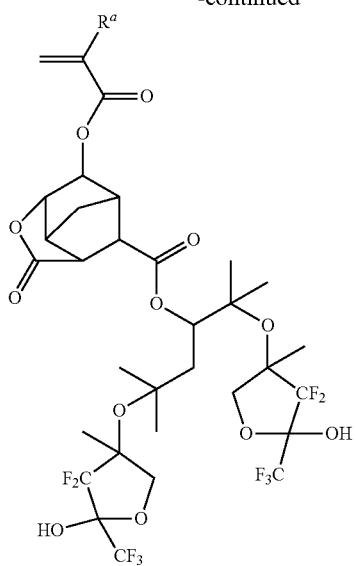
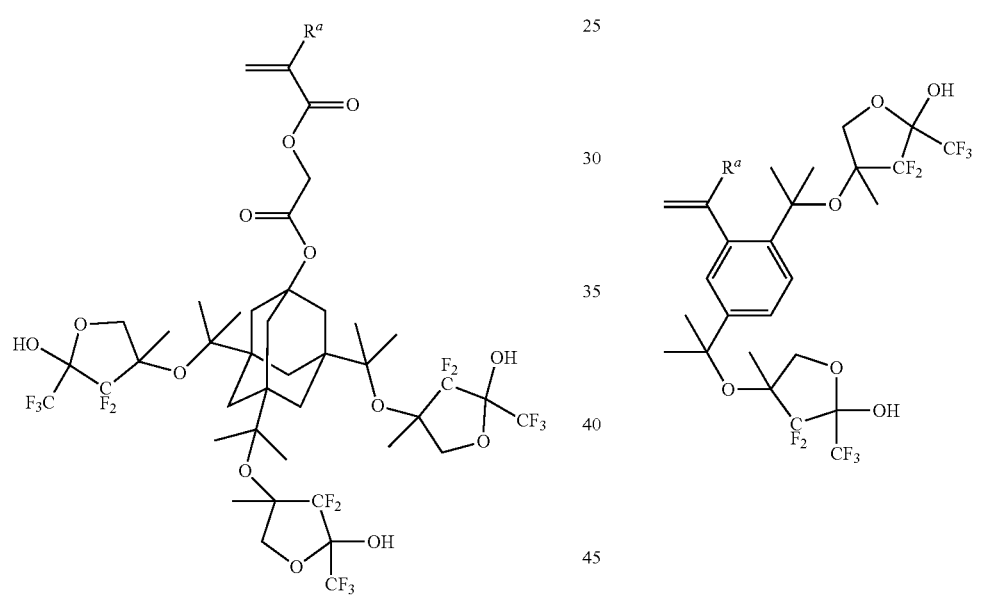
160
-continued
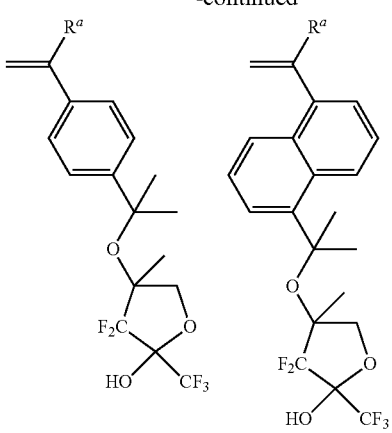
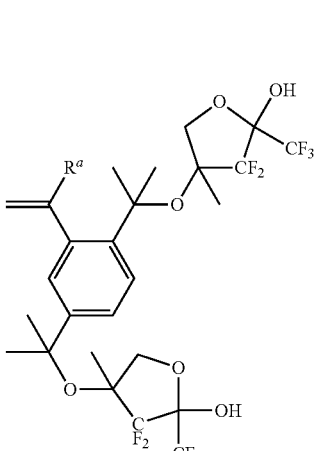
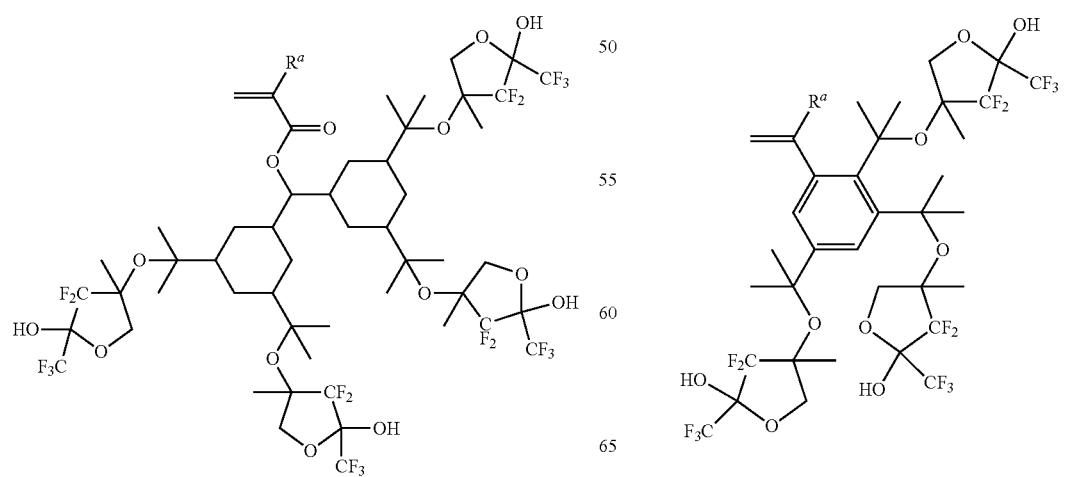
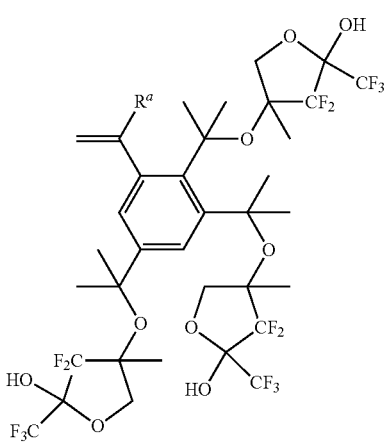

-continued

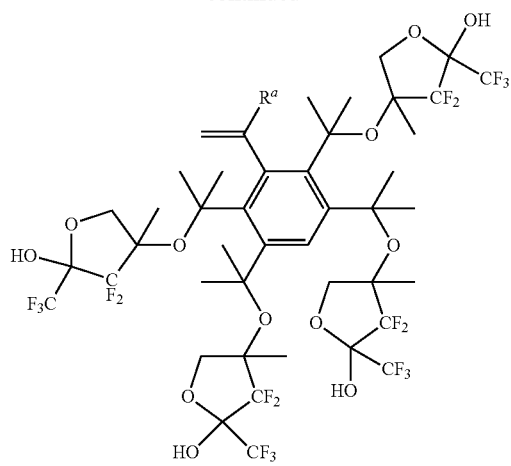

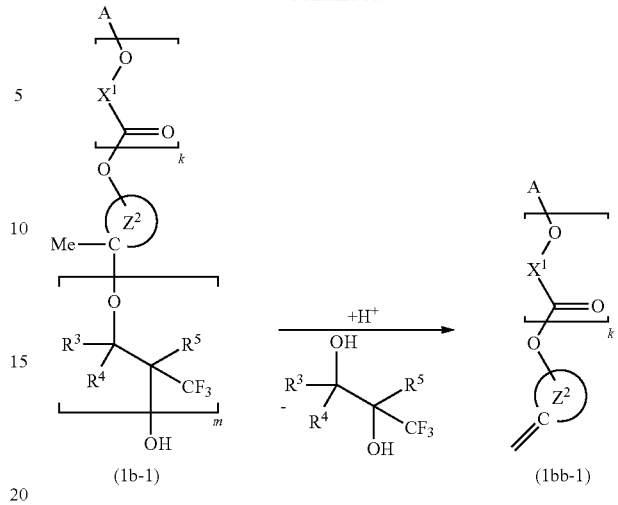

Herein R$^a$ is hydrogen, methyl or trifluoromethyl.

The monomer having formula (1a), (1b), (1aa) or (1bb) has an acid labile group of tertiary fluoroalkyl ether structure. For this reason, when a resist composition comprising a polymer derived from the monomer as a base resin is processed by lithography, elimination reaction of tertiary ether takes place under the action of strong acid generated in the exposed region, followed by olefin formation. This is illustrated in the reaction schemes below by referring to the compounds of formulae (1a-1) and (1b-1) corresponding to formulae (1a) and (1b) wherein R$^1$ and R$^6$ are methyl and m=1, respectively.

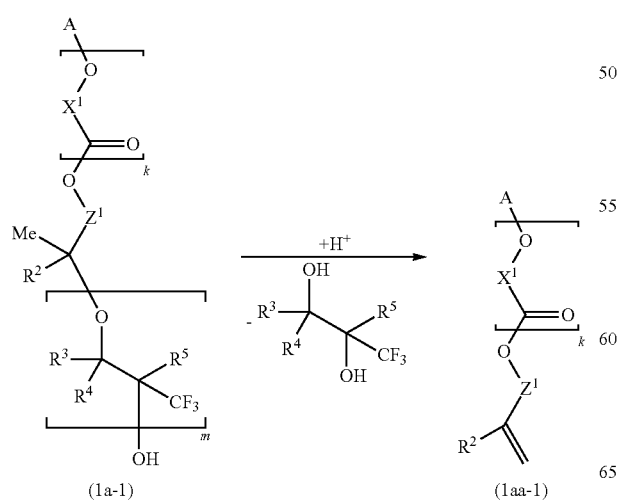

Herein A, X$^1$, R$^2$ to R$^5$, Z$^1$, Z$^2$, k and m are as defined above.

It is seen from the illustrated schemes that prior to exposure, the polymer derived front the monomer has a high affinity and solubility in alkaline developer because of the presence of 1,1,1,3,3,3-hexafluoro-2-propanol. After exposure, the exposed region reduces its solubility in alkaline developer because of elimination of 1,1,1,3,3,3-hexafluoro-2-propanol unit and olefin formation, and becomes insoluble in the developer. In the case of a compound having a cyclic hydrocarbon group in its skeleton, only a polarity switch occurs while retaining the robust alicyclic skeleton. Namely, a polymer comprising the inventive monomer becomes a base resin component which has a very high dissolution contrast relative to alkaline developer and does not necessarily need insolubilization by a crosslinker. After the polarity switch, a high carbon density and resin film thickness are maintained. This substantially eliminates drawbacks including bridge formation between pattern features and pattern collapse due to swell, which are problematic with negative resist materials of conventional polarity switch type and negative resist materials of crosslinking reaction type. Another advantage is etch resistance. Thus a finer size pattern can be resolved.

A prior patent document (JP 4448782) discloses a polymer comprising recurring units having a similar structure to the above formulae (1a) and (1b), as a base resin in a positive resist composition for immersion lithography. This patent document intends to use the polymer as a base resin in the positive resist composition wherein the base resin in the exposed region increases its solubility in alkaline developer. Actually, the polymer is used as a copolymer comprising recurring units of formula (I) shown below and recurring units in which (meth)acrylic acid having a very high affinity to alkaline developer is protected with an acid labile group. In formula (I) wherein L$_1$ is a single bond or a divalent linking group, it never happens that the fluoroalcohol unit undergoes elimination reaction under the action of acid. Therefore, the negative resist composition of the invention wherein the base resin in the exposed region decreases its solubility in alkaline developer and becomes insoluble in the developer is completely different from the prior technology.

Accordingly, the inventive polymer should be free of recurring units having formula (I).

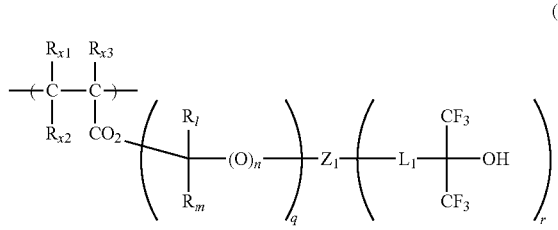

In formula (I), $R_{x1}$ to $R_{x3}$ are each independently hydrogen, fluorine, chlorine, cyano, alkyl or $-L_3-C(R_{f1})(R_{f2})Ra$; $R_{f1}$ and $R_{f2}$ are each independently hydrogen, fluorine or alkyl, at least one of $R_{f1}$ and $R_{f2}$ is fluorine or fluoroalkyl; Ra is hydrogen or hydroxyl; $L_3$ is a single bond, alkylene, —$CH_2$—O— or —$CH_2$—COO—; $R_l$ and $R_m$ are each independently hydrogen or alkyl; $Z_1$ is a single bond, alkylene, cycloalkylene or arylene; $L_1$ is a single bond or divalent linking group; n and q each are 0 or 1, and r is an integer of 1 to 6.

Also, another prior patent document (JP 5675664) discloses a recurring unit containing a 1,1,1,3,3,3-hexafluoro-2-propanol unit as the acid labile group. This patent document relates to a negative resist composition, but uses an organic solvent as the developer. Recurring units in which (meth)acrylic acid is protected with an acid labile group are essentially used while 1,1,1,3,3,3-hexafluoro-2-propanol units are introduced for the sole purpose of improving solvent solubility. After exposure, the acid labile group containing 1,1,1,3,3,3-hexafluoro-2-propanol unit is eliminated, leaving (meth)acrylic acid. On development with an organic solvent, the unexposed region is dissolved and the exposed region is left to form a negative pattern. Therefore, the negative resist composition of the invention wherein the base resin in the exposed region decreases its solubility in alkaline developer and becomes insoluble in the developer is completely different from the other prior technology.

Accordingly, the inventive polymer should be free of recurring units having formula (II).

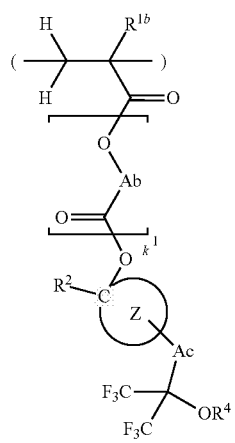

In formula (II), $R^{1b}$ is methyl; $R^2$ is a straight, branched or cyclic $C_1$-$C_{15}$ monovalent hydrocarbon group; Z is a divalent group which forms a substituted or unsubstituted cyclopropane, cyclobutane, cyclopentane, cyclohexane or norbornane ring with the carbon atom to which it is attached; Ab is a straight, branched or cyclic $C_1$-$C_6$ divalent hydrocarbon group; Ac is a single bond or a straight, branched or cyclic $C_1$-$C_{10}$ divalent hydrocarbon group; $R^4$ is hydrogen or a straight, branched or cyclic $C_1$-$C_{15}$ monovalent hydrocarbon group in which any constituent —$CH_2$— moiety may be replaced by —O— or —C(=O)—; and $k^1$ is 0 or 1.

In formula (1a), $Z^1$ is preferably an alicyclic group, especially cyclopentane, cyclohexane or adamantane ring since it is advantageous for control of acid diffusion length and etch resistance. Likewise, in formula (1b), the alicyclic unit constituted by atomic group $Z^2$ is preferably a cyclopentane, cyclohexane or adamantane ring.

The monomer having formula (1a) may be synthesized by reactions as shown in the reaction scheme below although the synthesis route is not limited thereto. Likewise, the monomer having formula (1b) may be synthesized in a similar reaction scheme although the synthesis route is not limited thereto. Synthesis of the monomer having formula (1a) is described in detail.

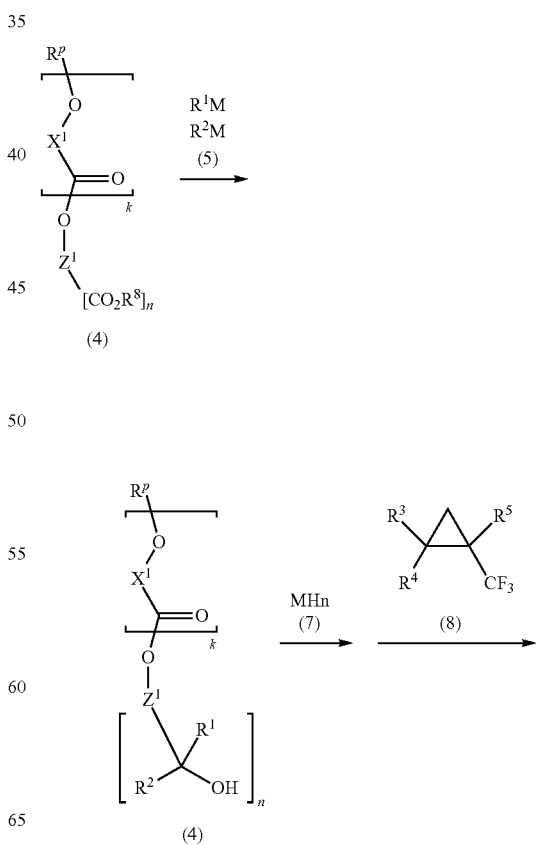

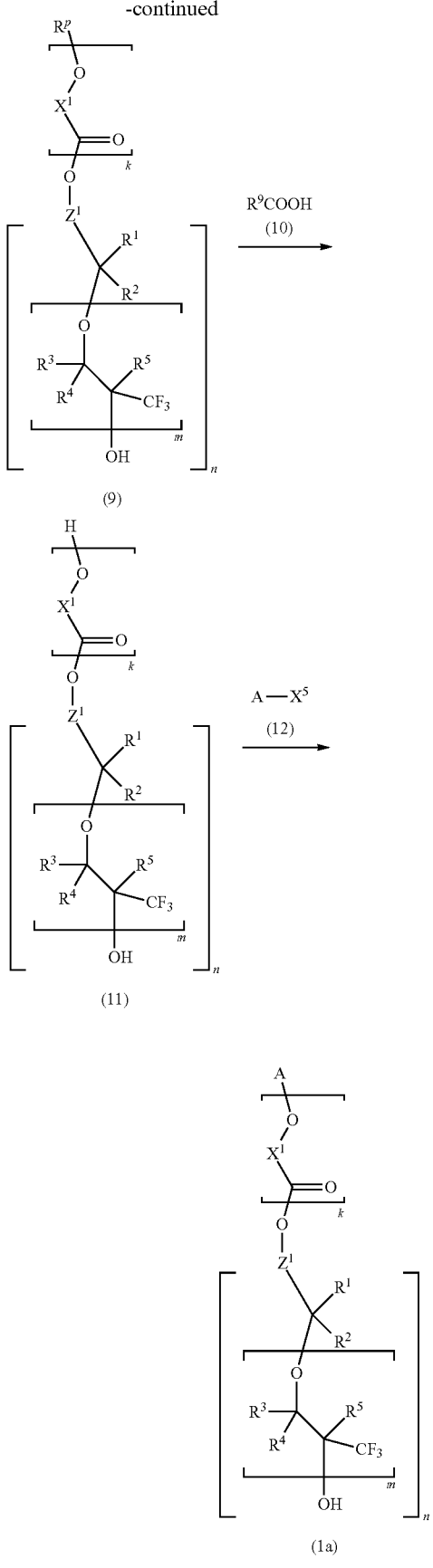

Herein $R^1$ to $R^5$, $X^1$, $Z^1$, k, m, and n are as defined above. $R^8$ is a straight, branched or cyclic $C_1$-$C_{10}$ monovalent hydrocarbon group. In view of reactivity with organometallic reagents $R^1M$ and $R^2M$, $R^8$ is preferably a straight monovalent hydrocarbon group, especially methyl or ethyl. $R^9$ is hydrogen or a straight, branched or cyclic $C_1$-$C_6$ divalent hydrocarbon group. $R^P$ is a protective group for an alcoholic hydroxyl group, $X^5$ is a halogen atom, hydroxyl group or acyloxy group. M is Li, Na, K, $MgX^{hal}$ or $ZnX^{hal}$ wherein $X^{hal}$ is a halogen atom.

The first stage is addition reaction of an ester compound (4) having a hydroxyl group protected in a well-known manner with an organometallic reagent (5) to form a tertiary alcohol-containing compound (6).

The protective group $R^P$ for an alcoholic hydroxyl group on the ester compound (4) may utilize ordinary organic synthesis reaction. Suitable protective groups for an alcoholic hydroxyl group include substituted methyl ether protective groups, substituted ethyl ether protective groups, substituted benzyl ether protective groups, silyl ether protective groups, ester protective groups, carbonate protective groups, and sulfonate protective groups. From the standpoints of stability to the organometallic reagents and ease of subsequent deprotection reaction, silyl ether protective groups are preferred. Suitable silyl ether protective groups include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, tris(trimethylsilyl)silyl, (2-hydroxystyryl)dimethylsilyl, (2-hydroxystyryl)diisopropylsilyl, t-butylmethoxyphenylsilyl, and t-butoxydiphenylsilyl. Inter alia, trimethylsilyl, triethylsilyl, triisopropylsilyl, and dimethylisopropylsilyl are preferred.

The reaction may be performed by a standard procedure. For example, protected hydroxy-ester compound (4) is dissolved in an ether solvent such as tetrahydrofuran or diethyl ether, then organometallic reagent (5) corresponding to substituent groups $R^1$ and $R^2$, for example, a Grignard reagent such as methylmagnesium chloride or ethylmagnesium chloride or alkyl-lithium reagent such as methyllithium is added to the solution, whereby addition reaction takes place to form tertiary alcohol compound (6). An appropriate amount of organometallic reagent (5) used is 2.0 to 10.0 moles, more preferably 2.0 to 5.0 moles per mole of the ester group of ester compound (4). More than 10.0 moles of organometallic reagent (5) may be disadvantageous in cost because of increased reactant expense. The reaction may be performed while cooling or heating if necessary, typically at a temperature of 0° C. to about the boiling point of the solvent. It is desirable from the standpoint of yield that the reaction time is determined so as to drive the reaction to completion by monitoring the reaction process by gas chromatography (GC) or silica gel thin-layer chromatography (TLC). Usually, the reaction time is about 0.5 to 24 hours. From the reaction mixture, the desired tertiary alcohol compound (6) is recovered through an ordinary aqueous workup. If necessary, the compound may be purified by a standard technique such as distillation, chromatography or recrystallization.

The second stage involves reaction of tertiary alcohol compound (6) with a metal hydride (7) to form a metal alkoxide and ring-opening reaction with a partially fluorinated 3-membered ring epoxy compound (8) to form a compound (9).

The reaction may be performed by a standard procedure. The metal hydride such as sodium hydride or potassium hydride is suspended in an ether solvent such as tetrahydrofuran. A dilution of the tertiary alcohol compound in a solvent such as tetrahydrofuran is added dropwise to the suspension to form a metal alkoxide. To the metal alkoxide solution, the partially fluorinated 3-membered ring epoxy compound (8) is added to form a fluorinated alcohol compound (9). An appropriate amount of the metal hydride used is 1.0 to 1.5 moles, more preferably 1.0 to 1.1 moles per mole of the tertiary alcohol compound. An appropriate amount of the partially fluorinated 3-membered ring epoxy compound (8) is 1.0 to 1.5 moles, more preferably 1.0 to 1.2 moles per mole of the tertiary alcohol compound. If the amount exceeds 1.5 moles, a product having 3 to 5 moles of the partially fluorinated 3-membered ring epoxy compound added per mole of the tertiary alcohol compound may form more, leading to a lowering of purity. The reaction may be performed while cooling or heating if necessary, typically at a temperature of 0 to 40° C. It is desirable from the standpoint of yield that the reaction time is determined so as to drive the reaction to completion by monitoring the reaction process by GC or silica gel TLC. Usually, the reaction time is about 6 to 24 hours. From the reaction mixture, the desired compound (9) is recovered through an ordinary aqueous workup. If necessary, the compound may be purified by a standard technique such as distillation, chromatography or recrystallization.

The third stage is deprotection of the protective group on compound (9) with a carboxylic acid (10) to form a diol (11).

The reaction may be performed by a standard procedure. The compound (9) is dissolved in an ether solvent, such as tetrahydrofuran optionally in admixture with water. Carboxylic acid (10) is added to the solution whereupon deprotection reaction takes place, yielding diol (11). Preferred examples of the carboxylic acid used herein include formic acid and acetic acid. The reaction may be performed while cooling or heating if necessary, typically in a range from room temperature to 60° C. It is desirable from the standpoint of yield that the reaction time is determined so as to drive the reaction to completion by monitoring the reaction process by GC or silica gel TLC. Usually, the reaction time is about 1 to 12 hours. From the reaction mixture, the desired diol (11) is recovered through an ordinary aqueous workup. If necessary, the compound may be purified by a standard technique such as distillation, chromatography or recrystallization.

The fourth stage is reaction of the hydroxyl group resulting from deprotection reaction at the third stage with an esterifying agent (12) to form monomer (1a).

The reaction may be performed by a standard procedure. The preferred esterifying agent (12) is an acid chloride of formula (12) wherein $X^5$ is chlorine, a carboxylic acid of formula (12) wherein $X^5$ is hydroxyl, or an acid anhydride of formula (12) wherein $X^5$ is acyloxy. When an acid chloride is used as the esterifying agent, the reaction may be performed in a solventless system or in a solvent (e.g., methylene chloride, acetonitrile, toluene or hexane) by sequentially or simultaneously adding diol (11), a corresponding acid chloride (e.g., methacryloyl chloride), and a base (e.g., triethylamine, pyridine or 4-dimethylaminopyridine), and optionally cooling or heating the reaction system. When a carboxylic acid is used as the esterifying agent, the reaction may be performed in a solvent (e.g., toluene or hexane) by heating diol compound (11) and a corresponding carboxylic acid (e.g., methacrylic acid) in the presence of an acid catalyst, and optionally removing water formed by the reaction from the reaction system. Examples of the acid catalyst used herein include mineral acids such as hydrochloric, acid, sulfuric acid, nitric acid and perchloric acid and organic acids such as p-toluenesulfonic acid and benzenesulfonic acid. When an acid anhydride is used as the esterifying agent, the reaction may be performed in a solventless system or in a solvent (e.g., methylene chloride, acetonitrile, toluene or hexane) by sequentially or simultaneously adding diol (11), a corresponding acid anhydride (e.g., methacrylic anhydride), and a base (e.g., triethylamine, pyridine or 4-dimethylaminopyridine), and optionally cooling or heating the reaction system. It is desirable from the standpoint of yield that the reaction time is determined, so as to drive the reaction to completion by monitoring the reaction process by GC or silica gel TLC. Usually, the reaction time is about 0.5 to 24 hours. From the reaction mixture, the desired monomer (1a) is recovered through an ordinary aqueous workup. If necessary, the monomer may be purified by a standard technique such as distillation, chromatography or recrystallization.

Polymer

The invention also provides a polymer comprising recurring units derived from the inventive monomer, specifically recurring units of at least one type selected from recurring units having formulae (2a) to (2d).

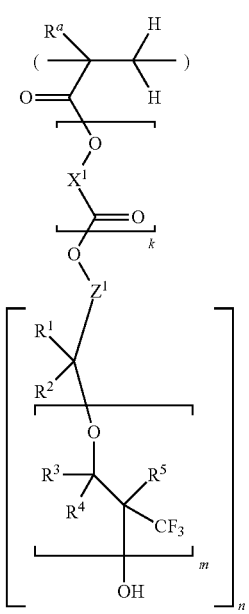

(2a)

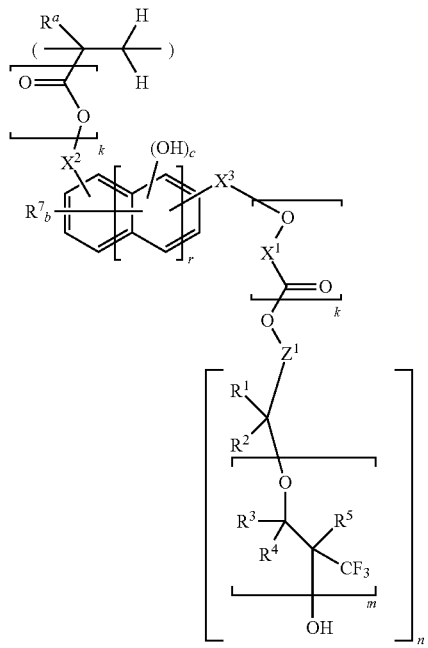

(2b)

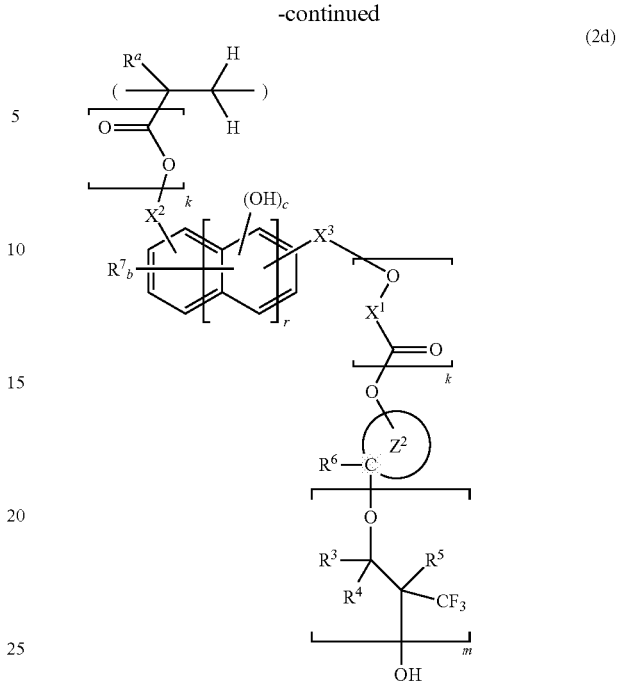

(2d)

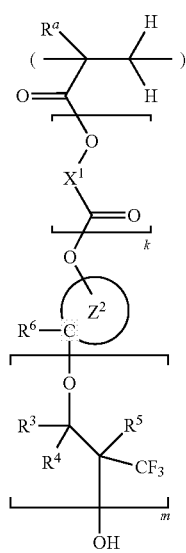

(2c)

Herein $R^a$ is hydrogen, methyl or trifluoromethyl. $R^1$ to $R^7$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$, $R^3$ and $R^4$, $R^3$ and $R^5$, or $R^4$ and $R^5$ may bond together to form an alicyclic group with the carbon atom to which they are attached. $X^1$ is a straight, branched or cyclic $C_1$-$C_{15}$ divalent hydrocarbon group in which any constituent —$CH_2$— moiety may be replaced by —O— or —C(=O)—. $X^2$ and $X^3$ are each independently a single bond or a straight, branched or cyclic $C_1$-$C_{15}$ divalent hydrocarbon group in which any constituent —$CH_2$— moiety may be replaced by —O— or —C(=O)—. $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, b is an integer meeting b≤5+2r−c, c is an integer of 1 to 3, k is 0 or 1, m is 1 or 2, n is an integer of 1 to 4, r is an integer of 0 to 2. $Z^2$ is an atomic group necessary to form a $C_3$-$C_{10}$ alicyclic group with the carbon atom to which it is attached, in which any constituent —$CH_2$— moiety may be replaced by —O— or —C(=O)—. In formulae (2a) to (2d), when the oxygen atom attached to group $Z^1$ or atomic group $Z^2$ forms a bond with the carbonyl carbon bonded to a polymerizable group or the linker —[O—$X^1$—C(=O)]—, a tertiary ester bond is not formed.

Examples of $R^a$, $R^1$ to $R^6$, $X^1$, $Z^1$, $Z^2$, k, m, and n are as described above. Examples of $R^7$, $X^2$, $X^3$, and r may also be similar ones.

Of the recurring units having formulae (2a) to (2d), recurring units having formulae (2aa) to (2dd) are preferred.

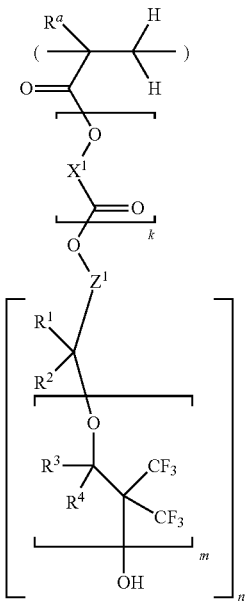
(2aa)

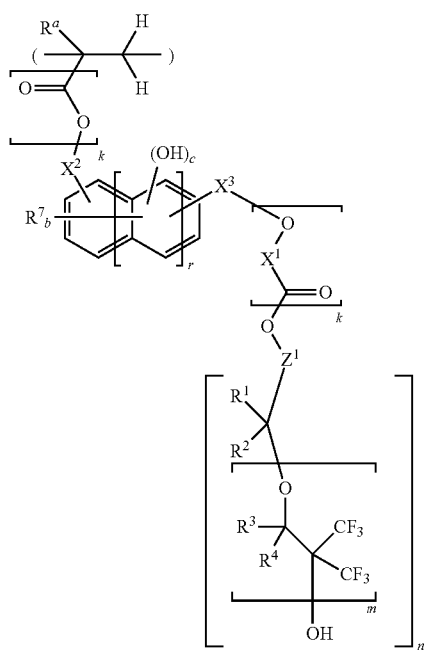
(2bb)

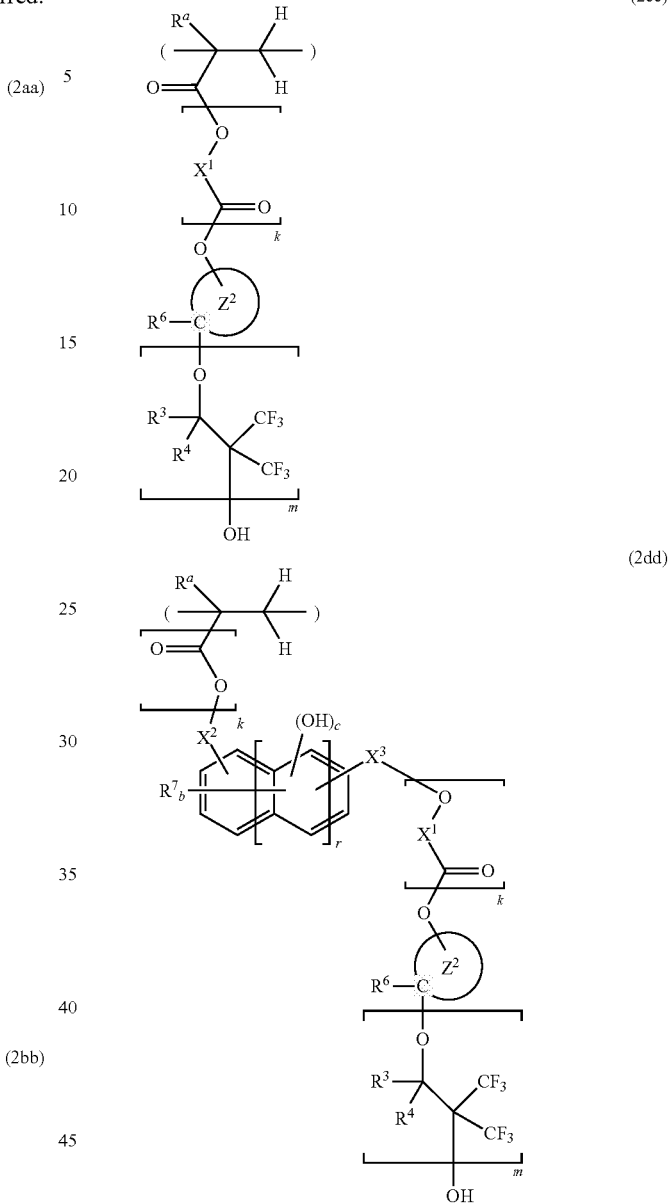

Herein $R^a$ is hydrogen, methyl or trifluoromethyl. $R^1$ to $R^4$, $R^6$ and $R^7$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$, or $R^3$ and $R^4$ may bond together to form an alicyclic group with the carbon atom to which they are attached. $X^1$ is a straight, branched or cyclic $C_1$-$C_{15}$ divalent hydrocarbon group in which any constituent —$CH_2$— moiety may be replaced by —O— or —C(=O)—. $X^2$ and $X^3$ are each independently a single bond or a straight, branched or cyclic $C_1$-$C_{15}$ divalent hydrocarbon group in which any constituent —$CH_2$— moiety may be replaced by —O— or —C(=O)—. $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, b is an integer meeting b≤5+2r−c, c is an integer of 1 to 3, k is 0 or 1, m is 1 or 2, n is an integer of 1 to 4, r is an integer of 0 to 2. $Z^2$ is an atomic group necessary to form a $C_3$-$C_{10}$ alicyclic group with the carbon atom to which it is attached, in which any constituent —$CH_2$— moiety may be replaced by —O— or —C(=O)—. In formulae (2aa) to (2dd), when the oxygen atom attached to group $Z^1$ or atomic group $Z^2$ forms a bond with the carbonyl carbon bonded to a polymerizable group or the linker —[O—$X^1$—C(=O)]—, a tertiary ester bond is not formed.

In addition to the recurring units (2a) to (2d), the inventive polymer may further comprise recurring units of at least one type selected from recurring units having formulae (A) to (D) for the purpose of solubility control.

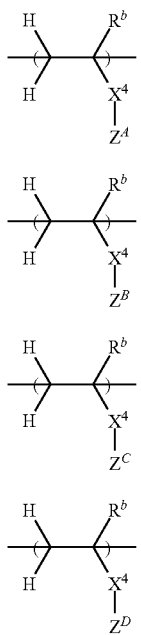

Herein $R^b$ is hydrogen, methyl or trifluoromethyl, $Z^A$ is a $C_1$-$C_{20}$ fluoroalcohol-containing group. $Z^B$ is a $C_1$-$C_{20}$ phenolic hydroxyl-containing group. $Z^C$ is a $C_1$-$C_{20}$ carboxyl-containing group. $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety, $X^4$ is a single bond, methylene, ethylene, phenylene, fluorinated phenylene, naphthylene, —O—$R^c$—, or —C(=O)—$Z^E$—$R^c$—, wherein $Z^E$ is oxygen or NH, and $R^c$ is a straight, branched or cyclic $C_1$-$C_6$ alkylene, straight, branched or cyclic $C_2$-$C_6$ alkenylene, phenylene or naphthylene group, which may contain a carbonyl, ester, ether or hydroxyl moiety.

The recurring unit of formula (A) has a fluoroalcohol-containing group having high affinity to alkaline aqueous solution. Preferred examples of the fluoroalcohol-containing unit include recurring units having a 1,1,1,3,3,3-hexafluoro-2-propanol residue and 2-hydroxy-2-trifluoromethyloxolane structure, as described in JP-A 2007-297590, JP-A 2008-111103, JP-A 2008-122932, and JP-A 2012-128067. Although these units have a tertiary alcoholic hydroxyl group or hemiacetal structure, they are not reactive with acid because of fluorine substitution.

Since the recurring units of formulae (A) to (D) are structural units having hydroxyl group's proton with a high acidity, the polymer becomes higher in alkaline solubility as the proportion of these units incorporated is increased. On the other hand, excessive incorporation of these units can adversely affect a polarity switch (or alkali insolubilizing effect) that is brought about by elimination reaction taking place in recurring unit of formula (2a) to (2d) by acid. Accordingly, the recurring units of formulae (A) to (D) are preferably incorporated, in such proportions that the alkali solubility of the unexposed region may be supplemented and the alkali insolubilizing effect of the exposed region not be impaired.

Illustrative, non-limiting examples of the recurring unit having formula (A) are shown below.

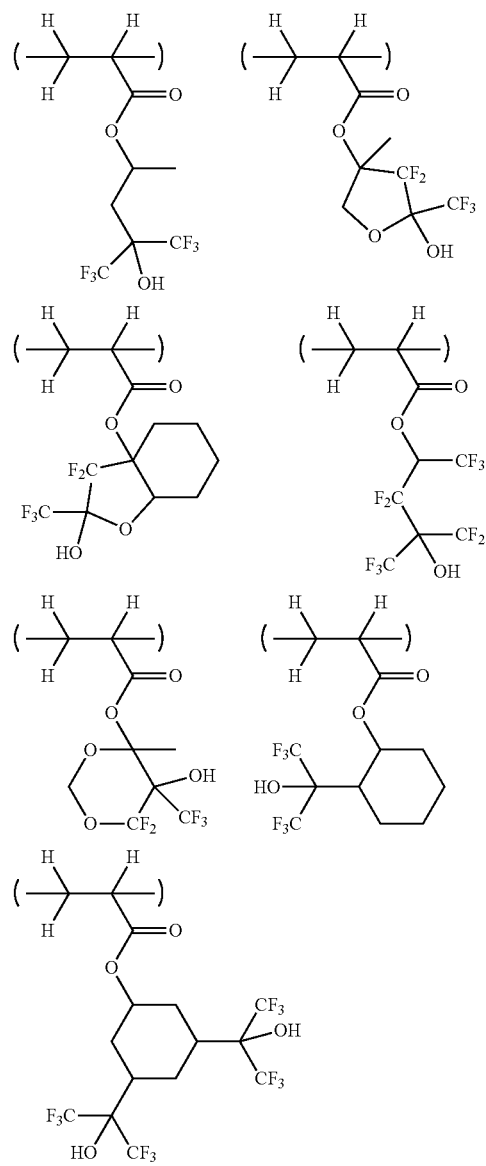

-continued
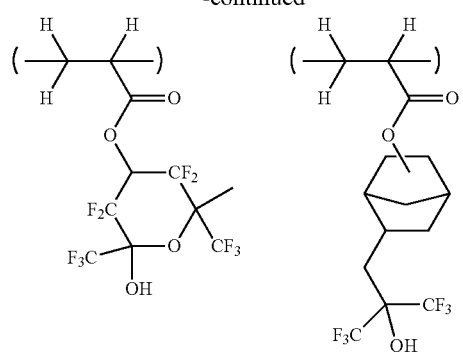
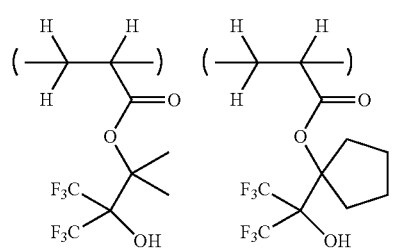
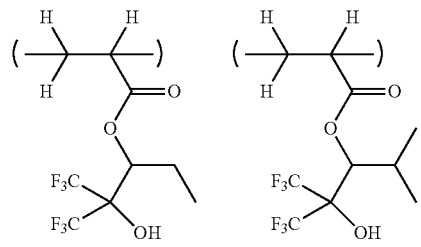
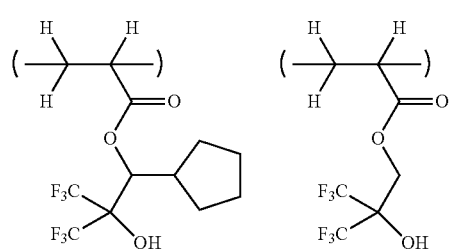
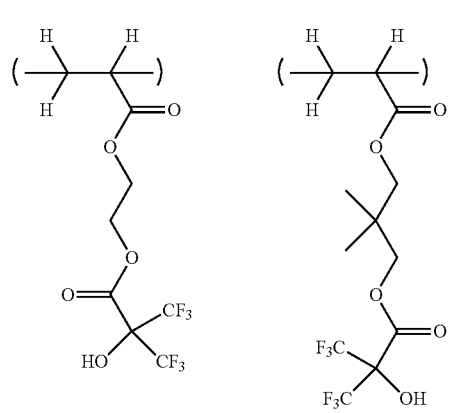
-continued
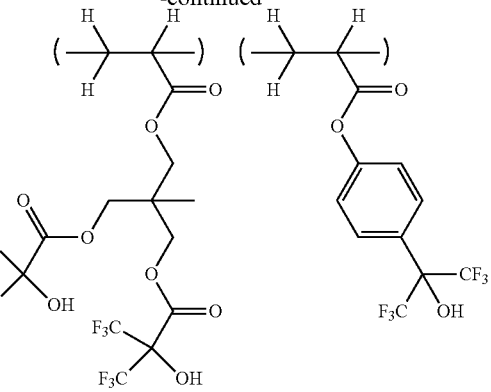
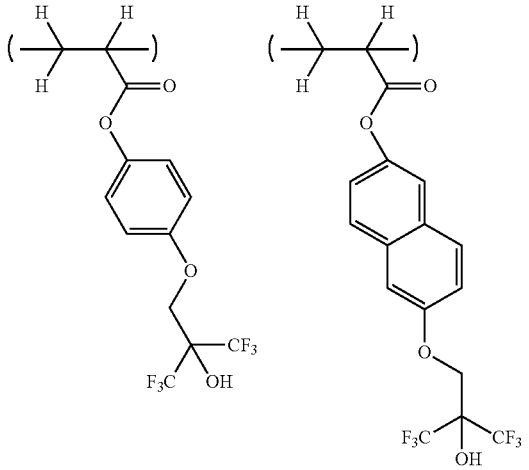
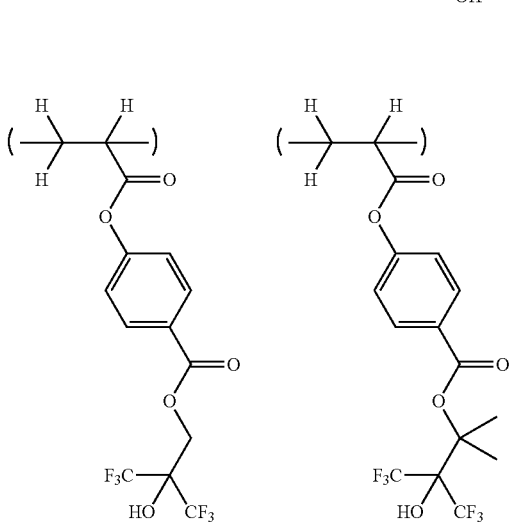
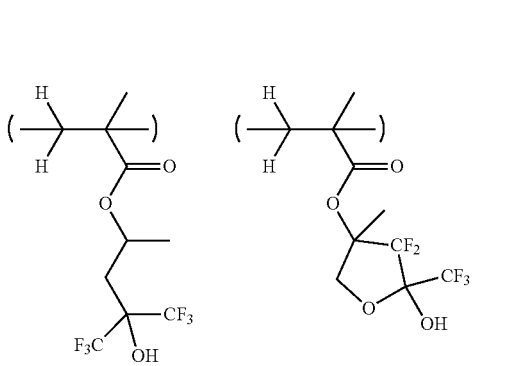

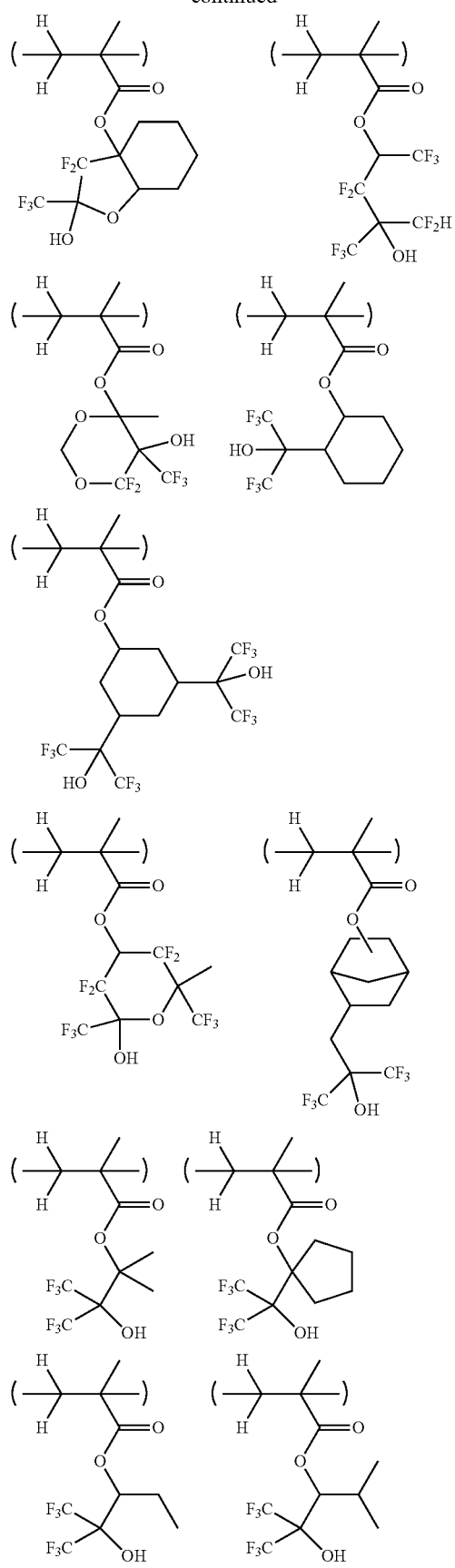
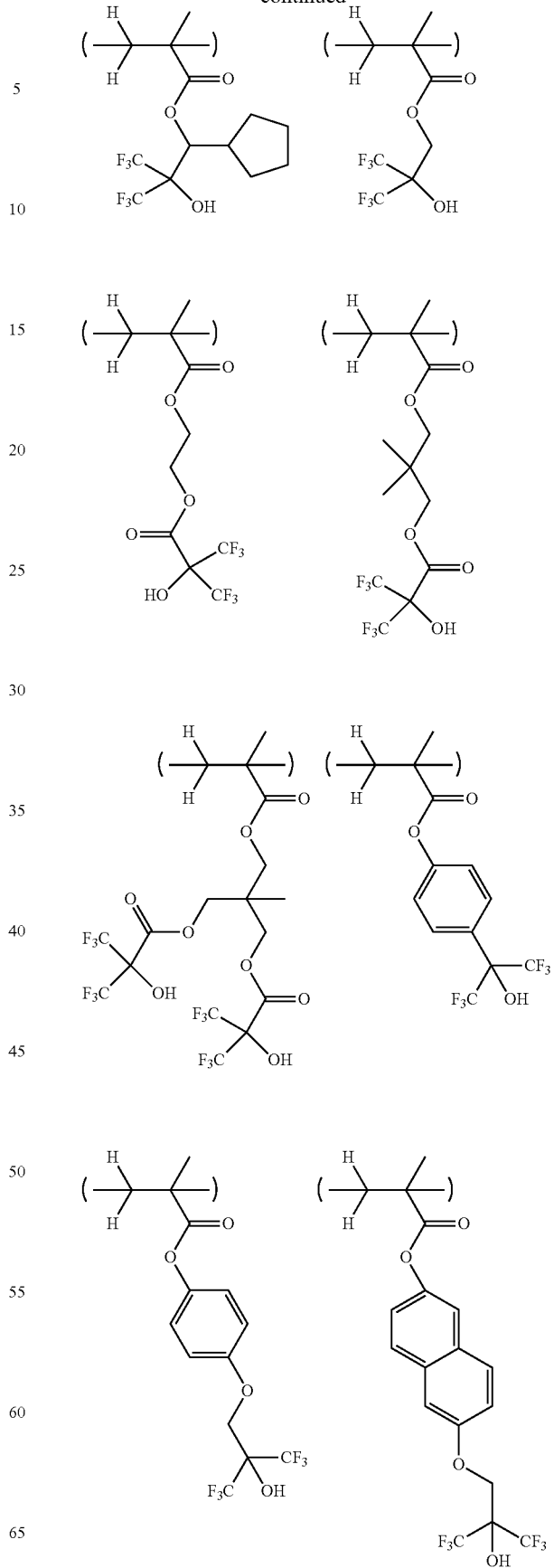

179
-continued
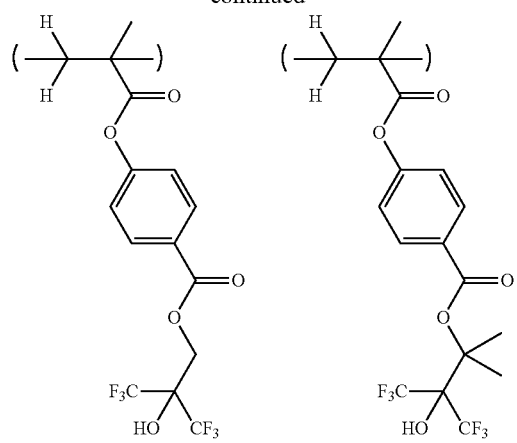
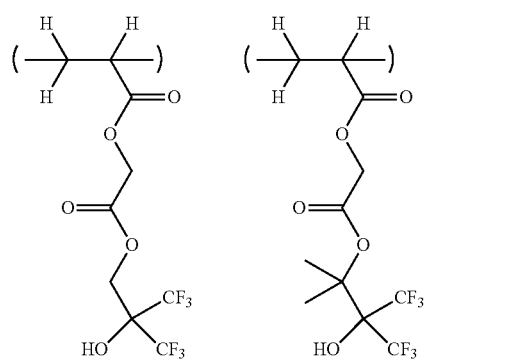
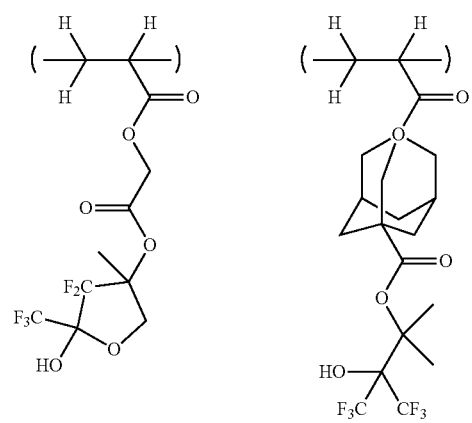
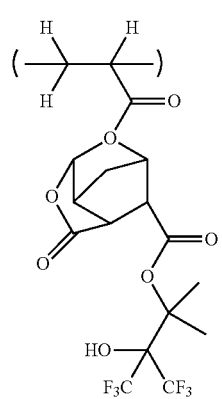
180
-continued
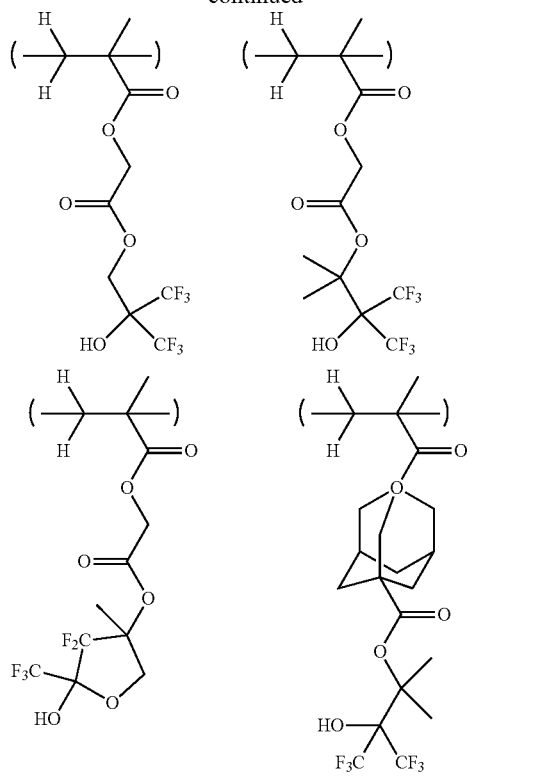
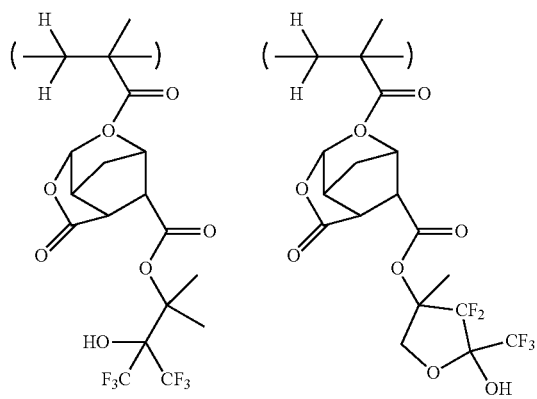
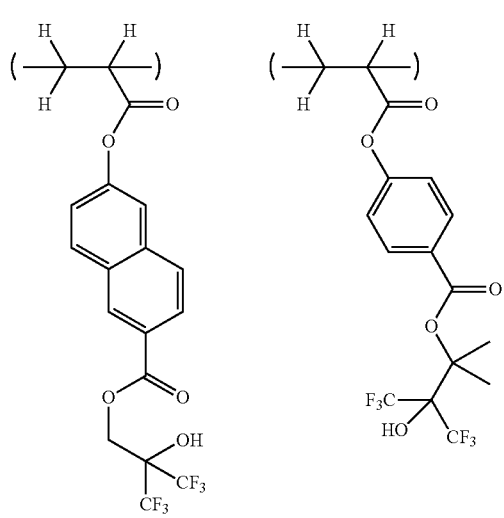

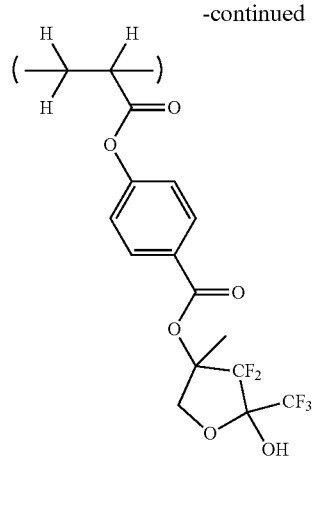
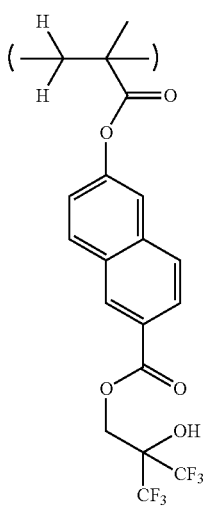
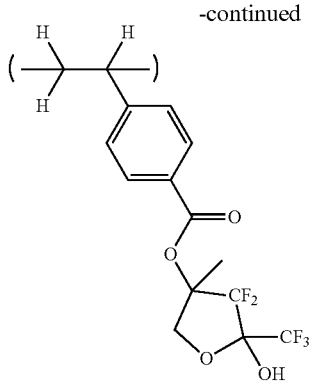
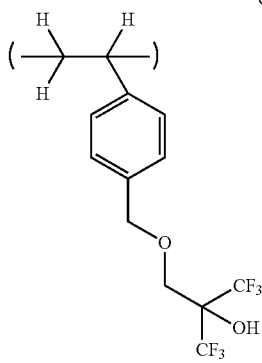
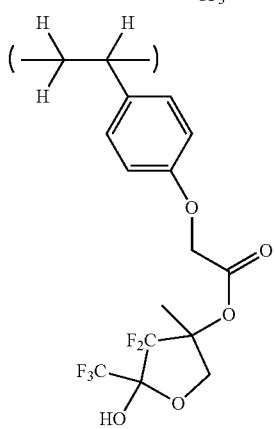
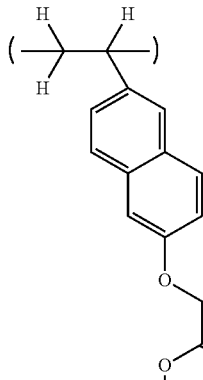

Illustrative, non-limiting examples of the recurring unit having formula (B) are shown below.
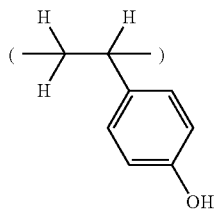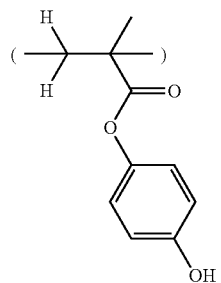
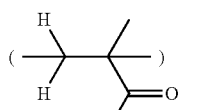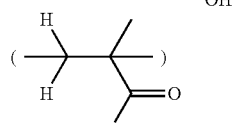
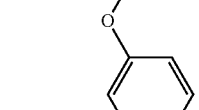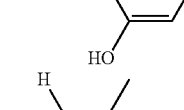
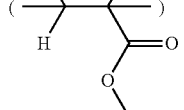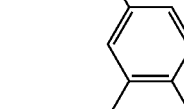
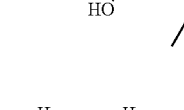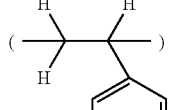
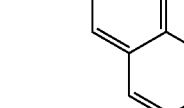
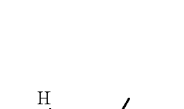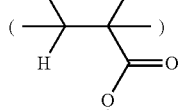
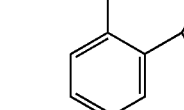
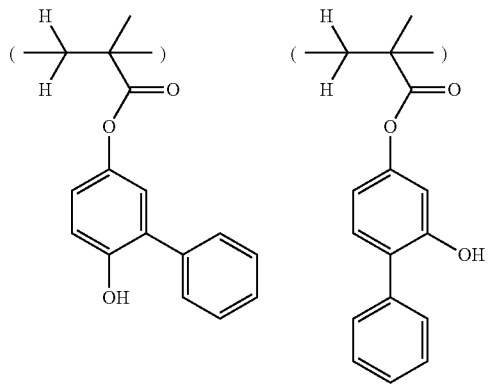
Illustrative, non-limiting examples of the recurring unit having formula (C) are shown below.
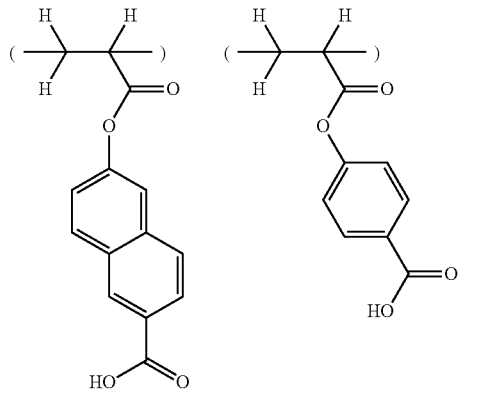

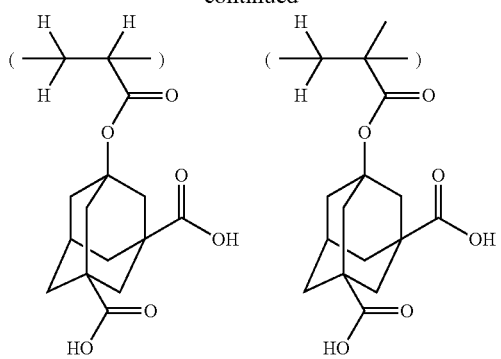
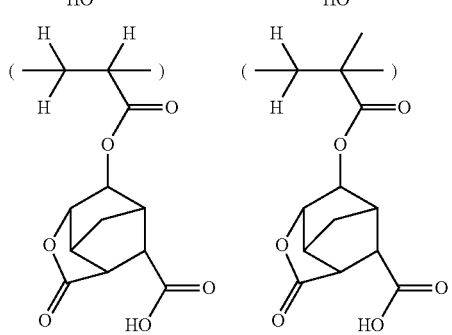
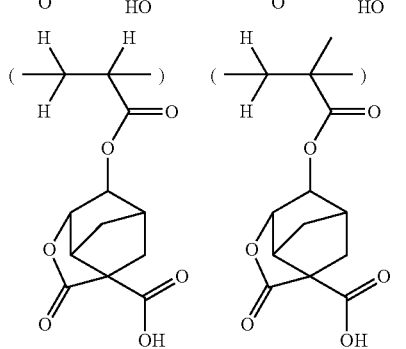

It is possible that the fluoroalcohol is protected with an acyl group or acid labile group in the polymer, so that the fluoroalcohol-containing unit corresponding to formula (A) may be generated by hydrolysis in alkaline developer or deprotection with the acid generated after exposure. Suitable such recurring units include the units described in JP-A 2012-128067 (U.S. Pat. No. 8,916,331), specifically units in paragraphs [0036]-[0040] and units (2a), (2b) and (2f) in paragraph [0041].

Illustrative, non-limiting examples of the recurring unit having formula (D) are shown below.

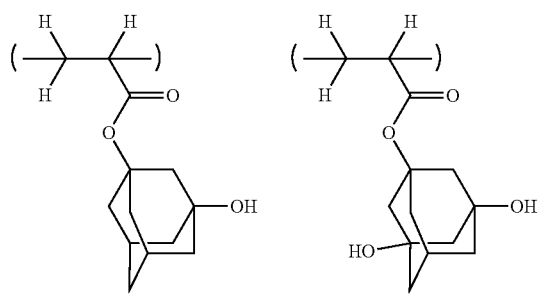

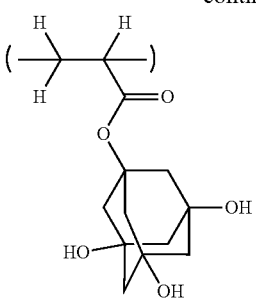
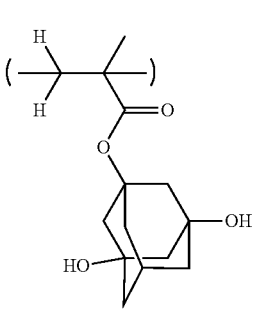
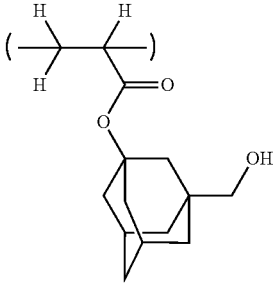
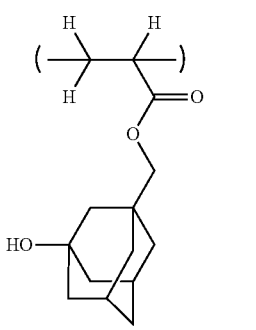
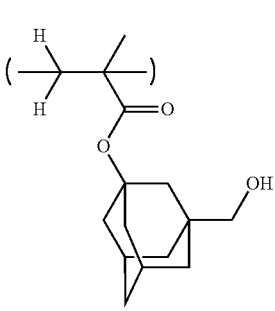

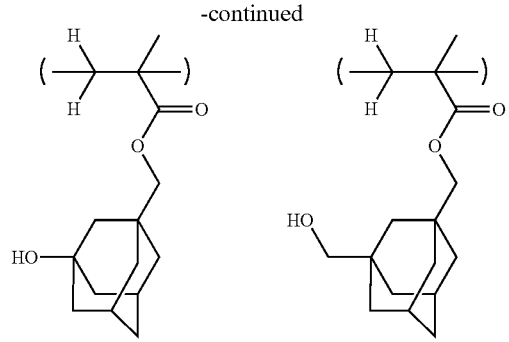
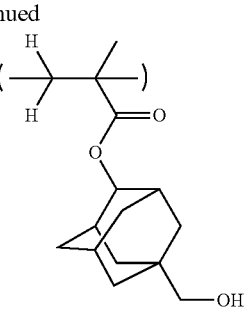
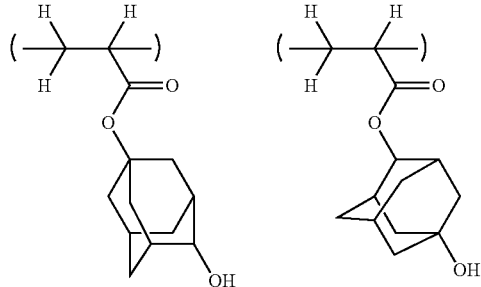
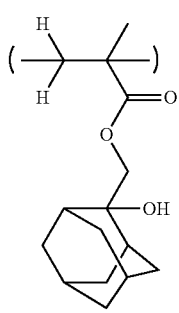
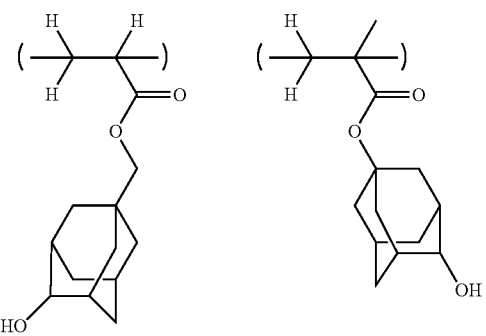
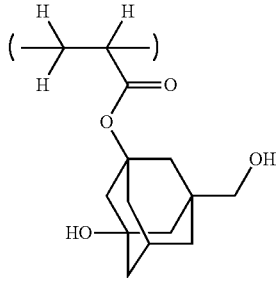
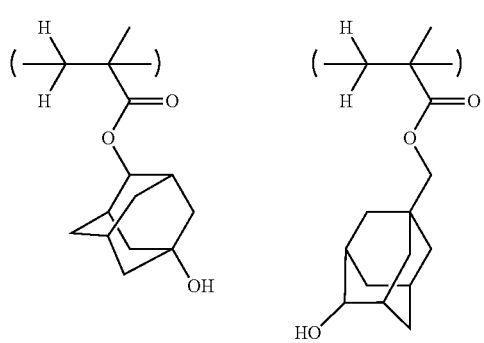
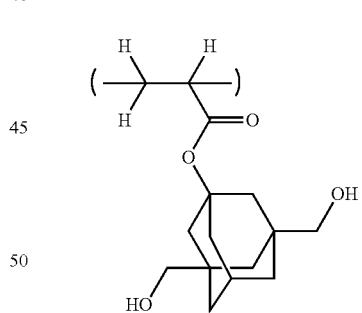
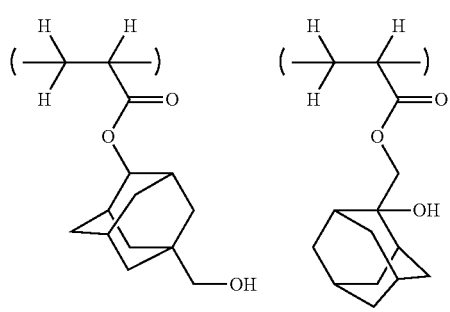
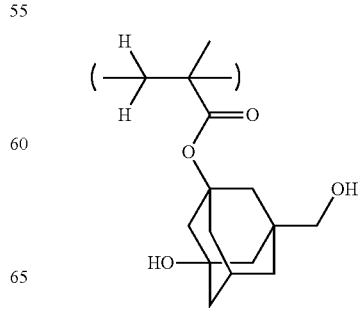

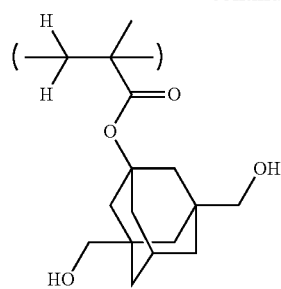
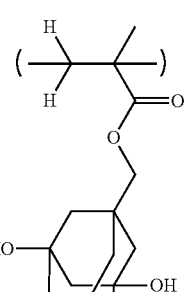
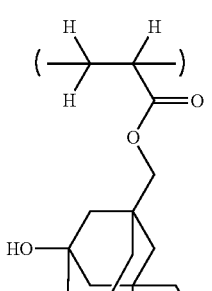
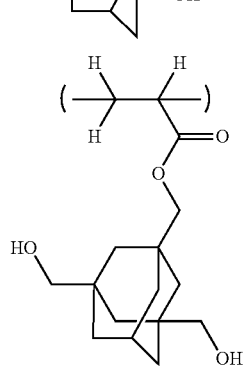
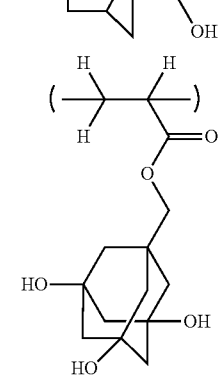
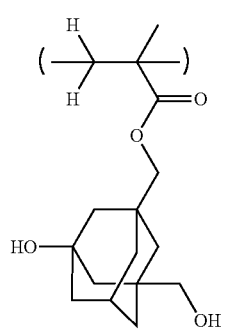
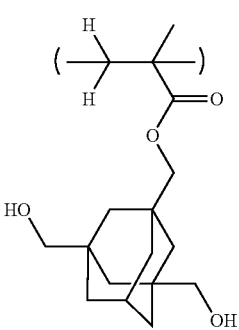
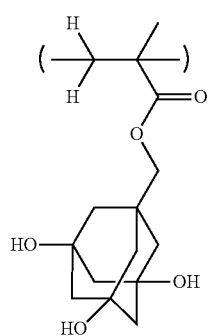
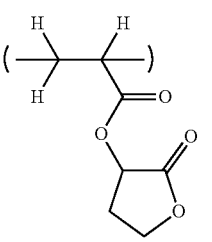
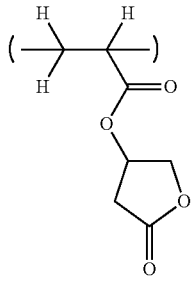
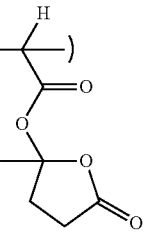
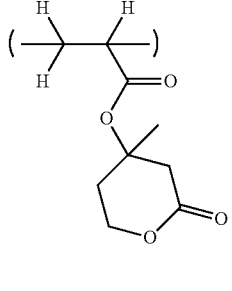
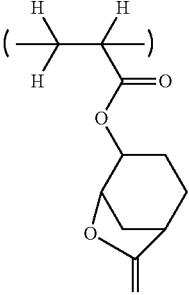
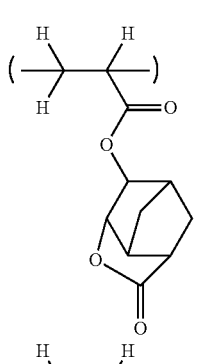
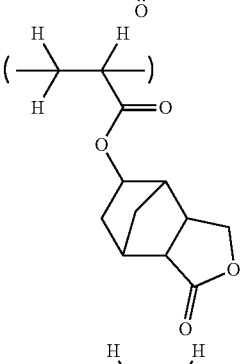
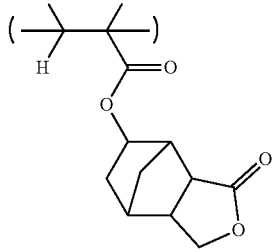
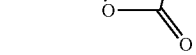
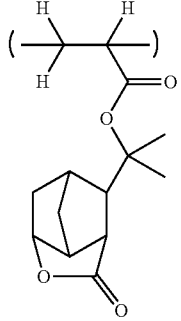
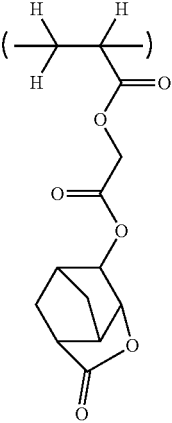

191
-continued
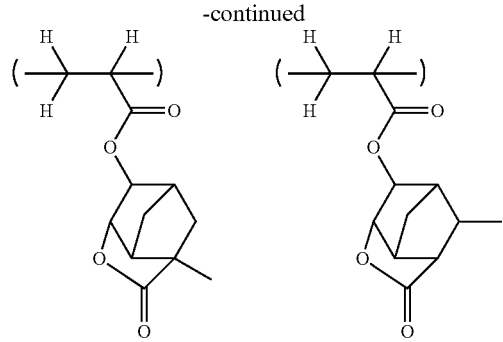
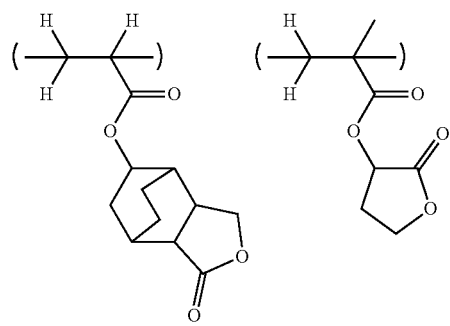
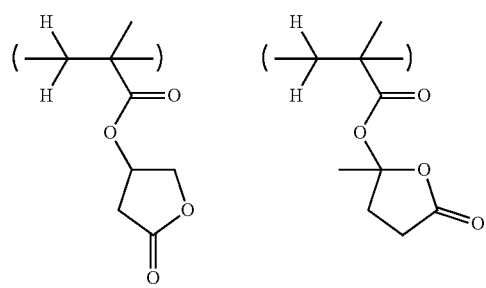
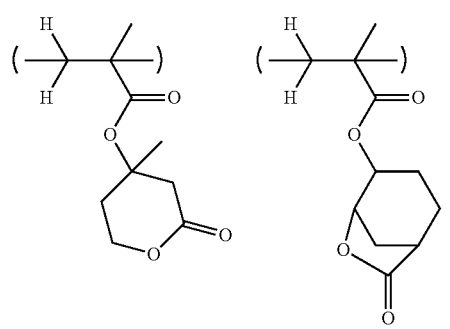
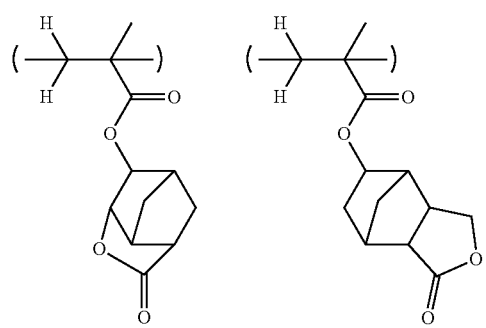
192
-continued
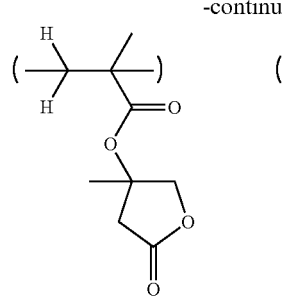
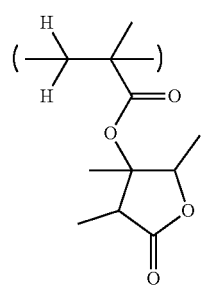
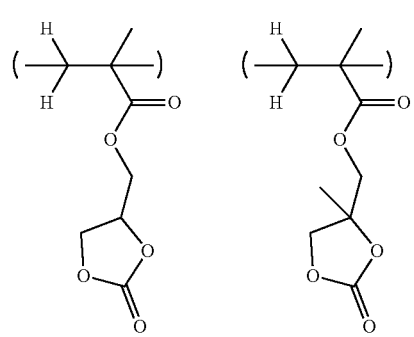
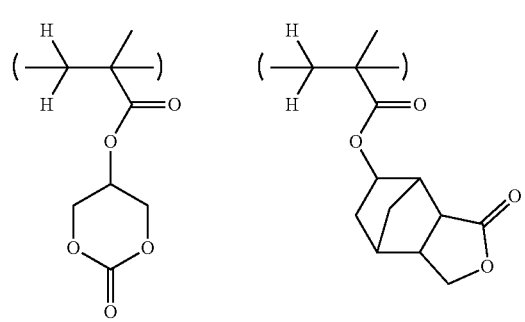
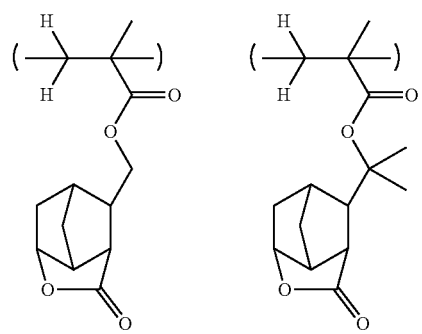

193
-continued
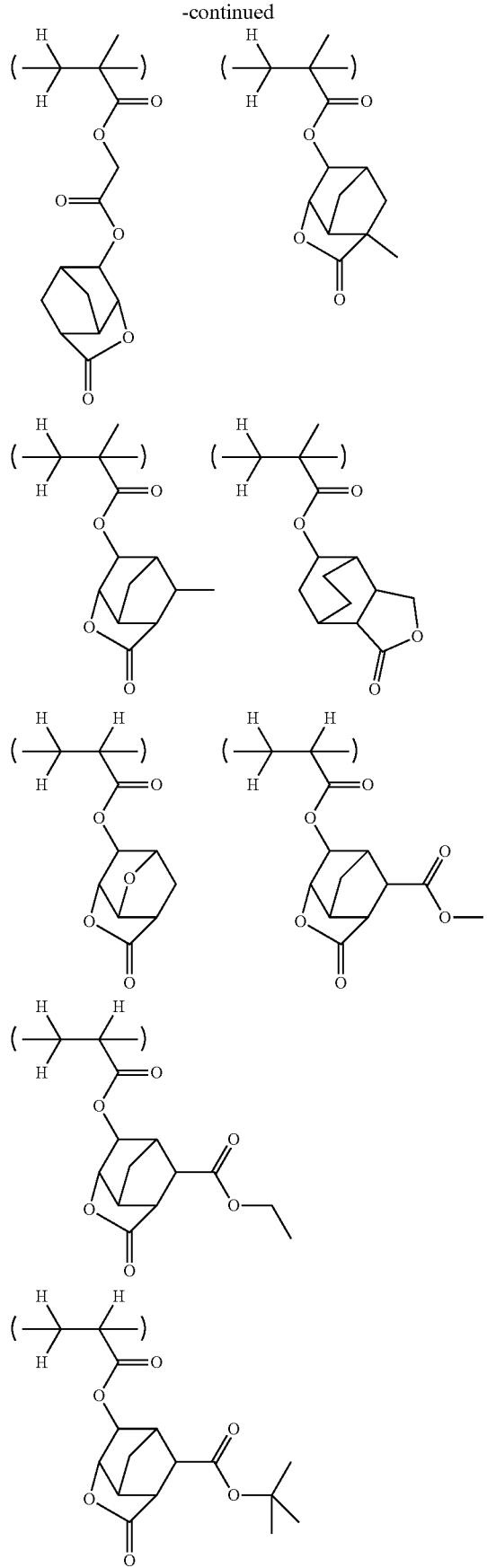
194
-continued
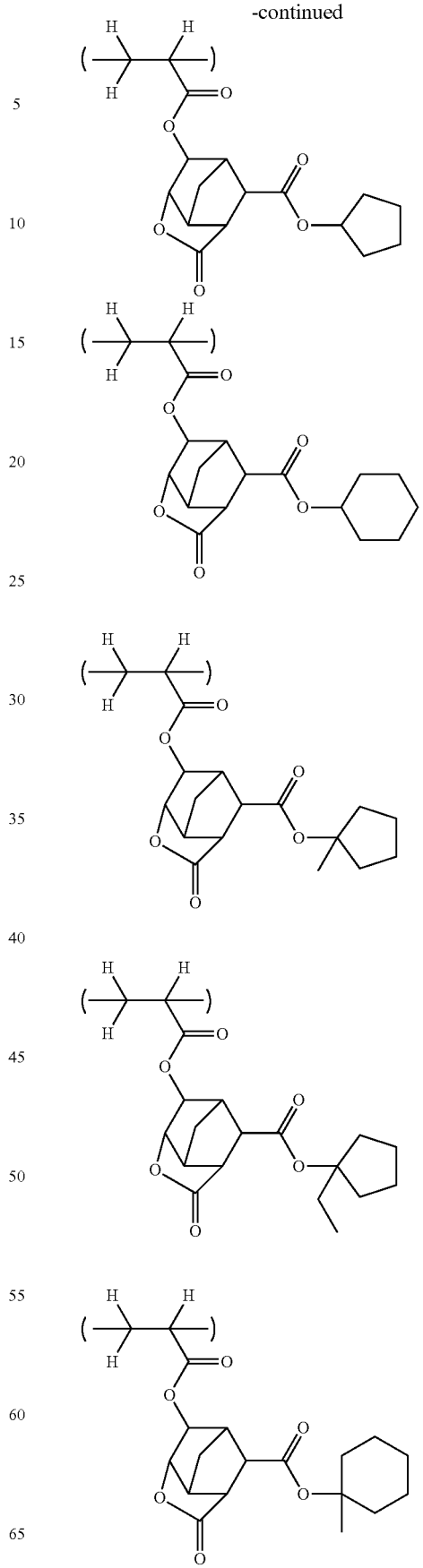

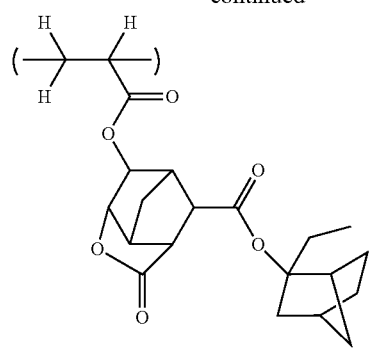
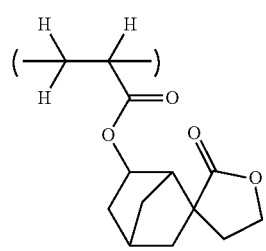
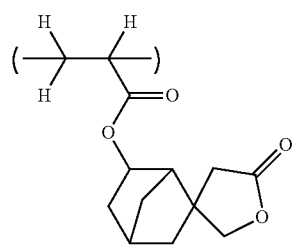
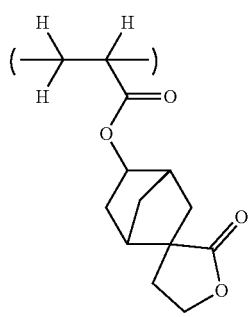
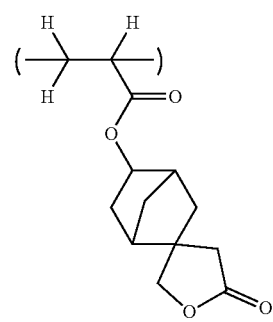
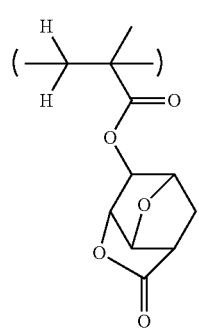
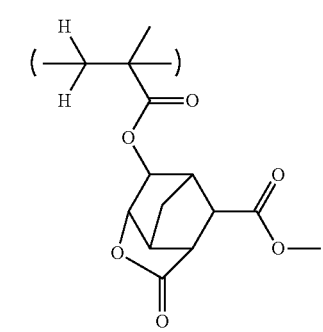
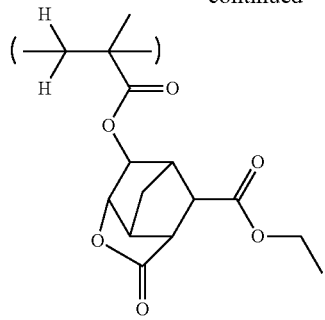
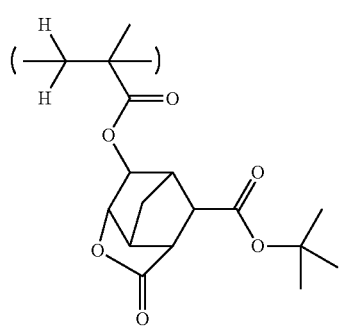
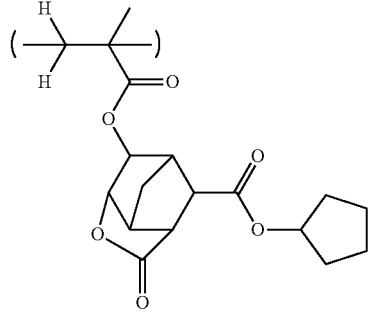
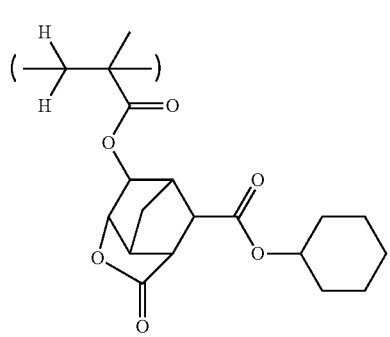
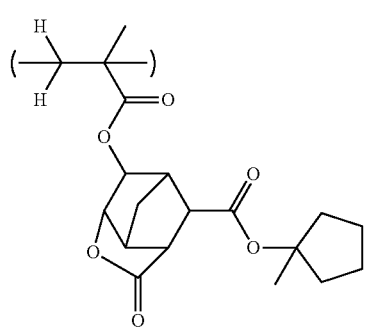

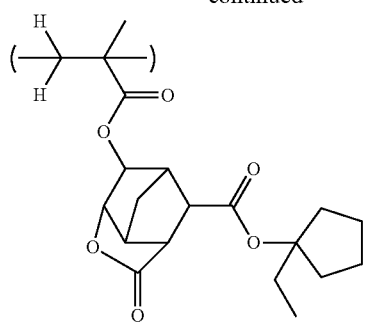
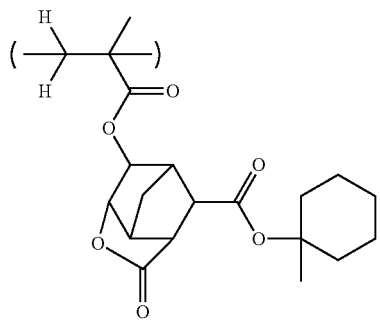
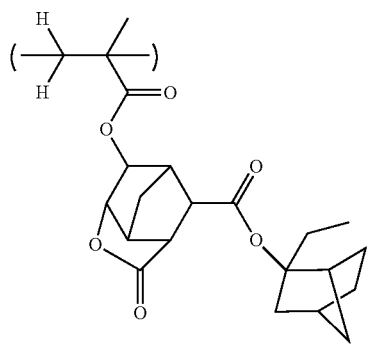
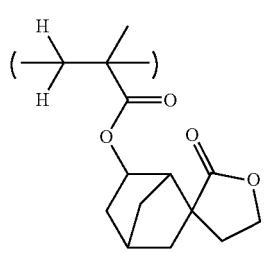
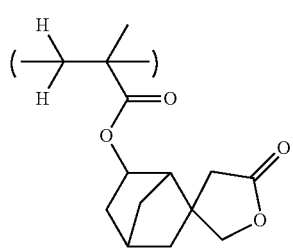
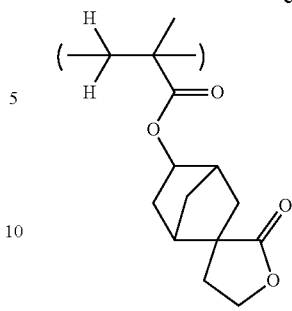
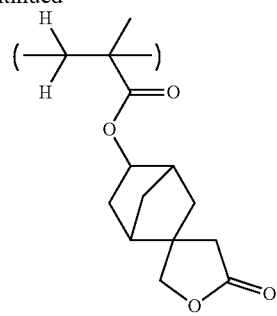
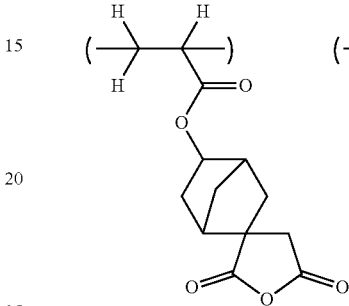
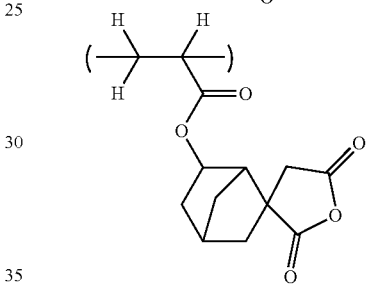
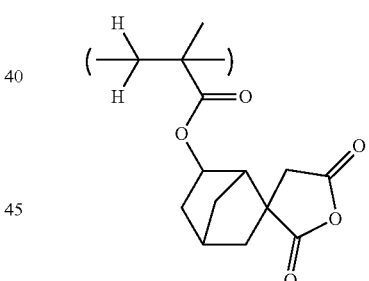
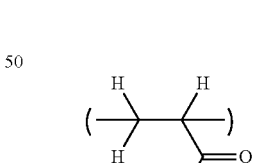
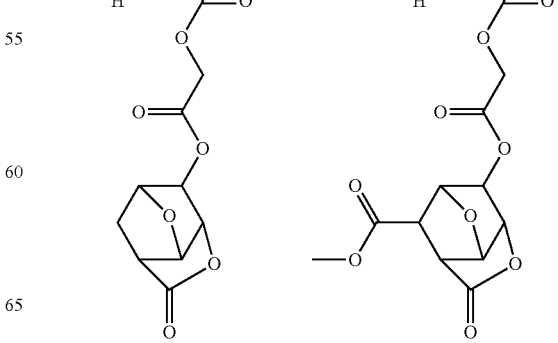

199
-continued
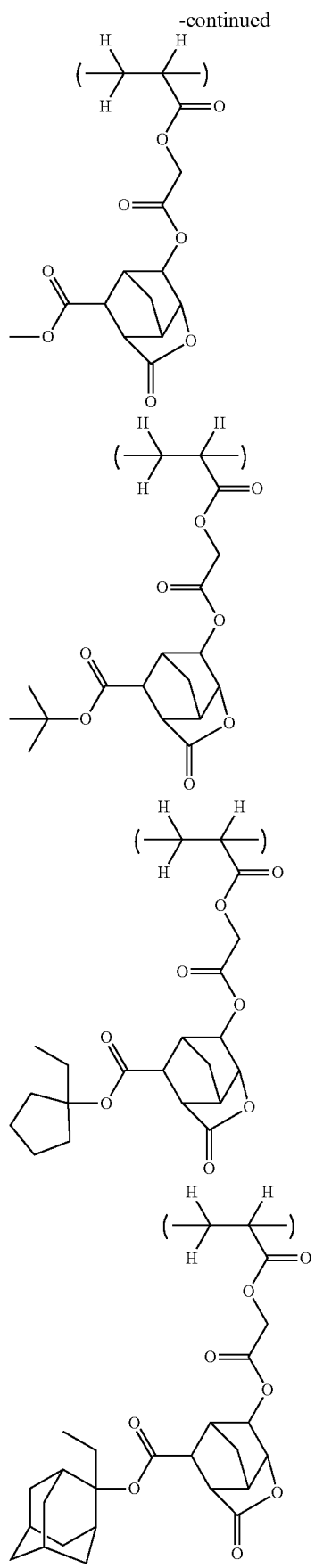
200
-continued
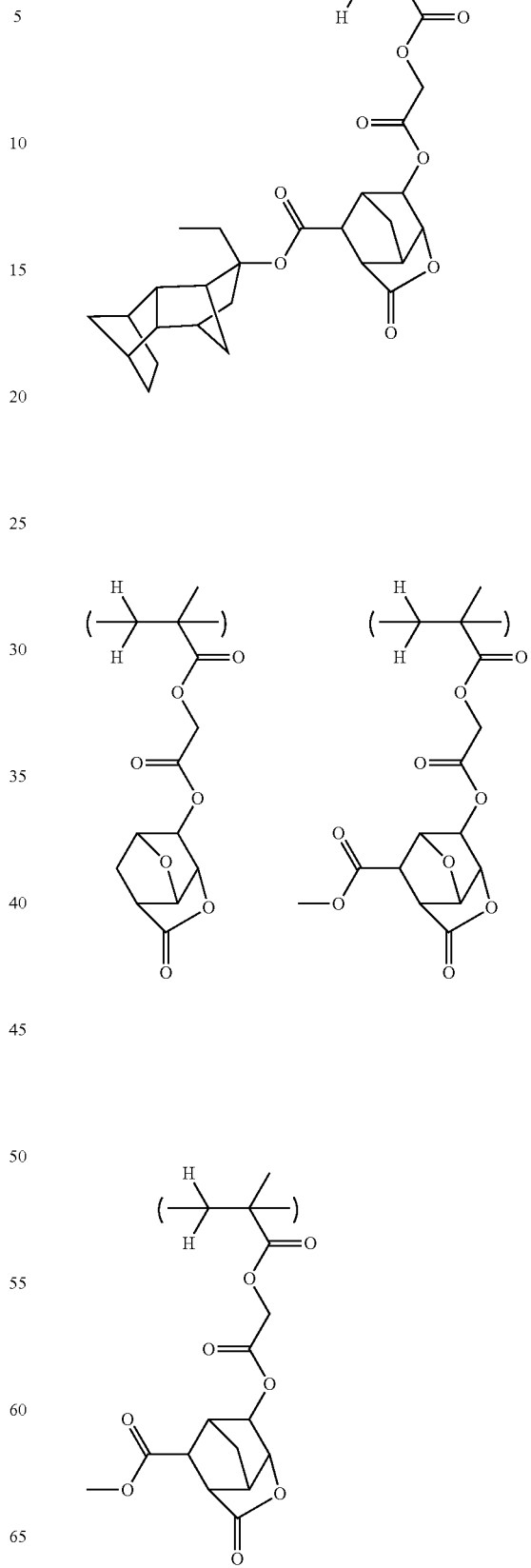

201
-continued
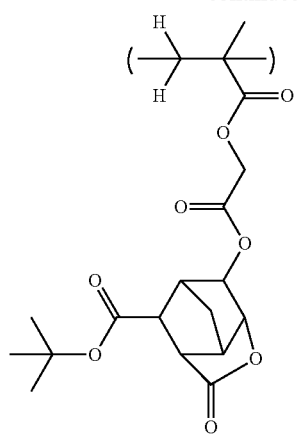
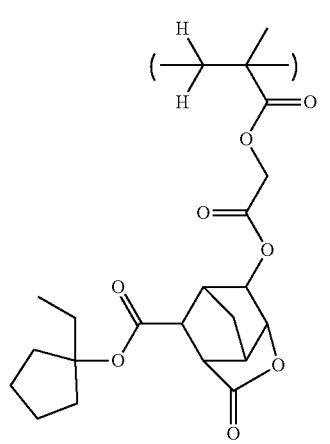
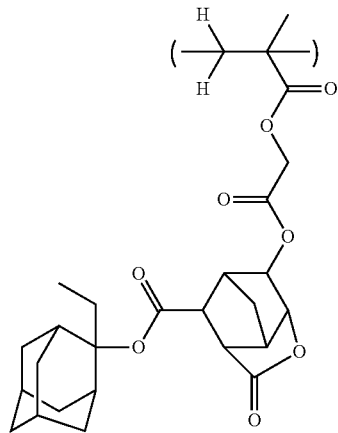
202
-continued
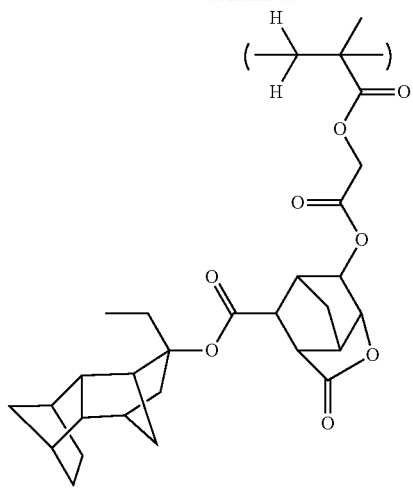
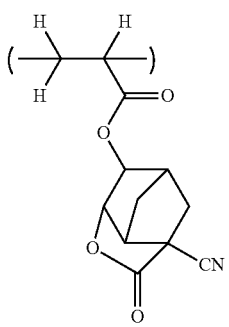 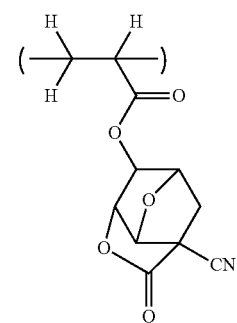
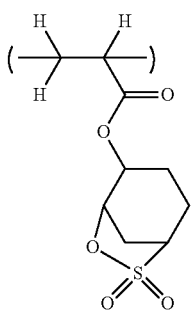 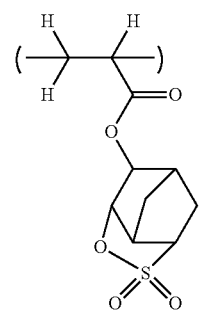
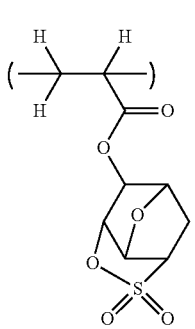 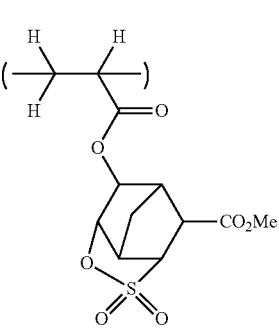

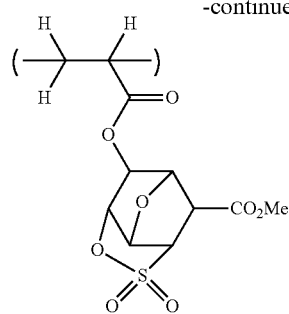
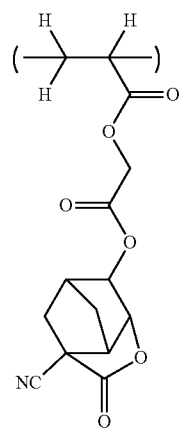
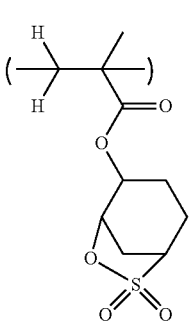
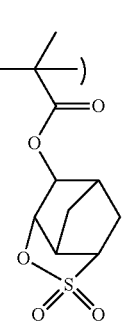
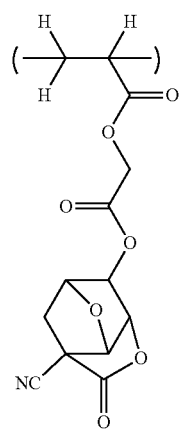
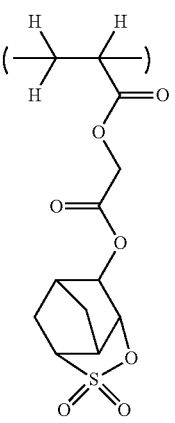
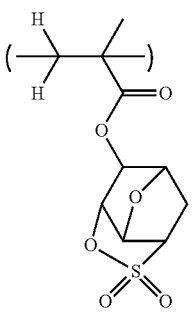
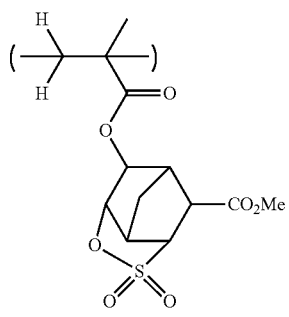
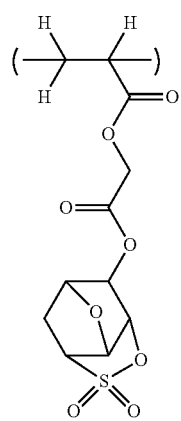
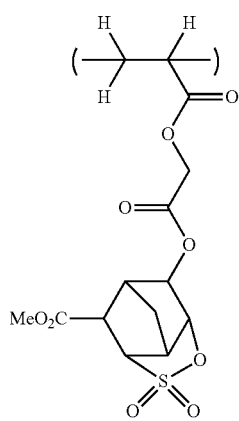
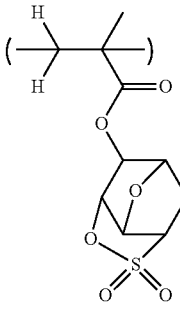
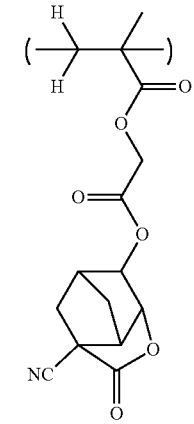
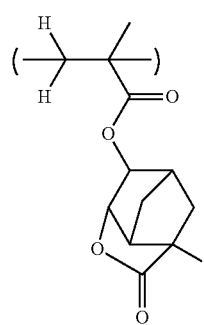
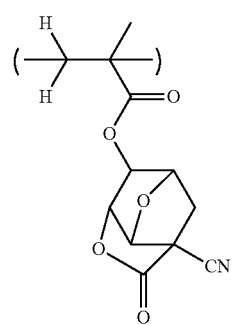
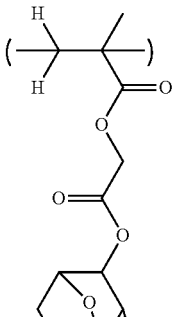
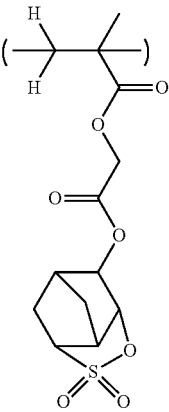

205
-continued
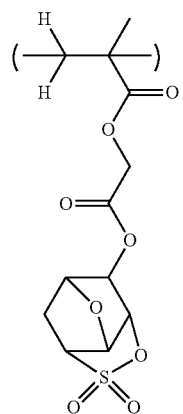 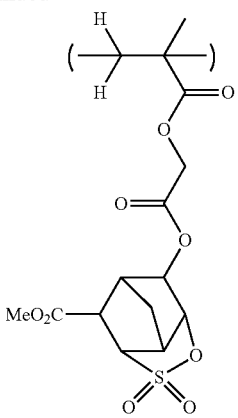
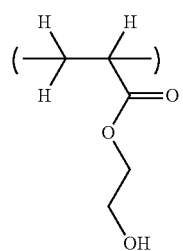 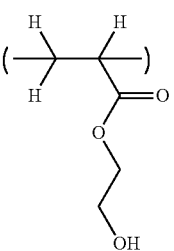
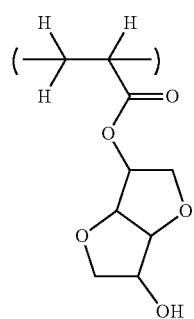 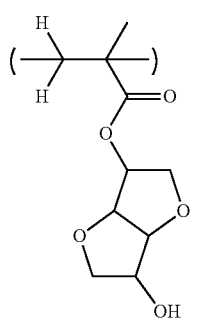
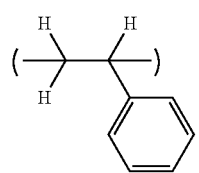 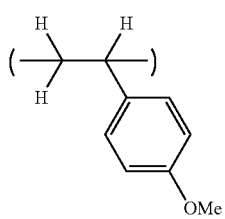
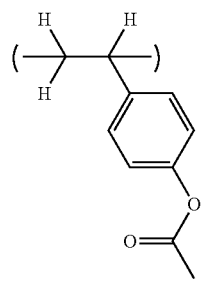 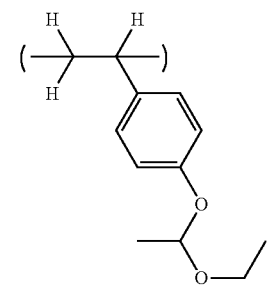
206
-continued
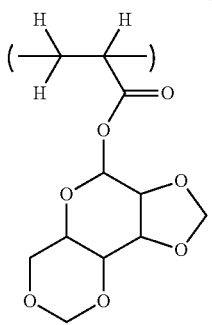 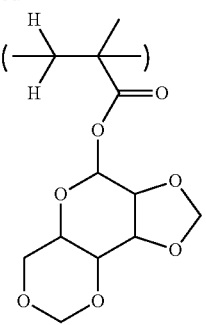
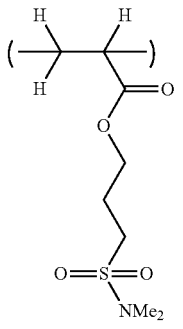 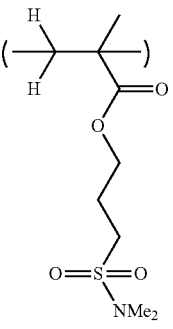
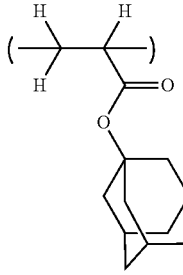 
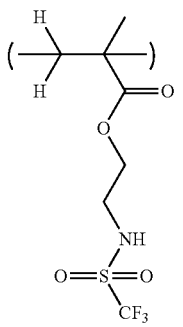 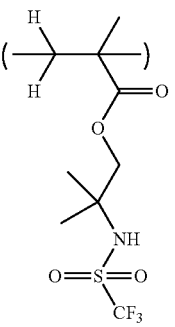
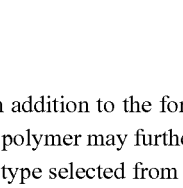 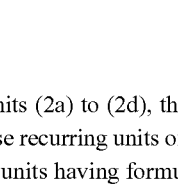
In addition to the foregoing units (2a) to (2d), the inventive polymer may further comprise recurring units of at least one type selected from recurring units having formulae (3a) to (3d).

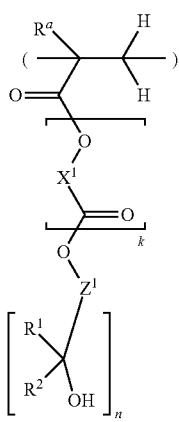

(3a)

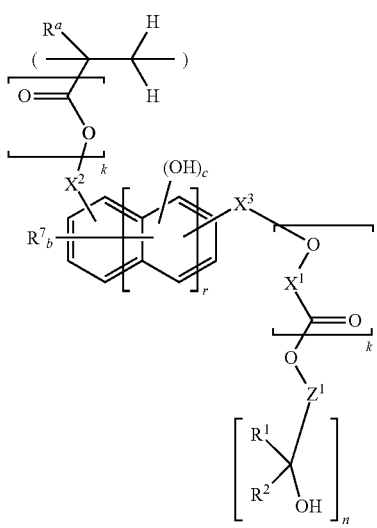

(3b)

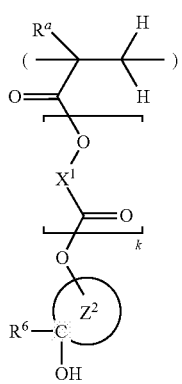

(3c)

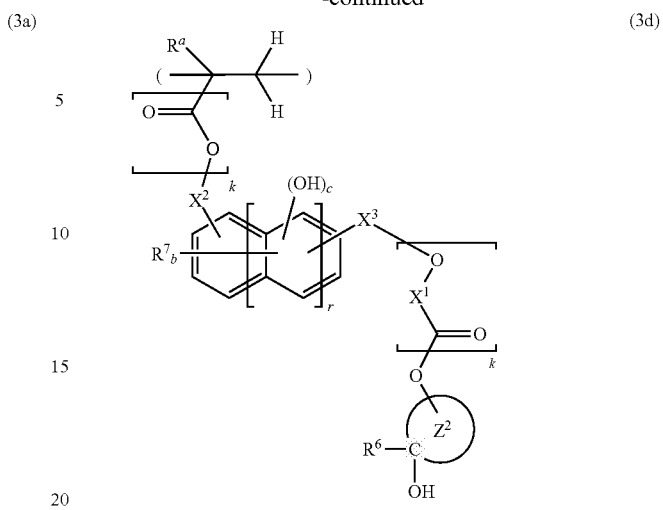

(3d)

Herein $R^a$ is hydrogen, methyl or trifluoromethyl. $R^1$ and $R^2$ are each independently a straight $C_1$-$C_{10}$ or branched or cyclic $C_3$-$C_{10}$ monovalent hydrocarbon group in which any constituent —$CH_2$— moiety may be replaced by —O— or —C(=O)—, a pair of $R^1$ and $R^2$ may bond together to form an alicyclic group with the carbon atom to which they are attached, $X^1$ is a straight, branched, or cyclic $C_1$-$C_{15}$ divalent hydrocarbon group in which any constituent —$CH_2$— moiety may be replaced by —O— or —C(=O)—. $X^2$ and $X^3$ are each independently a single bond or a straight, branched or cyclic $C_1$-$C_{15}$ divalent hydrocarbon group in which any constituent —$CH_2$— moiety may be replaced by —O— or —C(=O)—. $Z^1$ is a straight $C_1$-$C_{20}$ or branched or cyclic $C_3$-$C_{20}$, (n+1)-valent aliphatic hydrocarbon group in which any constituent —$CH_2$— moiety may be replaced by —O— or —C(=O)—, b is an integer meeting b≤5+2r–c, c is an integer of 1 to 3, k is 0 or 1, n is an integer of 1 to 4, r is an integer of 0 to 2. $Z^2$ is an atomic group necessary to form a $C_3$-$C_{10}$ alicyclic group with the carbon atom to which it is attached, in which any constituent —$CH_2$— moiety may be replaced by —O— or —C(=O)—. In formulae (3a) to (3d), when the oxygen atom attached to group $Z^1$ or atomic group $Z^2$ forms a bond with the carbonyl carbon bonded to a polymerizable group or the linker —[O—$X^1$—C(=O)]—, a tertiary ester bond is not formed.

Typical of the straight, branched or cyclic $C_1$-$C_{10}$ monovalent hydrocarbon group represented, by $R^1$ and $R^2$ are alkyl groups including methyl, ethyl, propyl, isopropyl, n-butyl, s-butyl, t-butyl, cyclopentyl, cyclohexyl, 2-ethylhexyl, n-octyl, norbornyl, tricyclodecanyl, and adamantyl.

When a pair of $R^1$ and $R^2$ bond together to form an alicyclic group with the carbon atom to which they are attached, suitable alicyclic groups include cyclopropane, cyclobutane, cyclopentane and cyclohexane.

Examples of the straight, branched or cyclic $C_1$-$C_{15}$ divalent hydrocarbon group represented by $X^1$ are given below, but not limited thereto.

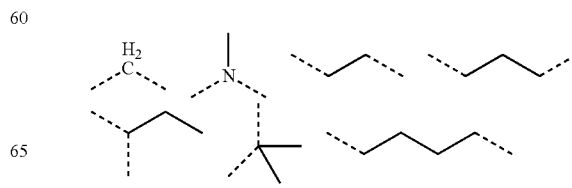

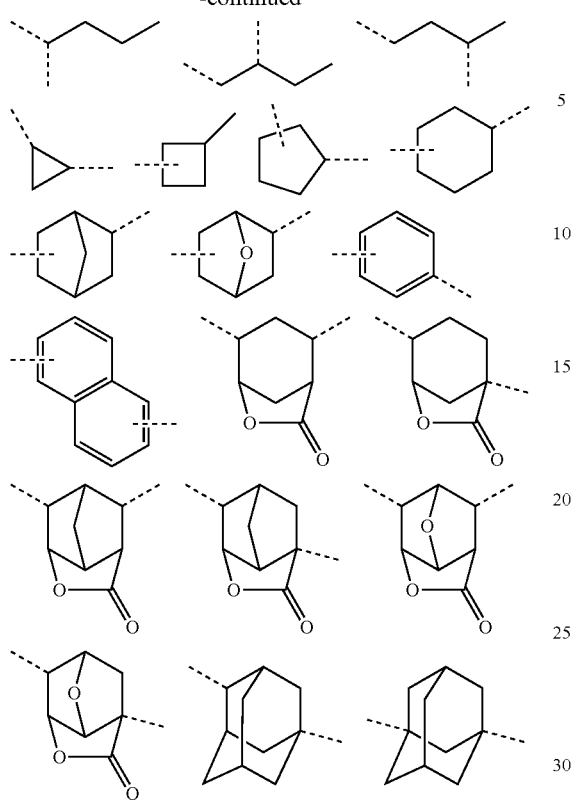
Examples of the straight $C_1$-$C_{20}$, or branched or cyclic $C_3$-$C_{20}$, (n+1)-valent aliphatic hydrocarbon group represented by $Z^1$ are given below, but not limited thereto.
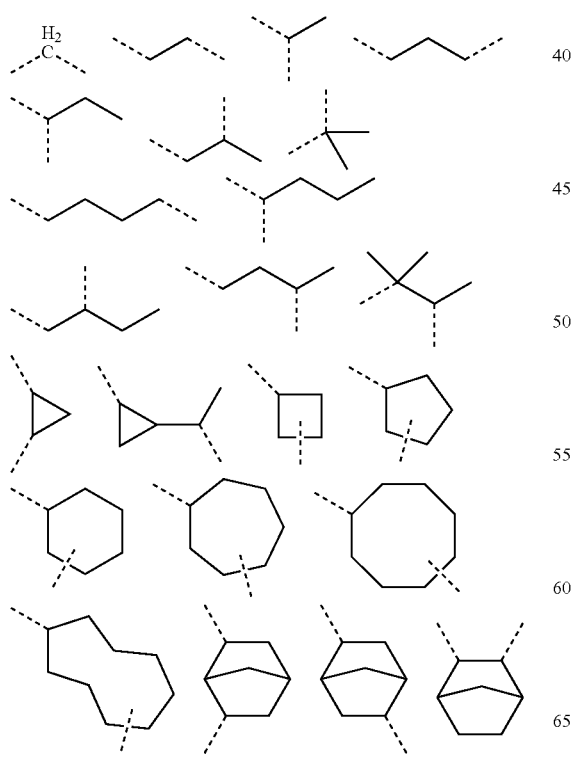
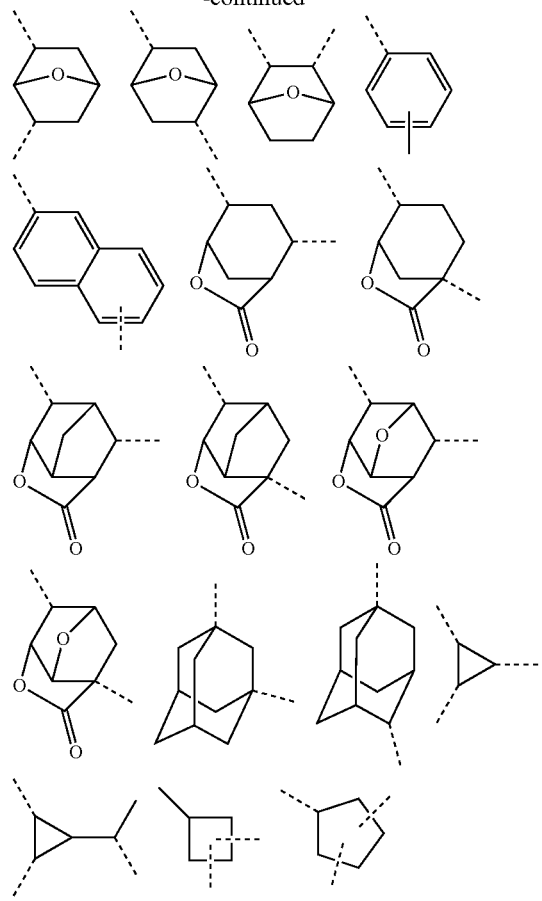
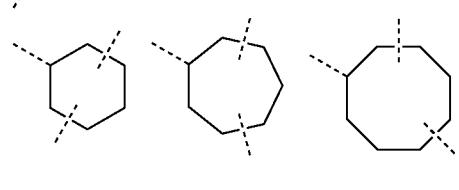
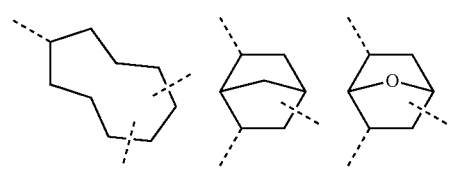
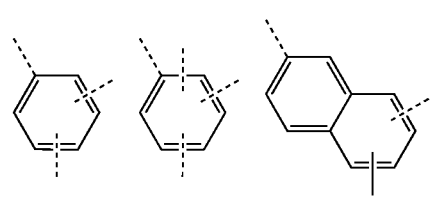
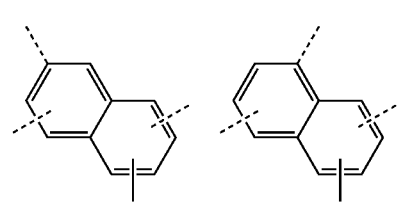

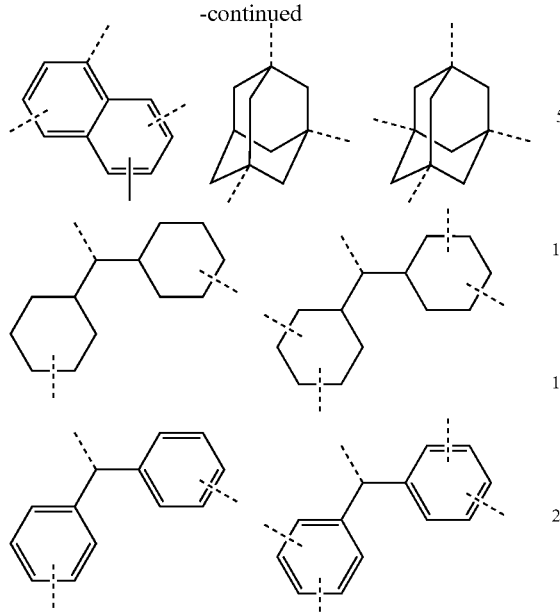

While $Z^2$ is an atomic group necessary to form a $C_3$-$C_{10}$ alicyclic group with the carbon atom to which it is attached, suitable alicyclic groups are as shown below.

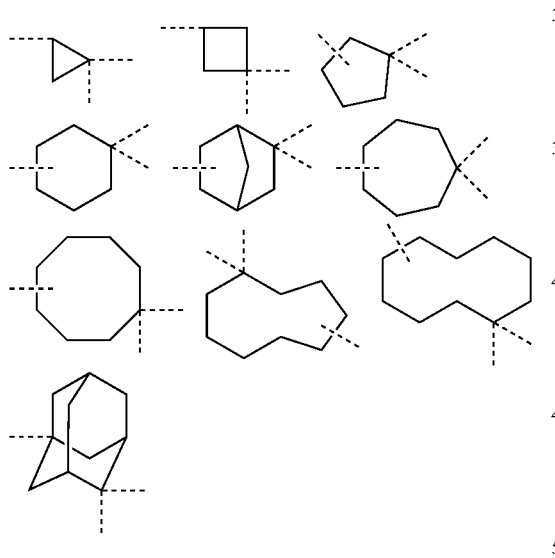

By incorporating recurring units of formulae (3a) to (3d) along with recurring units of formulae (2a) to (2d), the base resin in the unexposed region is further improved in the dissolution rate in alkaline developer. Like the units of formulae (2a) to (2d), the units of formulae (3a) to (3d) are units having 1 to 4 tertiary alcoholic hydroxyl groups serving as the acid labile group. Prior to exposure, these units have a high affinity and solubility in alkaline developer due to the presence of a plurality of highly polar, hydrophilic groups. After exposure, in the exposed region, dehydration reaction of tertiary alcohol takes place by the acid generated from the acid generator, so that a plurality of hydroxyl groups are lost. This suggests a substantial drop of solubility in alkaline developer, that is, the resin turns insoluble in the developer.

Examples of the recurring units of formulae (3a) to (3d) are shown below, but not limited thereto.

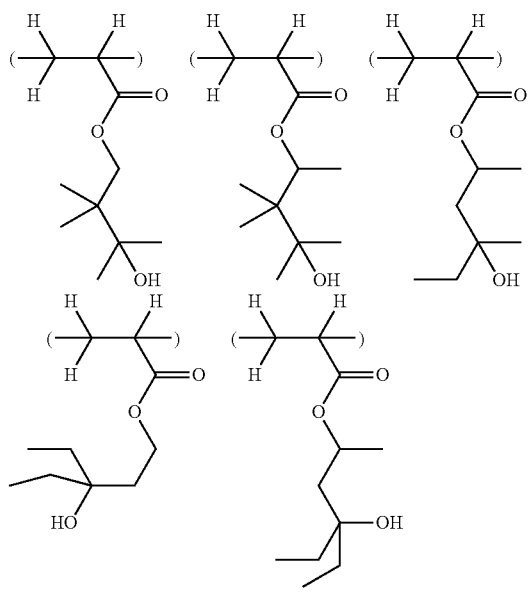
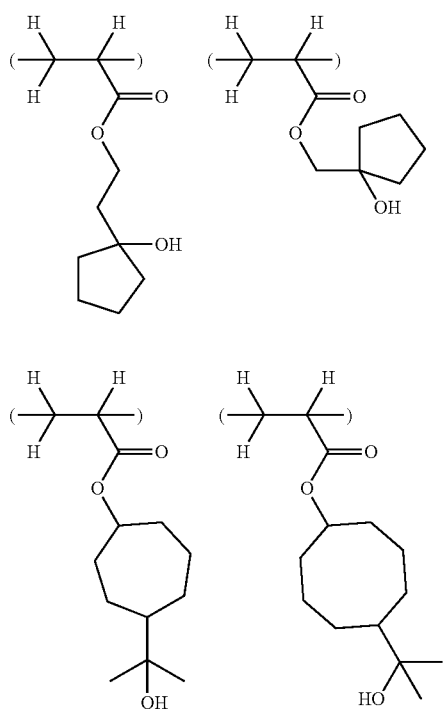
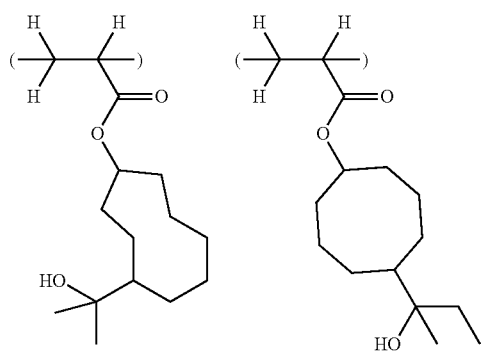

213
-continued
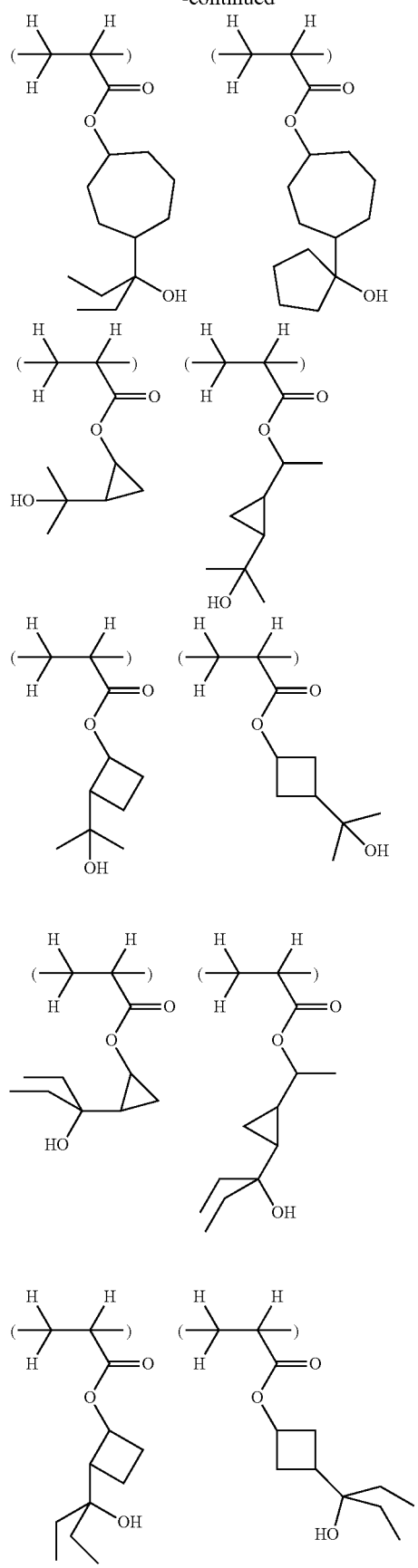
214
-continued
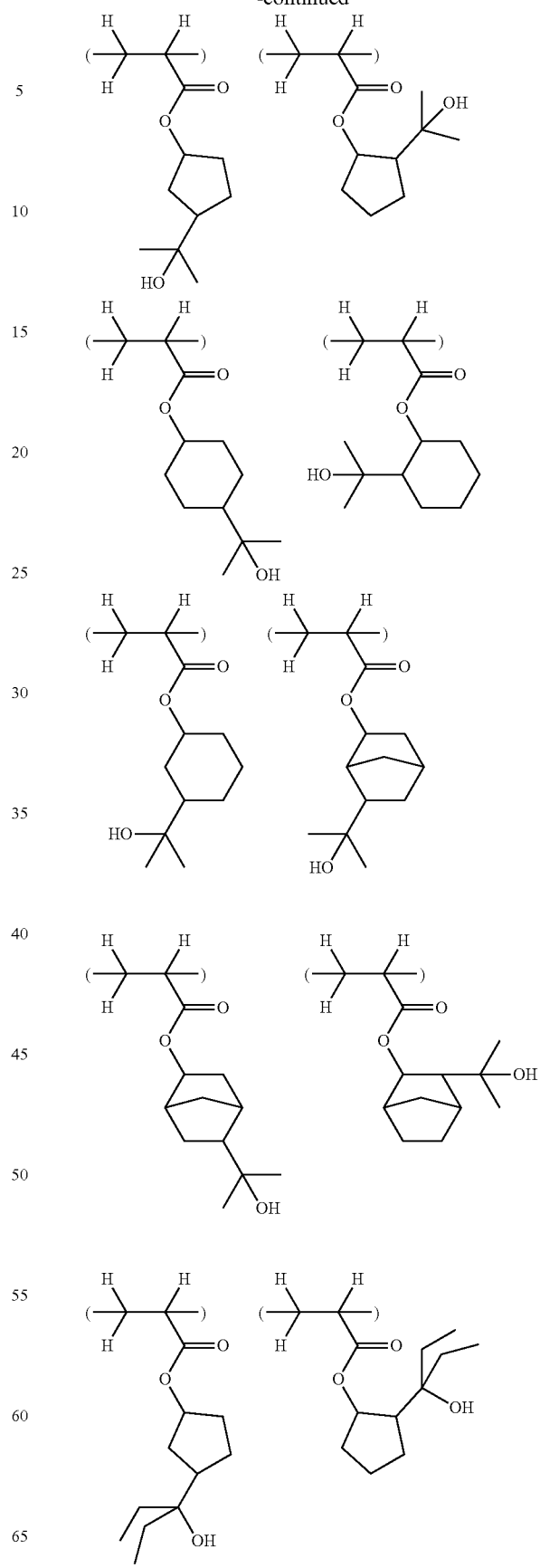

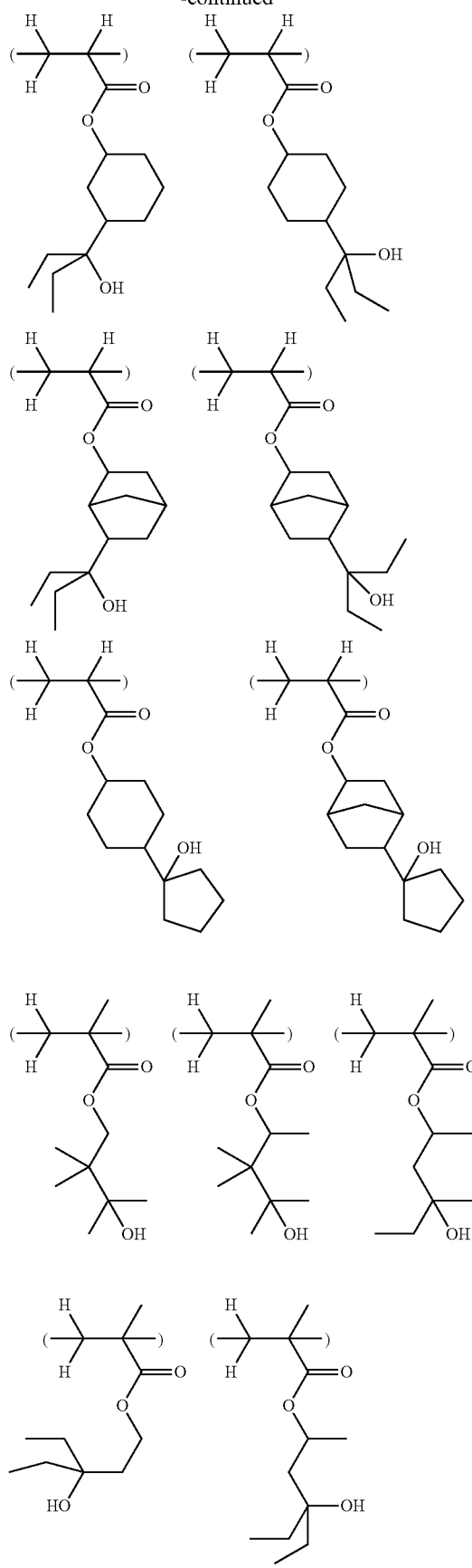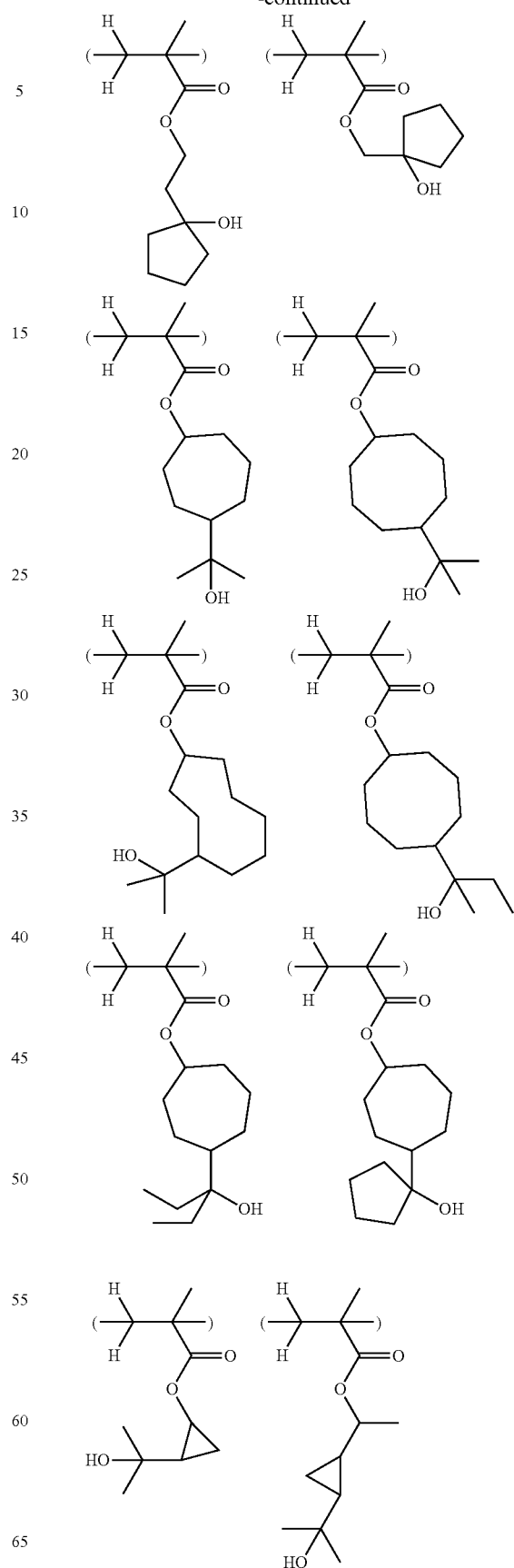

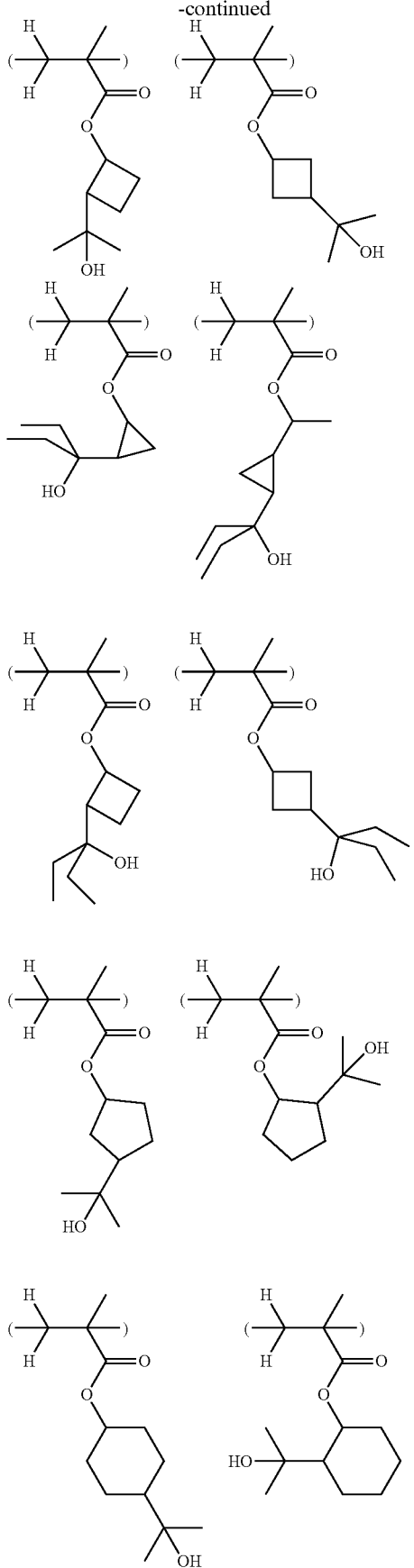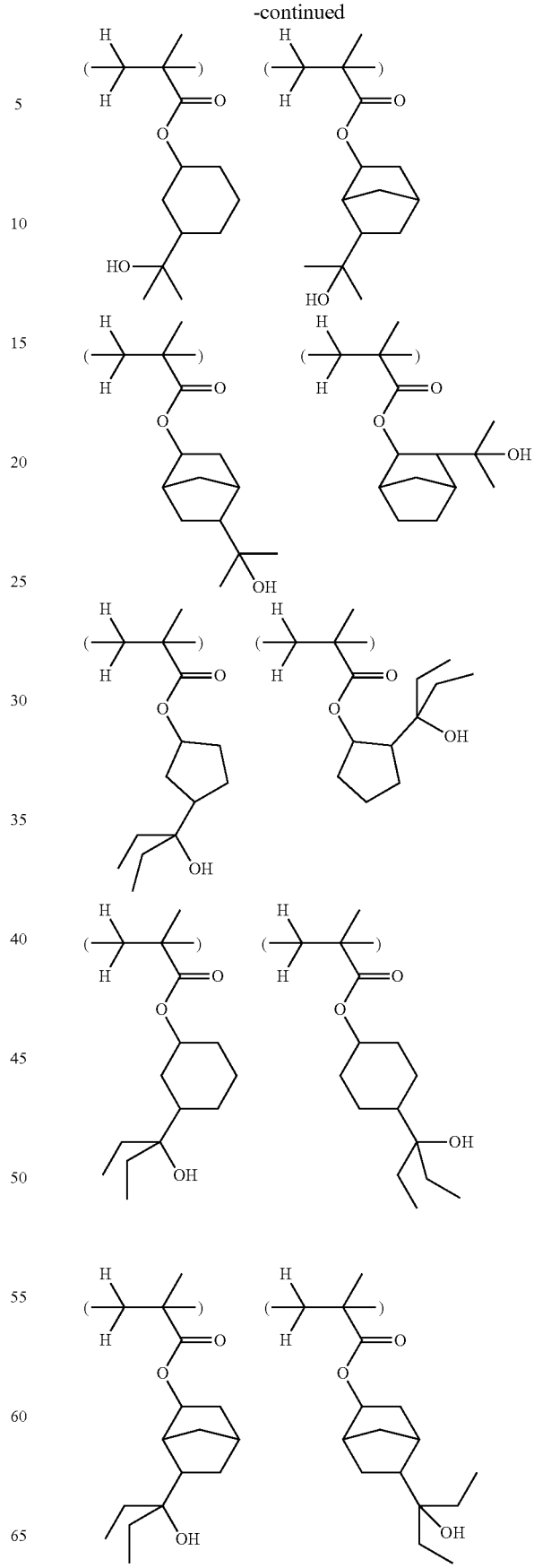

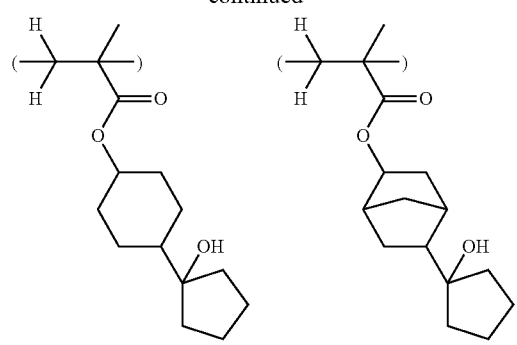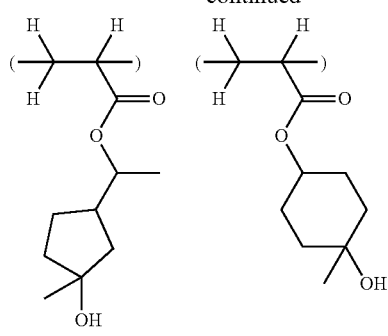

221
-continued
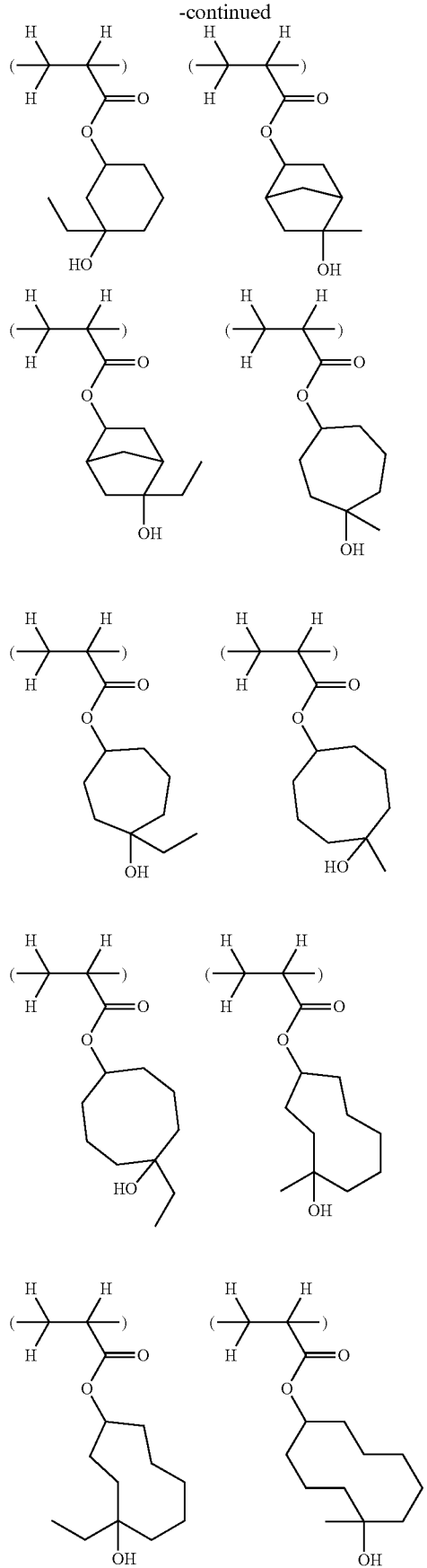
222
-continued
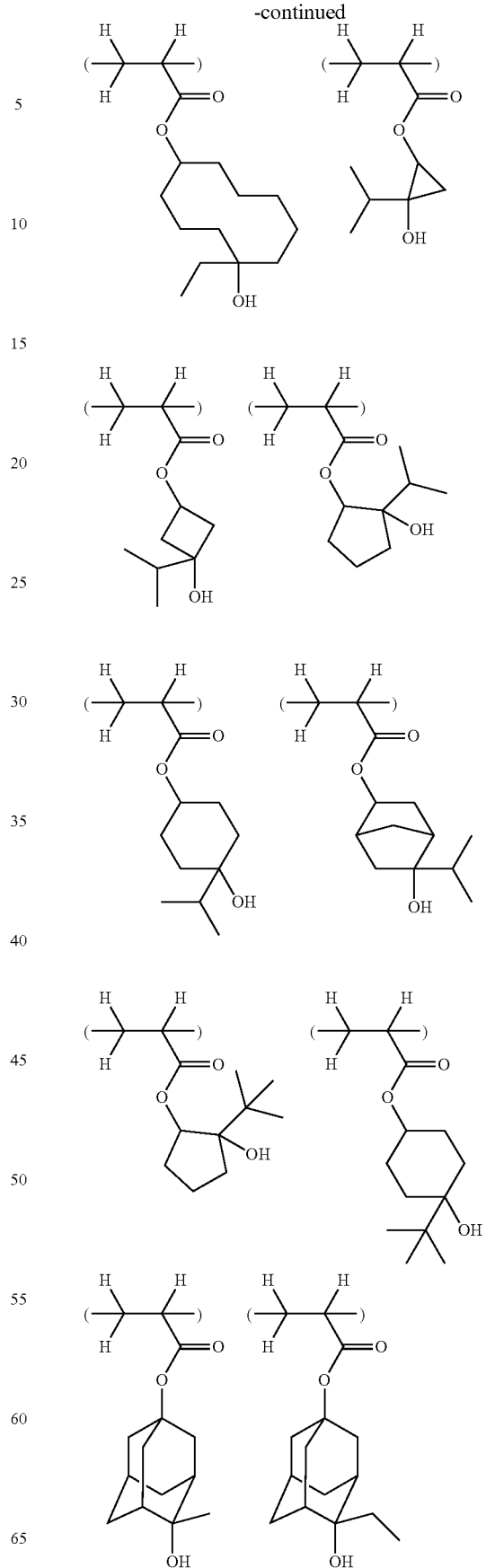

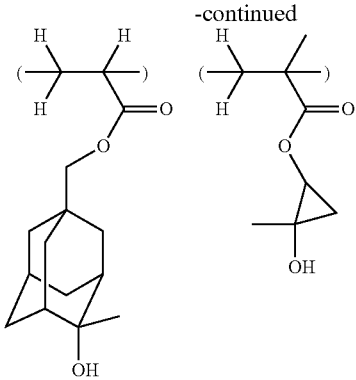
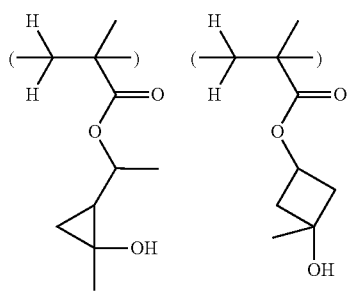
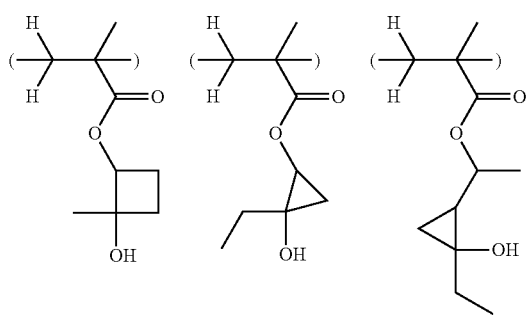
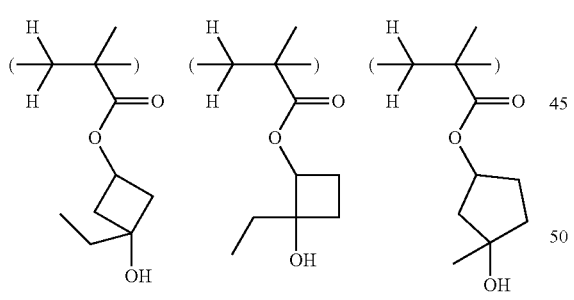
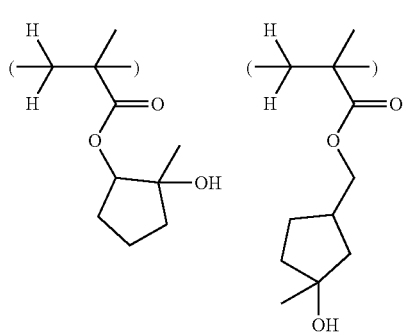
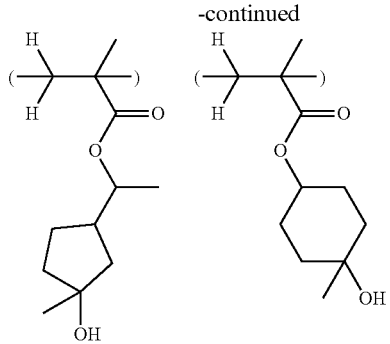
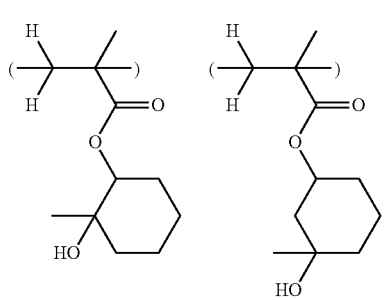
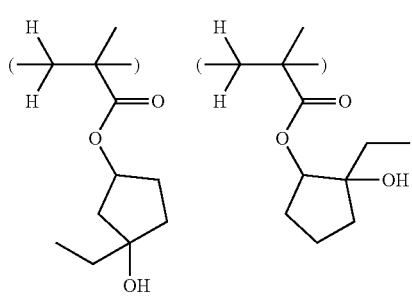
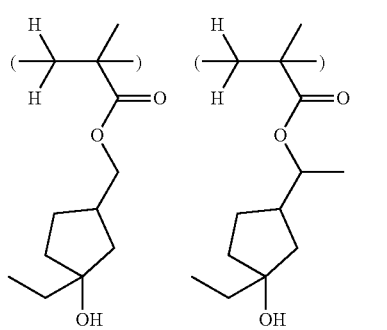
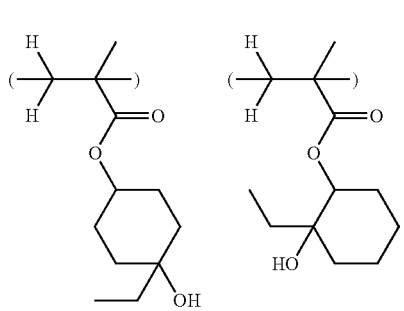

-continued
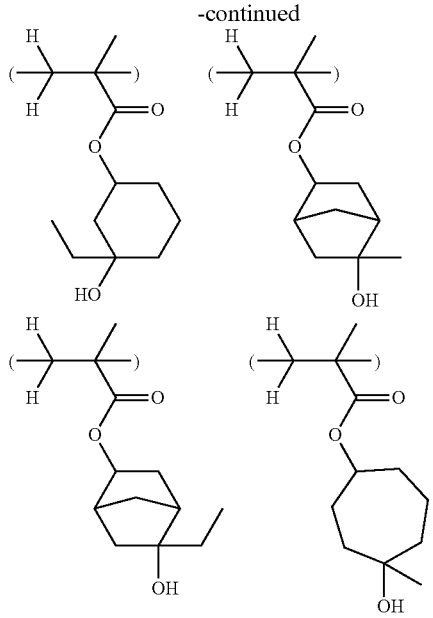
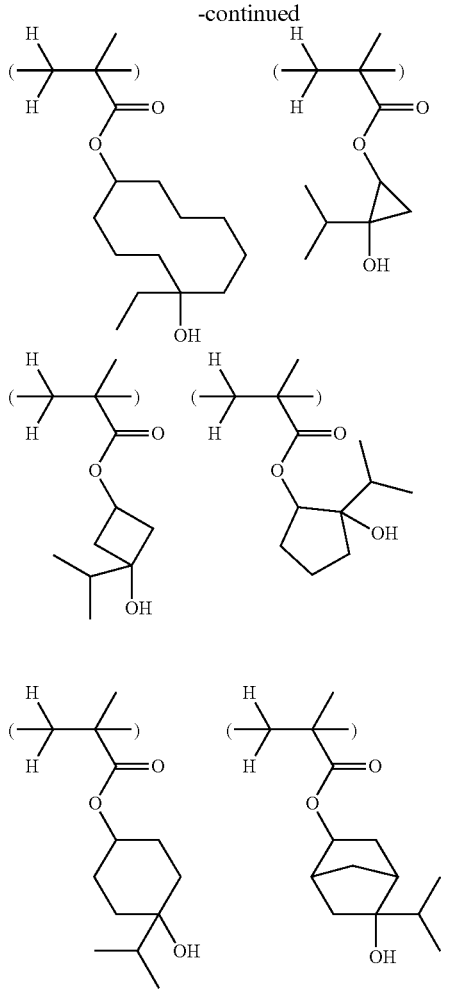
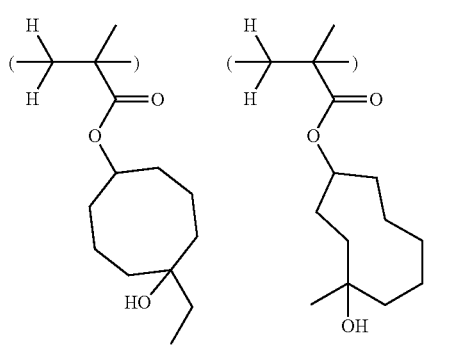
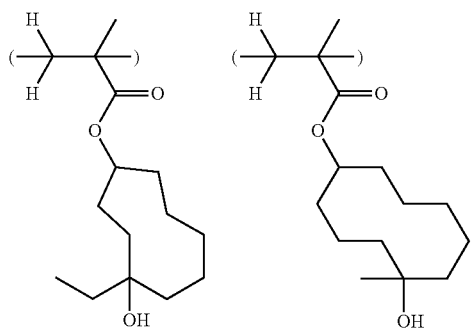
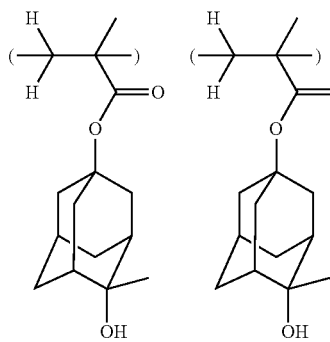

227
-continued
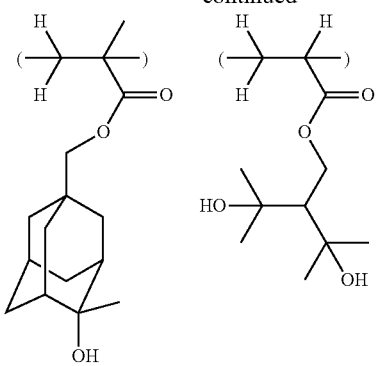
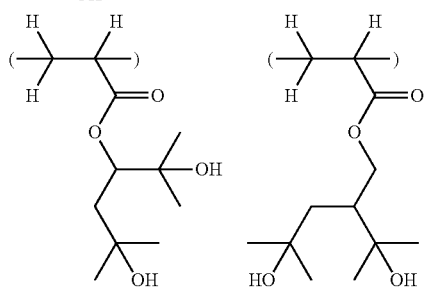
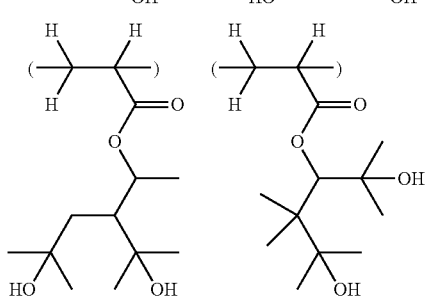
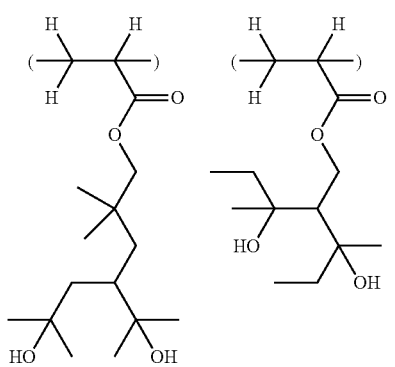
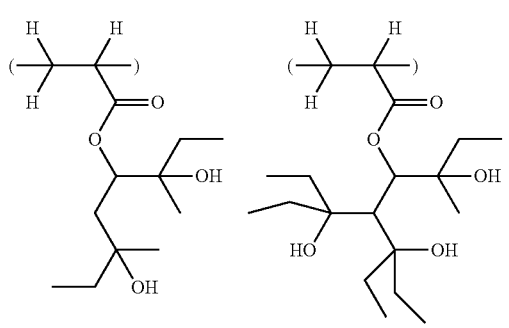
228
-continued
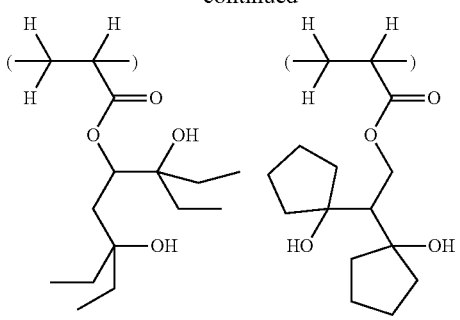
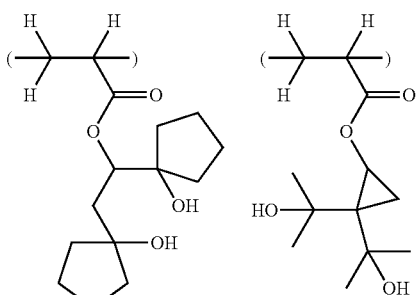
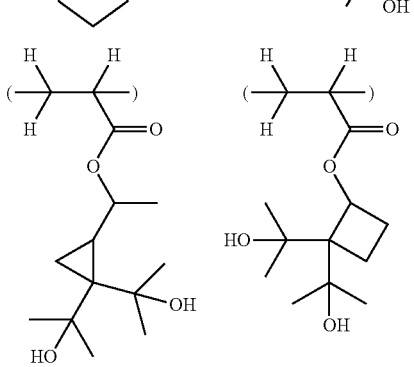
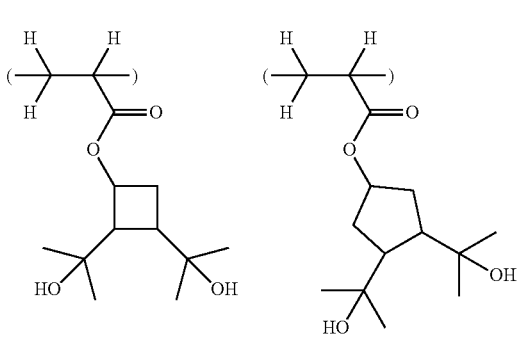
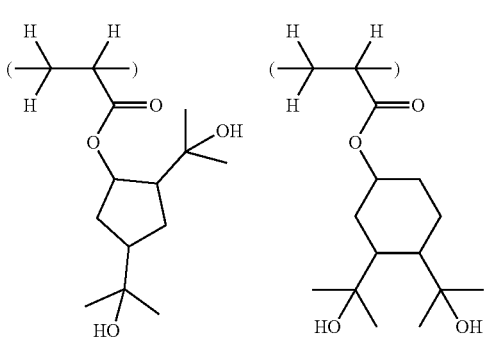

-continued
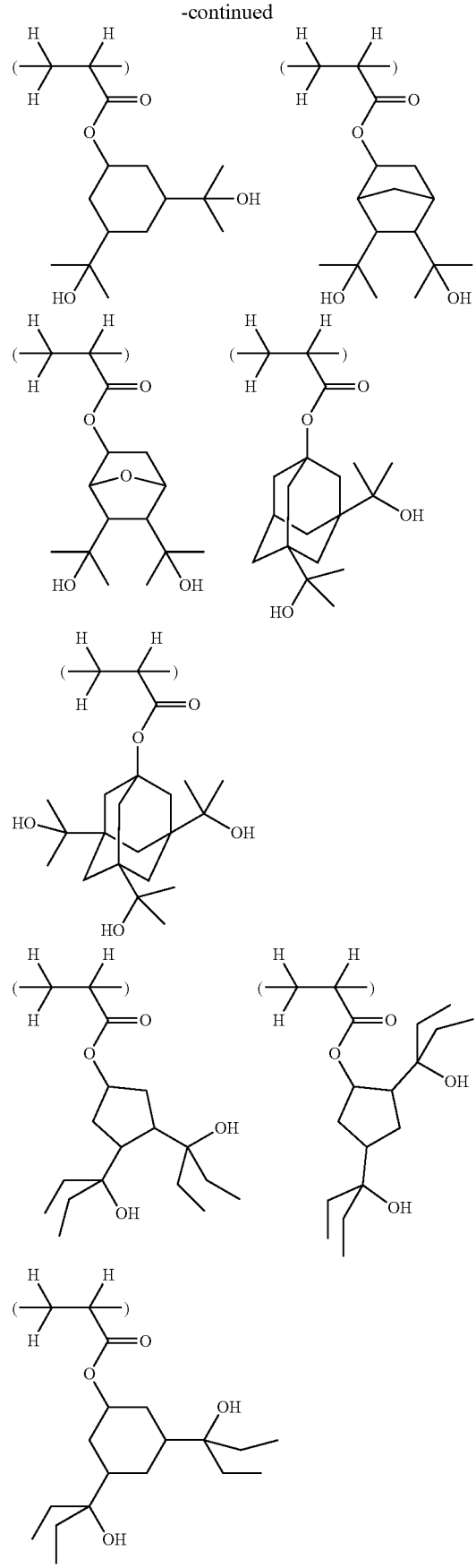
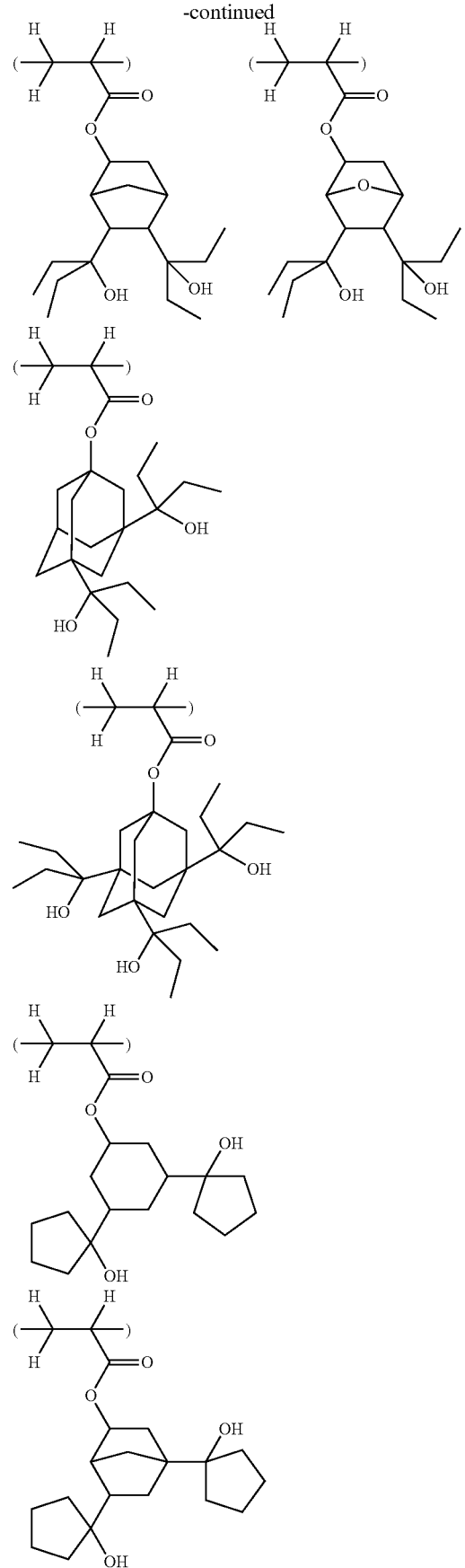

231
-continued
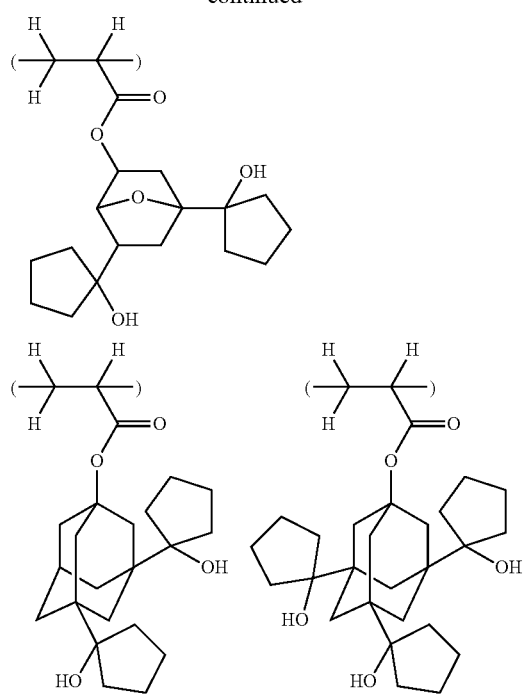
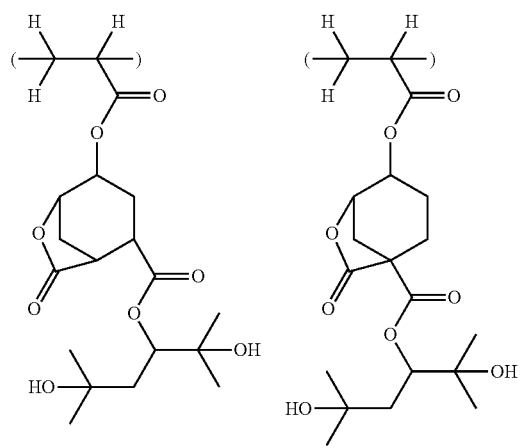
232
-continued
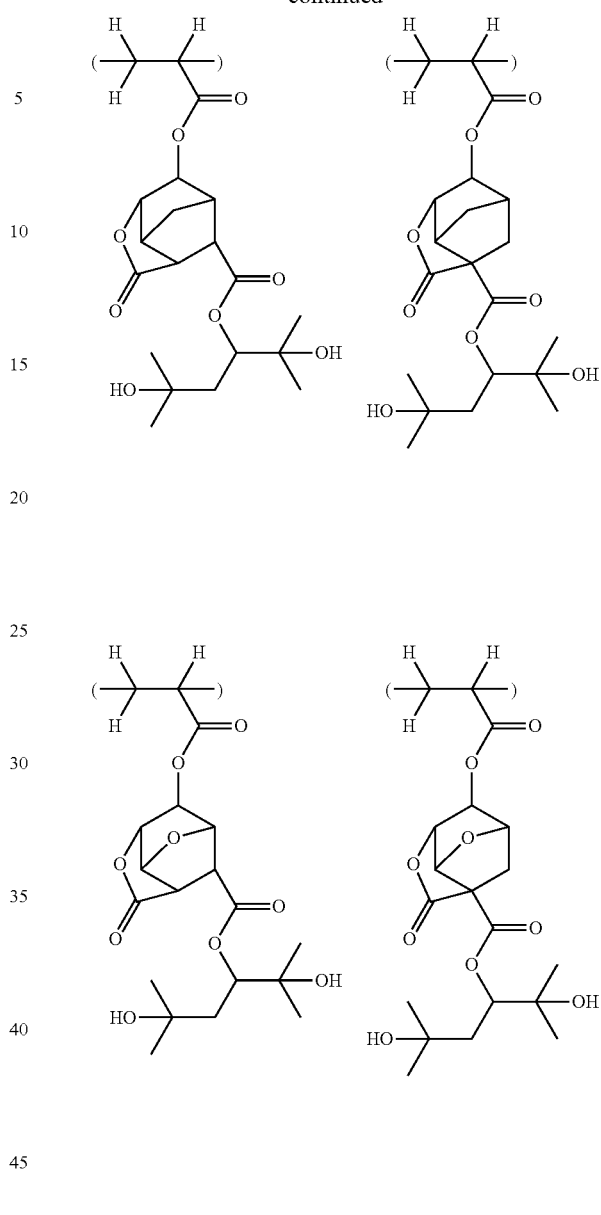
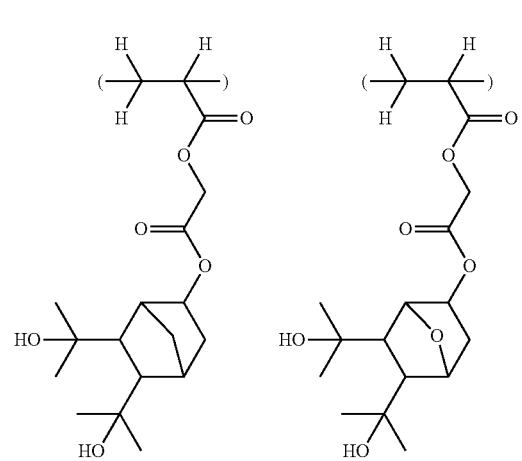

233
-continued
234
-continued
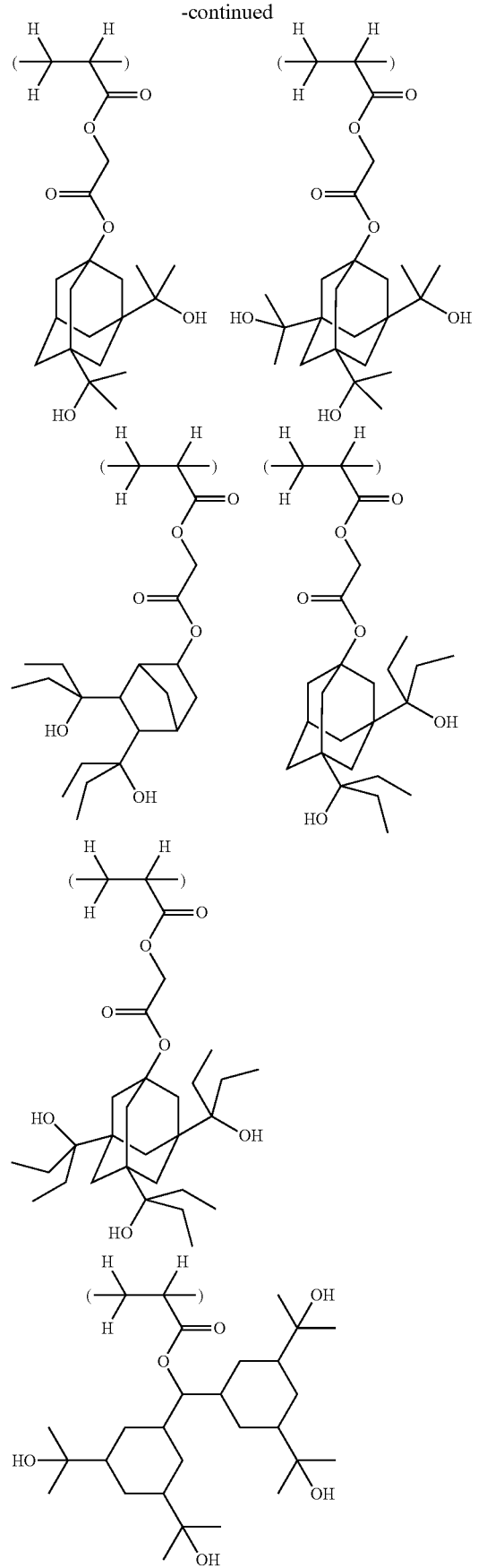
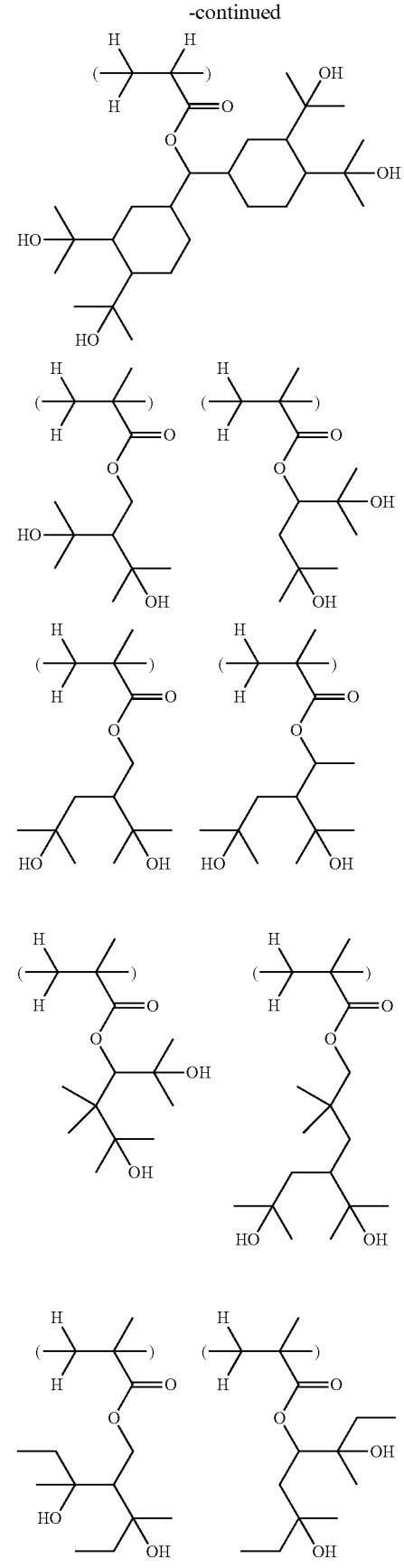

-continued
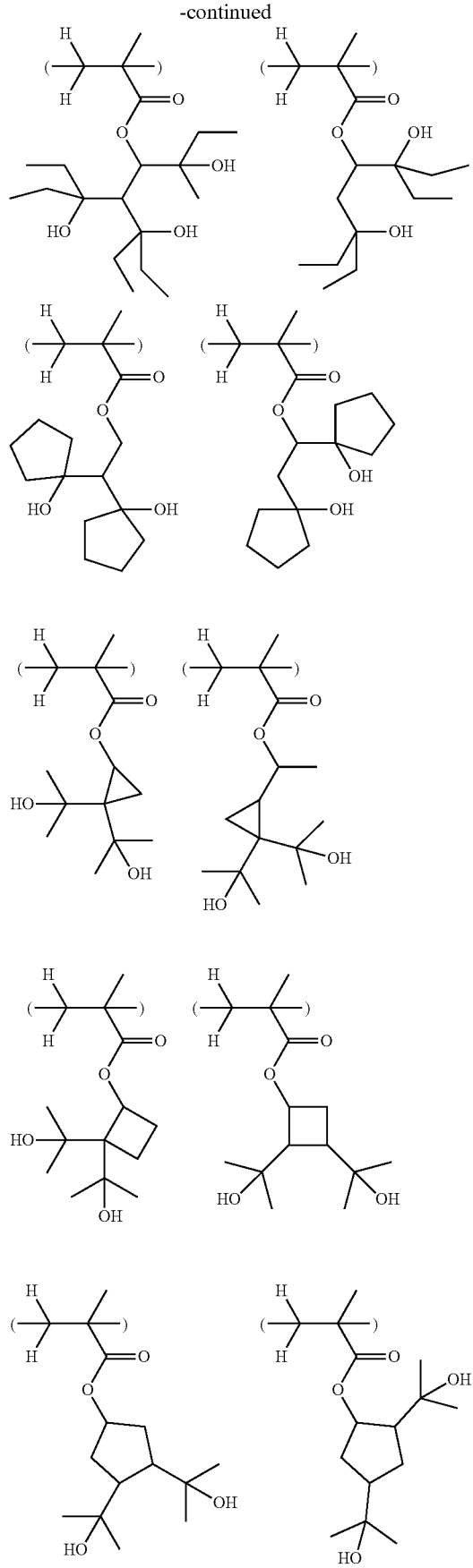
-continued
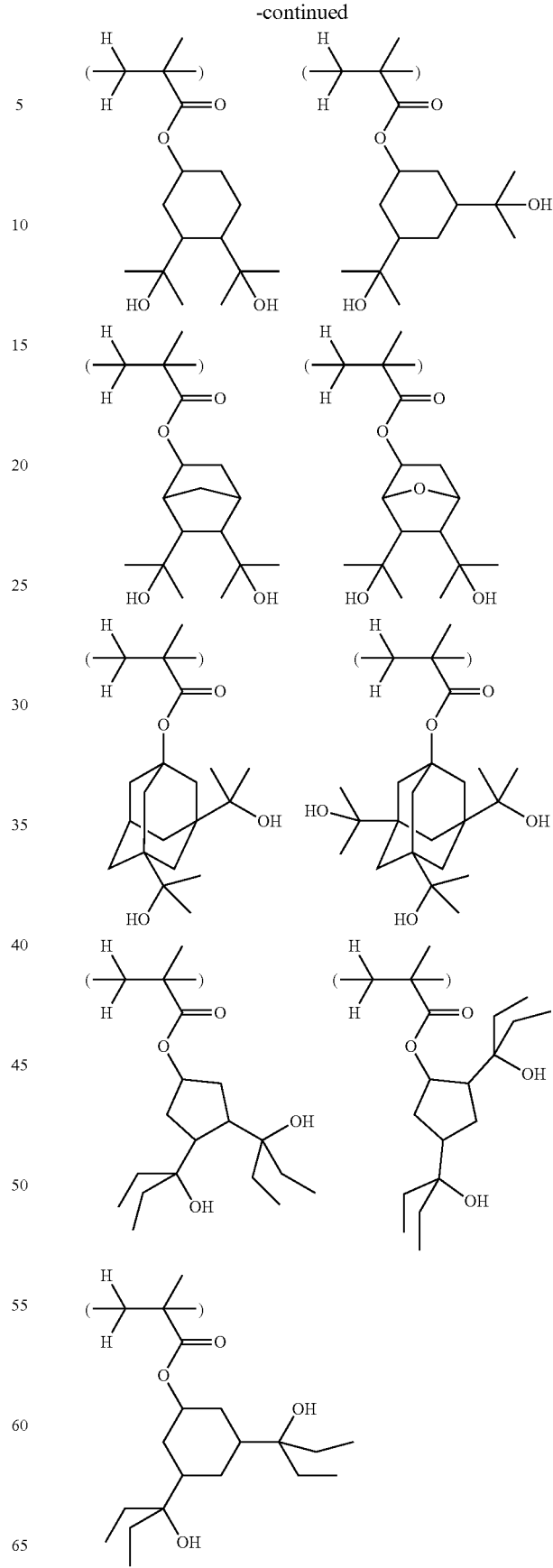

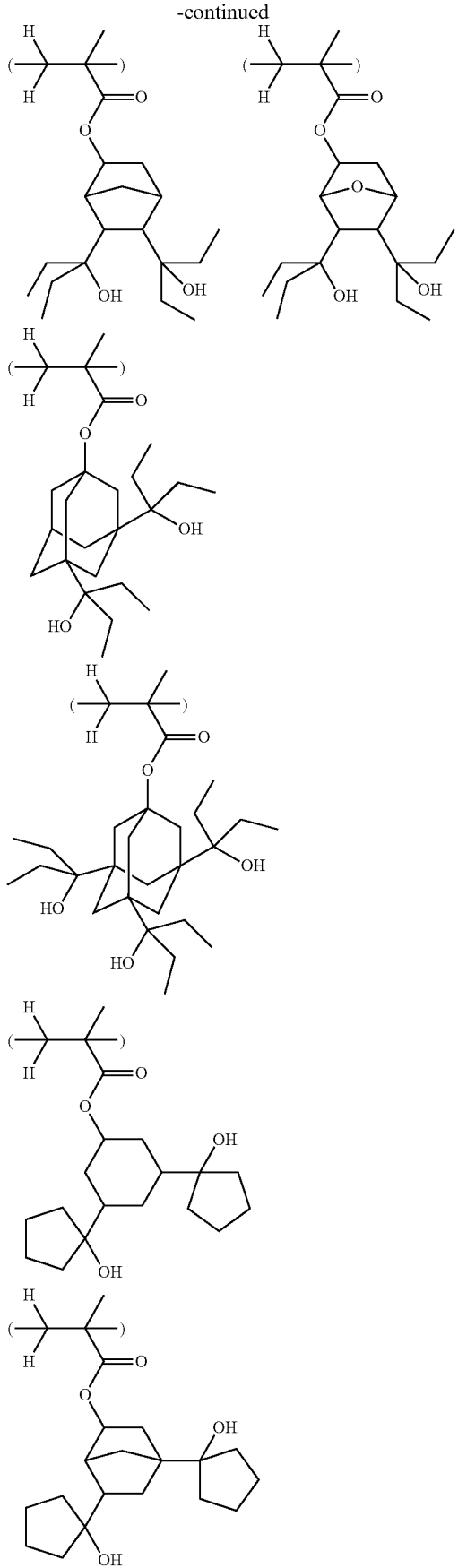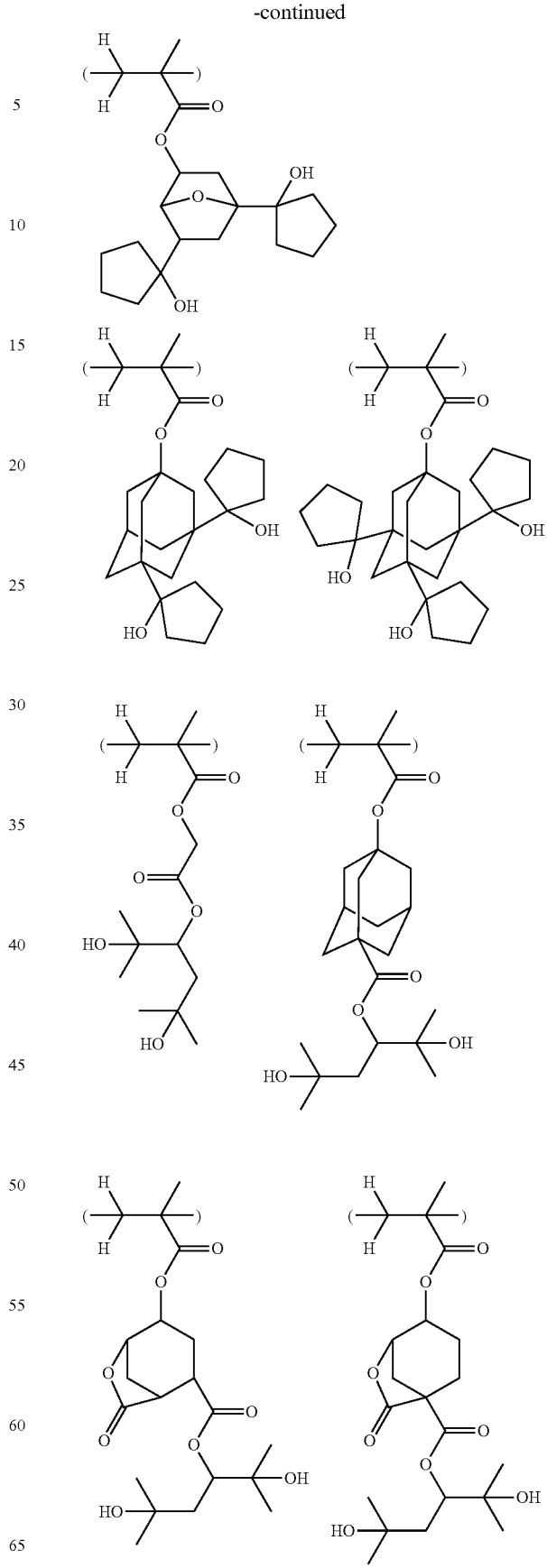

239
-continued
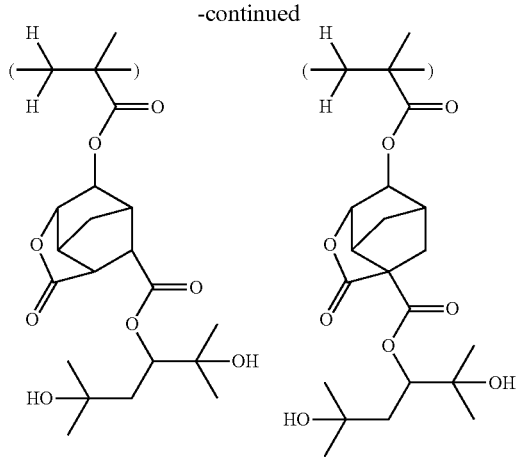
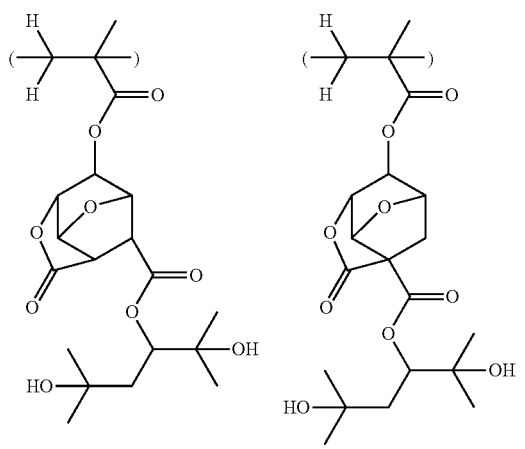
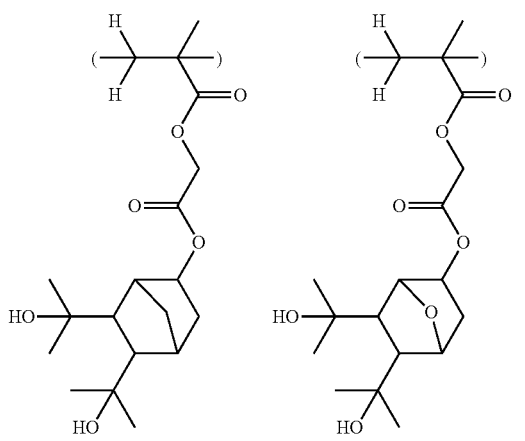
240
-continued
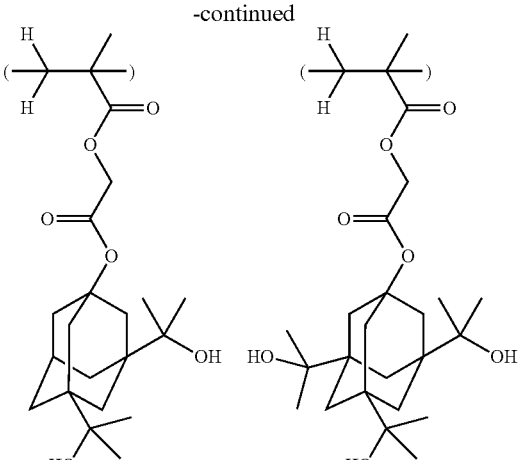
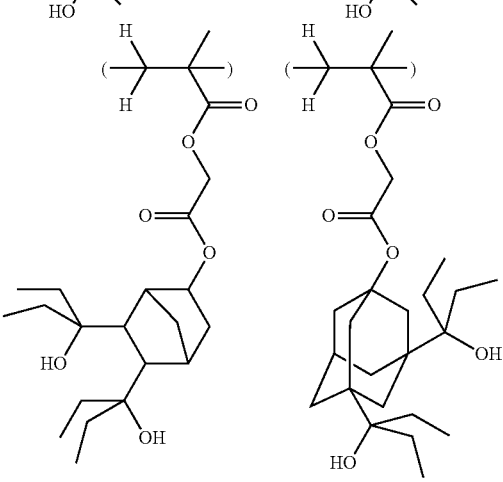
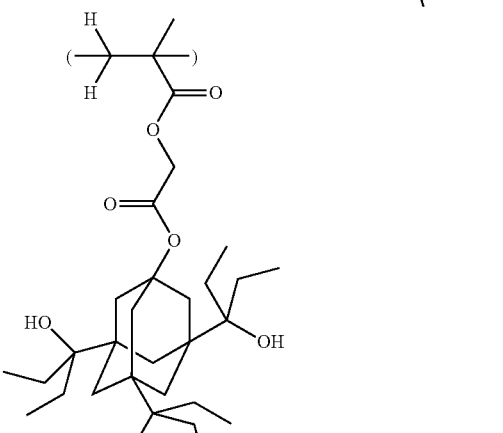
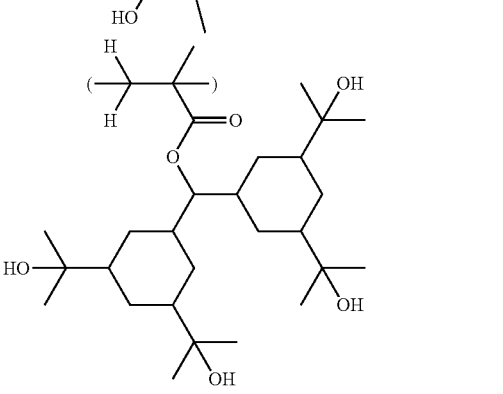

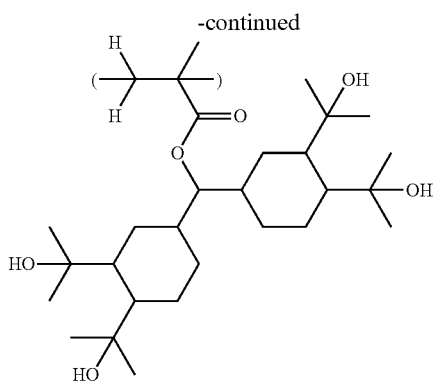

In addition to the foregoing units, the inventive polymer may further comprise recurring units of at least one type selected from recurring units having formulae (f1) to (f3).

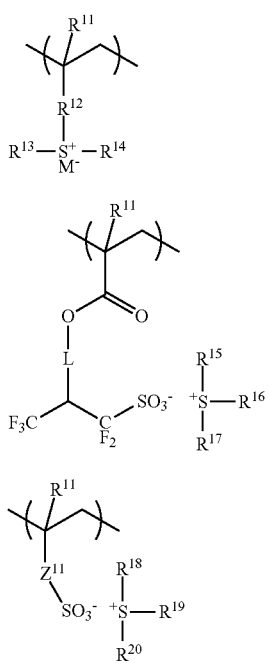

Herein $R^{11}$ is each independently hydrogen or methyl. $R^{12}$ is a single bond, phenylene, —O—$R^{21}$—, or —C(=O)—$Z^{22}$—$R^{21}$— wherein $Z^{22}$ is oxygen or NH and $R^{21}$ is a straight, branched or cyclic $C_1$-$C_6$ alkylene group, straight, branched or cyclic $C_2$-$C_6$ alkenylene group or phenylene group, which may contain a carbonyl (—CO—), ester (—COO—), ether (—O—) or hydroxyl moiety. L is a single bond or —$Z^{33}$—C(=O)—O— wherein $Z^{33}$ is a straight, branched or cyclic $C_1$-$C_{20}$ divalent hydrocarbon group which may be substituted with a heteroatom. $Z^{11}$ is a single bond, methylene, ethylene, phenylene, fluorinated phenylene, —O—$R^{22}$—, or —C(=O)—$Z^{44}$—$R^{22}$— wherein $Z^{44}$ is oxygen or NH and $R^{22}$ is a straight, branched or cyclic $C_1$-$C_6$ alkylene group, straight, branched or cyclic $C_2$-$C_6$ alkenylene group or phenylene group, which may contain a carbonyl, ester, ether or hydroxyl moiety. $R^{13}$ to $R^{20}$ are each independently a straight, branched or cyclic $C_1$-$C_{20}$ monovalent hydrocarbon group which may be substituted with or separated by a heteroatom. M" is a non-nucleophilic counter ion, $R^{13}$ to $R^{20}$ are each independently a straight, branched or cyclic $C_1$-$C_{20}$ monovalent hydrocarbon group which may be substituted with or separated by a heteroatom. Suitable monovalent hydrocarbon groups include alkyl groups such as methyl, ethyl, n-propyl, isopropyl, n-butyl, t-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl, and thienyl; and aralkyl groups such as benzyl, 1-phenylethyl, and 2-phenylethyl, with the aryl groups being preferred. Also included are modified forms of the foregoing groups in which at least one hydrogen atom (one or more or even all hydrogen atoms) is replaced by a heteroatom such as oxygen, sulfur, nitrogen or halogen, or in which a heteroatom such as oxygen, sulfur or nitrogen intervenes, and as a result, a hydroxyl group, cyano group, carbonyl group, ether bond, ester bond, sulfonic acid ester bond, carbonate bond, lactone ring, sultone ring, carboxylic acid anhydride, or haloalkyl group forms or intervenes. Also, a pair of $R^{13}$ and $R^{14}$ may bond together to form a ring with the sulfur atom to which they are attached, and any two or more of $R^{15}$, $R^{16}$ and $R^{17}$, or any two or more of $R^{18}$, $R^{19}$ and $R^{20}$ may bond together to form a ring with the sulfur atom to which they are attached.

When L is —$Z^{33}$—C(=O)—O—, examples of the optionally heteroatom-substituted, straight, branched or cyclic $C_1$-$C_{20}$ divalent hydrocarbon group represented by $Z^{33}$ are shown below, but not limited thereto.

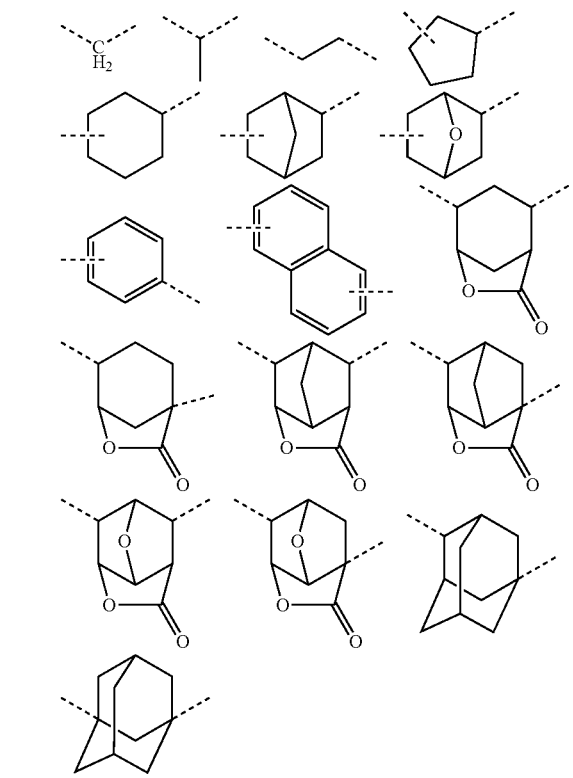

When a pair of $R^{13}$ and $R^{14}$ bond together to form a ring with the sulfur atom to which they are attached, and any two or more of $R^{15}$, $R^{16}$ and $R^{17}$, or any two or more of $R^{18}$, $R^{19}$ and $R^{20}$ bond together to form a ring with the sulfur atom to which they are attached, examples of the ring are shown below, but not limited thereto.

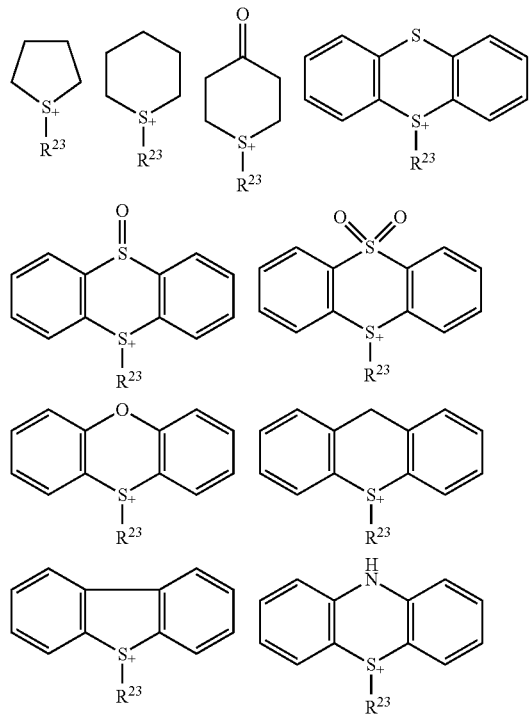

In the formulae, $R^{23}$ is a straight, branched or cyclic $C_1$-$C_{20}$ monovalent hydrocarbon group which may be substituted with or separated by a heteroatom. Suitable monovalent hydrocarbon groups are as exemplified above for $R^{13}$ to $R^{20}$.

Illustrative, non-limiting examples of the sulfonium cation in formulae (f2) and (f3) are given below.

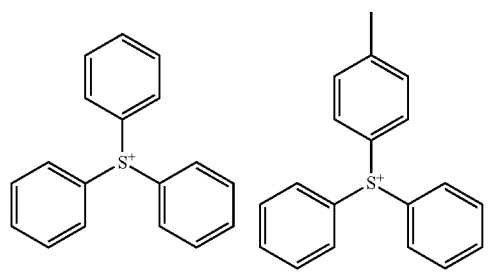

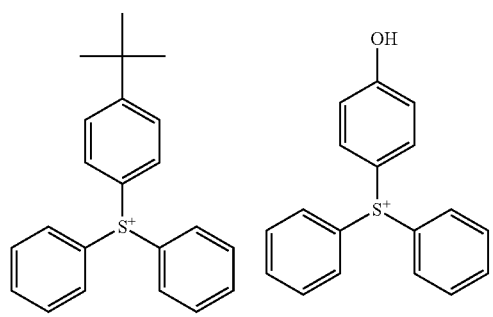

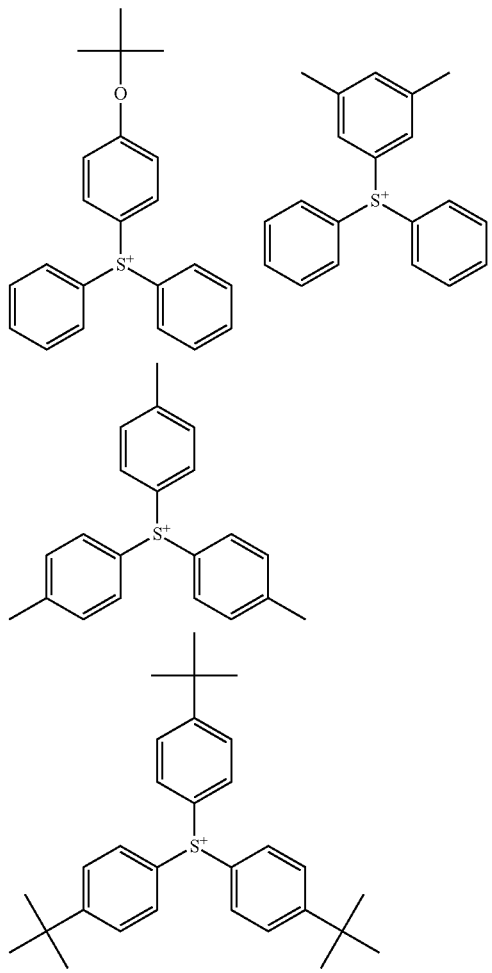

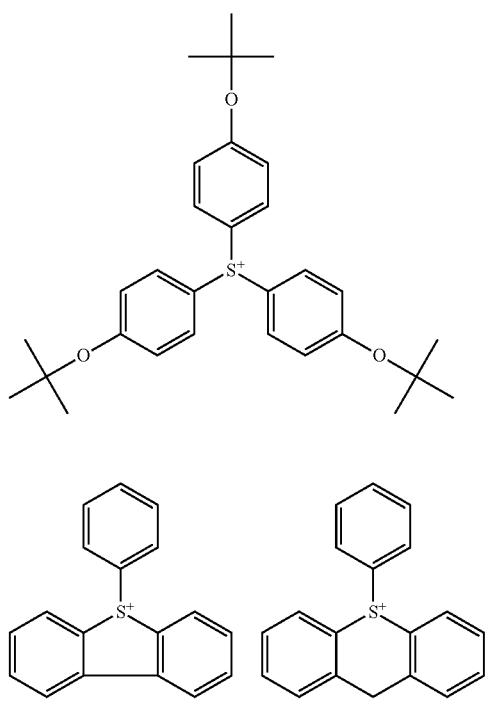

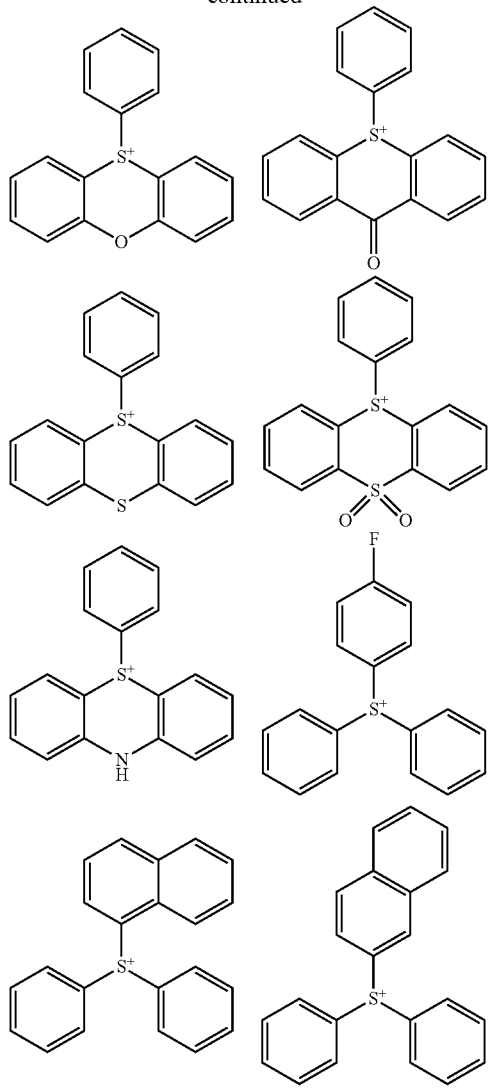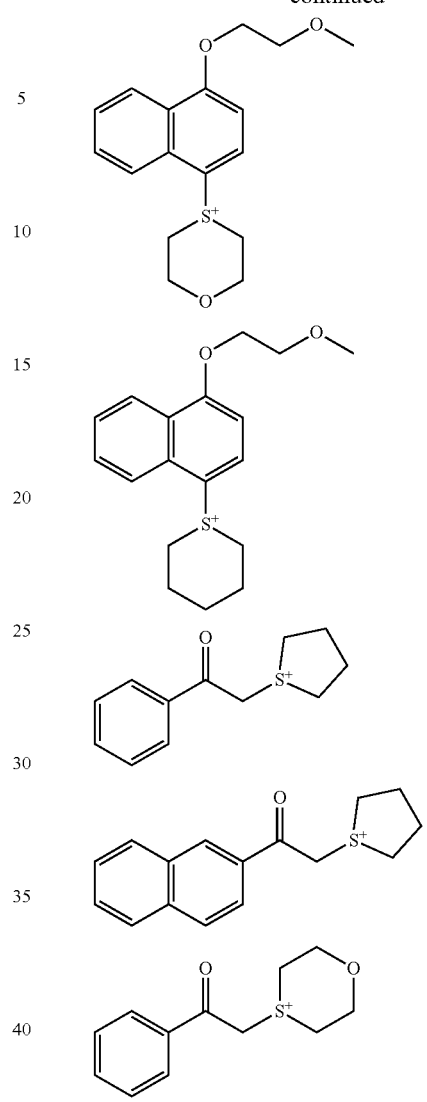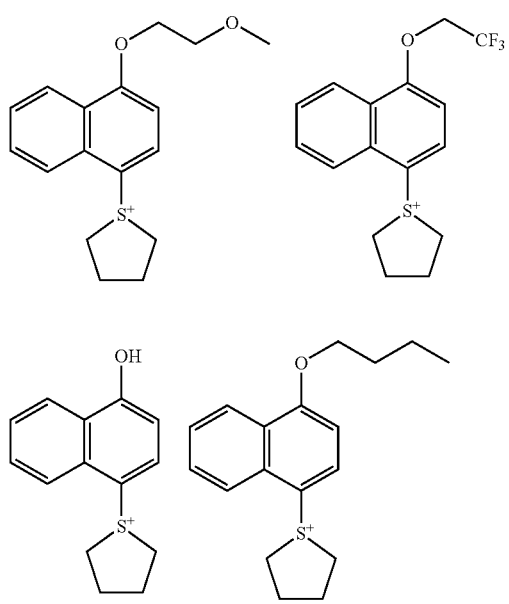

Examples of the non-nucleophilic counter ion represented by M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; and methidates such as tris(trifluoromethylsulfonyl)methide and tris(perfluoroethylsulfonyl)methide.

Also included are a sulfonate which is fluorinated at α-position as represented by the formula (F-1) and a sulfonate which is fluorinated at α- and β-positions as represented by the formula (F-2).

$$R^{31}-CF_2-SO_3^- \quad (F\text{-}1)$$

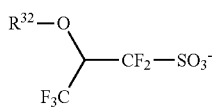

(F-2)

In formula (F-1), $R^{31}$ is hydrogen, or a straight, branched or cyclic $C_1$-$C_{20}$ alkyl group, straight, branched or cyclic $C_2$-$C_{20}$ alkenyl group or $C_6$-$C_{20}$ aryl group, which may have an ether, ester, carbonyl moiety, lactone ring or fluorine atom. In formula (F-2), $R^{32}$ is hydrogen, or a straight, branched or cyclic $C_1$-$C_{30}$ alkyl group, straight, branched or cyclic $C_2$-$C_{30}$ acyl group, straight, branched or cyclic $C_2$-$C_{20}$ alkenyl group, $C_6$-$C_{20}$ aryl group or $C_6$-$C_{20}$ aryloxy group, which may have an ether, ester, carbonyl moiety or lactone ring.

Furthermore, recurring units (g) having an oxirane or oxetane ring may be copolymerized. When recurring units (g) are copolymerized, it is expected that when the polymer is used in a resist composition, the exposed region of a resist film is crosslinked, leading to improvements in insolubilization in alkaline developer and etch resistance of negative pattern. Examples of recurring units (g) having an oxirane or oxetane ring are shown below, but not limited thereto.

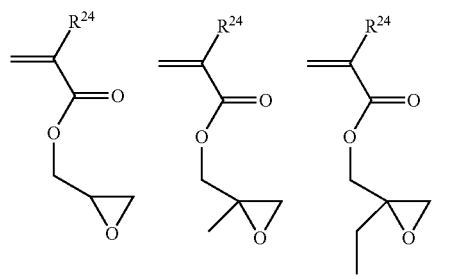

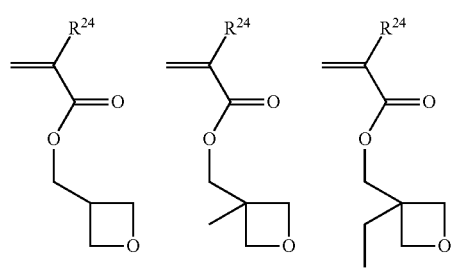

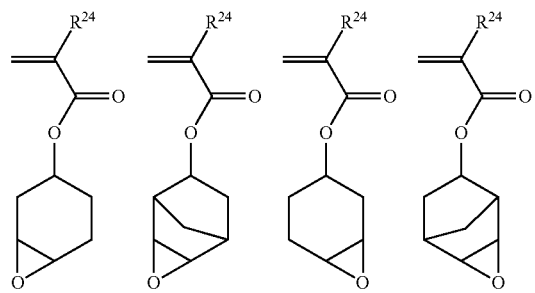

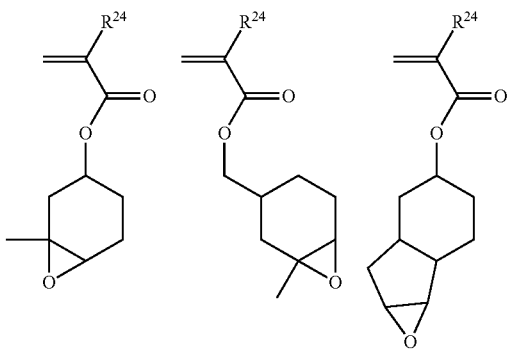

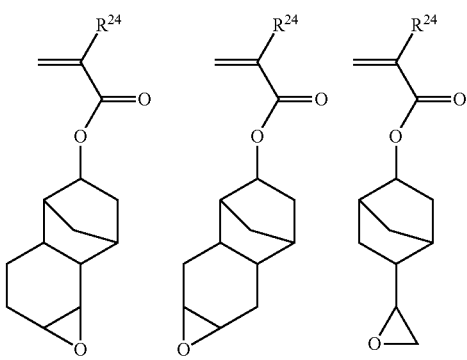

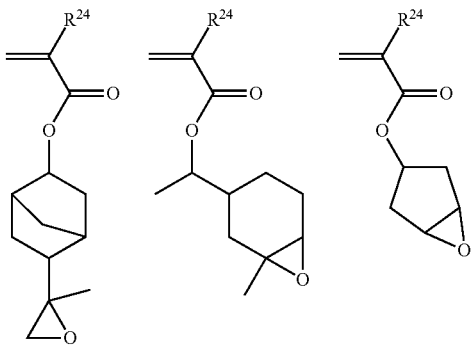

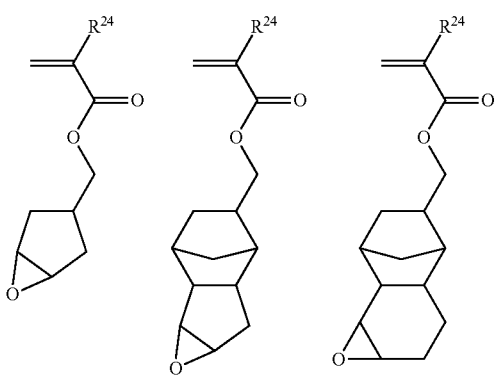

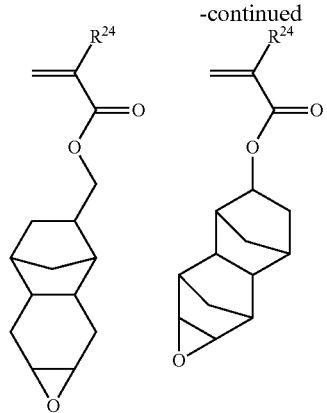
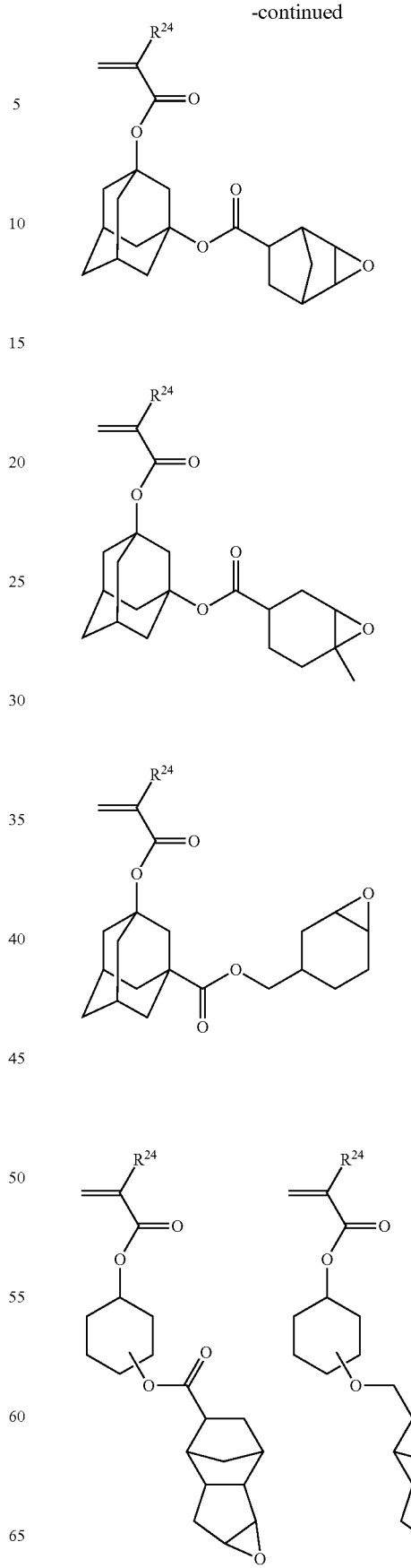

-continued

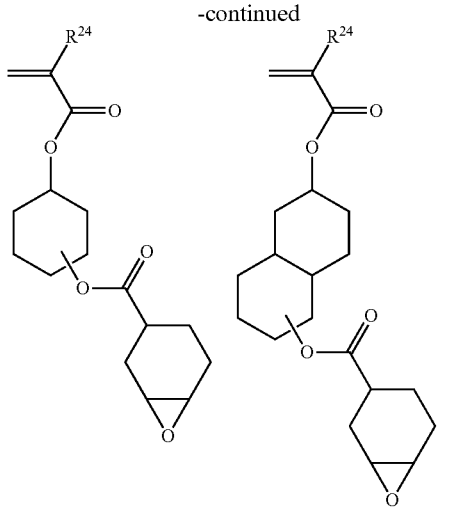
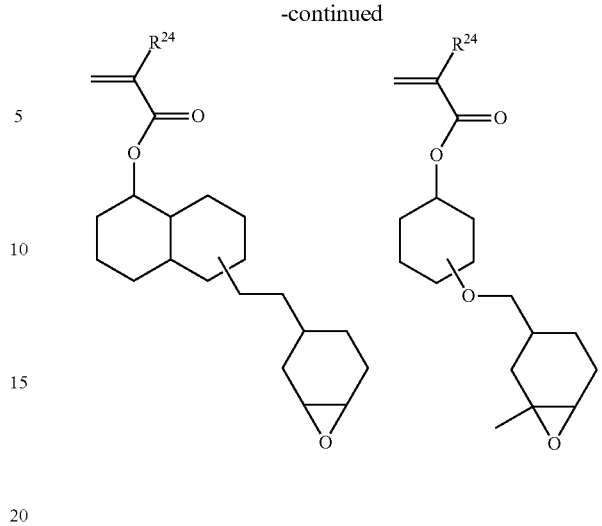
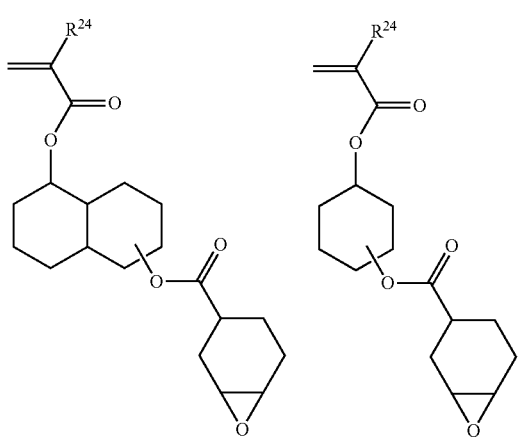
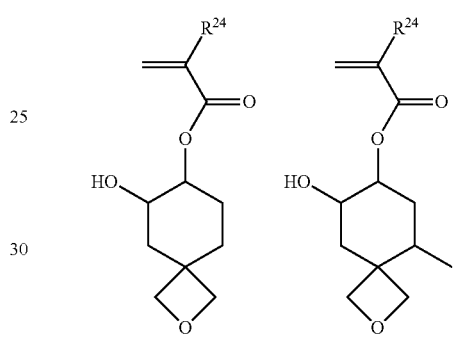
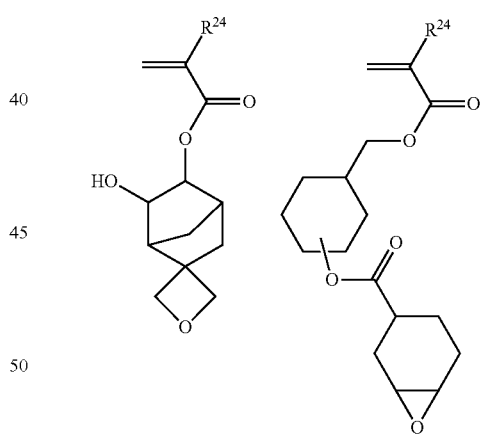
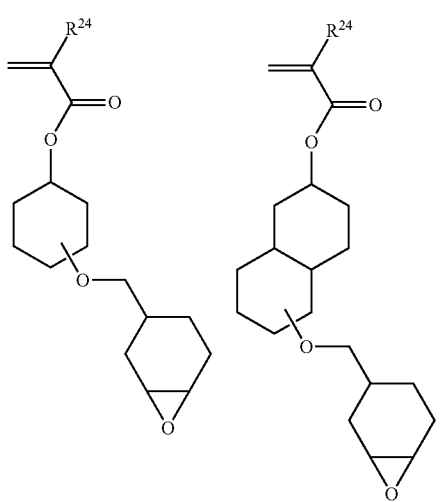

Herein $R^{24}$ is hydrogen, methyl or trifluoromethyl.

In addition to the foregoing units, the polymer may further comprise recurring units (h) derived from carbon-to-carbon double bond-bearing monomers. Examples include recurring units derived from substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers shown below.

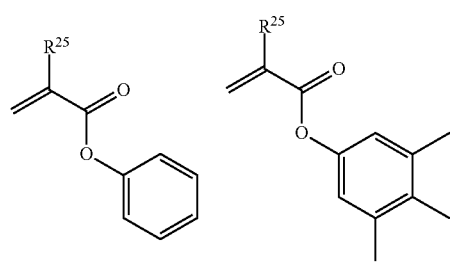
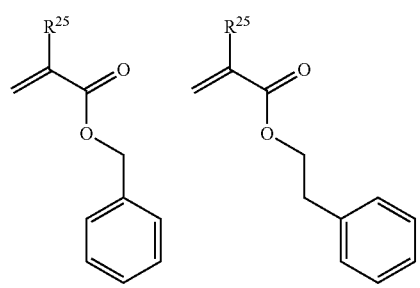
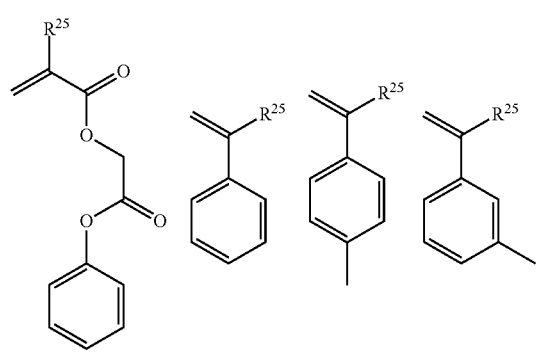
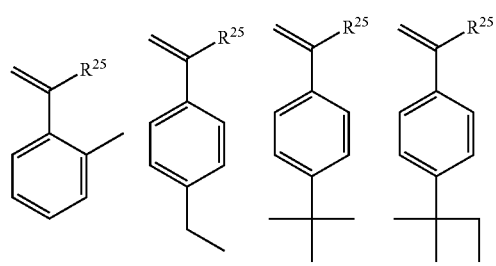
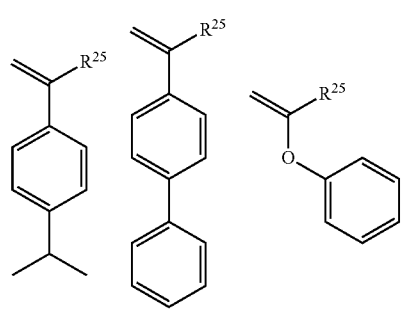
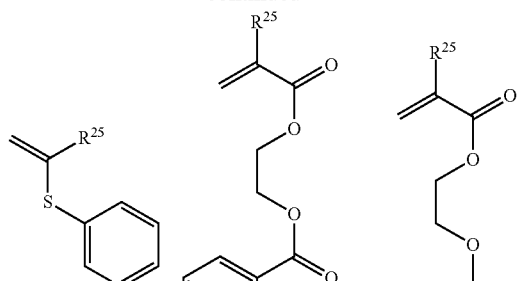
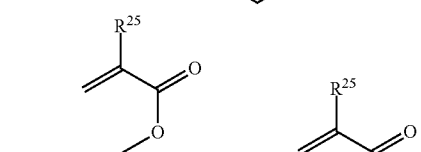
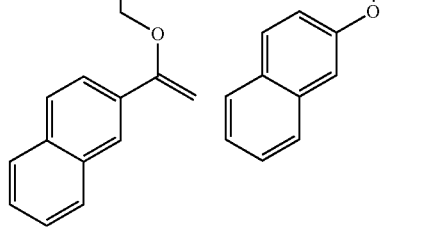
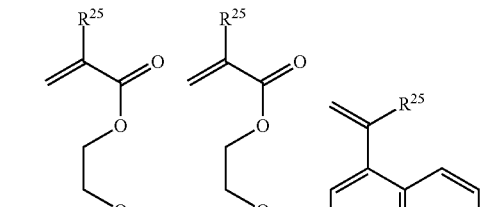
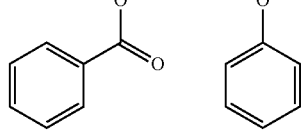
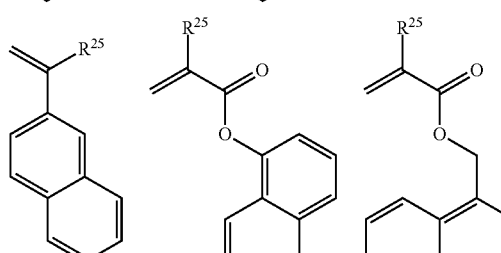
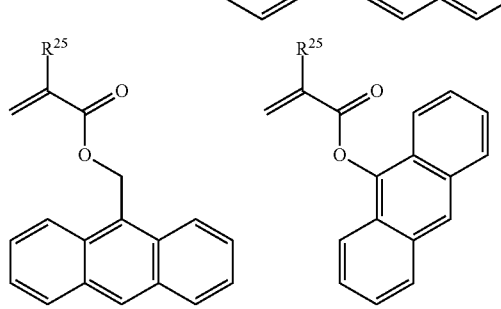

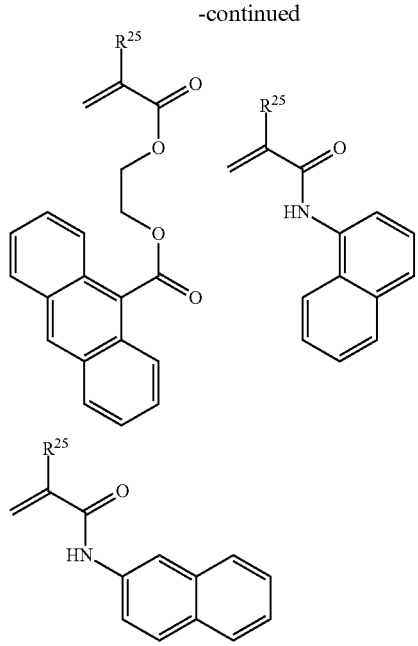
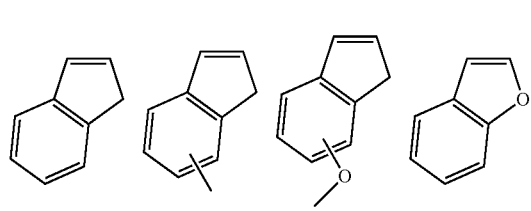
Herein R²⁵ is hydrogen, methyl or trifluoromethyl.
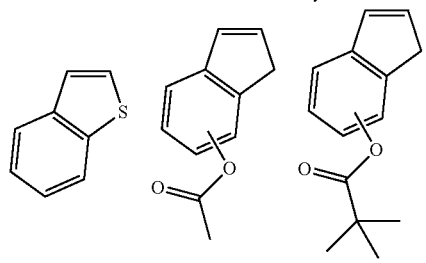
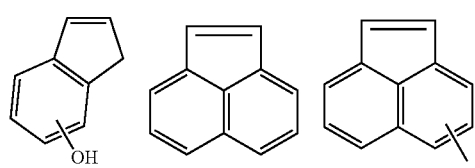
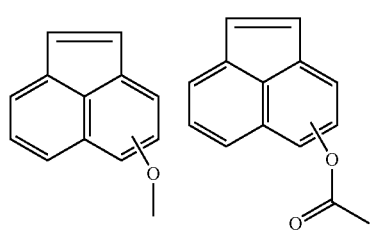
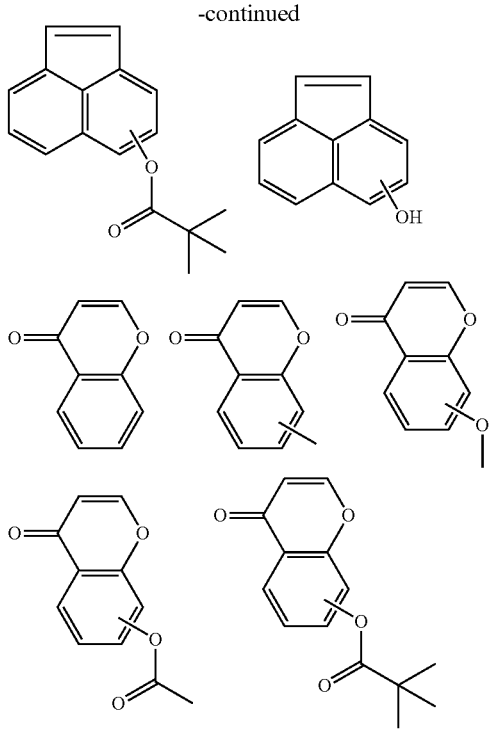
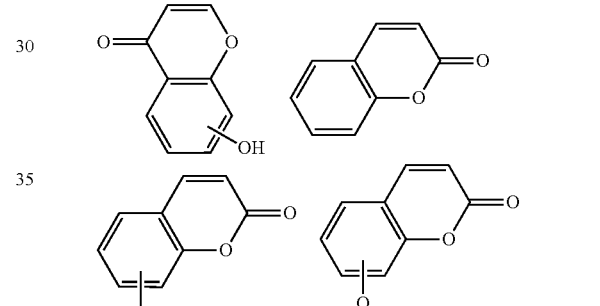
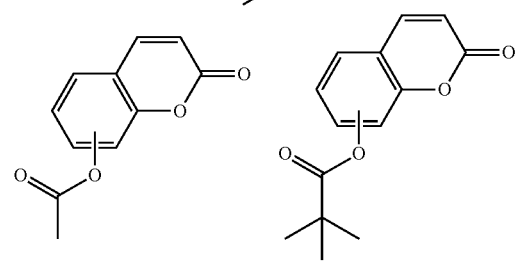
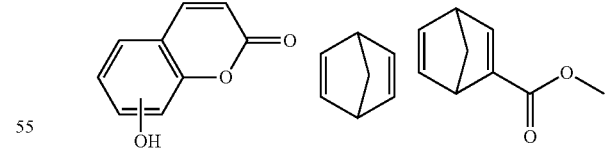
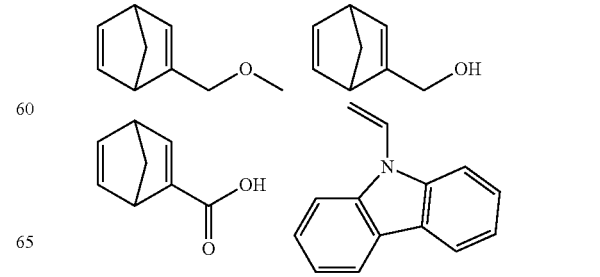

-continued

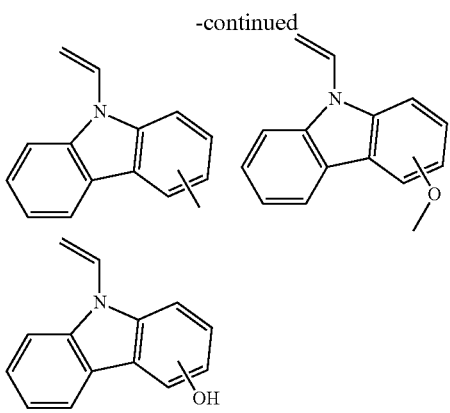

In the polymer, the recurring units derived from the inventive monomer and other monomers are preferably incorporated in the following molar fractions (mol %):
(I) more than 0 mol % to 100 mol %, preferably 5 to 80 mol %, and more preferably 10 to 60 mol % of constituent units of at least one type derived from monomer of formula (1a), (1b), (1aa) or (1bb);
(II) 0 mol % to less than 100 mol %, preferably 0 to 90 mol %, and more preferably 0 to 80 mol % of constituent units of at least one type selected from units (3a) to (3d), if incorporated, at least 1 mol %, especially at least 4 mol %;
(III) 0 mol % to less than 100 mol %, preferably 5 to 95 mol %, and more preferably 10 to 90 mol % of constituent units of at least one type selected from units (A) to (D), if incorporated, at least 4 mol %, especially at least 5 mol %;
(IV) 0 to 30 mol %, preferably 0 to 20 mol %, and more preferably 0 to 10 mol % of constituent units of at least one type selected from units (f1) to (f3), if incorporated, at least 1 mol %; and
(V) 0 to 80 mol %, preferably 0 to 70 mol %, and more preferably 0 to 50 mol % of constituent units of at least one type selected from units (g) and (h).

The polymer may be synthesized by any desired methods, for example, by dissolving one or more monomers corresponding to the selected recurring units in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethyl-valeronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, a copolymer may be obtained by dissolving hydroxystyrene or hydroxyvinylnaphthalene and another monomer(s) in an organic solvent, adding a radical polymerization initiator, and heat polymerization. Alternatively, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to polyhydroxystyrene or hydroxypolyvinylnaphthalene. For alkaline hydrolysis, a base such as aqueous ammonia or triethylamine may be used. The reaction temperature is −20 to 100° C., preferably 0 to 60° C., and the reaction time is 0.2 to 100 hours, preferably 0.5 to 20 hours.

The polymer should preferably have a weight average molecular weight (Mw) in the range of 1,000 to 500,000, and more preferably 3,000 to 50,000, as measured versus polystyrene standards by GPC using tetrahydrofuran solvent. Outside the range, there may result an extreme decline of etch resistance, a failure to provide a differential dissolution rate before and after exposure, and a lowering of resolution. Also preferably, the polymer has a molecular weight distribution or dispersity (Mw/Mn) of 1.20 to 2.20, more preferably 1.30 to 1.80.

Resist Composition

The inventive polymer is advantageously used as a base resin in a resist composition. Specifically, the polymer is used as a base resin and combined with any desired components including an organic solvent, acid generator, dissolution regulator, basic compound, surfactant, and acetylene alcohol to formulate a resist composition.

The resist composition comprising the inventive polymer has a very high sensitivity in that the dissolution rate in alkaline developer of the polymer in the exposed region is reduced by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified resist composition capable of utilizing acid catalyzed reaction, the composition has a higher sensitivity and is further improved in the properties described above.

Inclusion of a dissolution regulator may lead to an increased difference in dissolution rate between exposed and unexposed regions and a further improvement in resolution. Addition of a basic compound may be effective in suppressing the diffusion rate of acid in the resist film, achieving a further improvement in resolution. Addition of a surfactant may improve or control the coating characteristics of the resist composition.

The resist composition may include an acid generator in order for the composition to function as a chemically amplified negative resist composition. Typical of the acid generator used herein is a photoacid generator (PAG) capable of generating an acid in response to actinic light or radiation. Preferably the PAG is used in an amount of 0.5 to 30 parts, more preferably 1 to 20 parts by weight per 100 parts by weight of the base resin. The PAG is any compound capable of generating an acid upon exposure to high-energy radiation. The preferred photoacid generators include the sulfonium salts and PAGs described in JP-A 2009-269953 and the PAGs described in JP 3995575. Any sulfonium salt, iodonium salt, sulfonyldiazomethane, N-sulfonyloxyimide, and oxime-O-sulfonate acid generators may be used. These compounds may be used alone or in admixture. Examples of the acid generated by the acid generator include sulfonic acids, imidic acids and methide acids. Of these, sulfonic acids which are fluorinated at α-position are most commonly used. Fluorination at α-position is not essential when the acid labile group used is an acetal group susceptible to deprotection. Where the base polymer having recurring units (f1), (f2) or (f3) of acid generator copolymerized therein is used, the acid generator of addition type is not essential.

The preferred acid generators are those having the general formulae (Z1) and (Z2).

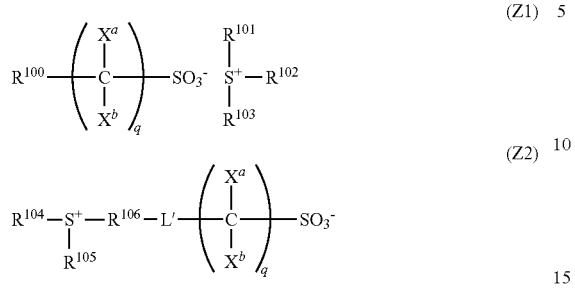

Herein $R^{100}$ is hydrogen, fluorine, or a straight, branched or cyclic $C_1$-$C_{35}$ monovalent hydrocarbon group which may be substituted with or separated by a heteroatom, $X^a$ and $X^b$ are each independently hydrogen, fluorine, or trifluoromethyl, q is an integer of 1 to 4. $R^{101}$, $R^{102}$, and $R^{103}$ are each independently an optionally substituted, straight or branched $C_1$-$C_{10}$ alkyl, $C_1$-$C_{10}$ oxoalkyl or $C_2$-$C_{10}$ alkenyl group, or an optionally substituted $C_6$-$C_{18}$ aryl, $C_7$-$C_{19}$ aralkyl or aryloxoalkyl group, or any two or more of $R^{101}$, $R^{102}$, and $R^{103}$ may bond together to form a ring with the sulfur atom to which they are attached. $R^{104}$ and $R^{105}$ are each independently a straight, branched or cyclic $C_1$-$C_{20}$ monovalent hydrocarbon group which may be substituted with or separated by a heteroatom, or $R^{104}$ and $R^{105}$ may bond together to form a ring with the sulfur atom to which they are attached. $R^{106}$ is a straight, branched or cyclic $C_1$-$C_{20}$ divalent hydrocarbon group which may be substituted with or separated by a heteroatom. L' is a single bond or a straight, branched or cyclic $C_1$-$C_{20}$ divalent hydrocarbon group which may be substituted with or separated by a heteroatom.

Also preferred are acid generators having the general formulae (Z3) and (Z4).

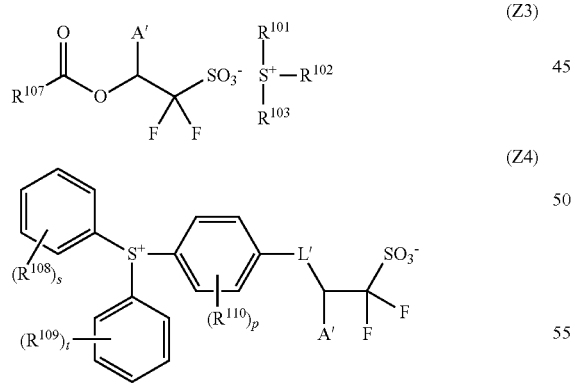

Herein A' is hydrogen or trifluoromethyl. $R^{101}$, $R^{102}$, and $R^{103}$ are as defined above. $R^{107}$ is a straight, branched or cyclic $C_1$-$C_{35}$ monovalent hydrocarbon group which may be substituted with or separated by a heteroatom. $R^{108}$, $R^{109}$, and $R^{110}$ are each independently hydrogen or a straight, branched or cyclic $C_1$-$C_{20}$ monovalent hydrocarbon group which may be separated by a heteroatom. Each of s and t is an integer of 0 to 5, p is an integer of 0 to 4. L' is a single bond, ether bond, or a straight, branched or cyclic $C_1$-$C_{20}$ divalent hydrocarbon group which may be substituted with or separated by a heteroatom.

When the acid generator is one having formula (Z3) or (Z4), preferably formula (Z3) or (Z4) wherein A' is trifluoromethyl, a pattern with improved properties, for example, a line-and-space pattern having low roughness (LWR) and improved control of acid diffusion length or a hole pattern having improved roundness and dimensional control can be formed.

Illustrative, non-limiting examples of the acid generators having formulae (Z1) to (Z4) are shown below. Notably A' is as defined above, and Ac stands for acetyl.

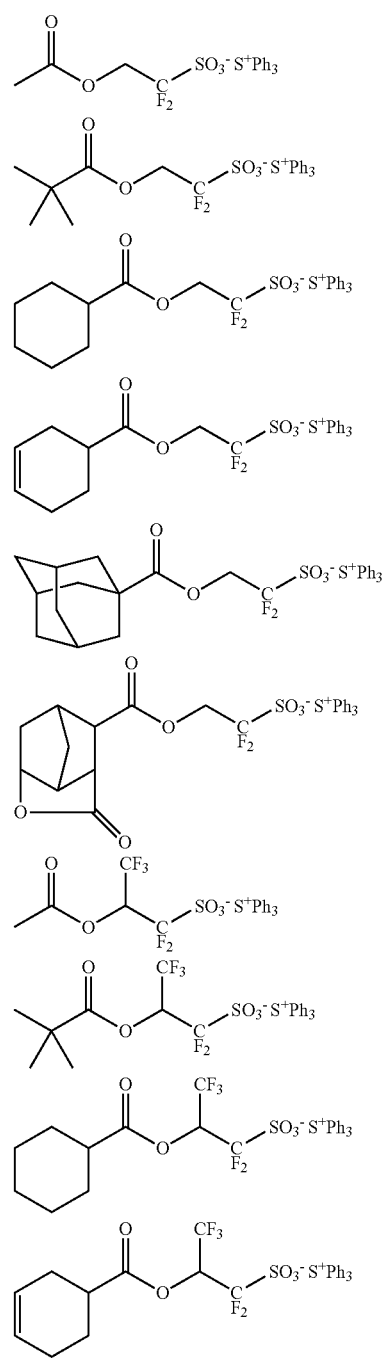

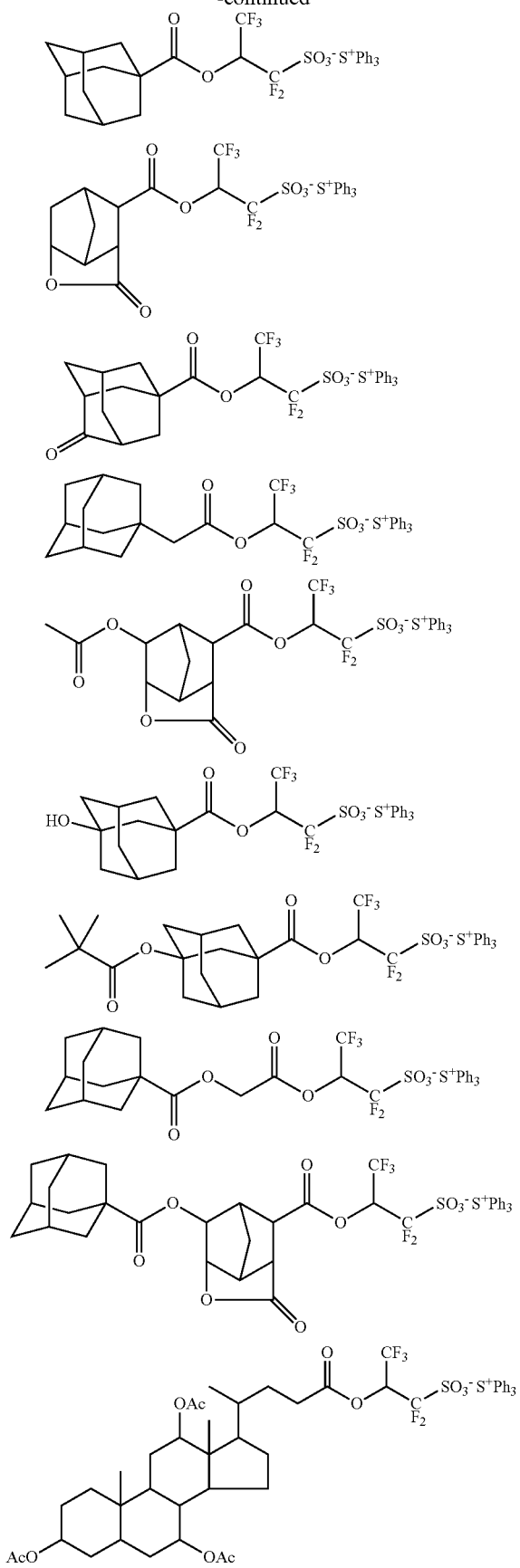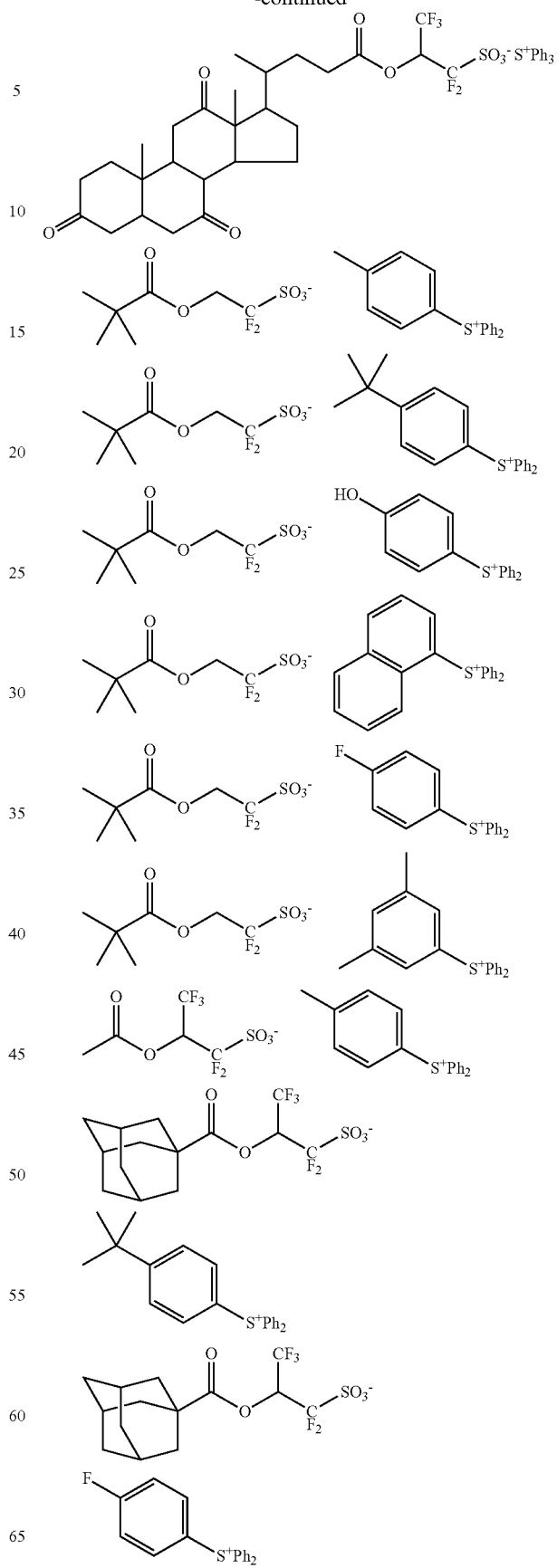

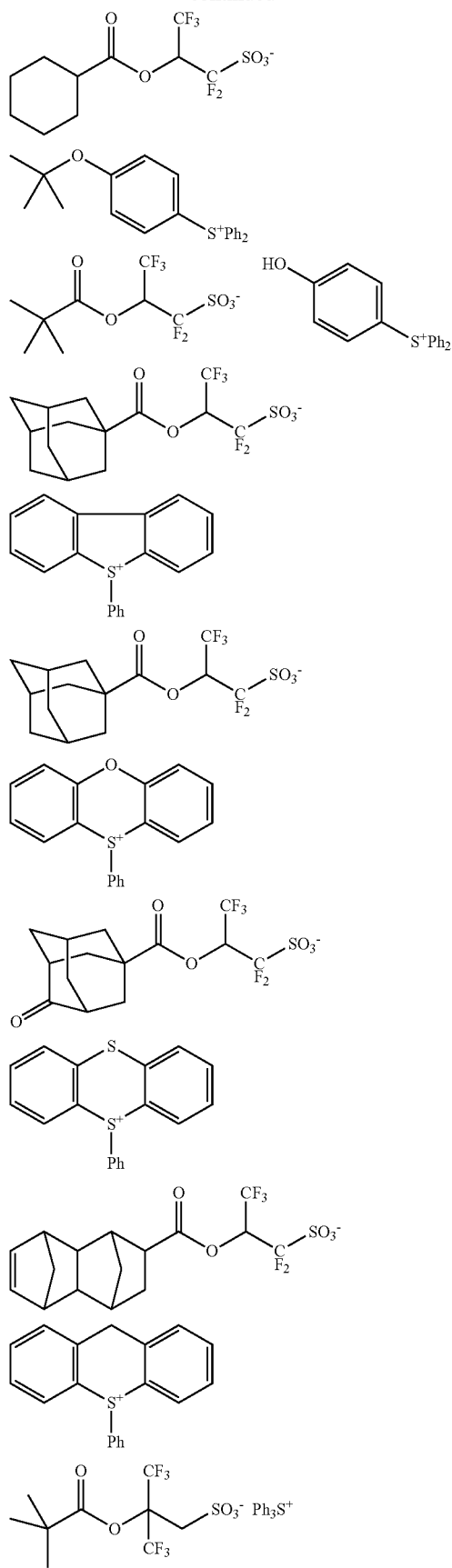
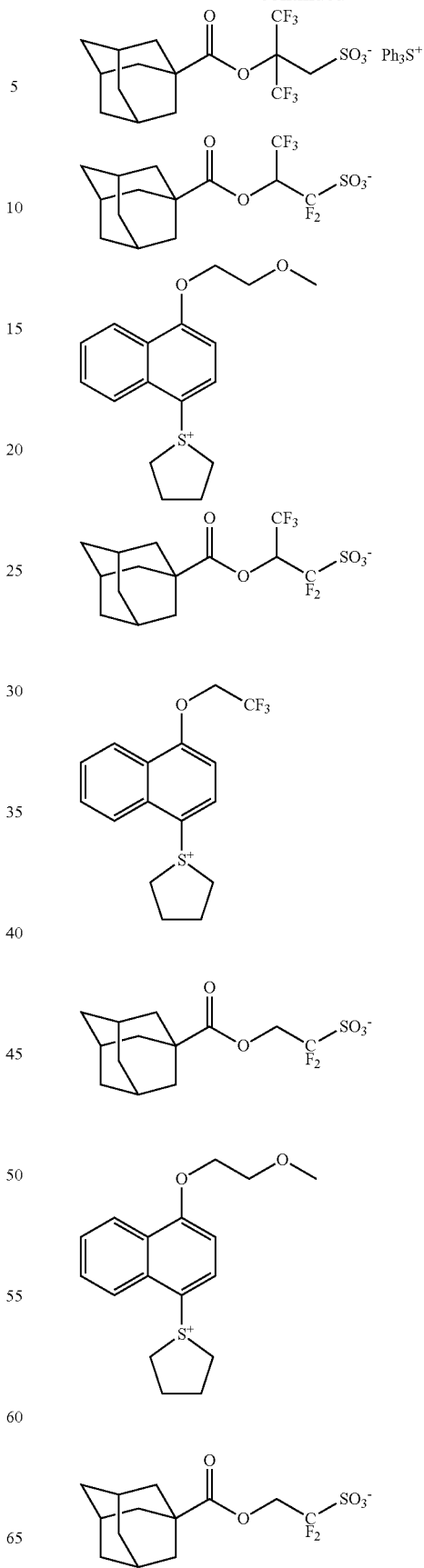

265
-continued
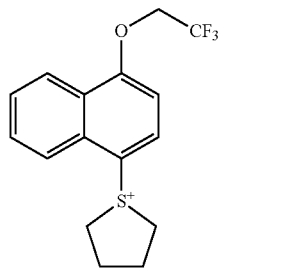
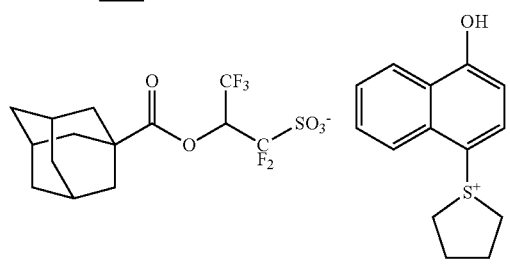
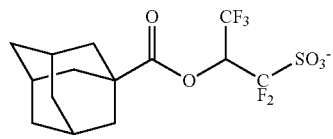
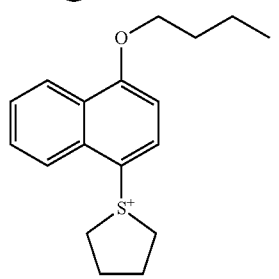
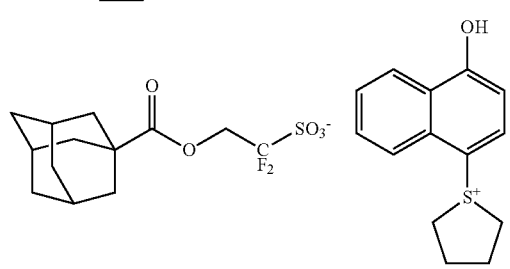
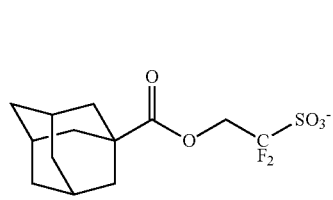
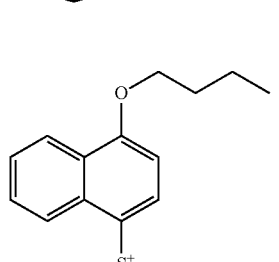
266
-continued
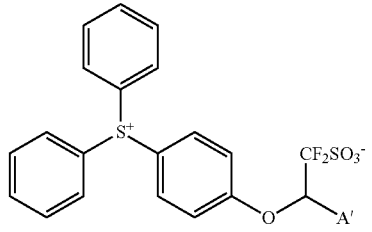
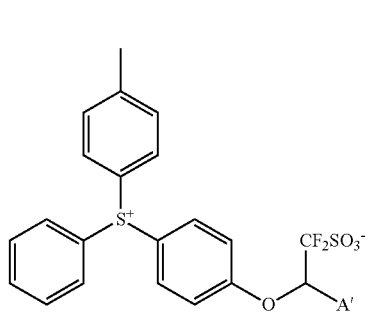
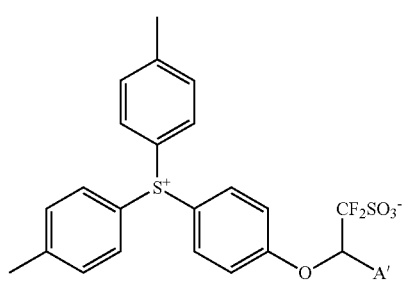
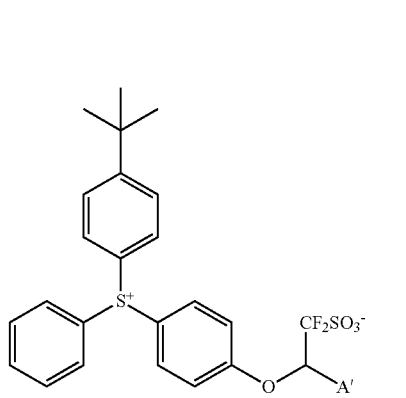
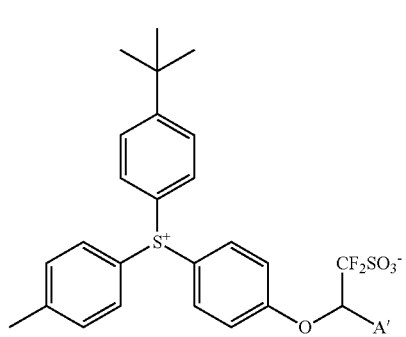

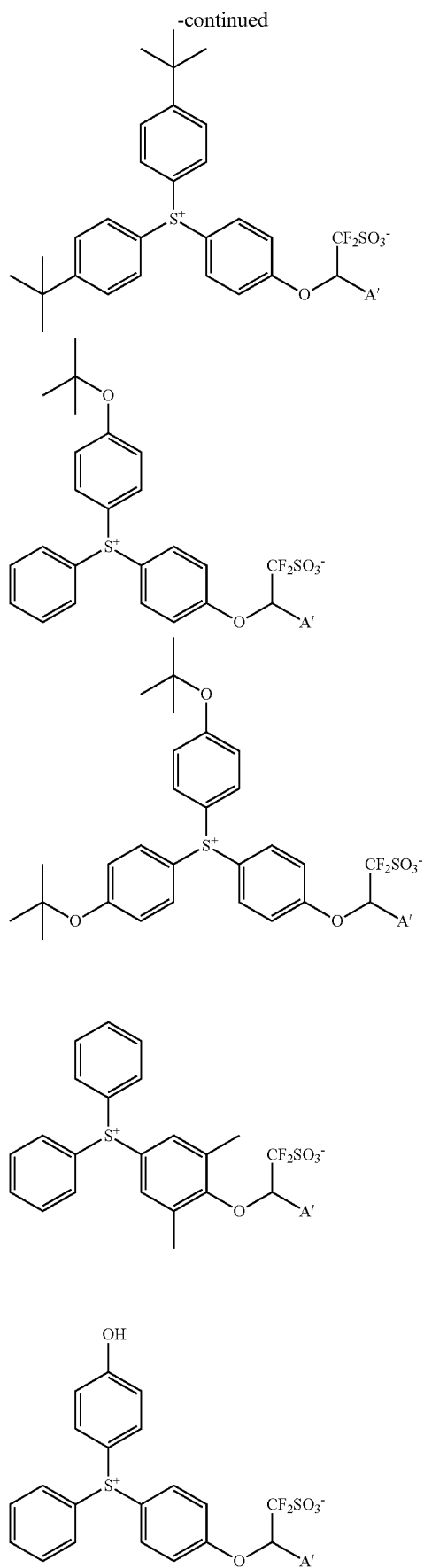
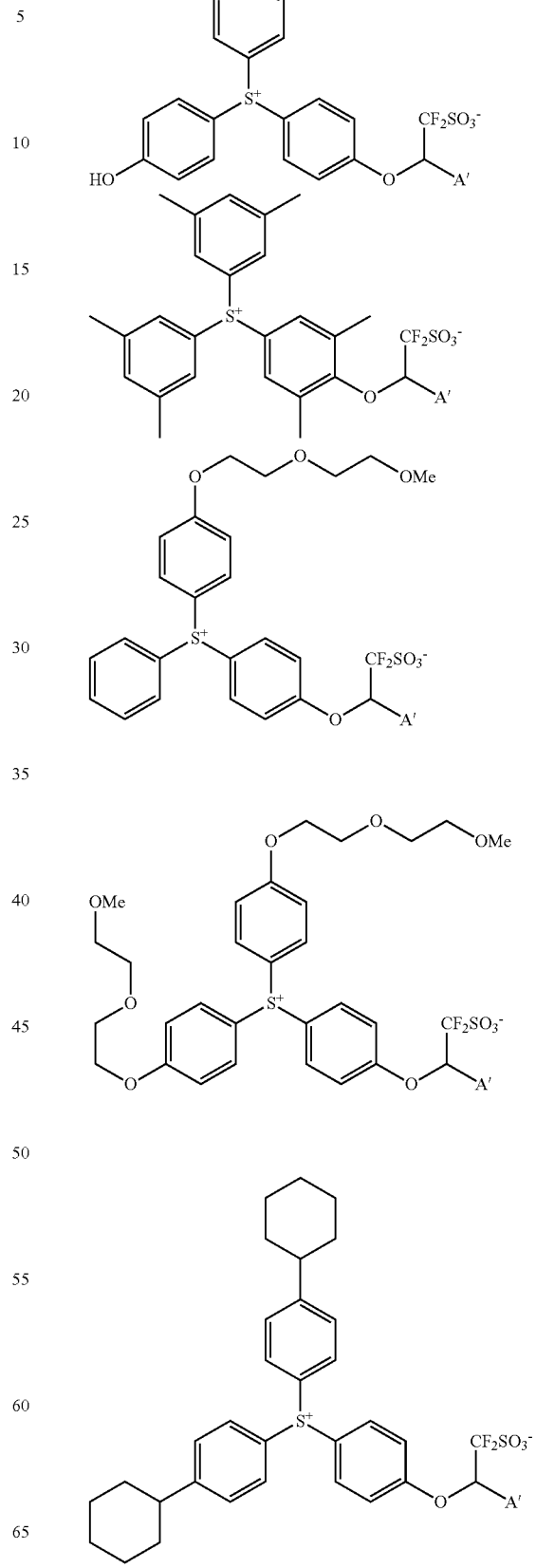

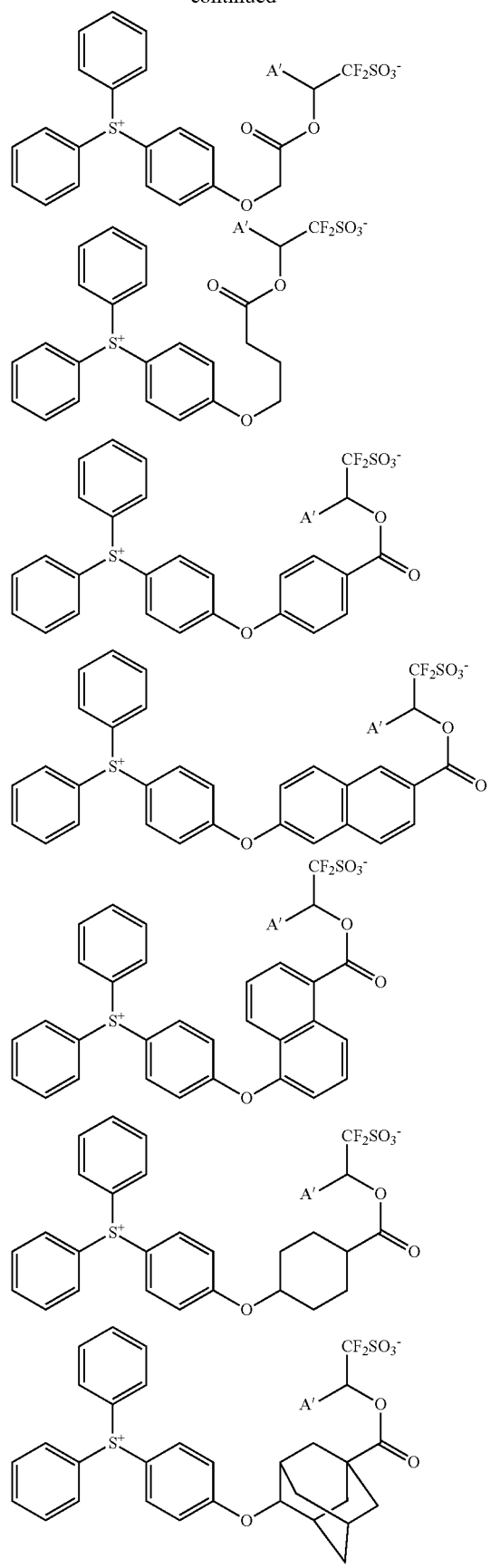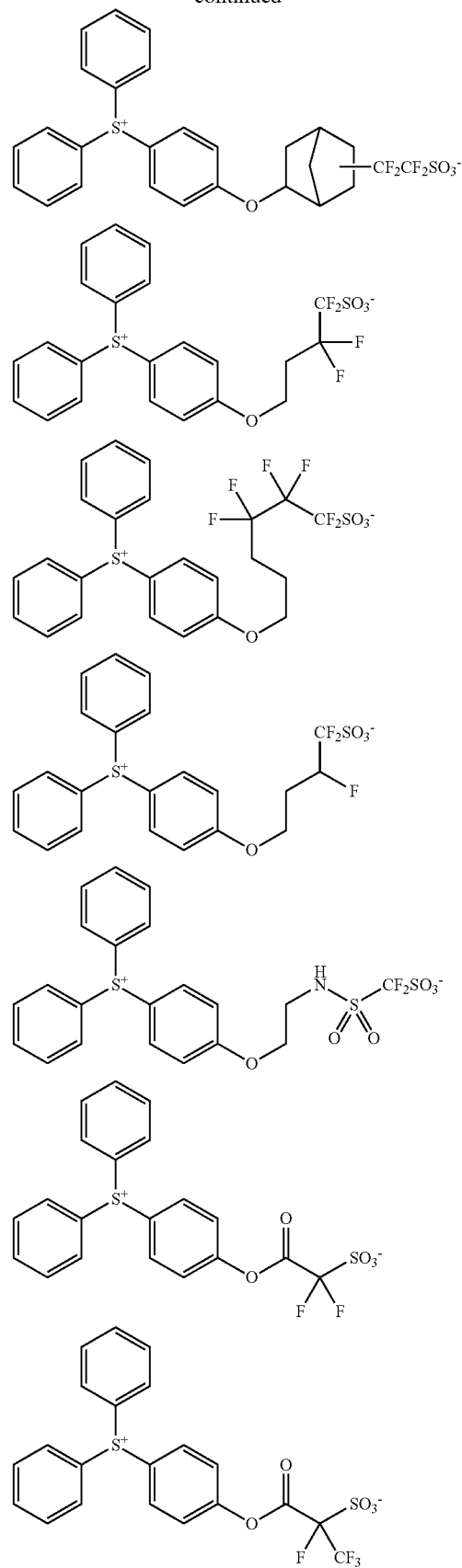

Suitable organic solvents include ketones such as cyclohexanone, cyclopentanone, methyl-2-n-pentyl ketone, and diacetone alcohol; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, methyl lactate, ethyl lactate, n-butyl lactate, ethyl pyruvate, butyl acetate, methyl 3-methoxypropionate, ethyl 3-ethoxypropionate, t-butyl acetate, tert-butyl propionate, propylene glycol mono-t-butyl ether acetate, methyl 2-hydroxyisobutyrate, isopropyl 2-hydroxyisobutyrate, isobutyl 2-hydroxyisobutyrate, and n-butyl 2-hydroxyisobutyrate; and lactones such as γ-butyrolactone, which may be used alone or in admixture.

Examples of the basic compound used herein include primary, secondary, and tertiary amine compounds as described in JP-A 2008-111103 (U.S. Pat. No. 7,537,880), paragraphs [0146]-[0164], specifically amine compounds having a hydroxyl, ether, ester, lactone, cyano or sulfonic ester group, and compounds having a carbamate group as described in JP 3790649.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acids as described in US 2013034813 (JP-A 2013-037092) may be used as the quencher. Where an α-position non-fluorinated sulfonic acid salt or carboxylic acid salt and an α-position fluorinated sulfonic acid, imide acid, or methide acid generated by a PAG are co-present, salt exchange occurs to generate an α-position non-fluorinated sulfonic acid or carboxylic acid. Since this α-position non-fluorinated sulfonic acid or carboxylic acid has an insufficient acid strength to induce deprotection reaction to the resist resin, the relevant sulfonium salt, iodonium salt or ammonium salt functions as a quencher. In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed area, further improved focus margin or DOF and satisfactory dimensional control.

In case the polarity switching unit of formula (1a), (1b), (1aa) or (1bb) in the base resin has a high reactivity with acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Illustrative, non-limiting examples of the α-position non-fluorinated sulfonic acid salt and carboxylic acid salt are given below.

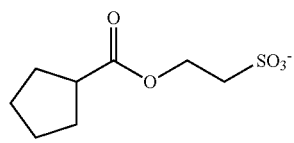

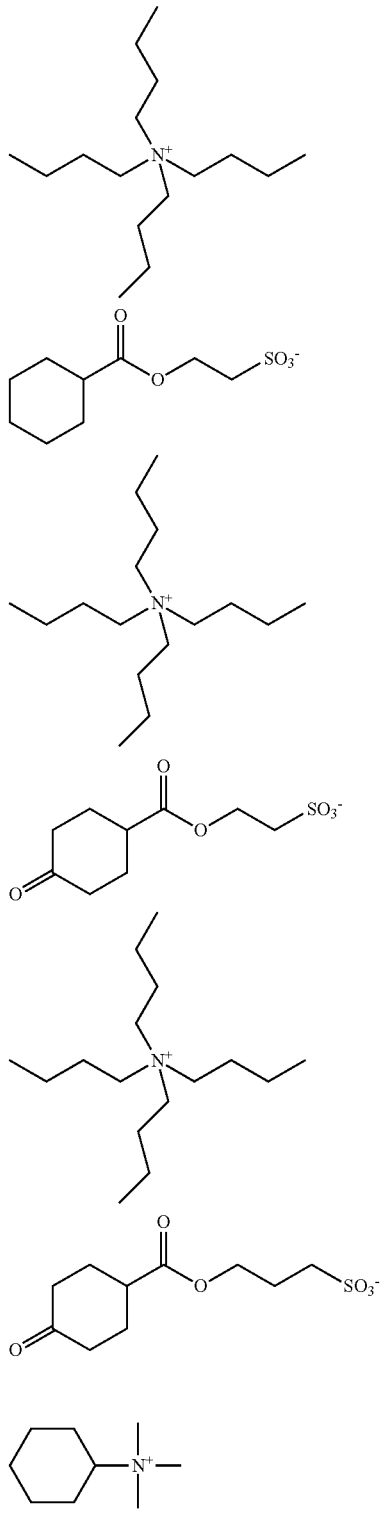

273
-continued
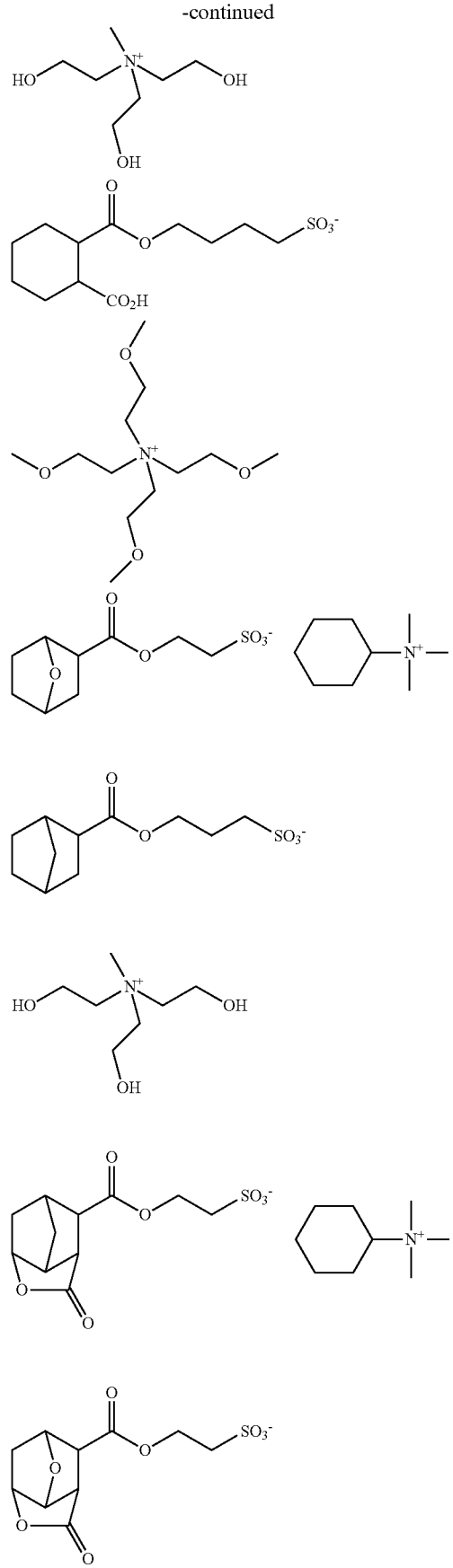
274
-continued
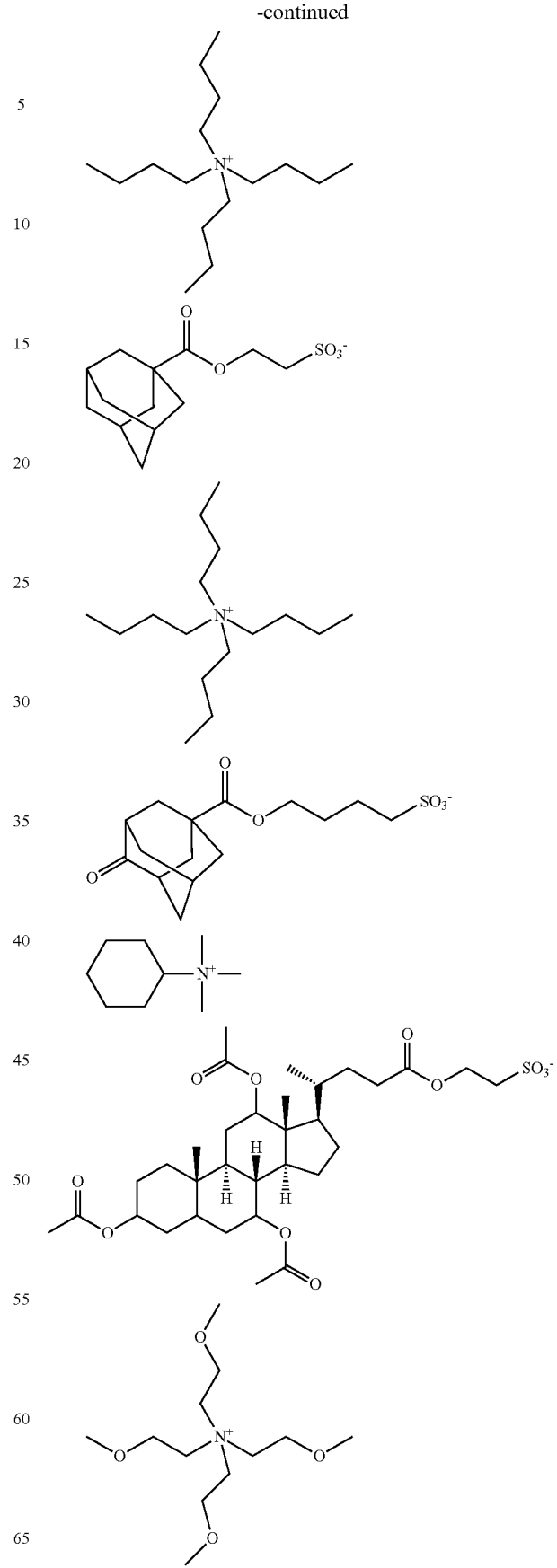

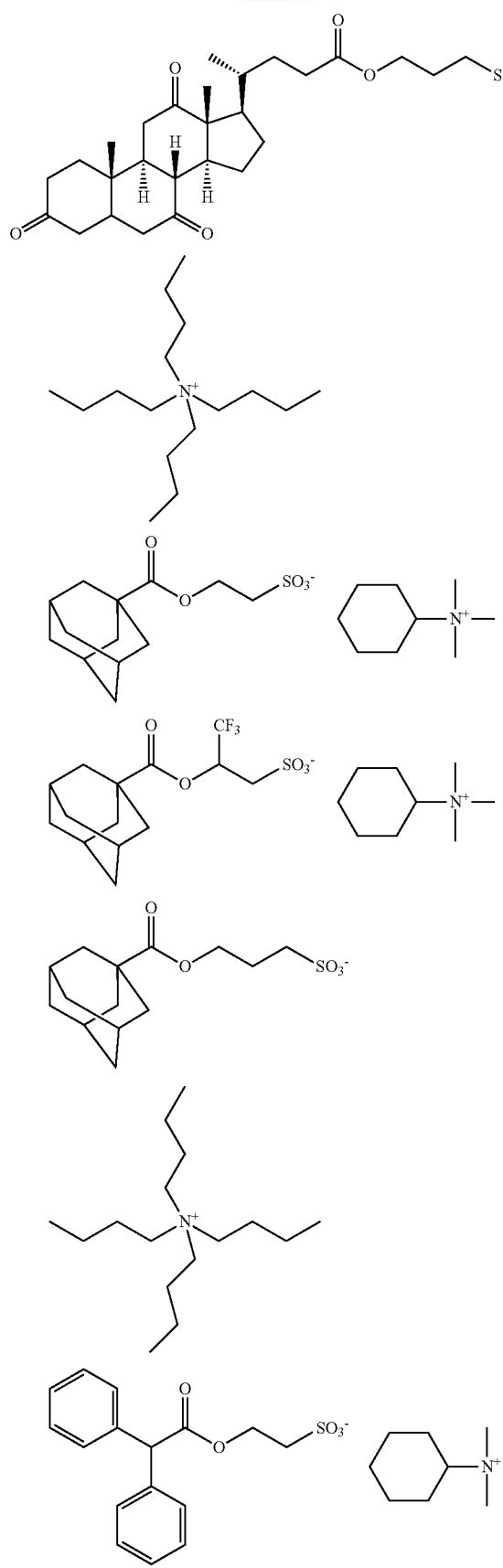
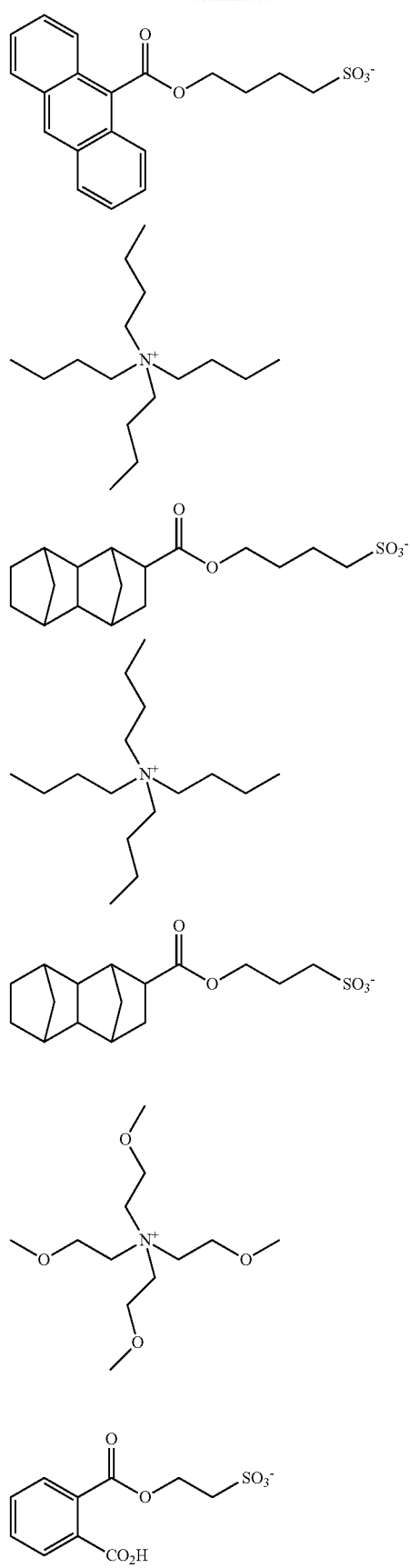

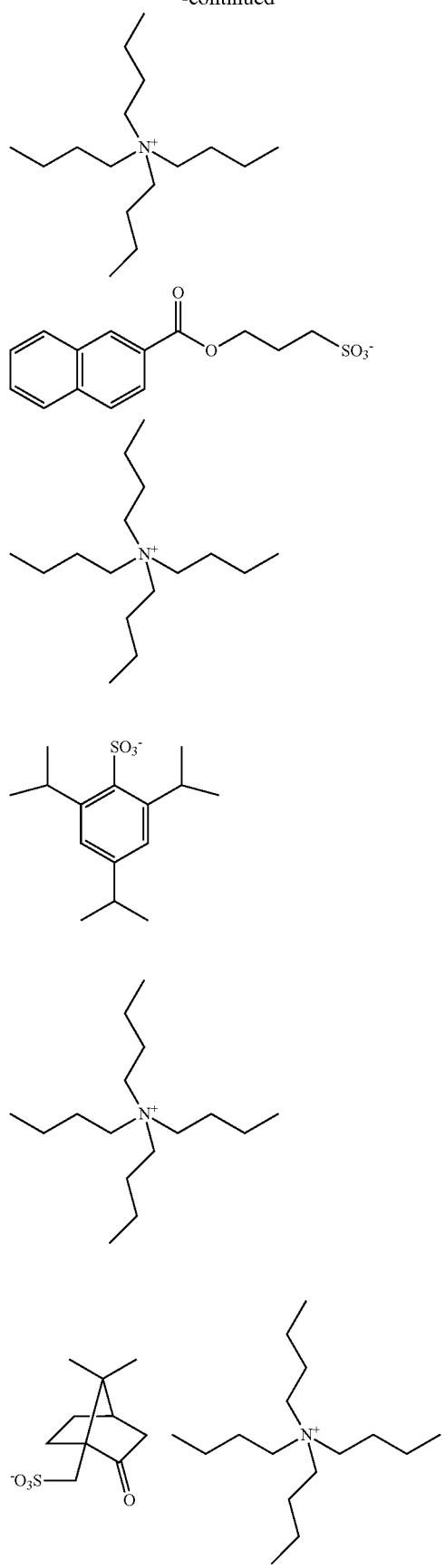
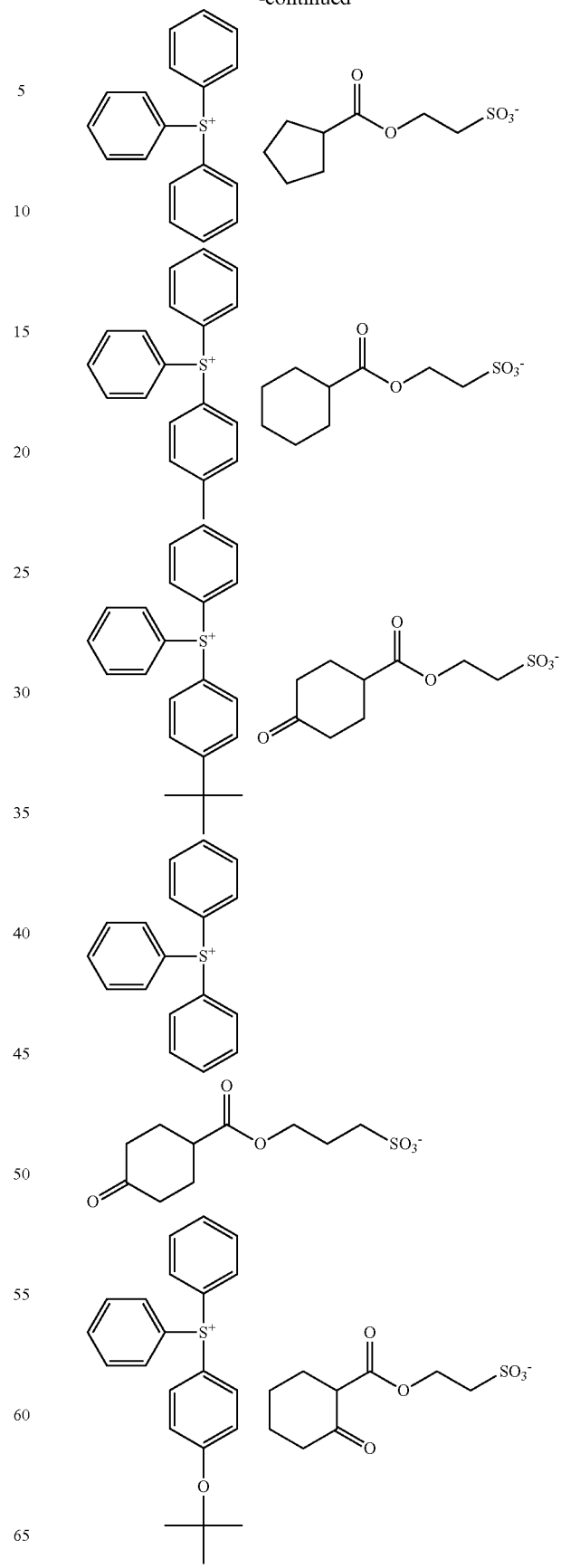

279
-continued
280
-continued
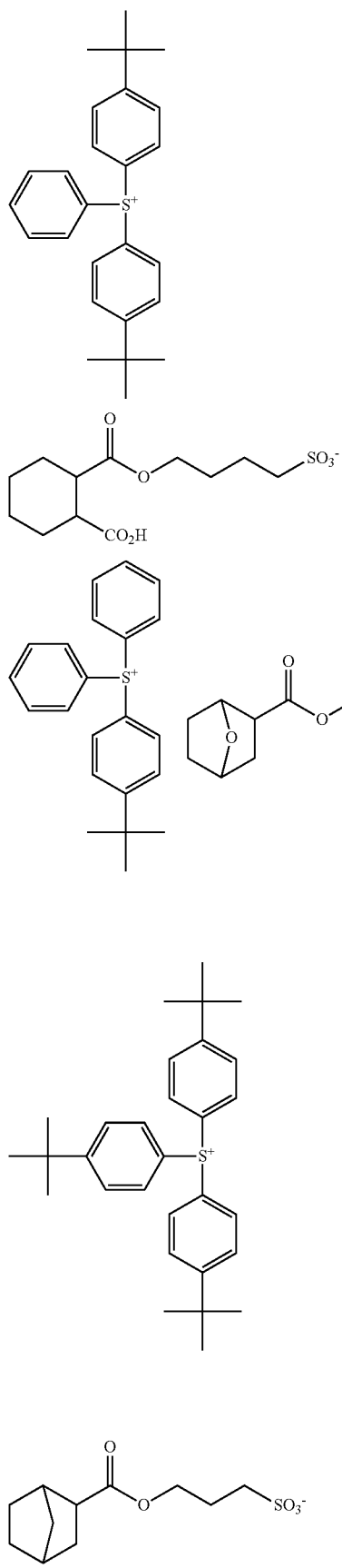
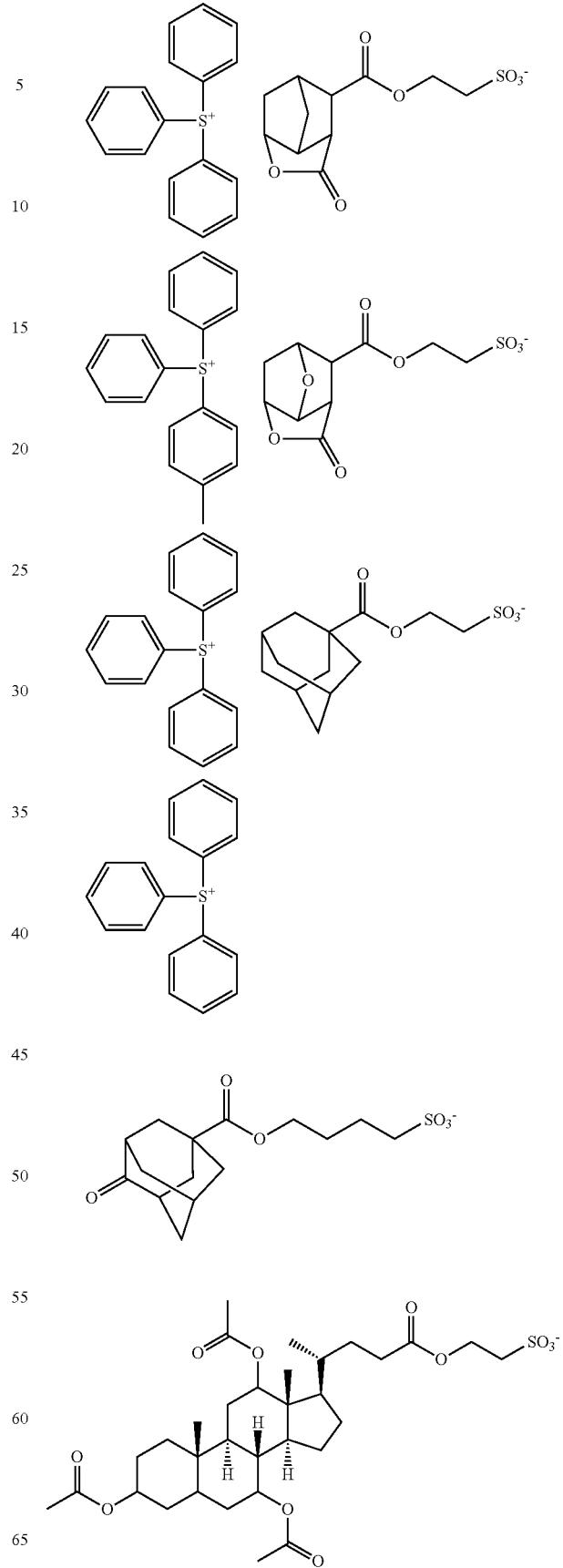

281
-continued
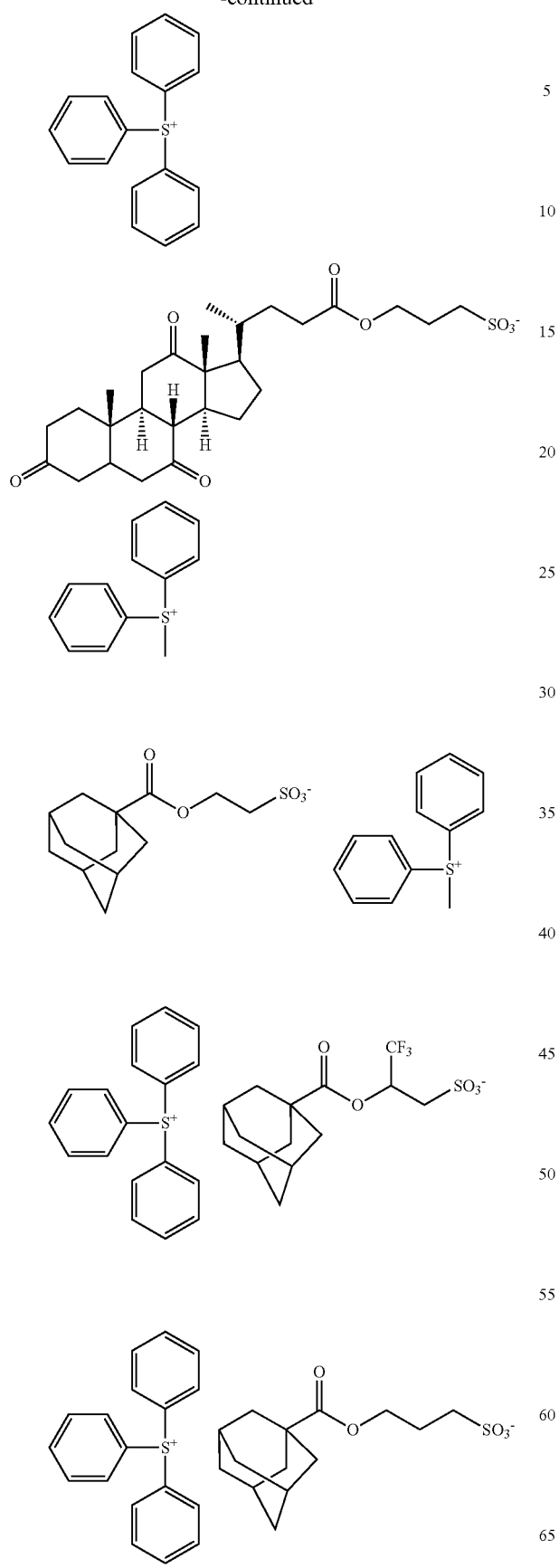
282
-continued
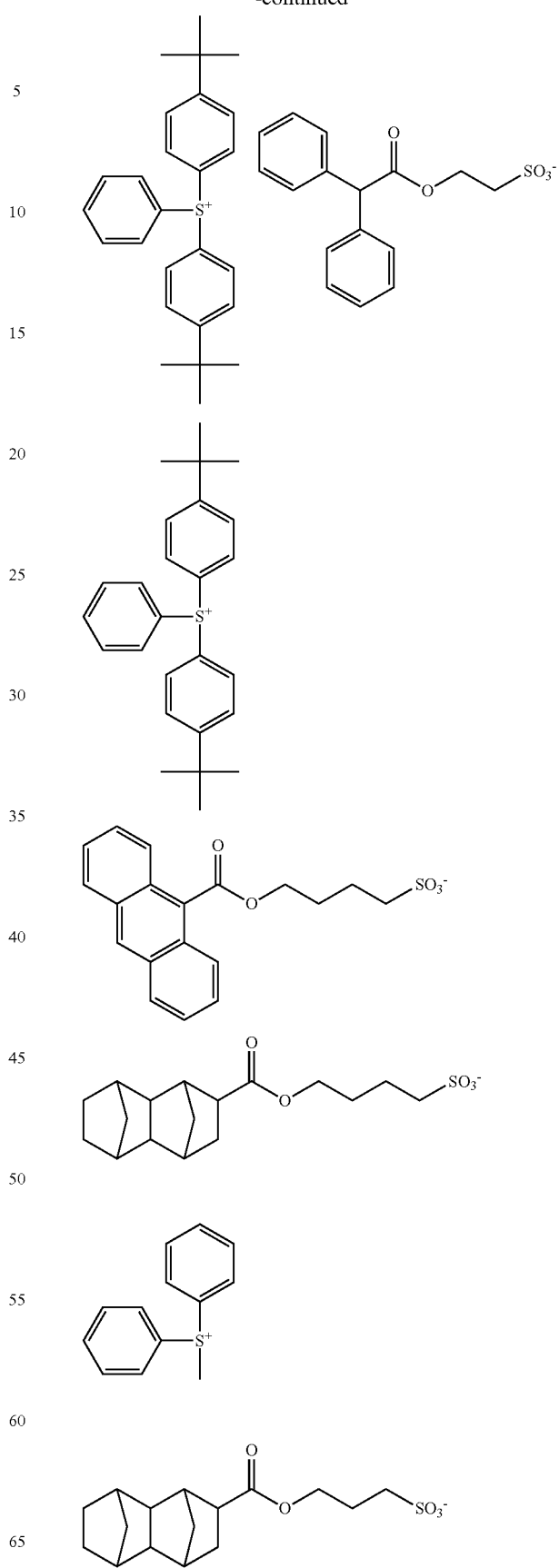

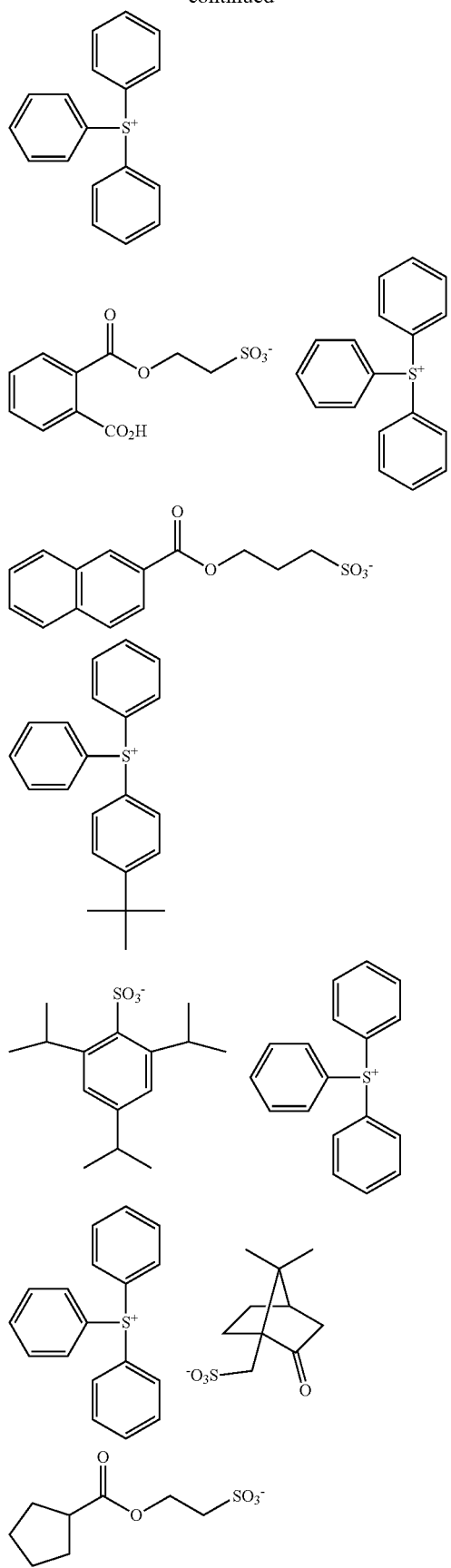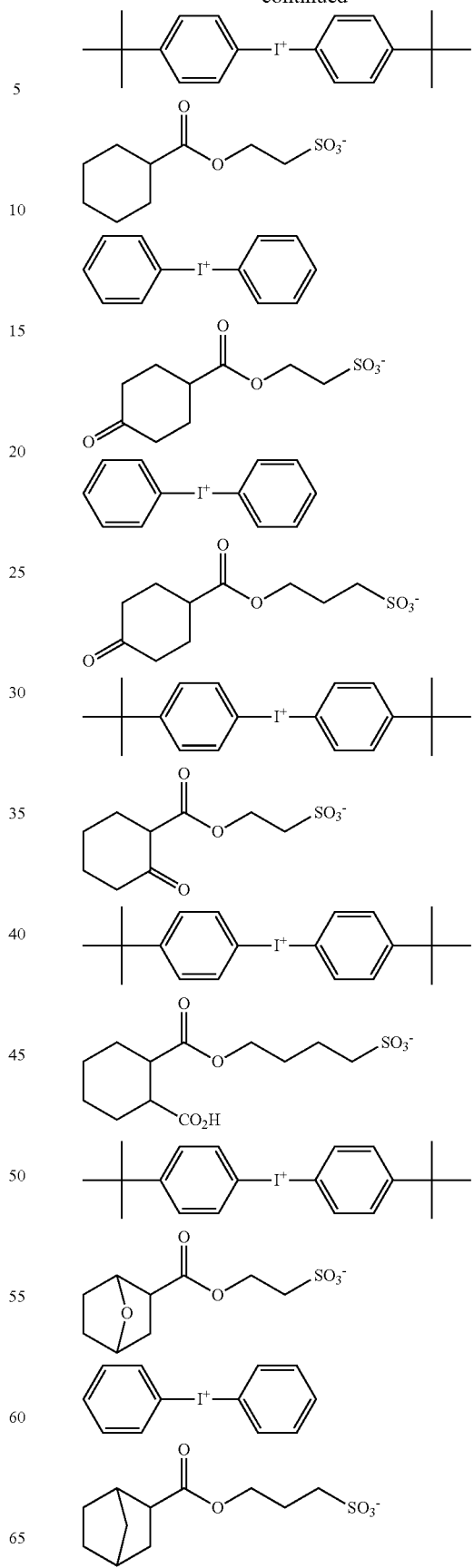

-continued
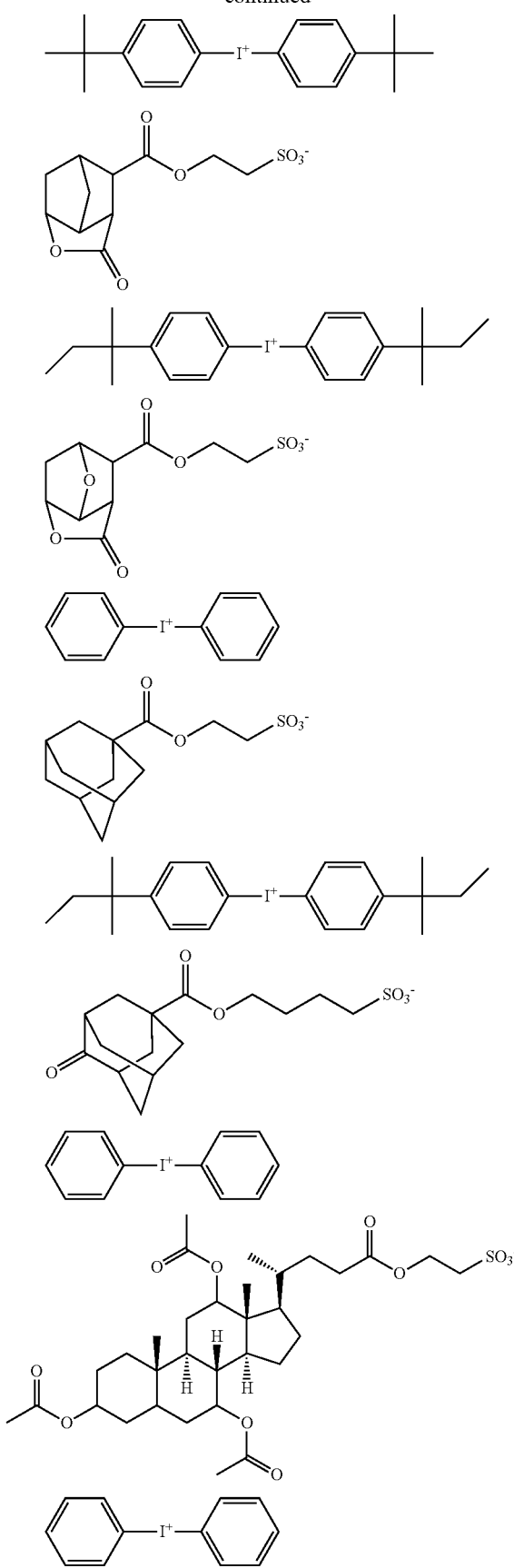
-continued
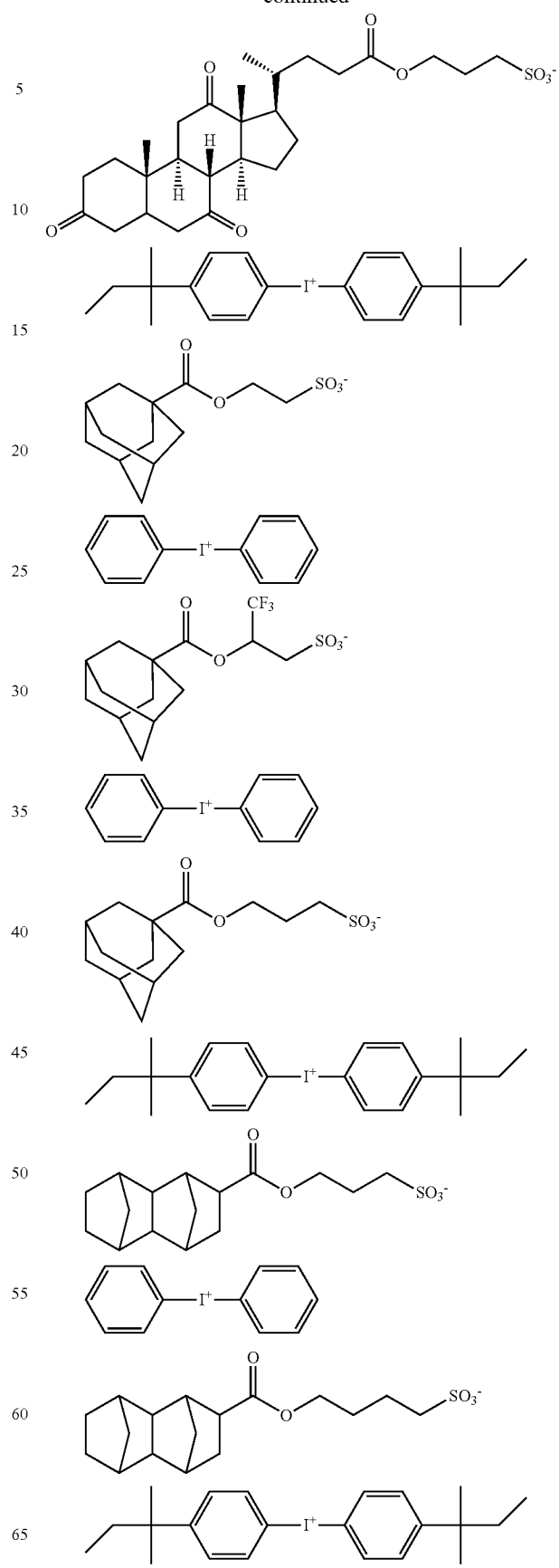

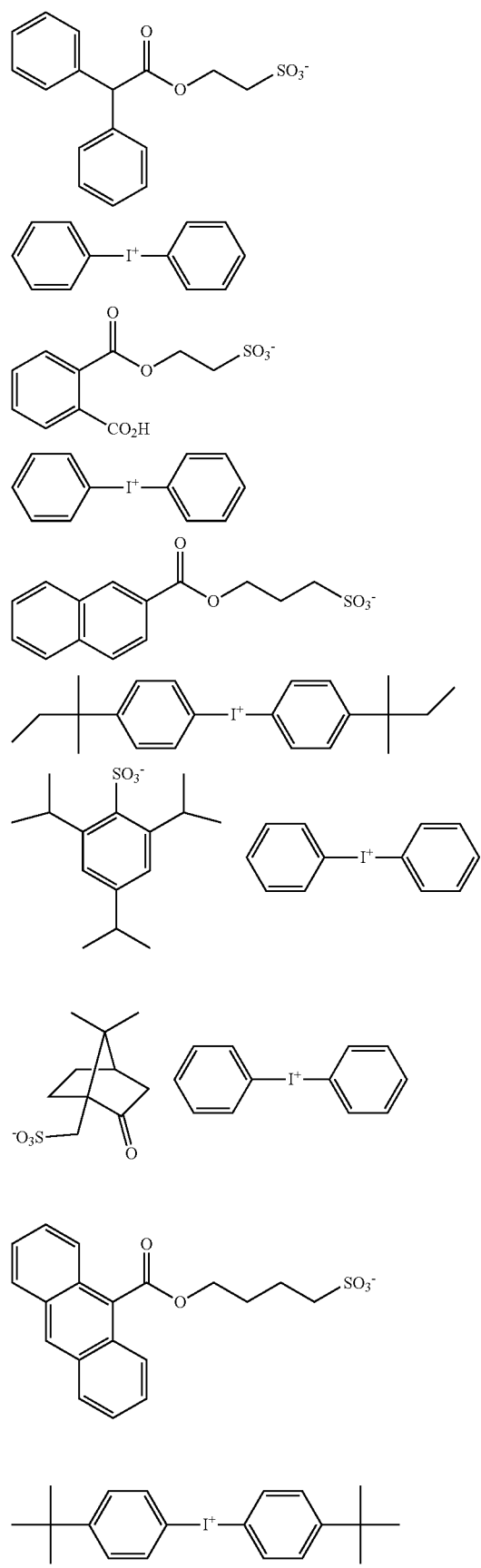
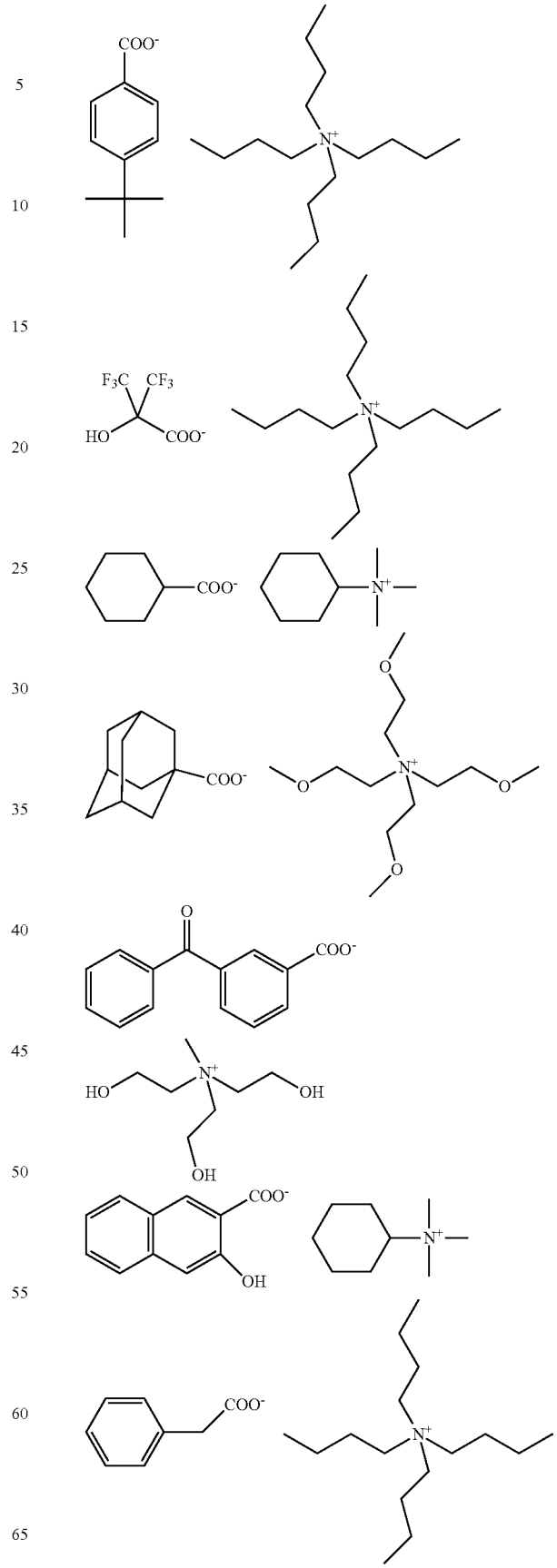

289
-continued
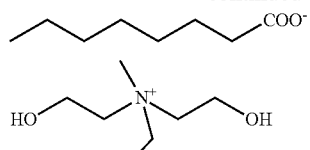
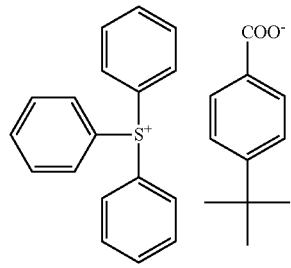
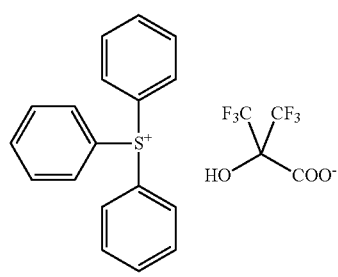
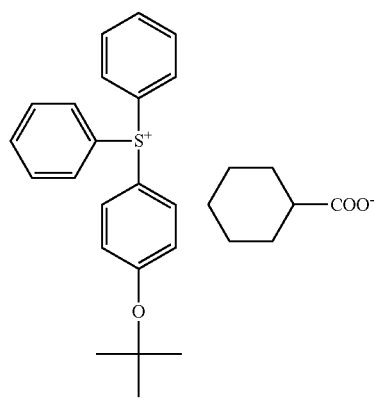
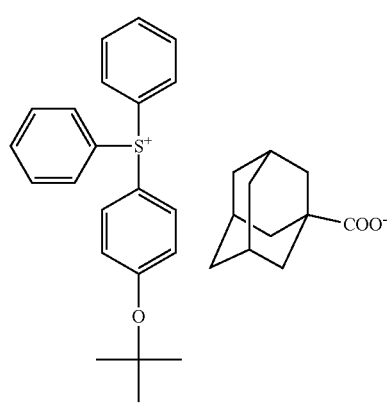
290
-continued
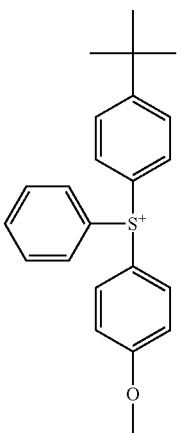
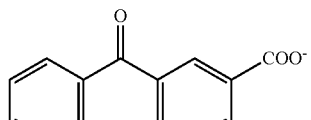
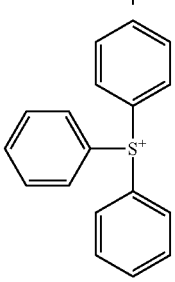
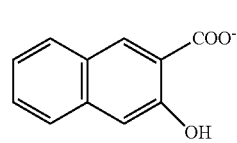
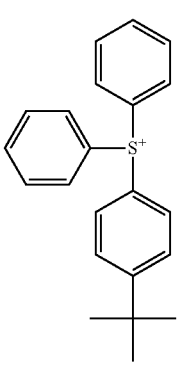
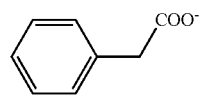
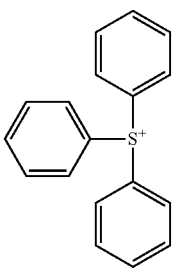
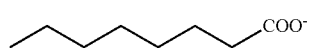
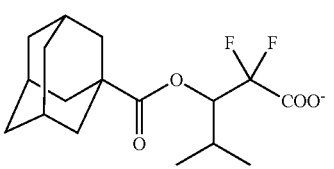

291
-continued
292
-continued
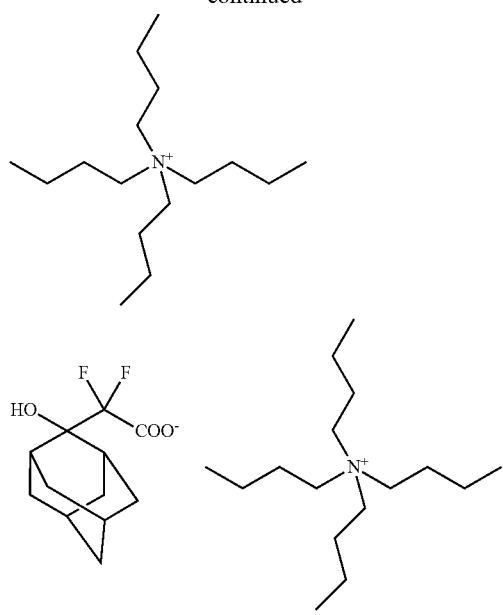
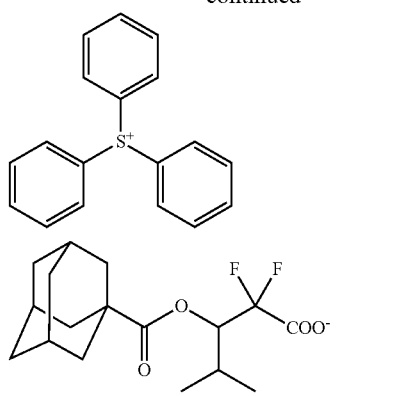
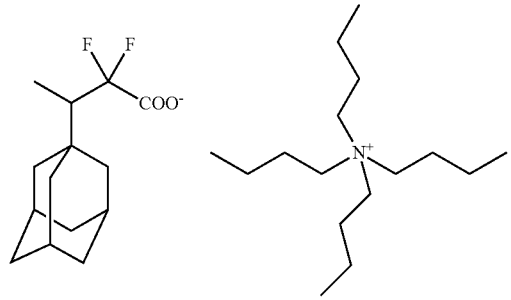
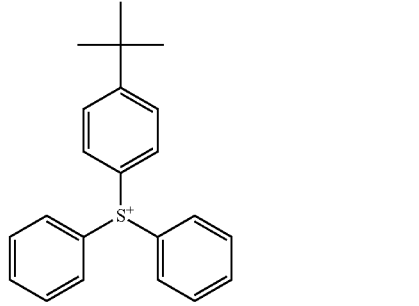
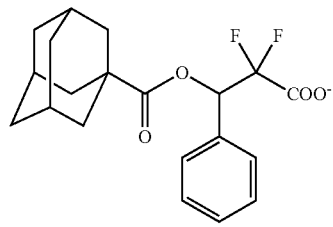
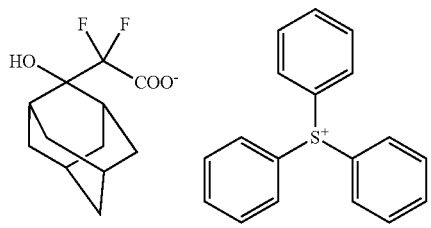
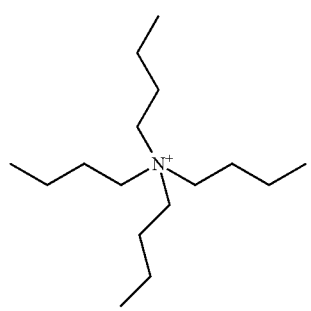
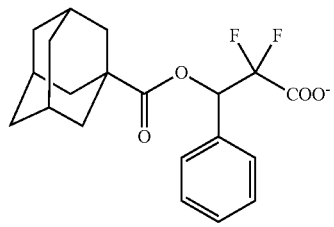
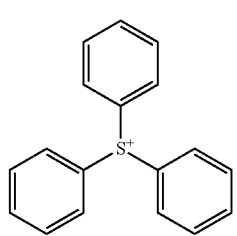
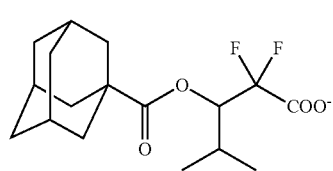
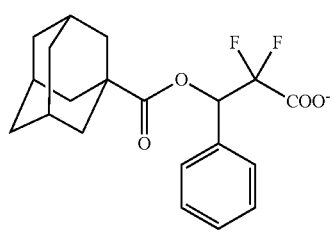

-continued

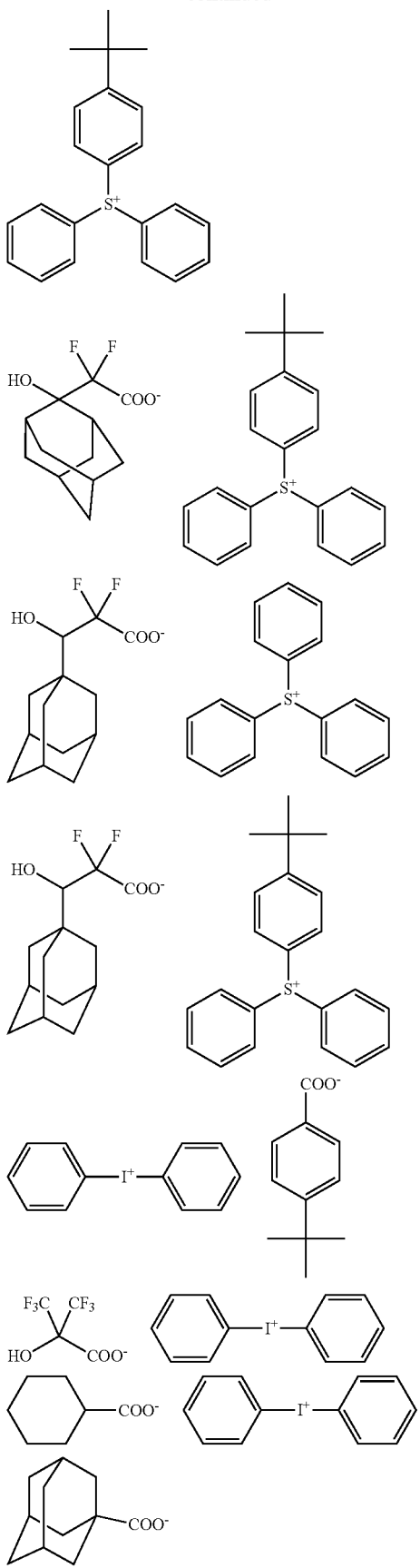

-continued

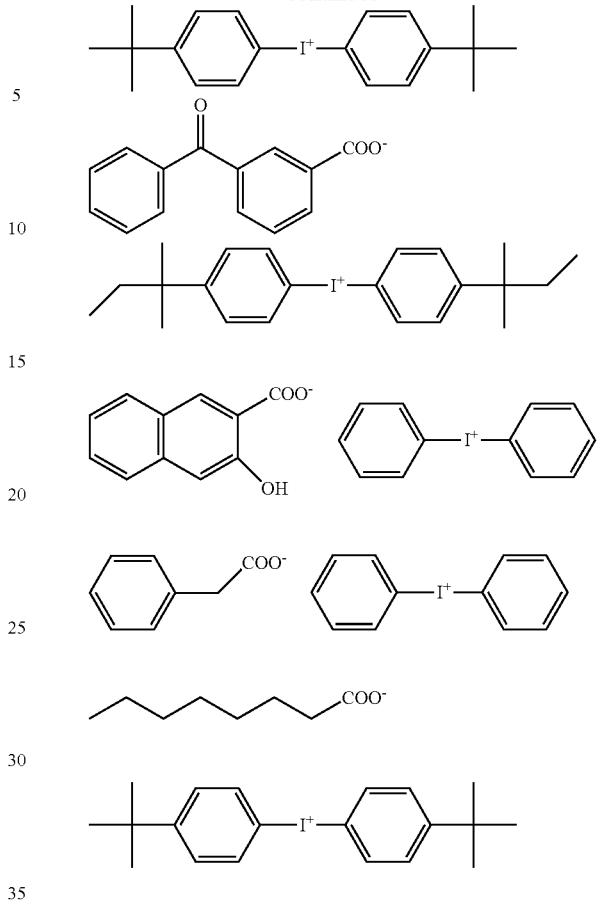

Exemplary surfactants are described in JP-A 2008-111103, paragraphs [0165]-[0166]. Exemplary dissolution regulators are described in JP-A 2008-122932 (US 2008090172), paragraphs [0155]-[0178], and exemplary acetylene alcohols in paragraphs [0179]-[0182].

Notably, an appropriate amount of the organic solvent used is 50 to 10,000 parts, preferably 100 to 5,000 parts by weight, an appropriate amount of the dissolution regulator is 0 to 50 parts, preferably 0 to 40 parts by weight, and an appropriate amount of the basic compound is 0 to 100 parts, preferably 0.001 to 50 parts by weight, per 100 parts by weight of the base resin. Amounts of the surfactant and acetylene alcohol may be determined as appropriate for a particular purpose.

Also a polymeric additive may be added for improving the water repellency on surface of a resist film as spin coated. This water repellency improver may be used in the topcoatless immersion lithography. These water repellency improvers have a specific structure with a 1,1,1,3,3,3-hexafluoro-2-propanol residue and are described in JP-A 2007-297590, JP-A 2008-111103, JP-A 2008-122932, JP-A 2012-128067, and JP-A 2013-057836.

The water repellency improver is described in more detail. Preferred are a homopolymer consisting of fluorine-containing units of one type, a copolymer consisting of fluorine-containing units of more than one type, and a copolymer consisting of fluorine-containing units and other units. Suitable fluorine-containing units and other units are shown below, but not limited thereto. Notably $R^{55}$ is hydrogen or methyl.

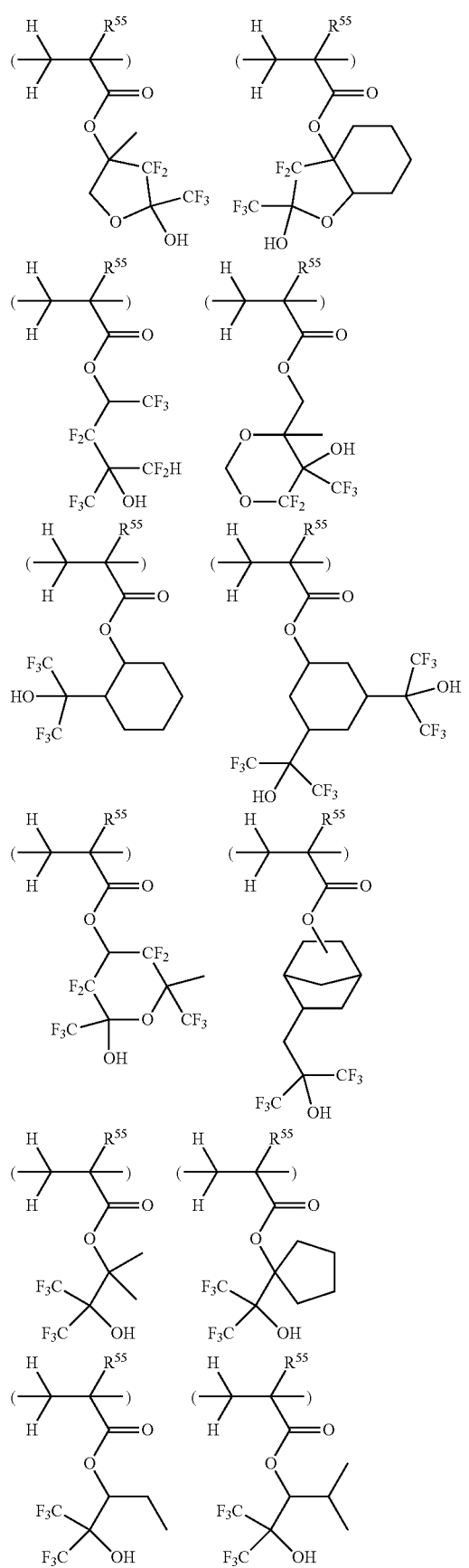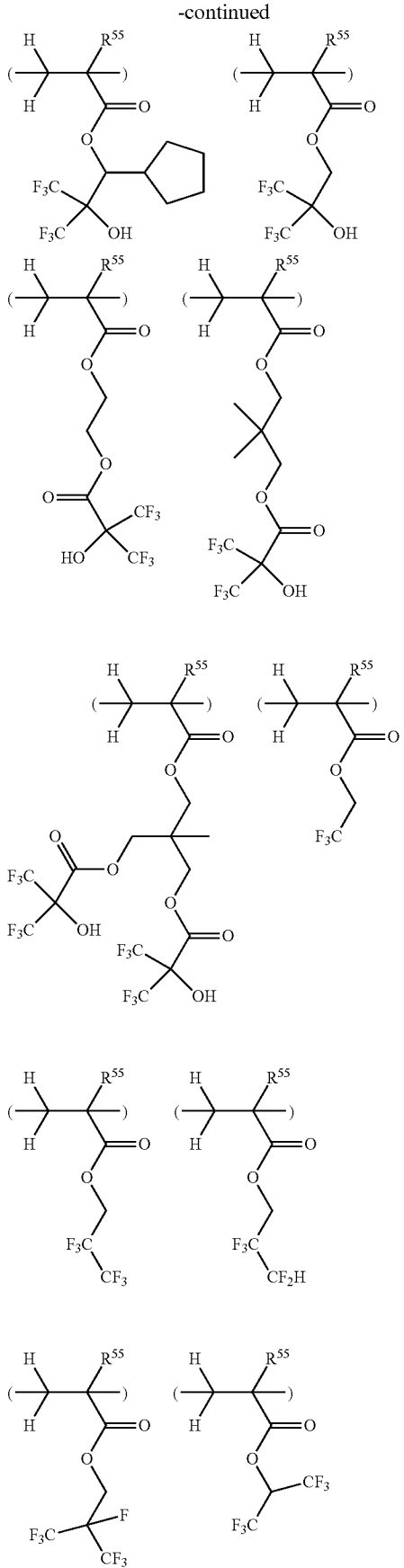

297
-continued
298
-continued
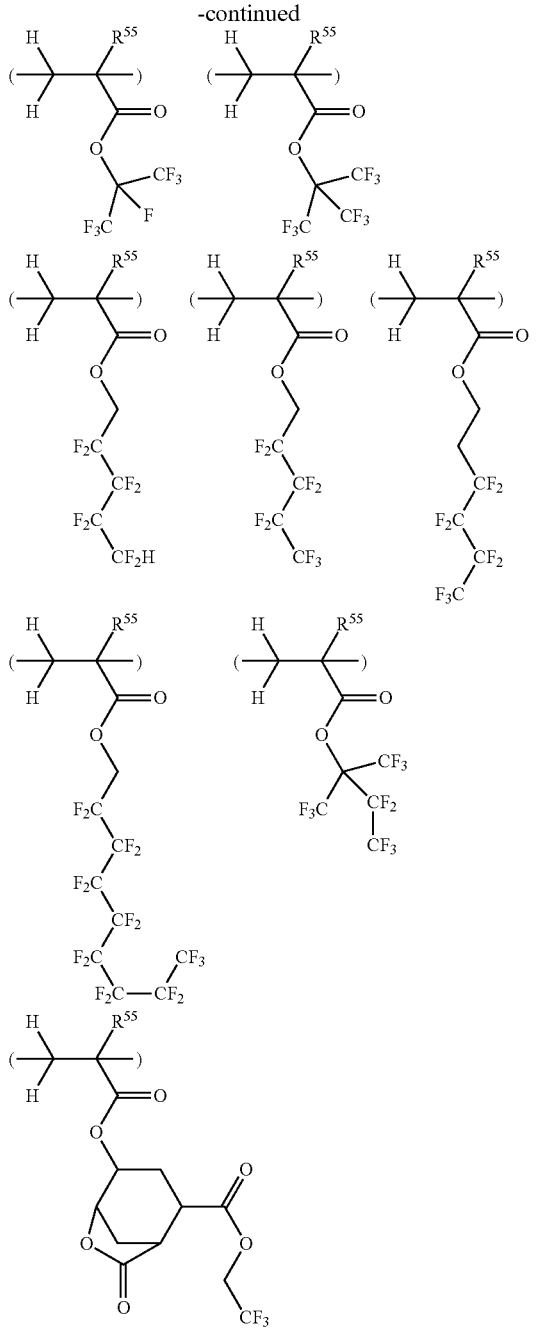
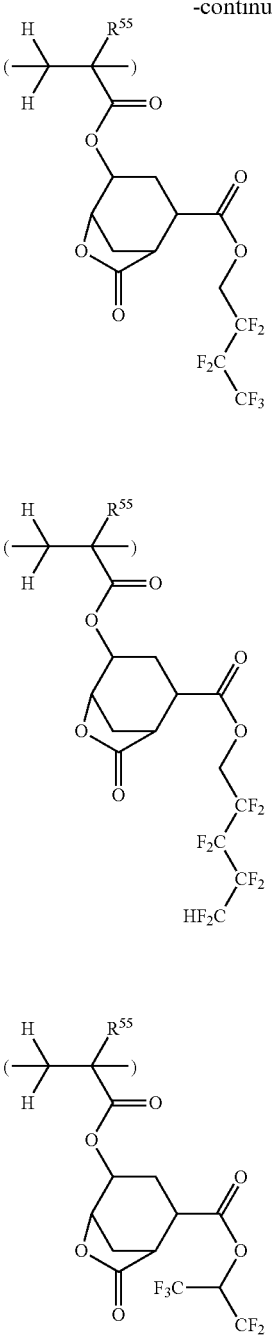
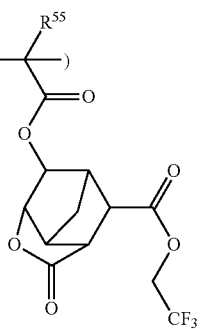

299
-continued
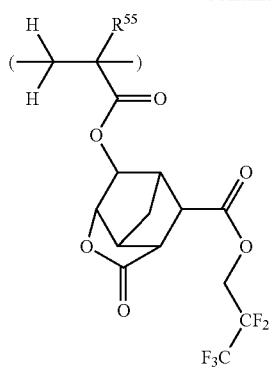
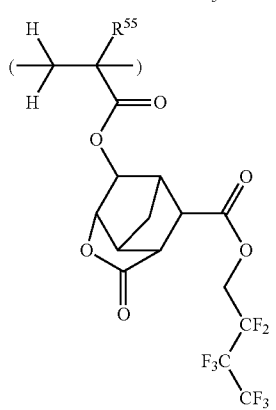
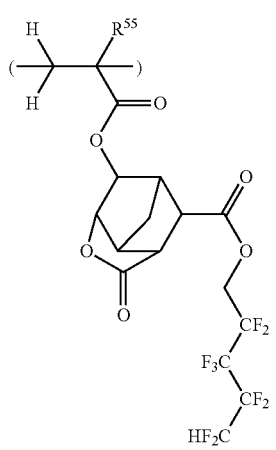
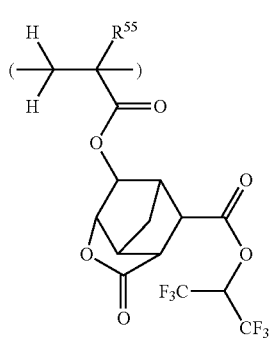
300
-continued
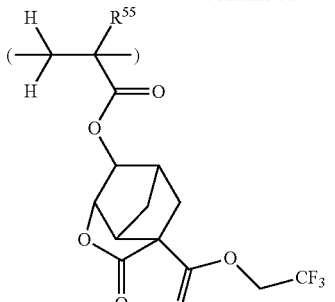
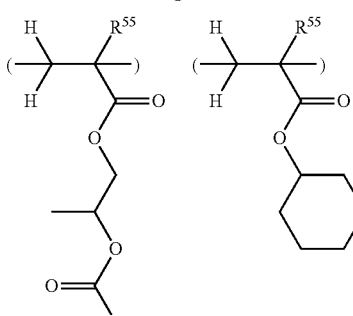
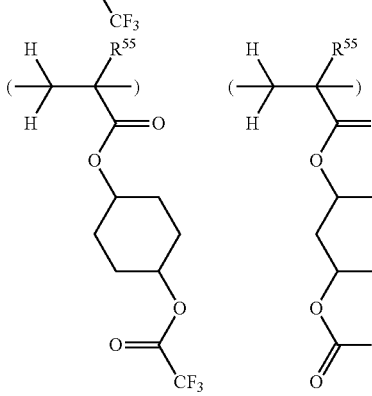
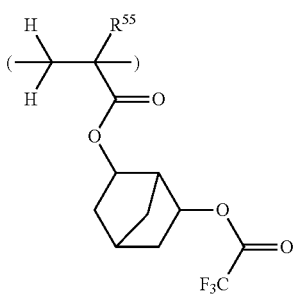
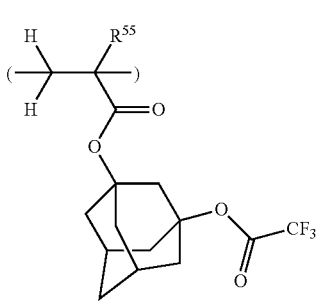

301
-continued
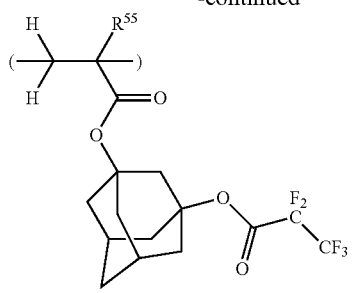
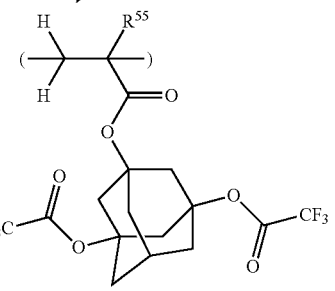
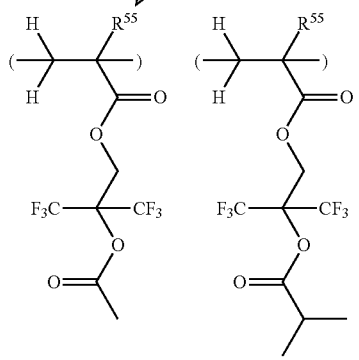
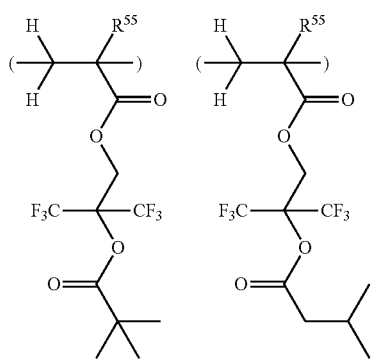
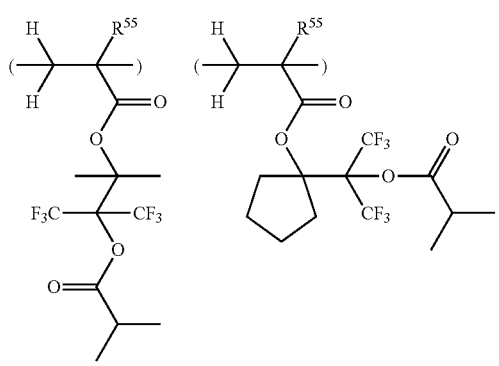
302
-continued
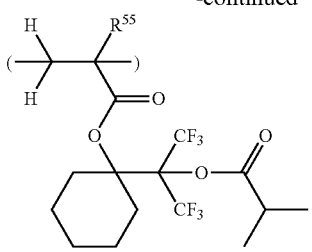
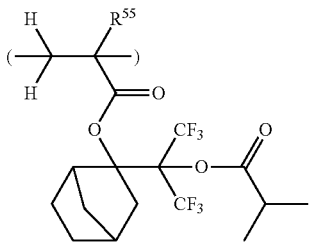
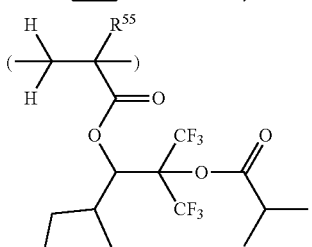
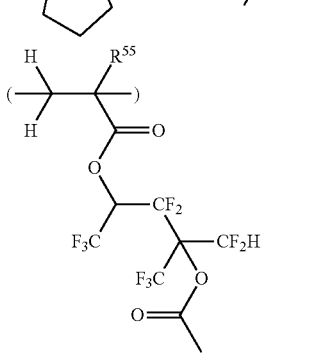
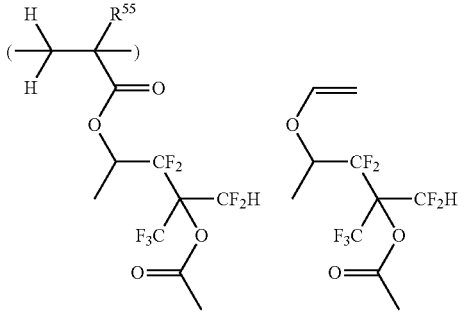
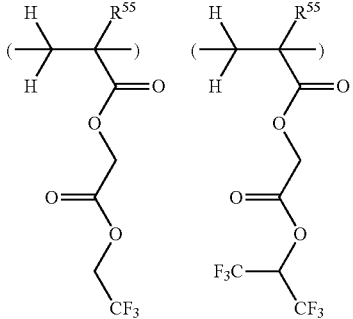

-continued
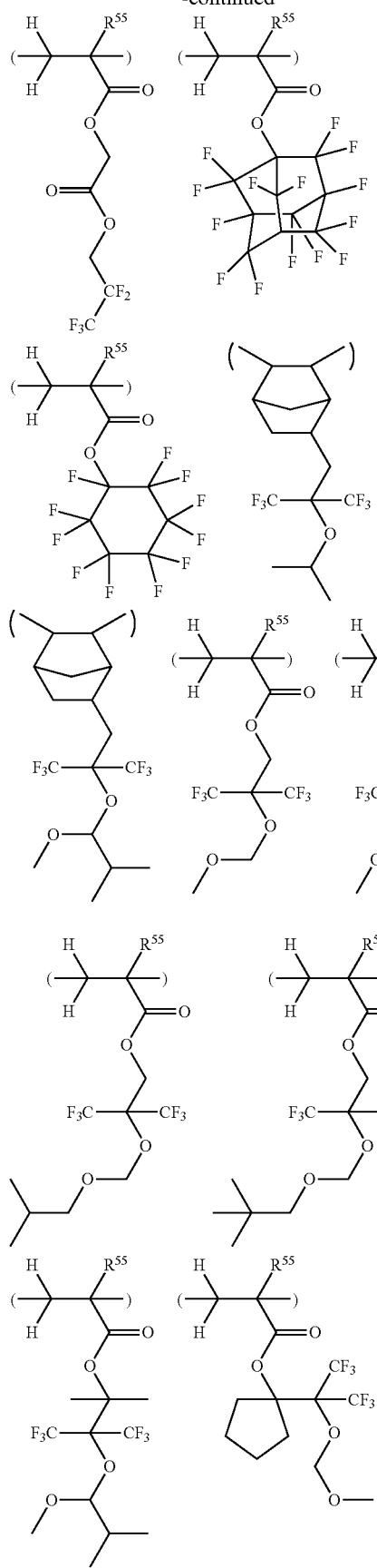
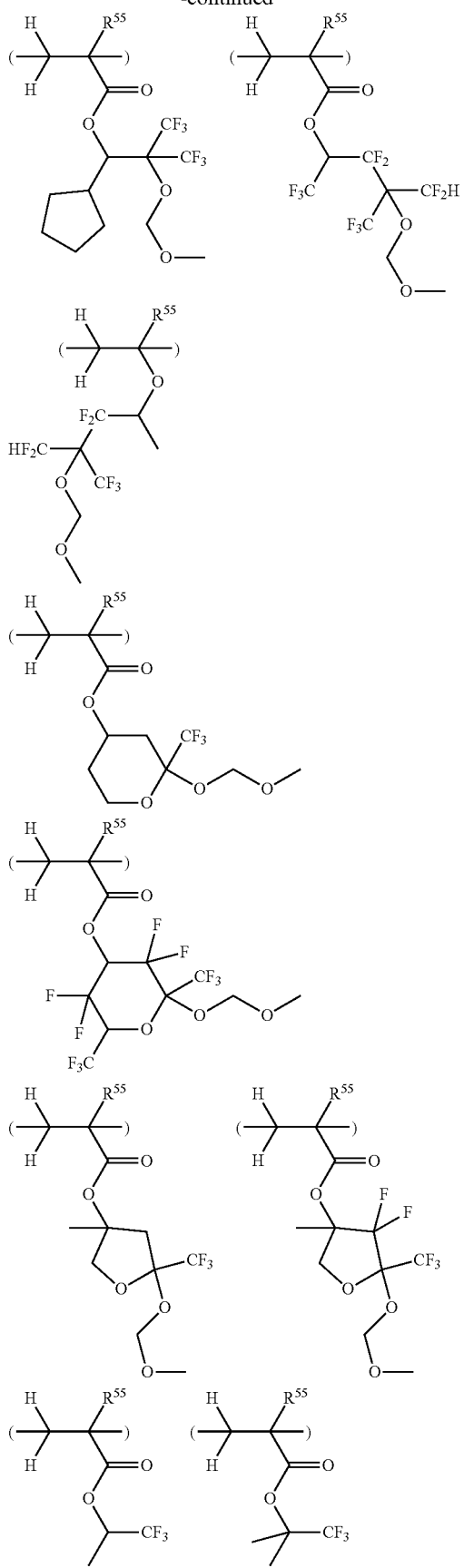

305
-continued
306
-continued
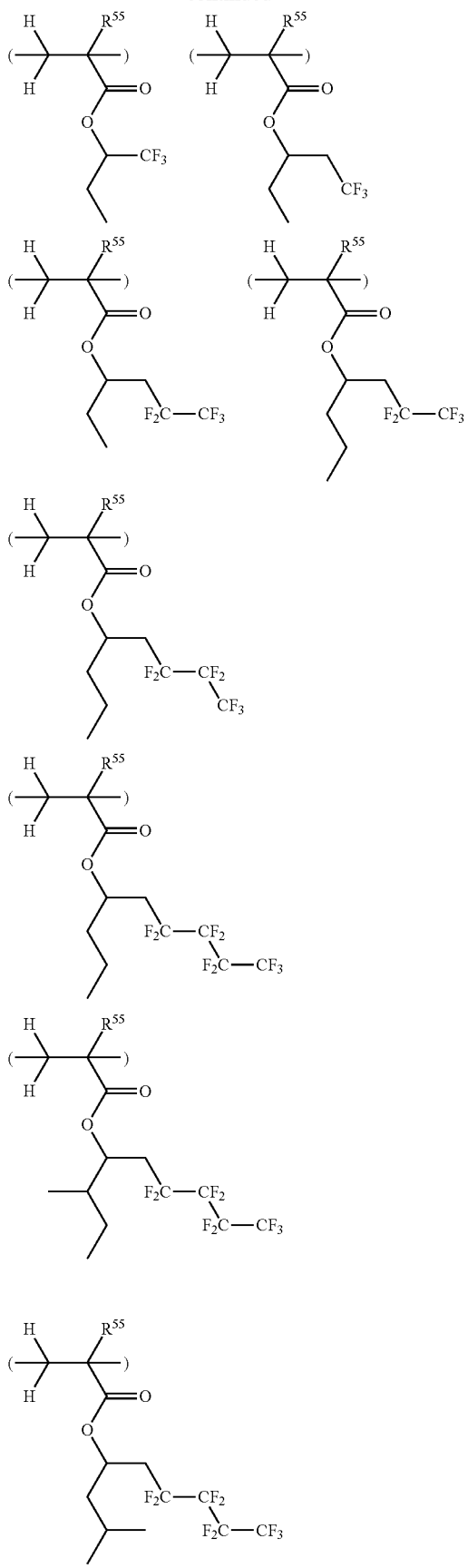
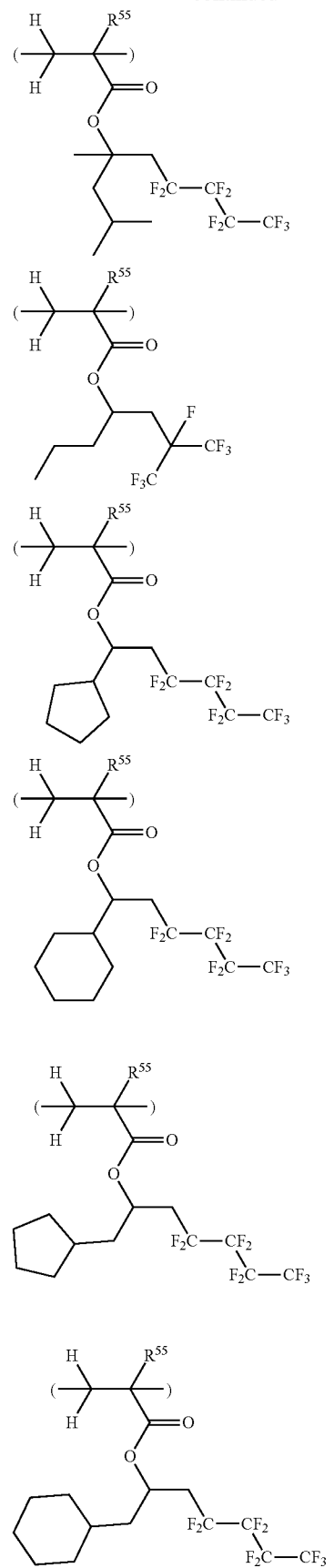

307
-continued
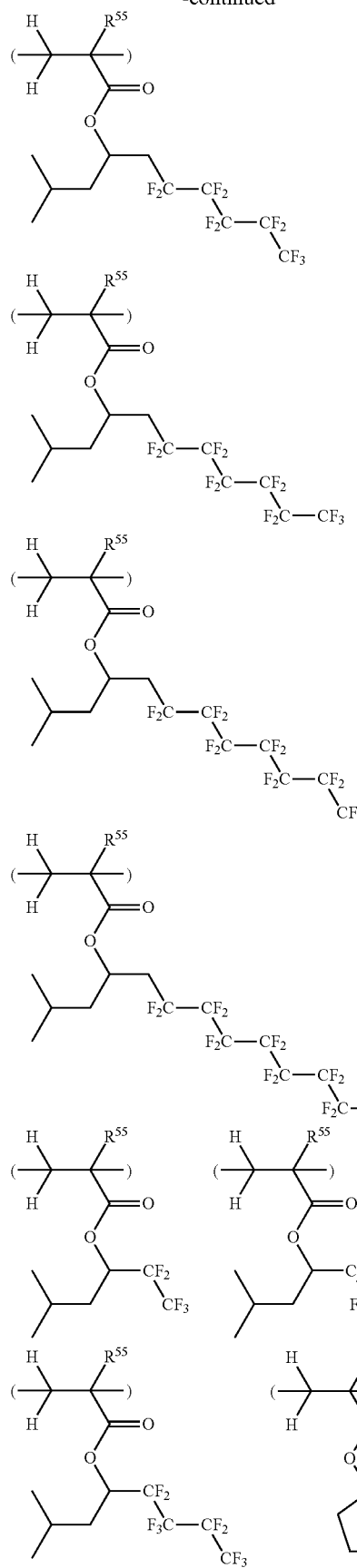
308
-continued
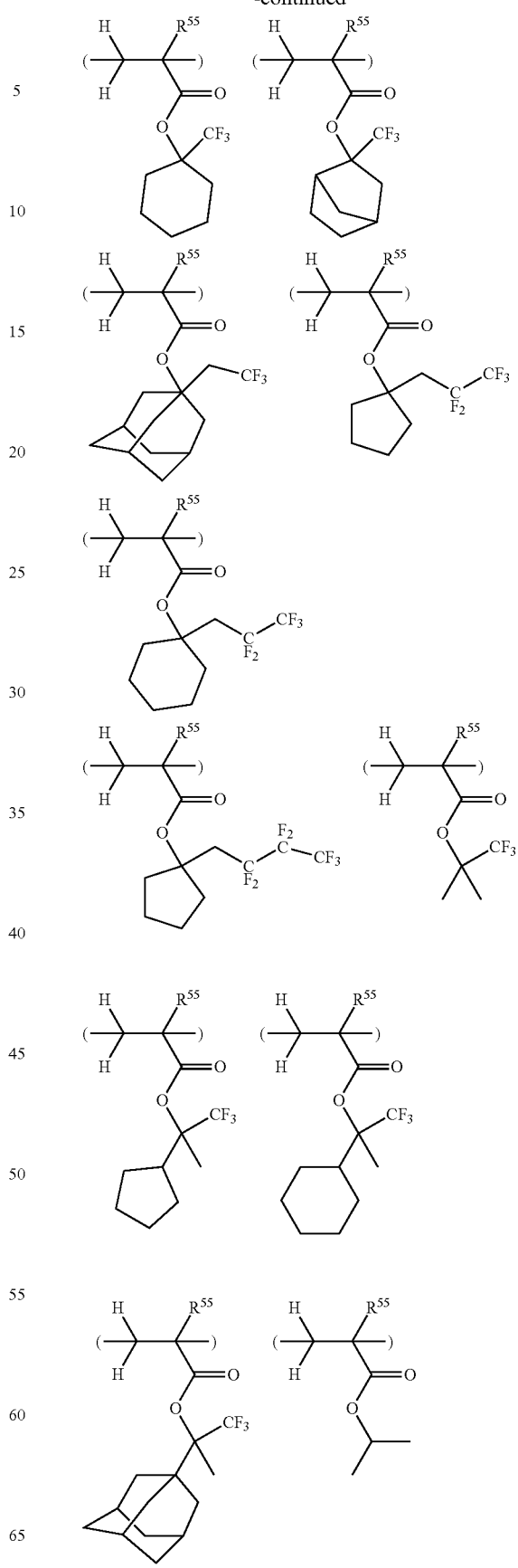

-continued

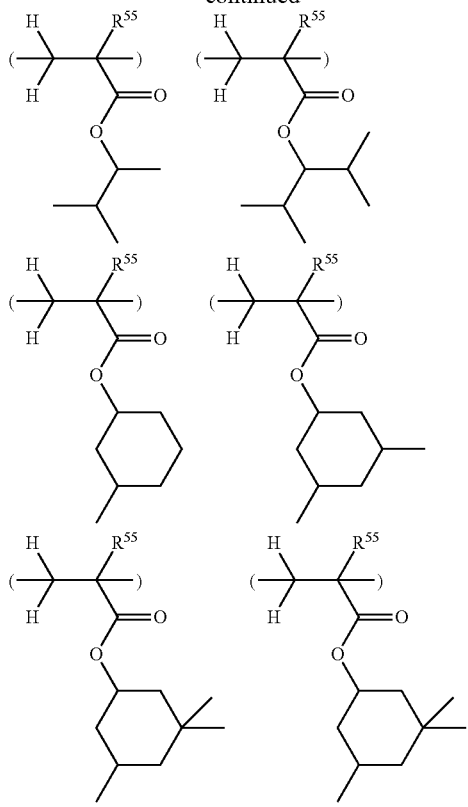

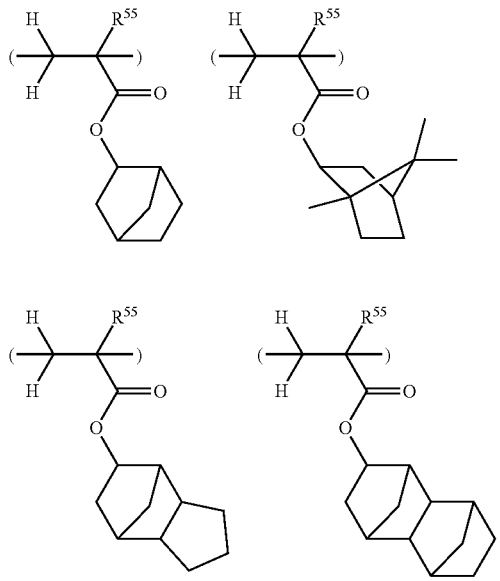

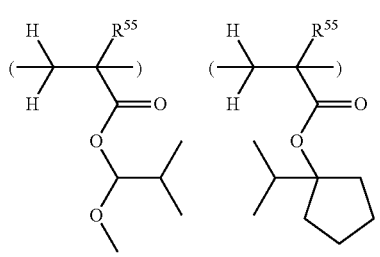

-continued

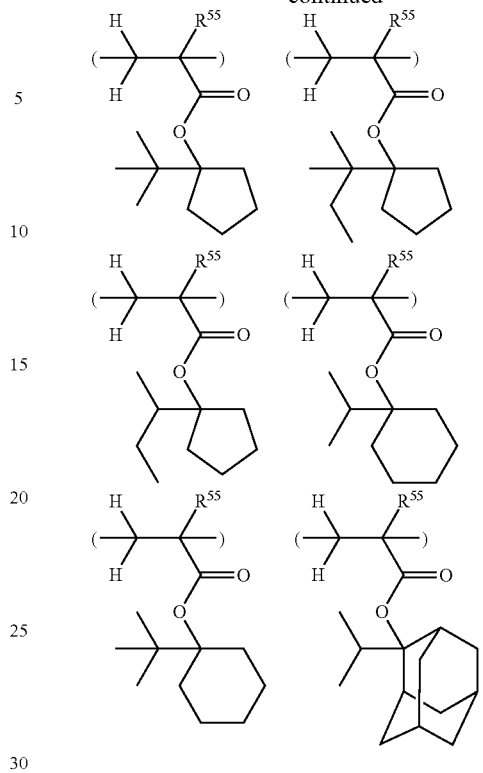

The water repellency improver to be added to the resist composition should be soluble in alkaline aqueous solution as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, any hole pattern opening failure after development, and bridging of a line-and-space pattern. An appropriate amount of the water repellency improver is 0.1 to 20 parts, preferably 0.5 to 10 parts by weight per 100 parts by weight of the base resin.

Though optional, a crosslinker may be added to the resist composition to facilitate formation of a negative pattern via a polarity switch of the inventive polymer. Suitable crosslinkers are described in JP-A 2006-145755. The crosslinker is preferably used in such an amount as not to interfere with high resolution performance by a polarity switch and solubility change induced by dehydration reaction of the recurring unit derived from the inventive monomer. An appropriate amount of the crosslinker is 1 to 30 parts, preferably 3 to 20 parts by weight per 100 parts by weight of the base resin.

Process

The resist composition comprising the inventive polymer, typically chemically amplified resist composition comprising the inventive polymer, optionally a basic compound and an acid generator, in an organic solvent is used in the fabrication of various integrated circuits. Pattern formation using the resist composition may be performed by well-known lithography processes. The process generally involves coating, prebaking, exposure, PEB, and development. If necessary, any additional steps may be added.

The negative resist composition is first applied onto a substrate on which an integrated circuit is to be formed (e.g., Si, $SiO_2$, SiN, SiON, TiN, WSi, BPSG, SOG, or a multilayer film including silicon-containing antireflective coating or organic hydrocarbon film) or a substrate on which a mask circuit is to be formed (e.g., Cr, CrO, CrON, MoSi, or $SiO_2$) by a suitable coating technique such as spin coating, roll coating, flow coating, dipping, spraying or doctor coating. The coating is prebaked on a hot plate preferably at a temperature of 60 to 150° C. for 10 seconds to 30 minutes, more preferably at 80 to 120° C. for 30 seconds to 20 minutes. The resulting resist film is generally 0.01 to 2.0 μm thick.

The resist film is then exposed to a desired pattern of high-energy radiation such as UV, deep-UV, EB, x-ray, excimer laser light, γ-ray, synchrotron radiation, EUV or soft x-ray, directly or through a mask. The exposure dose is preferably about 1 to 200 mJ/cm², more preferably about 10 to 100 mJ/cm², or about 0.1 to 100 μC/cm², more preferably about 0.5 to 50 μC/cm². The resist film is further baked (PEB) on a hot plate preferably at 60 to 150° C. for 10 seconds to 30 minutes, more preferably at 80 to 120° C. for 30 seconds to 20 minutes.

Thereafter the resist film is developed in an alkaline developer for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed region is not dissolved in the developer whereas the resist film in the unexposed region is dissolved. In this way, the desired negative pattern is formed on the substrate. After the development step, the patterned resist film is rinsed with water, preferably for 3 seconds to 3 minutes, more preferably 5 seconds to 2 minutes, by conventional techniques such as dip, puddle and spray techniques. It is appreciated that the resist composition of the invention is best suited for micro-patterning using such high-energy radiation as KrF and ArF excimer laser, EB, EUV, soft, x-ray, x-ray, γ-ray and synchrotron radiation.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the Invention are given below by way of illustration and not by way of limitation. The abbreviation "pbw" is parts by weight, THF stands for tetrahydrofuran, and DMF for dimethylformamide. For all polymers, Mw and Mn are determined versus polystyrene standards by GPC using THF solvent, and dispersity Mw/Mn is computed therefrom.

[1] Synthesis of Monomers

Example 1

Synthesis of Monomer 1

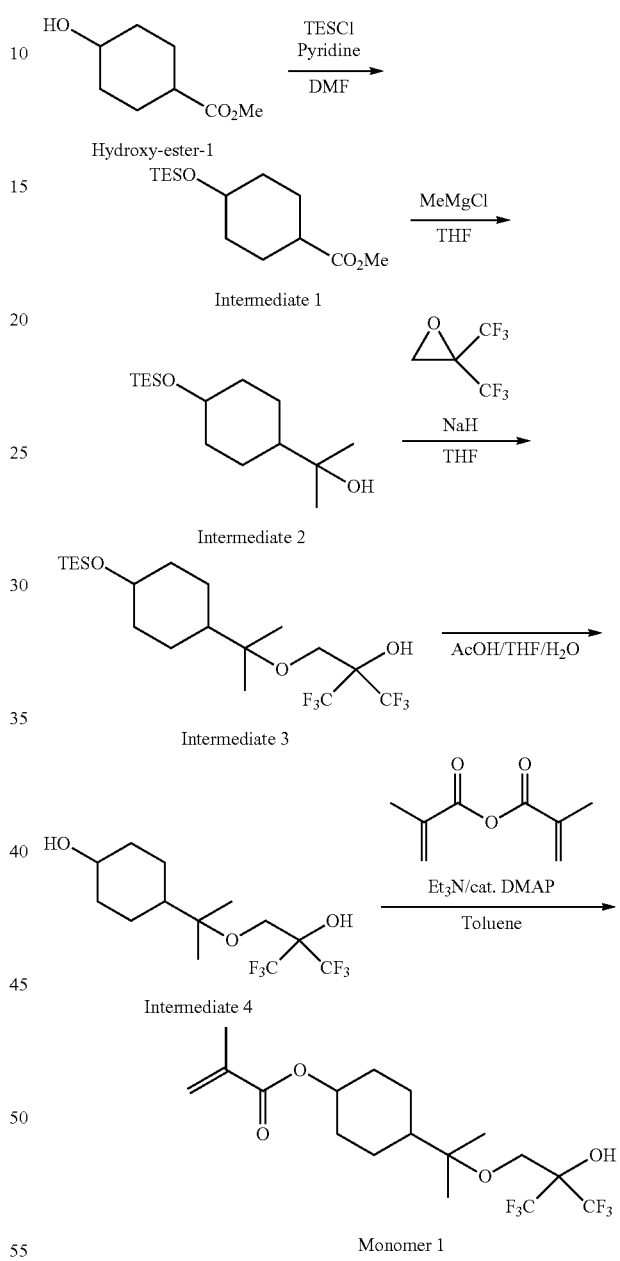

Example 1-1

Synthesis of Intermediate 1

In nitrogen atmosphere, 285 g of triethylsilyl chloride was added dropwise to a solution of 290 g of Hydroxy-ester 1 in 157 g of pyridine and 1,125 g of DMF which was cooled in an ice bath. At the end of dropwise addition, the contents were stirred at room temperature for 7 hours. The reaction solution was again cooled in an ice bath, to which 1,200 g of water was added dropwise to quench the reaction. This was followed by ordinary aqueous workup, solvent distillation, and vacuum distillation, obtaining 392 g of Intermediate 1 as colorless clear oil (yield 80%). The product was measured for boiling point and infrared (IR) spectrum and the main isomer analyzed by nuclear magnetic resonance ($^1$H-NMR) spectroscopy, with the results shown below.

b.p.: 90° C./4 Pa

IR (D-ATR):

ν=3592, 2912, 2876, 1738, 1458, 1435, 1415, 1356, 1310, 1235, 1196, 1167, 1117, 1095, 1050, 1016, 894, 871, 851, 834, 812, 795, 742, 727, 619, 596 cm$^{-1}$ $^1$H-NMR (600 MHz, in DMSO-d$_6$):

δ=3.85 (1H, m), 3.57 (3H, s), 2.32 (1H, m), 1.80 (4H, m), 1.51 (4H, m), 0.90 (9H, t), 0.53 (6H, q) ppm Example 1-2

Synthesis of Intermediate 2

In nitrogen atmosphere, a dilute solution of 342 g of Intermediate 1 (isomer mixture) in 400 mL of THF was added dropwise to a THF solution of methylmagnesium chloride which had been prepared from 73 g of magnesium, chloromethane and 1,200 mL of THF, at 25-45° C. The contents were stirred at 50° C. for 10 hours. Then the reaction solution was ice cooled, to which a mixture of 300 g of ammonium chloride and 1,800 g of 3.0 wt % hydrochloric acid aqueous solution was added dropwise to quench the reaction. This was followed by ordinary aqueous workup, solvent distillation, and vacuum distillation, obtaining 295 g of Intermediate 2 as colorless clear oil (yield 90%). The product was measured for boiling point and IR spectrum and the main isomer analyzed by $^1$H-NMR spectroscopy, with the results shown below.

b.p.: 90° C./5 Pa

IR (D-ATR):

ν=3379, 2952, 2938, 2912, 2876, 1460, 1444, 1414, 1378, 1296, 1237, 1196, 1146, 1102, 1051, 1016, 956, 930, 913, 871, 833, 310, 757, 742, 726, 694, 627 cm$^{-1}$ $^1$H-NMR (600 MHz in DMSO-d$_6$):

δ=3.96 (1H, m), 3.93 (1H, s), 1.63 (2H, m), 1.46 (2H, m), 1.35 (4H, m), 1.14 (1H, m), 0.99 (6H, s), 0.90 (9H, t), 0.52 (6H, q) ppm Example 1-3

Synthesis of Intermediate 3

In nitrogen atmosphere, a solution of 55 g of Intermediate 2 (isomer mixture) in 100 mL of THF was added dropwise to 9.6 g of sodium hydride in 100 ml of THF at 50° C. The contents were stirred at 80° C. for 6 hours. Then the reaction solution was cooled at 25° C., to which 44 g of 2,2-bistrifluoromethyloxirane was added dropwise. Stirring was continued at 40° C. for 36 hours. The reaction solution was cooled, to which 100 g of saturated ammonium chloride aqueous solution was added to quench the reaction. This was followed by ordinary aqueous workup, solvent distillation, and vacuum; distillation, obtaining 70 g of Intermediate 3 as colorless clear oil (yield 78%). The product was measured for boiling point and IR spectrum and the main isomer analyzed by $^1$H-NMR spectroscopy, with the results shown below.

b.p.: 105° C./7 Pa

IR (D-ATR):

ν=3462, 2953, 2915, 2878, 1461, 1445, 1415, 1373, 1324, 1266, 1213, 1166, 1140, 1095, 1052, 1030, 1004, 931, 907, 889, 861, 833, 808, 772, 758, 743, 727, 714, 680, 599, 567 cm$^{-1}$ $^1$H-NMR (600 MHz in DMSO-d$_6$):

δ=7.72 (1H, brs), 3.96 (1H, m), 3.64 (2H, s), 1.62 (2H, m), 1.43-1.30 (7H, m), 1.04 (6H, s), 0.90 (9H, t), 0.52 (6H, q) ppm Example 1-4

Synthesis of Intermediate 4

In nitrogen atmosphere, a solution containing 70 g of Intermediate 3 (isomer mixture), 70 mL of acetic acid, 70 mL of THF and 17.5 mL of water was stirred at 60° C. for 12 hours. Then the reaction solution was cooled, to which 100 mL of water was added to quench the reaction. The reaction solution was extracted with 200 mL of toluene. This was followed by ordinary aqueous workup, solvent distillation, and vacuum distillation, obtaining 46 g of Intermediate 4 as colorless clear oil (yield 87%). The product was measured for boiling point and IR spectrum and the main isomer analyzed by $^1$H-NMR spectroscopy, with the results shown below.

b.p.: 90° C./4 Pa

IR (D-ATR):

ν=3489, 3307, 3083, 2946, 1481, 1465, 1448, 1413, 1369, 1321, 1289, 1257, 1212, 1162, 1114, 1097, 1074, 1039, 1027, 1018, 990, 980, 954, 941, 907, 880, 825, 787, 762, 721, 710, 683, 669, 610, 589, 574, 566 cm$^{-1}$ $^1$H-NMR (600 MHz in DMSO-d$_6$):

δ=7.62 (1H, brs), 4.11 (1H, d), 3.80 (1H, m), 3.62 (2H, s), 1.67 (2H, m), 1.45-1.24 (7H, dm), 1.02 (6H, s) ppm Example 1-5

Synthesis of Monomer 1

In nitrogen atmosphere, 11 g of methacrylic anhydride was added dropwise to a solution containing 18 g of Intermediate 4 (isomer mixture), 13 g of triethylamine, 0.06 g of dimethylaminopyridine, and 45 g of toluene at 40° C. The contents were stirred at 50° C. for 12 hours. Then the reaction solution was ice cooled, to which 15 g of water was added dropwise to quench the reaction. This was followed by ordinary aqueous workup, solvent distillation, and purification by silica gel column chromatography, obtaining 12 g of Monomer 1 as colorless clear oil (5 step yield 28%, isomer ratio 87/13). The product was measured for boiling point and IR spectrum and the main isomer analyzed by $^1$H-NMR spectroscopy, with the results shown below.

b.p.: 90° C./4 Pa

IR (D-ATR):

ν=3446, 2947, 2875, 1712, 1637, 1450, 1386, 1369, 1322, 1298, 1260, 1213, 1168, 1093, 1069, 1027, 991, 935, 919, 876, 816, 763, 716, 702, 684, 601, 573, 561 cm$^{-1}$ $^1$H-NMR (600 MHz in DMSO-d$_6$):

δ=7.76 (1H, brs), 6.01 (1H, s), 5.62 (1H, s), 4.94 (1H, m), 3.65 (2H, s), 1.95-1.75 (5H, m), 1.56-1.46 (4H, m), 1.39-1.31 (3H, m), 1.08 (6H, s) ppm

Example 2

Synthesis of Monomer 2

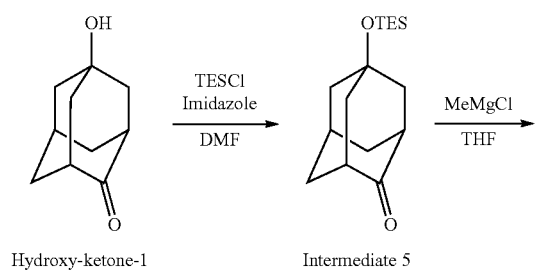

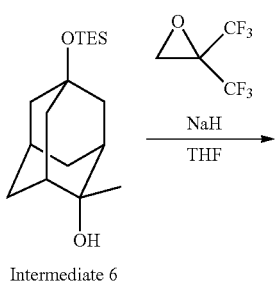

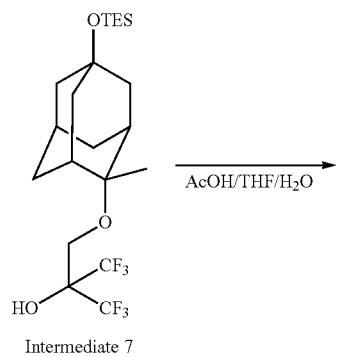

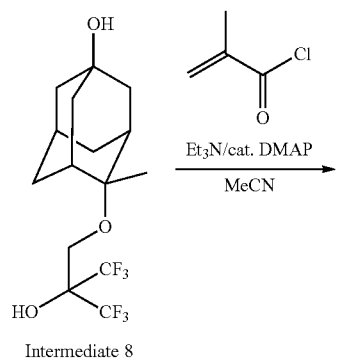

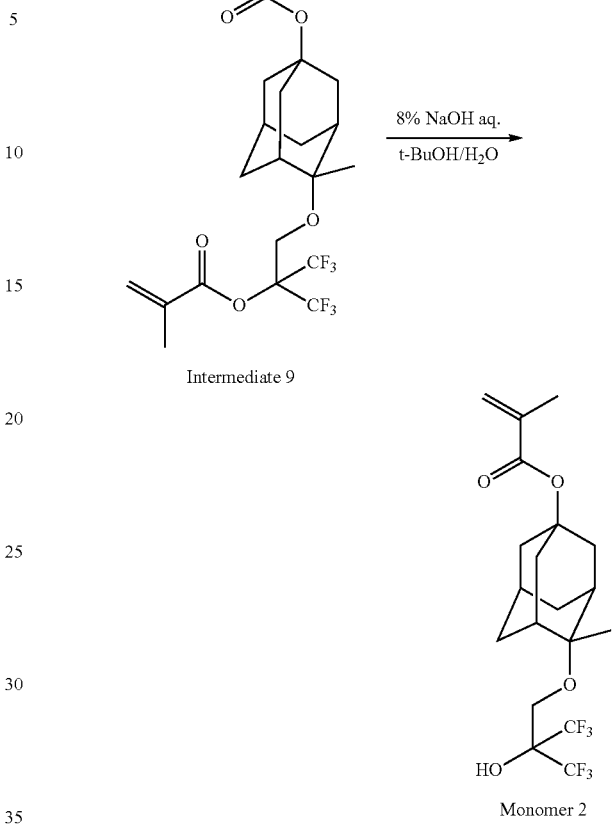

Example 2-1

Synthesis of Intermediate 5

In nitrogen atmosphere, 83 g of triethylsilyl chloride was added dropwise to a solution containing 83 g of Hydroxy-ketone 1, 41 g of imidazole and 160 g of DMF which was cooled in an ice bath. At the end of dropwise addition, the contents were stirred at room temperature for 6 hours. The reaction solution was again cooled in an ice bath, to which 200 g of water was added dropwise to quench the reaction. This was followed by ordinary aqueous workup and solvent distillation, obtaining 143 g of Intermediate 5 as oil (crude yield 97%). Without further purification, Intermediate 5 was used in the subsequent reaction.

Example 2-2

Synthesis of Intermediate 6

In nitrogen atmosphere, a dilute solution of 341 g of Intermediate 5 in 100 mL of THF was added dropwise to a 3.0 M methylmagnesium chloride THF solution (conventionally prepared) at 25-45° C. The contents were stirred at 50° C. for 5 hours. Then the reaction solution was ice cooled, to which a mixture of 142 g of ammonium chloride and 800 g of 3.0 wt % hydrochloric acid aqueous solution was added dropwise to quench the reaction. This was followed by ordinary aqueous workup, solvent distillation, and vacuum distillation, obtaining 327 g of Intermediate 6 as colorless clear oil (yield 90%).

Example 2-3

Synthesis of Intermediate 7

In nitrogen atmosphere, a solution of 138 g of Intermediate 6 (isomer mixture) in 250 mL of THF was added dropwise to 22 g of sodium hydride in 140 ml of THF at 50° C. The contents were stirred at 80° C. for 6 hours. Then the reaction solution was cooled at 25° C., to which 99 g of 2,2-bistrifluoromethyloxirane was added dropwise. Stirring was continued at 40° C. for 46 hours. The reaction solution was cooled, to which 400 g of saturated ammonium chloride aqueous solution was added to quench the reaction. This was followed, by ordinary aqueous workup, solvent distillation, and vacuum distillation, obtaining 217 g of Intermediate 7 as colorless clear oil (yield 98%).

2-4

Synthesis of Intermediate 8

In nitrogen atmosphere, a solution containing 211 g of Intermediate 7 (isomer mixture), 420 mL of acetic acid, 210 mL of THF and 210 mL of water was stirred at 60° C. for 16 hours. Then the reaction solution was cooled, to which 250 mL of water was added to quench the reaction. The reaction solution was extracted with 1,000 mL of toluene. This was followed by ordinary aqueous workup, solvent distillation, and purification by silica gel column chromatography, obtaining 140 g of Intermediate 8 as colorless clear oil (yield 98%).

Example 2-5

Synthesis of Intermediate 9

In nitrogen atmosphere, 113 g of methacrylic acid chloride was added dropwise to a solution containing 157 g of Intermediate 8 (isomer mixture), 175 g of triethylamine, 5.3 g of 4-dimethylaminopyridine and 450 mL of acetonitrile at 40° C. The contents were stirred at 60° C. for 3 hours. The reaction solution was ice cooled, to which 500 g of water was added dropwise to quench the reaction. This was followed by ordinary aqueous workup and solvent distillation, obtaining 181 g of Intermediate 9 as oil (yield 83%). Without further purification, Intermediate 9 was used in the subsequent reaction.

Example 2-6

Synthesis of Monomer 2

In nitrogen atmosphere, 363 g of 8% sodium hydroxide aqueous solution was added dropwise to a solution of 181 g of Intermediate 9 (isomer mixture) in 900 g of t-butanol at room temperature. The contents were stirred at room temperature for 3 hours. Then the reaction solution was ice cooled, to which 133 g of 20 wt % hydrochloric acid aqueous solution was added dropwise to quench the reaction. The reaction solution was extracted with 1,000 mL of toluene. This was followed by ordinary aqueous workup, solvent distillation, and crystallization, obtaining 147 g of Monomer 2 as white crystal (6 step yield 60%, isomer ratio 66/34).

The product was measured for IR spectrum and the main isomer analyzed by $^1$H-NMR spectroscopy, with the results shown below.

IR (D-ATR):

ν=3278, 3012, 2960, 2925, 2306, 2873, 1681, 1628, 1485, 1448, 1408, 1380, 1345, 1329, 1312, 1293, 1275, 1259, 1215, 1189, 1156, 1121, 1103, 1091, 1061, 1041, 1032, 1010, 985, 947, 934, 921, 897, 881, 868, 817, 736, 715, 700, 680, 640, 589 cm$^{-1}$ $^1$H-NMR (600 MHz in DMSO-d$_6$):

δ=7.85 (1H, s), 5.91 (1H, s), 5.58 (1H, s), 3.70 (2H, s), 2.29 (2H, m), 2.09-1.89 (9H, m), 1.81 (3H, s), 1.38 (2H, m), 1.35 (3H, s) ppm Example 3

Synthesis of Monomer 2

Monomers 3 to 12, shown below, were similarly synthesized using the corresponding reactants.

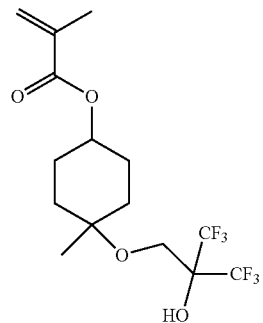

Monomer 3

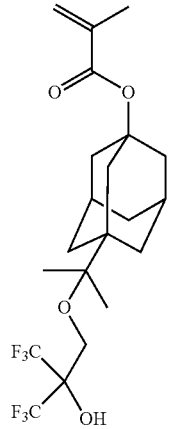

Monomer 4

Monomer 5
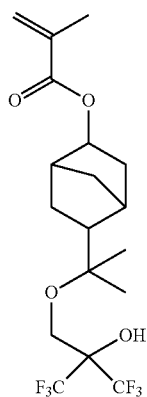
Monomer 6
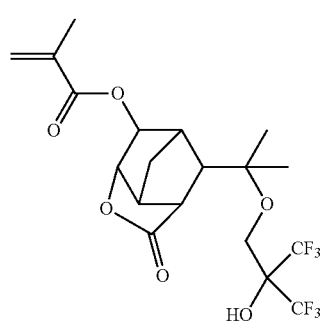
Monomer 7
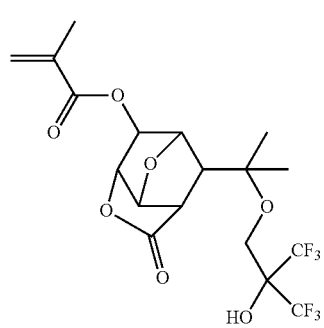
Monomer 9
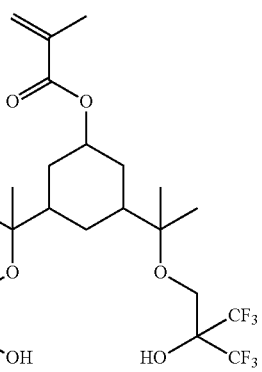
Monomer 10
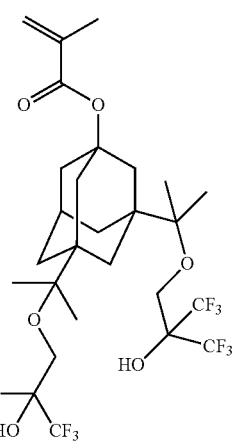
Monomer 11
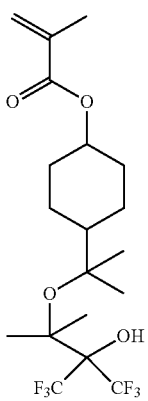

-continued

Monomer 12

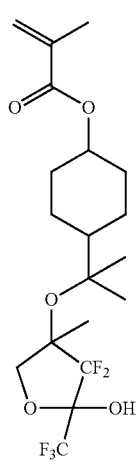

[2] Synthesis of Polymers

Each of polymers (Polymers 1 to 23 and Comparative Polymers 1 to 12) for use in resist compositions was prepared by combining monomers in cyclopentanone solvent, effecting copolymerization reaction, crystallizing from hexane, washing with hexane several times, isolation and drying. The polymer was analyzed for composition by $^1$H-NMR and $^{13}$C-NMR spectroscopy.

Example 4

Polymer 1
Mw=8,600
Mw/Mn−1.67

Polymer 1

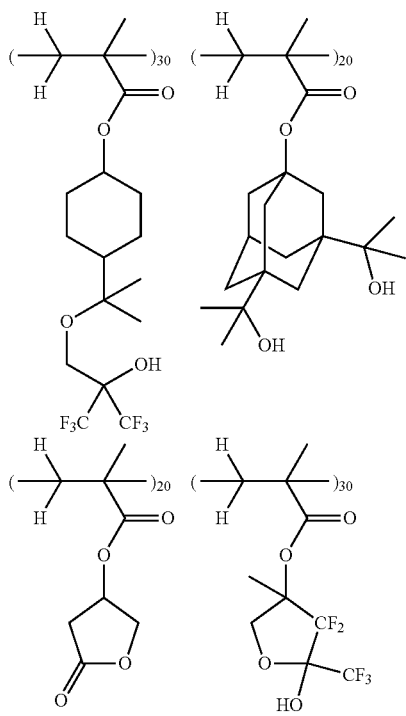

Example 5

Polymer 2
Mw=8,400
Mw/Mn=1.65

Polymer 2

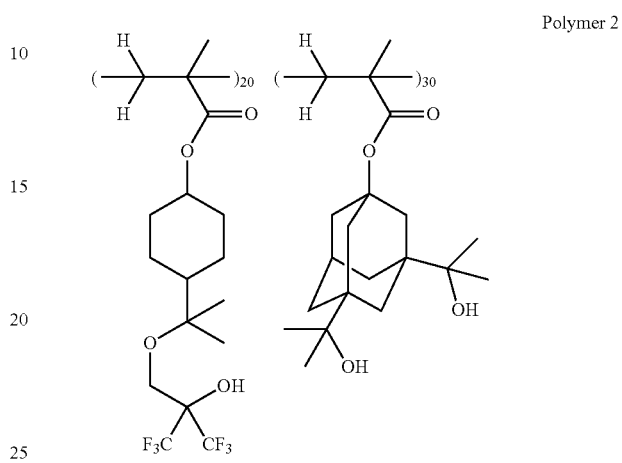

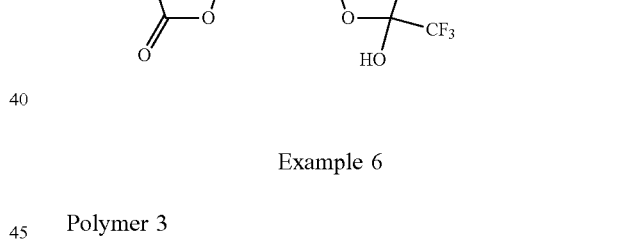

Example 6

Polymer 3
Mw=8,300
Mw/Mn=1.67

Polymer 3

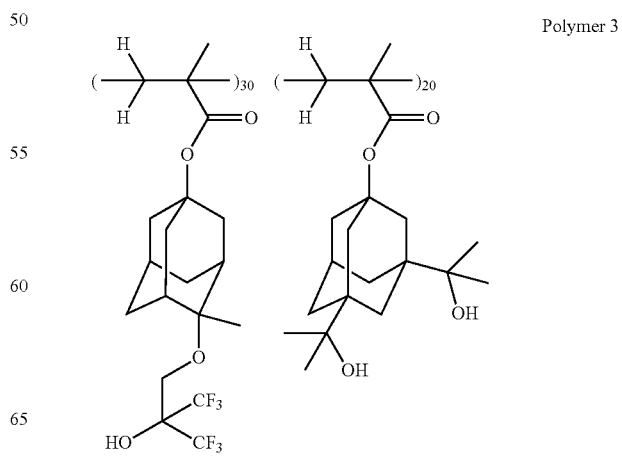

-continued
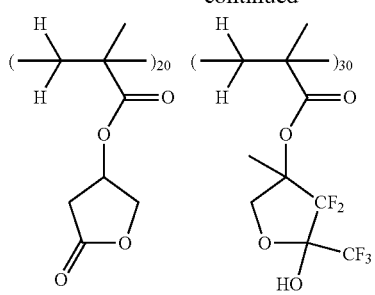
Example 7
Polymer 4
Mw=8,300
Mw/Mn=1.66
Polymer 4
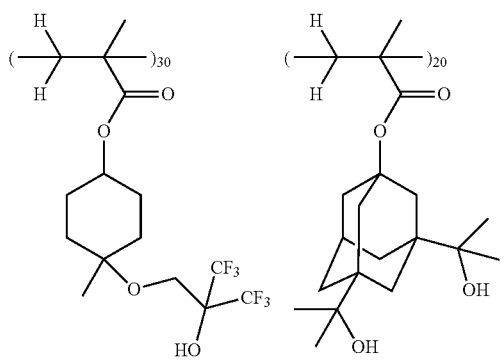
Example 8
Polymer 5
Mw=8,500
Mw/Mn=1.66
Polymer 5
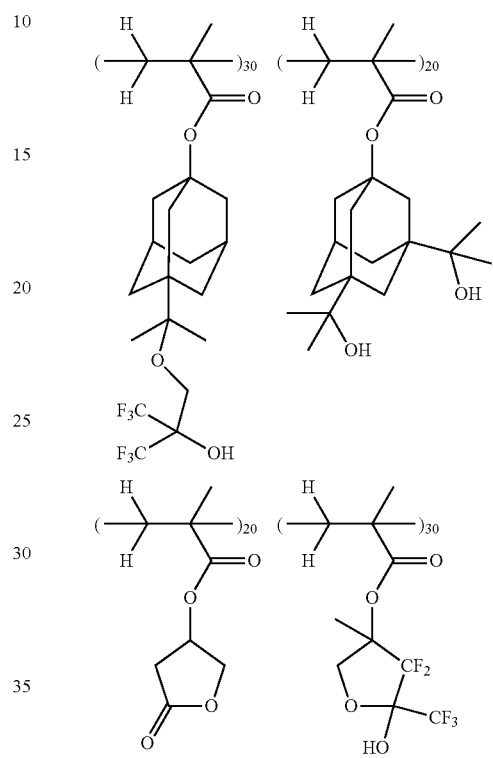
Example 9
Polymer 6
Mw=8,900
Mw/Mn=1.71
Polymer 6
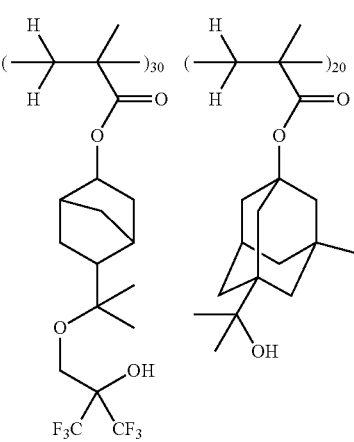
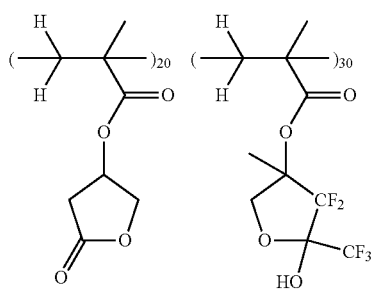

-continued
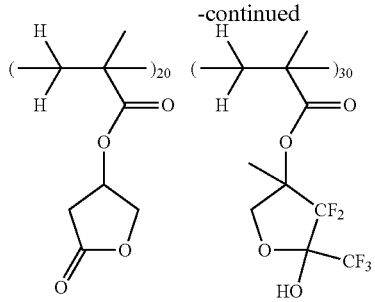
Example 10
Polymer 7
Mw=8,800
Mw/Mn=1.72
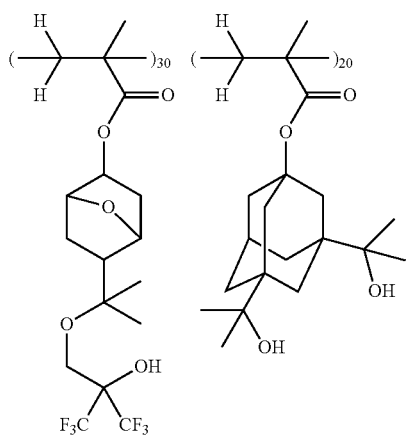
Polymer 7
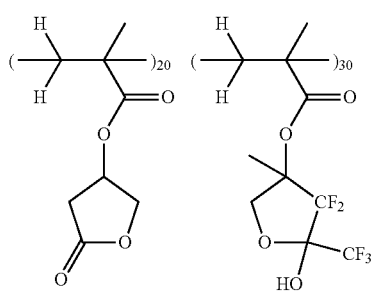
Example 11
Polymer 8
Mw=8,500
Mw/Mn=1.68
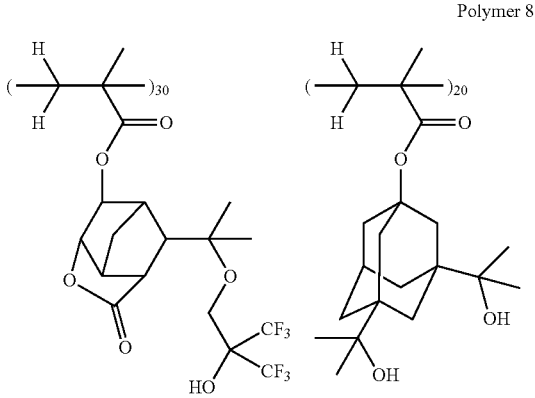
Polymer 8
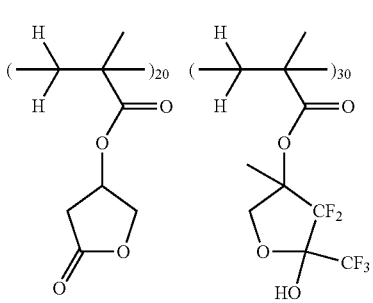
Example 12
Polymer 9
Mw=8,700
Mw/Mn=1.70
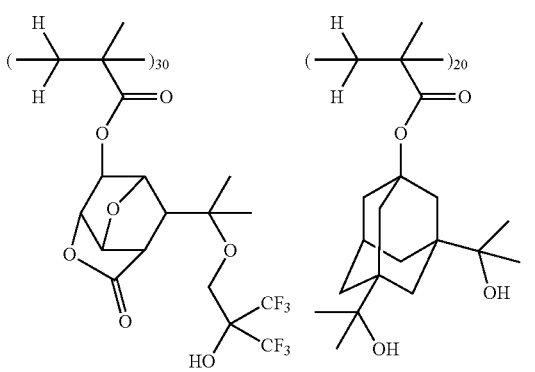
Polymer 9

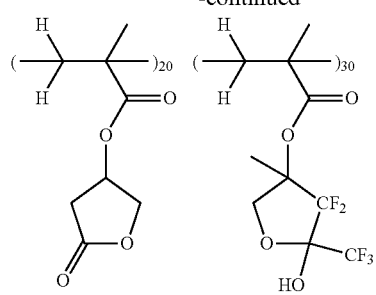
Example 13
Polymer 10
Mw=8,800
Mw/Mn=1.69
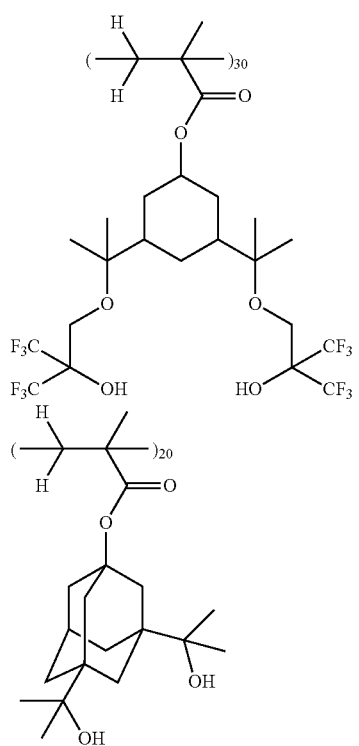
Polymer 10
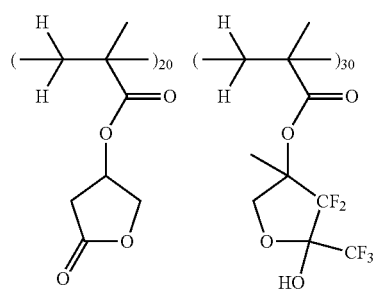
Example 14
Polymer 11
Mw=9,000
Mw/Mn=1.76
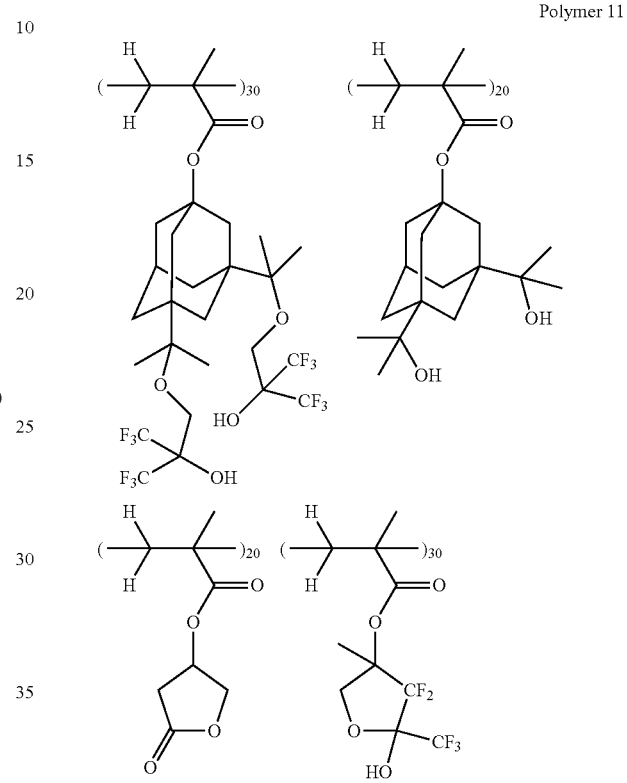
Polymer 11
Example 15
Polymer 12
Mw=8,700
Mw/Mn=1.70
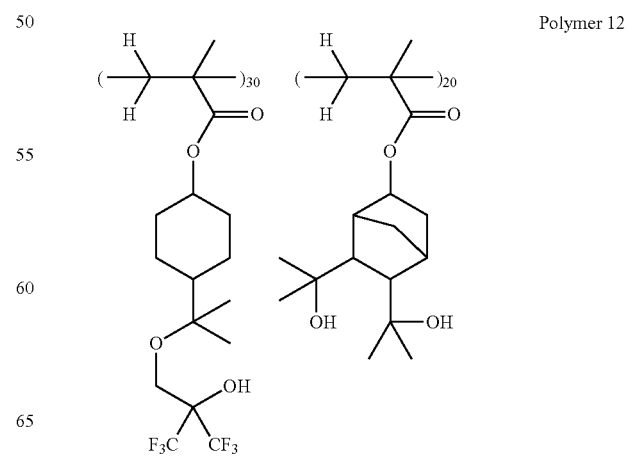
Polymer 12

-continued
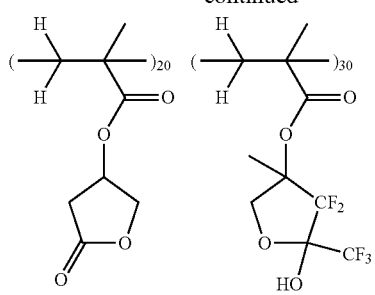
Example 16
Polymer 13
Mw=8,300
Mw/Mn=1.66
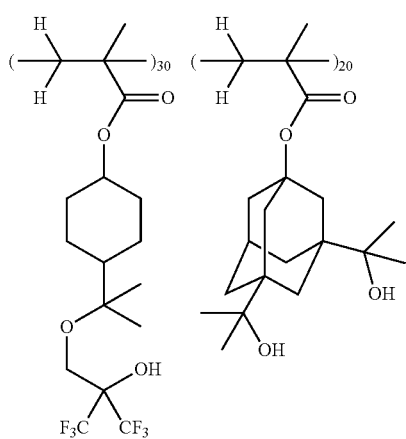
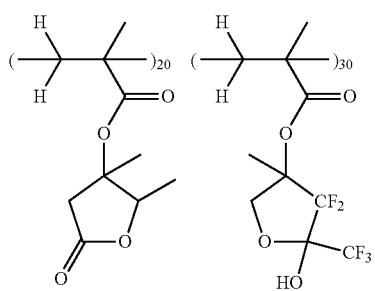
Example 17
Polymer 14
Mw=8,500
Mw/Mn=1.65
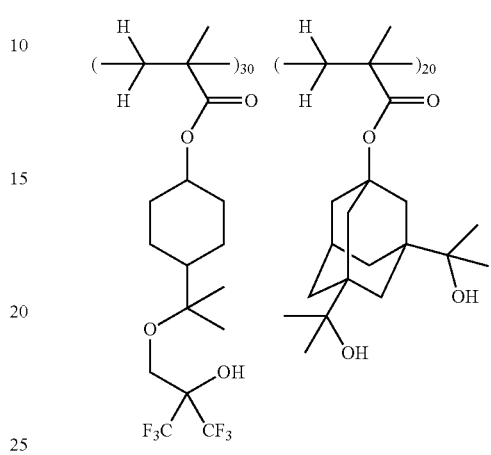
Polymer 14
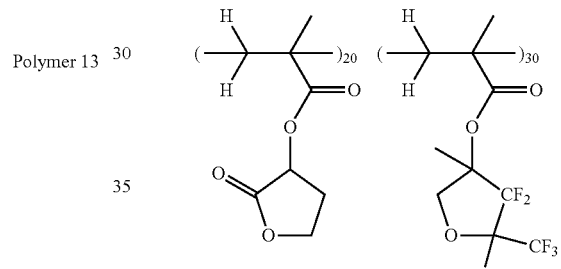
Polymer 13
Example 18
Polymer 15
Mw=8,800
Mw/Mn=1.71
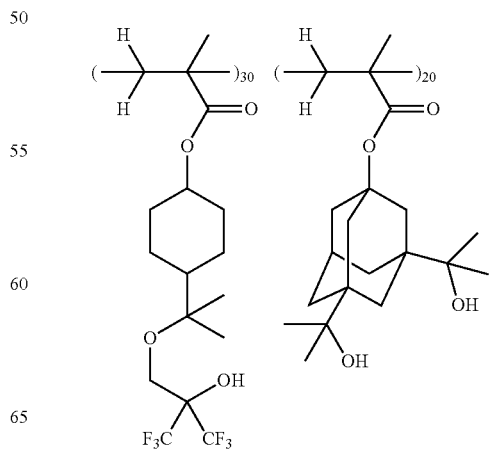
Polymer 15

-continued
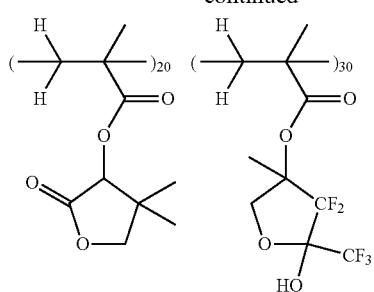
Example 19
Polymer 16
Mw=8,700
Mw/Mn=1.69
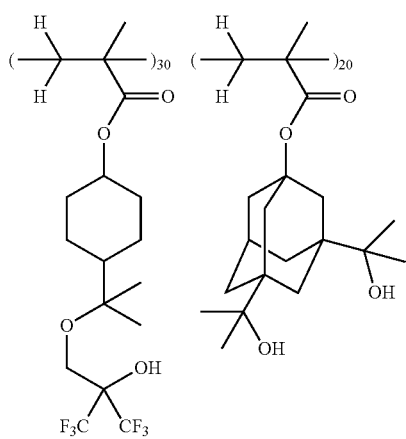
Polymer 16
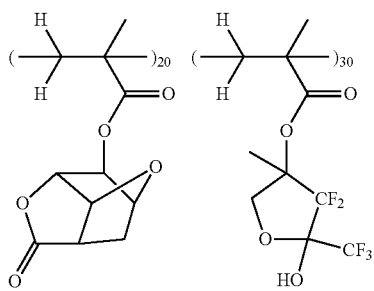
Example 20
Polymer 17
Mw=8,600
Mw/Mn=1.70
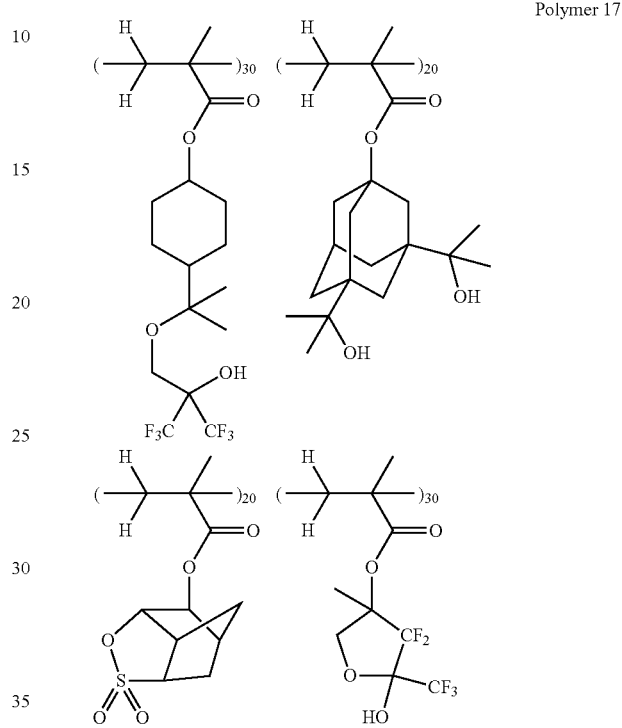
Polymer 17
Example 21
Polymer 18
Mw=8,700
Mw/Mn=1.68
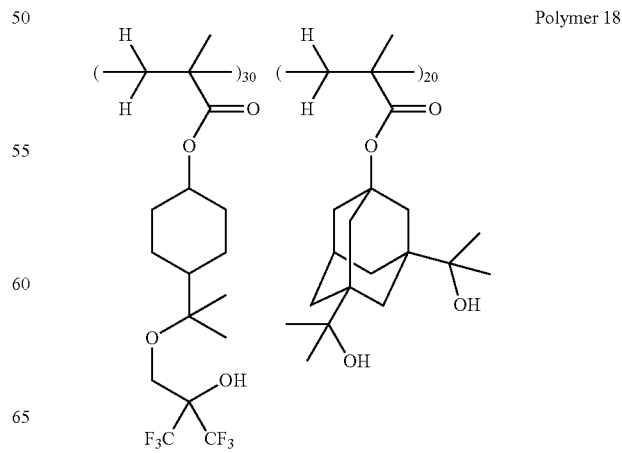
Polymer 18

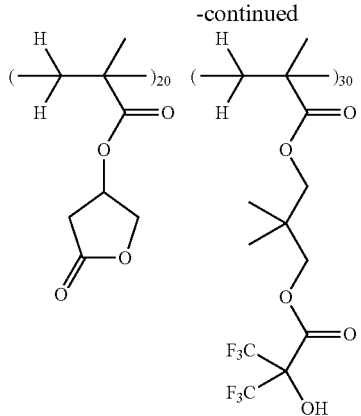
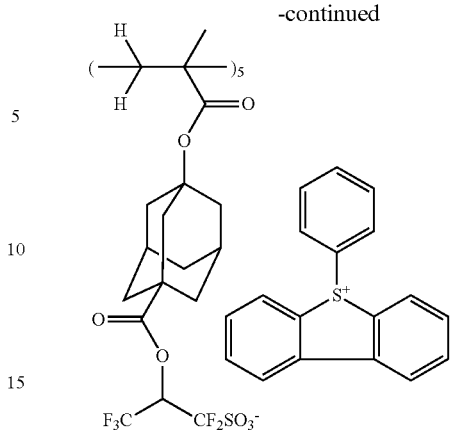
Example 22
Polymer 19
Mw=9,000
Mw/Mn=1.72
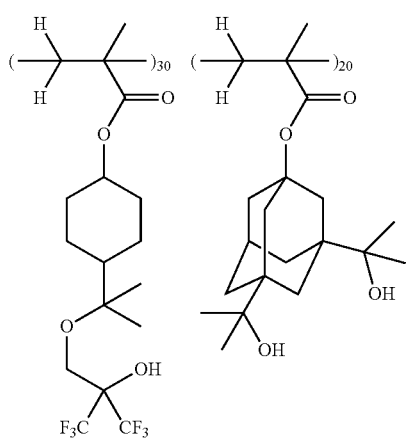
Polymer 19
Example 23
Polymer 20
Mw=8,500
Mw/Mn=1.67
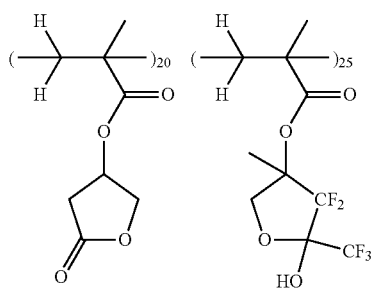
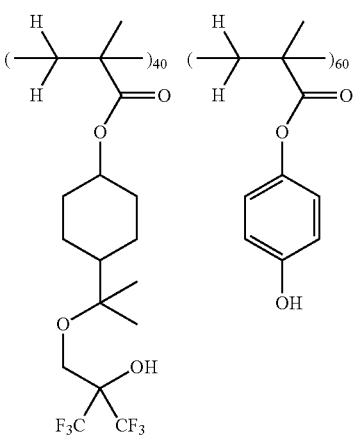
Polymer 20

Example 24
Polymer 21
Mw=8,400
Mw/Mn=1.66
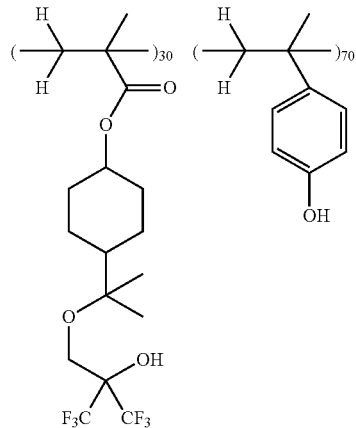
Polymer 21
Example 25
Polymer 22
Mw=8,300
Mw/Mn=1.62
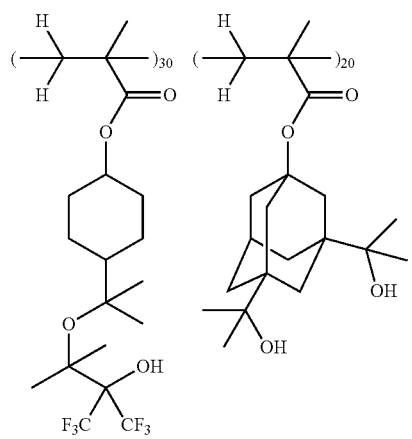
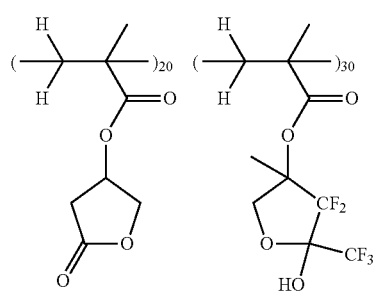
Polymer 22
Example 26
Polymer 23
Mw=8,700
Mw/Mn=1.64
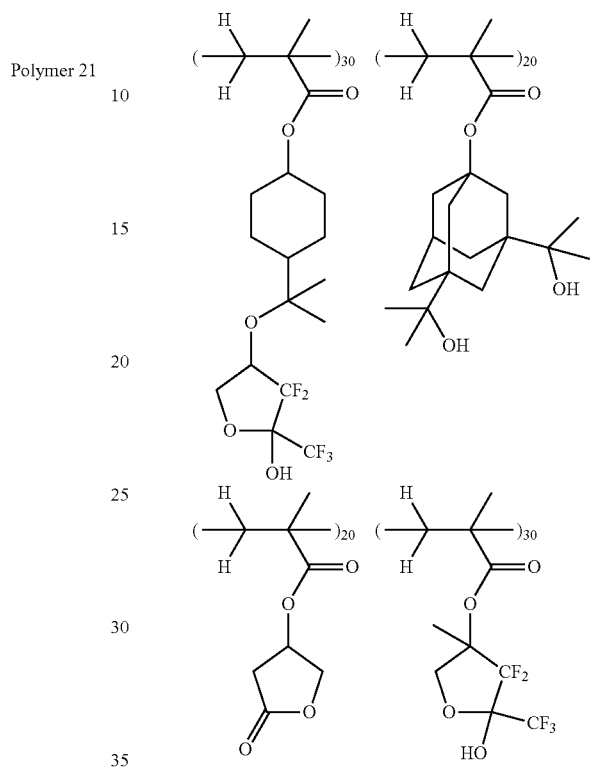
Polymer 23
Comparative Example 1
Comparative Polymer 1
Mw=8,400
Mw/Mn=1.65
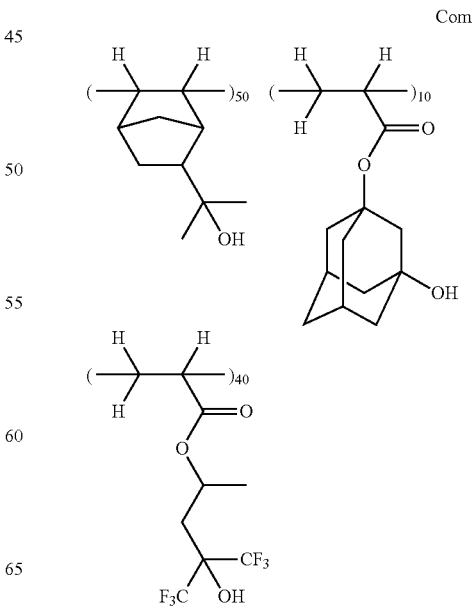
Comparative Polymer 1

Comparative Example 2
Comparative Polymer 2
Mw=8,500
Mw/Mn=1.63
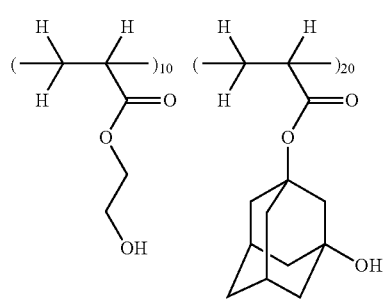
Comparative Polymer 2
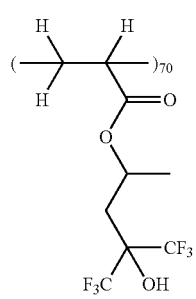
Comparative Example 3
Comparative Polymer 3
Mw=8,700
Mw/Mn=1.65
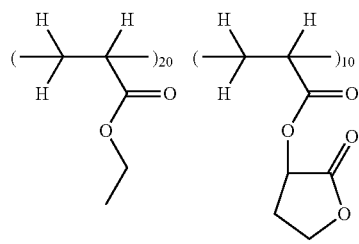
Comparative Polymer 3
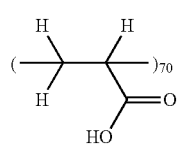
Comparative Example 4
Comparative Polymer 4
Mw=8,600
Mw/Mn=1.62
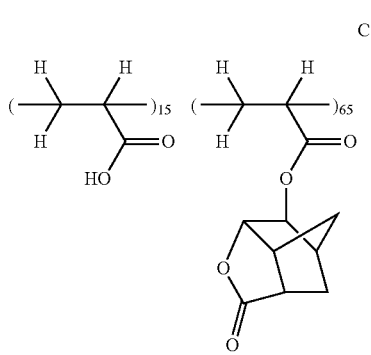
Comparative Polymer 4
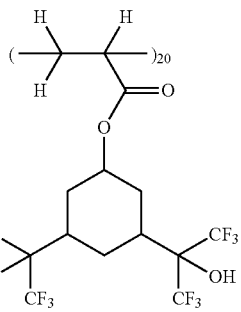
Comparative Example 5
Comparative Polymer 5
Mw=8,400
Mw/Mn=1.66
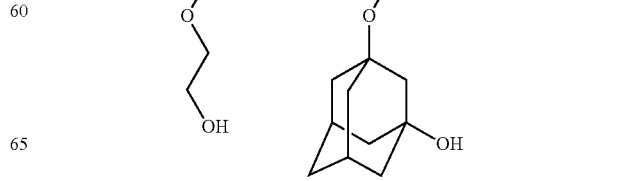
Comparative Polymer 5

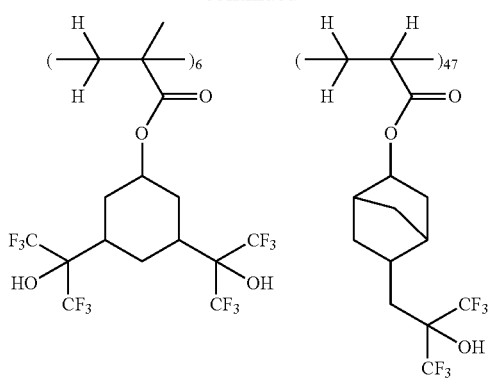
Comparative Example 6
Comparative Polymer 6
Mw=8,600
Mw/Mn=1.63
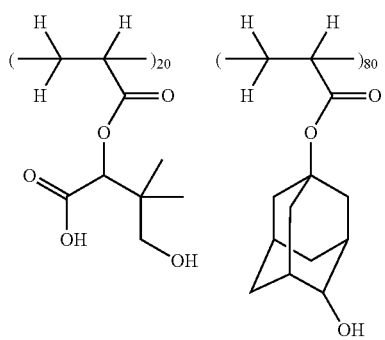
Comparative Example 7
Comparative Polymer 7
Mw=8,600
Mw/Mn=1.63
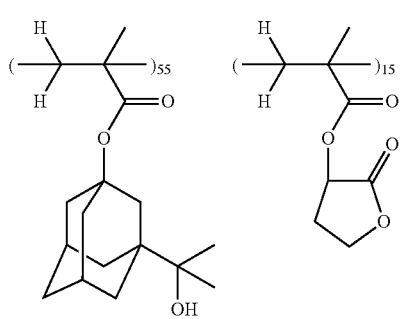
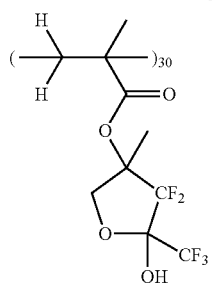
Comparative Example 8
Comparative Polymer 8
Mw=8,500
Mw/Mn=1.61
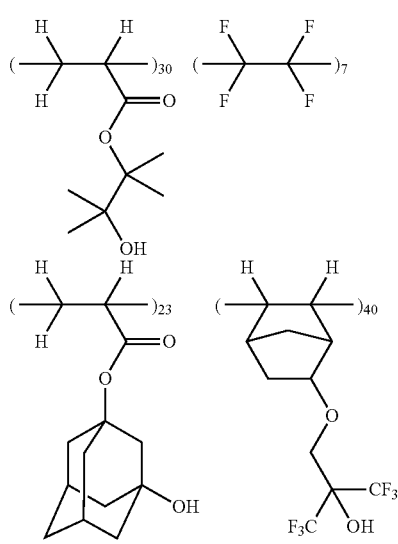
Comparative Example 9
Comparative Polymer 9
Mw=8,400
Mw/Mn=1.65
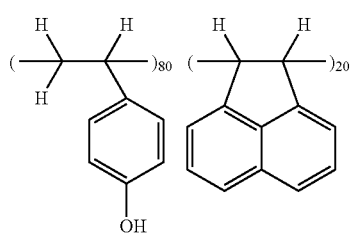

Comparative Example 10

Comparative Polymer 10
Mw=8,400
Mw/Mn=1.65

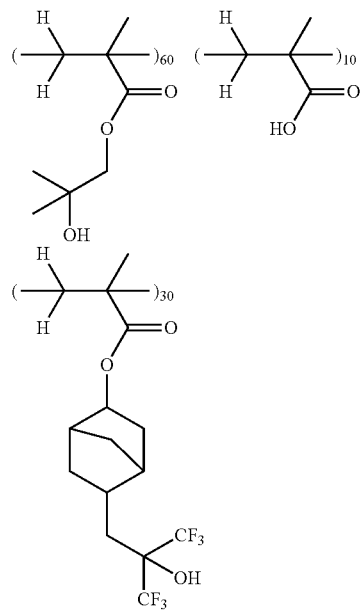

Comparative Polymer 10

Comparative Example 11

Comparative Polymer 11
Mw=9,800
Mw/Mn=2.53

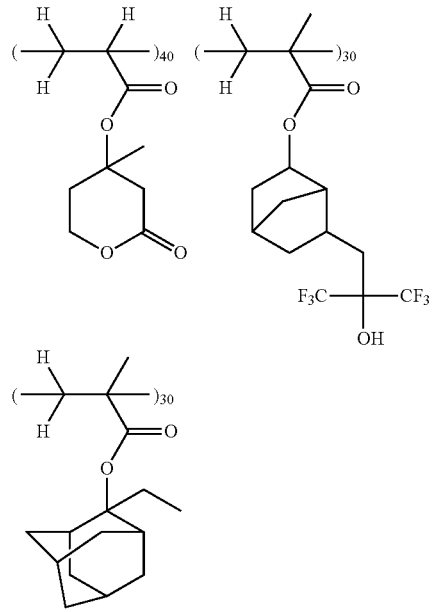

Comparative Polymer 11

Comparative Example 12

Comparative Polymer 12
Mw=12,000
Mw/Mn=2.01

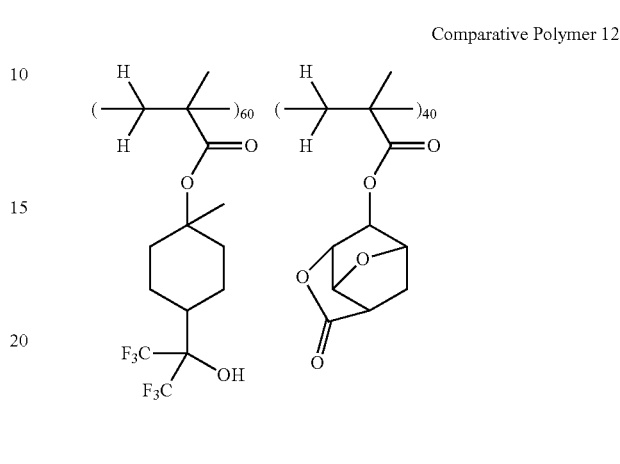

Comparative Polymer 12

[3] Preparation of Resist Compositions

Examples 27 to 49 & Comparative Examples 13 to 24

Resist compositions R-01 to R-35 were prepared by using inventive Polymers 1 to 23 or Comparative Polymers 1 to 12 as the base resin, dissolving the polymer and other components in a solvent in accordance with the recipe shown in Tables 1 and 2, and filtering through a Teflon® filter having a pore size of 0.2 µm.

In Tables 1 and 2, acid generator (PAG-1 to 4), water-repellent polymer (SF-1), sensitivity regulator (Q-1 to 4), crosslinker (XL-1), and solvent are as identified below.

Photoacid Generator: PAG-1 to PAG-4

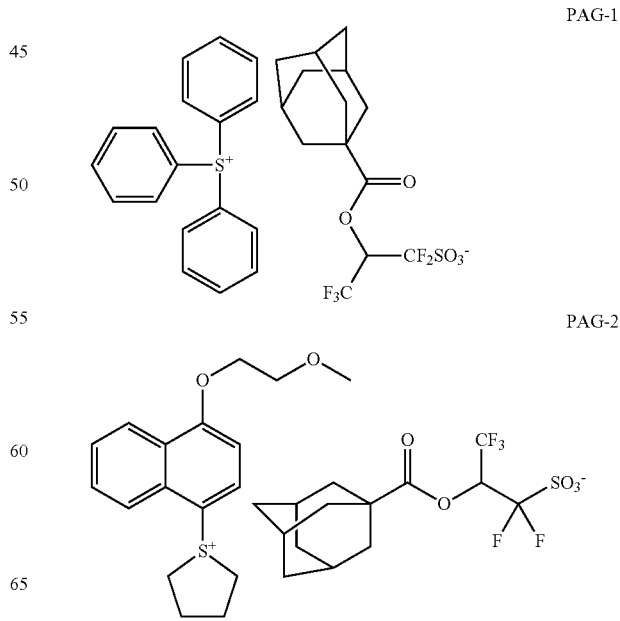

PAG-1

PAG-2

PAG-3
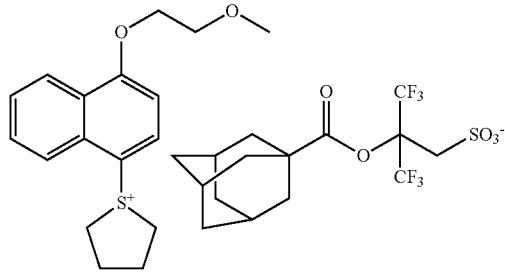
PAG-4
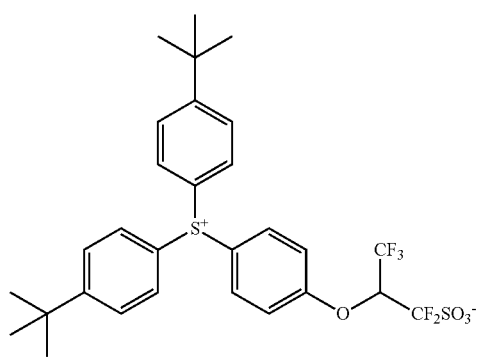
Sensitivity Regulator: Q-1 to Q-4
Q-1
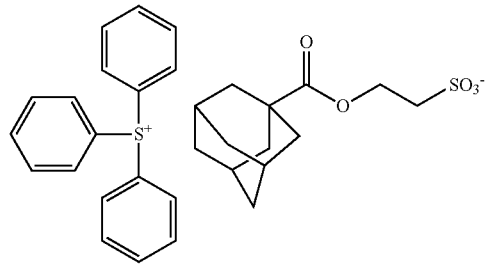
Q-2
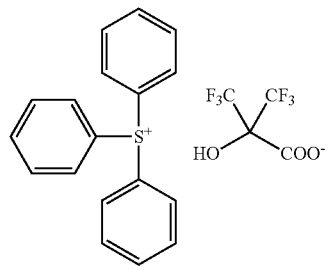
Q-3
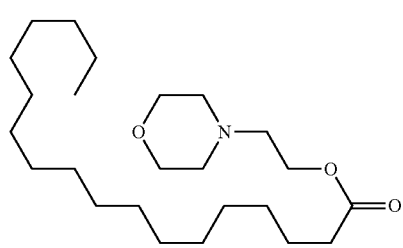
Q-4
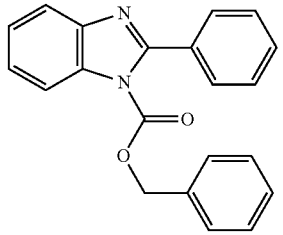
Water-Repellent Polymer: SF-1
  Mw=8,700
  Mw/Mn=1.85
SF-1
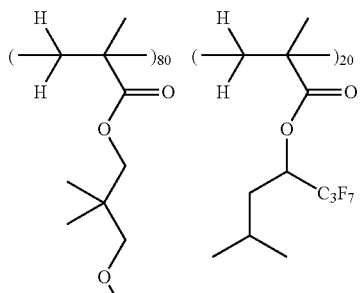
Crosslinker: XL-1
XL-1
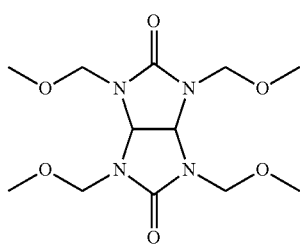
Solvent
  PGEE: propylene glycol monoethyl ether
  DAA: diacetone alcohol
  GBL: γ-butyrolactone

TABLE 1

|  | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|
| Example 27 | R-01 | Polymer 1 (100) | PAG-4 (5.0) | Q-2 (3.5) | SF-1 (5.0) | — | PGEE (2,000) DAA (400) GBL (100) |
| 28 | R-02 | Polymer 2 (100) | PAG-4 (5.0) | Q-2 (3.5) | SF-1 (5.0) | — | PGEE (2,000) DAA (400) GBL (100) |
| 29 | R-03 | Polymer 3 (100) | PAG-1 (5.0) | Q-2 (3.5) | SF-1 (5.0) | — | PGEE (2,000) DAA (400) GBL (100) |
| 30 | R-04 | Polymer 4 (100) | PAG-3 (5.0) | Q-1 (3.5) | SF-1 (5.0) | — | PGEE (2,000) DAA (400) GBL (100) |
| 31 | R-05 | Polymer 5 (100) | PAG-3 (5.0) | Q-2 (3.5) | SF-1 (5.0) | — | PGEE (2,000) DAA (400) GBL (100) |
| 32 | R-06 | Polymer 6 (100) | PAG-2 (5.0) | Q-3 (3.5) | SF-1 (5.0) | — | PGEE (2,000) DAA (400) GBL (100) |
| 33 | R-07 | Polymer 7 (100) | PAG-4 (5.0) | Q-2 (3.5) | SF-1 (5.0) | — | PGEE (2,000) DAA (400) GBL (100) |
| 34 | R-08 | Polymer 8 (100) | PAG-4 (5.0) | Q-3 (3.5) | SF-1 (5.0) | — | PGEE (2,000) DAA (400) GBL (100) |
| 35 | R-09 | Polymer 9 (100) | PAG-3 (5.0) | Q-4 (3.5) | SF-1 (5.0) | — | PGEE (2,000) DAA (400) GBL (100) |
| 36 | R-10 | Polymer 10 (100) | PAG-2 (5.0) | Q-3 (3.5) | SF-1 (5.0) | — | PGEE (2,000) DAA (400) GBL (100) |
| 37 | R-11 | Polymer 11 (100) | PAG-3 (5.0) | Q-2 (3.5) | SF-1 (5.0) | — | PGEE (2,000) DAA (400) GBL (100) |
| 38 | R-12 | Polymer 12 (100) | PAG-1 (5.0) | Q-4 (3.5) | SF-1 (5.0) | — | PGEE (2,000) DAA (400) GBL (100) |
| 39 | R-13 | Polymer 13 (100) | PAG-3 (5.0) | Q-2 (3.5) | SF-1 (5.0) | — | PGEE (2,000) DAA (400) GBL (100) |
| 40 | R-14 | Polymer 14 (100) | PAG-3 (5.0) | Q-2 (3.5) | SF-1 (5.0) | — | PGEE (2,000) DAA (400) GBL (100) |
| 41 | R-15 | Polymer 15 (100) | PAG-3 (5.0) | Q-2 (3.5) | SF-1 (5.0) | — | PGEE (2,000) DAA (400) GBL (100) |
| 42 | R-16 | Polymer 16 (100) | PAG-3 (5.0) | Q-2 (3.5) | SF-1 (5.0) | — | PGEE (2,000) DAA (400) GBL (100) |
| 43 | R-17 | Polymer 17 (100) | PAG-3 (5.0) | Q-2 (3.5) | SF-1 (5.0) | — | PGEE (2,000) DAA (400) GBL (100) |
| 44 | R-18 | Polymer 18 (100) | PAG-3 (5.0) | Q-2 (3.5) | SF-1 (5.0) | — | PGEE (2,000) DAA (400) GBL (100) |

TABLE 2

|  | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|
| Example 45 | R-19 | Polymer 19 (100) | PAG-3 (5.0) | Q-2 (3.5) | SF-1 (5.0) | — | PGEE (2,000) DAA (400) GBL (100) |
| 46 | R-20 | Polymer 20 (100) | PAG-3 (5.0) | Q-4 (3.5) | SF-1 (5.0) | XL-1 (5.0) | PGEE (2,000) DAA (400) GBL (100) |
| 47 | R-21 | Polymer 21 (100) | PAG-3 (5.0) | Q-2 (3.5) | SF-1 (5.0) | — | PGEE (2,000) DAA (400) GBL (100) |

TABLE 2-continued

| | | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
| | 48 | R-22 | Polymer 22 (100) | PAG-4 (5.0) | Q-2 (3.5) | SF-1 (5.0) | — | PGEE (2,000) DAA (400) GBL (100) |
| | 49 | R-23 | Polymer 23 (100) | PAG-4 (5.0) | Q-2 (3.5) | SF-1 (5.0) | — | PGEE (2,000) DAA (400) GB L(100) |
| Comparative Example | 13 | R-24 | Comparative Polymer 1 (100) | PAG-1 (5.0) | Q-2 (3.5) | SF-1 (5.0) | — | PGEE (2,000) DAA (400) GBL (100) |
| | 14 | R-25 | Comparative Polymer 2 (100) | PAG-2 (5.0) | Q-1 (3.5) | SF-1 (5.0) | XL-1 (5.0) | PGEE (2,000) DAA (400) GBL (100) |
| | 15 | R-26 | Comparative Polymer 3 (100) | PAG-3 (5.0) | Q-3 (3.5) | SF-1 (5.0) | XL-1 (5.0) | PGEE (2,000) DAA (400) GBL (100) |
| | 16 | R-27 | Comparative Polymer 4 (100) | PAG-4 (5.0) | Q-3 (3.5) | SF-1 (5.0) | XL-1 (5.0) | PGEE (2,000) DAA (400) GBL (100) |
| | 17 | R-28 | Comparative Polymer 5 (100) | PAG-3 (5.0) | Q-3 (3.5) | SF-1 (5.0) | XL-1 (5.0) | PGEE (2,000) DAA (400) GBL (100) |
| | 18 | R-29 | Comparative Polymer 6 (100) | PAG-3 (5.0) | Q-3 (3.5) | SF-1 (5.0) | — | PGEE (2,000) DAA (400) GBL (100) |
| | 19 | R-30 | Comparative Polymer 7 (100) | PAG-4 (5.0) | Q-4 (3.5) | SF-1 (5.0) | — | PGEE (2,000) DAA (400) GBL (100) |
| | 20 | R-31 | Comparative Polymer 8 (100) | PAG-3 (5.0) | Q-3 (3.5) | SF-1 (5.0) | XL-1 (5.0) | PGEE (2,000) DAA (400) GBL (100) |
| | 21 | R-32 | Comparative Polymer 9 (100) | PAG-4 (5.0) | Q-4 (3.5) | SF-1 (5.0) | XL-1 (5.0) | PGEE (2,000) DAA (400) GBL (100) |
| | 22 | R-33 | Comparative Polymer 10 (100) | PAG-3 (5.0) | Q-3 (3.5) | SF-1 (5.0) | — | PGEE (2,000) DAA (400) GBL (100) |
| | 23 | R-34 | Comparative Polymer 11 (100) | PAG-4 (5.0) | Q-4 (3.5) | SF-1 (5.0) | XL-1 (5.0) | PGEE (2,000) DAA (400) GBL (100) |
| | 24 | R-35 | Comparative Polymer 12 (100) | PAG-4 (5.0) | Q-3 (3.5) | SF-1 (5.0) | XL-1 (5.0) | PGEE (2,000) DAA (400) GBL (100) |

[4] Evaluation of Swell Quantity of Resist During Development, by the QCM (Quartz Crystal Microbalance) Technique Examples 50 to 53 & Comparative Example 25

The above-prepared resist solution (in Tables 1 and 2) was spin coated on a QCM substrate and baked on a hot plate at 100° C. for 60 seconds to form a resist film of 100 nm thick. The resist film was exposed by means of an ArF open-frame exposure system in a dose varying stepwise from 1 mJ/cm$^2$ to 13 mJ/cm$^2$ by an increment of 1 mJ/cm$^2$ and baked (PEB) on a hot plate at the temperature shown in Table 3 for 60 seconds. The QCM substrate was set on a quartz oscillator microbalance instrument RDA-Qz3 for resist development analysis (Litho Tech Japan Co., Ltd.). Development in a 2.38 wt % TMAH aqueous solution was carried out, during which a variation of thickness of resist film was observed as a function of development time. From graphs in which a film thickness variation was plotted relative to development time for each dose, the exposure dose corresponding to the maximum swell quantity and the maximum swell ratio (maximum, swell quantity standardized per initial film thickness) are determined, with the results shown in Table 3. A smaller value of maximum swell ratio indicates that the swell of resist film is suppressed.

TABLE 3

| | | Resist | PEB temp. (° C.) | Dose (mJ/cm$^2$) | Maximum swell ratio (%) |
|---|---|---|---|---|---|
| Example | 50 | R-01 | 100 | 9 | 109 |
| | 51 | R-02 | 100 | 8 | 112 |
| | 52 | R-03 | 120 | 10 | 140 |
| | 53 | R-04 | 120 | 9 | 132 |
| Comparative Example | 25 | R-22 | 100 | 7 | 191 |

As is evident from Table 3, the resist compositions within the scope of the invention show lower maximum swell ratios than the comparative resist compositions.

[5] ArF Lithography Patterning Test 1

Examples 54 to 67 & Comparative Examples 26 to 37

On a silicon wafer which had been coated with antireflective coating ARC29A (Nissan Chemical Industries, Ltd.) to a thickness of 78 nm, the resist composition (in Tables 1 and 2) was spin coated, then baked on a hot plate at 100° C. for 60 seconds to form a resist film of 100 nm thick. Using an ArF excimer laser scanner NSR-S307E (Nikon Corp., NA 0.85, σ0.93/0.74, annular illumination), exposure was performed through a 6% halftone phase shift mask bearing a line-and-space pattern with a space width of 90 nm and a pitch of 180 nm, a space width of 80 nm and a pitch of 160 nm or a space width of 70 nm and a pitch of 140 nm (on-safer size) or a trench pattern with a space width of 90 nm and a pitch of 1,650 nm (on-wafer size) while varying the dose and focus (dose pitch: 1 mJ/cm², focus pitch: 0.025 µm). After the exposure, the wafer was baked (PEB) at the temperature shown in Table 4 for 60 seconds and puddle developed in 2.38 wt % TMAH aqueous solution for 30 seconds. The wafer was rinsed with deionized water and spin dried, forming a negative pattern. The L/S patterns and trench pattern after development were observed under TD-SEM S-9380 (Hitachi Kitechnologies, Ltd.).

Evaluation of Sensitivity

As an index of sensitivity, the optimum dose (Eop, mJ/cm²) which provided an L/S pattern with a space width of 90 nm and a pitch of 180 nm was determined. A smaller dose value indicates a higher sensitivity.

Evaluation of Exposure Latitude (EL)

The exposure dose which provided an L/S pattern with a space width of 90 nm±10% (i.e., 81 nm to 99 nm) was determined. EL (%) is calculated from the exposure doses according to the following equation:

$$EL(\%)=(|E1-E2|/Eop)\times 100$$

wherein E1 is an exposure dose which provides an L/S pattern with a space width of 81 nm and a pitch of 180 nm, E2 is an exposure dose which provides an L/S pattern with a space width of 99 nm and a pitch of 180 nm, and Eop is the optimum exposure dose which provides an L/S pattern with a space width of 90 nm and a pitch of 180 nm.

Evaluation of Line Width Roughness (LWR)

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Depth of Focus (DOF)

As an index of DOF, a range of focus which provided a trench pattern with a space width of 90 nm±10% (i.e., 81 to 99 nm) was determined. A greater value indicates a wider DOF.

Evaluation of Resolution

Resolution is the minimum size that can be resolved among the L/S patterns with a size from 70 nm to 90 nm (pitch 140 to 180 nm). A smaller value indicates better resolution.

The results are shown in Table 4.

TABLE 4

|  | Resist | PEB temp. (° C.) | Eop (mJ/cm²) | EL (%) | LWR (nm) | DOF (µm) | Resolution (nm) |
| --- | --- | --- | --- | --- | --- | --- | --- |
| Example 54 | R-01 | 100 | 38.5 | 15.3 | 6.5 | 0.18 | 70 |
| 55 | R-02 | 100 | 36.5 | 10 | 6.7 | 0.18 | 70 |
| 56 | R-03 | 120 | 40.5 | 14.5 | 7.3 | 0.18 | 70 |
| 57 | R-04 | 120 | 38.4 | 16.3 | 7.1 | 0.18 | 70 |
| 58 | R-10 | 120 | 50.5 | 9.8 | 7.6 | 0.16 | 80 |
| 59 | R-11 | 100 | 43.5 | 12.3 | 8.3 | 0.14 | 70 |
| 60 | R-12 | 105 | 33.5 | 14.5 | 6.9 | 0.16 | 80 |
| 61 | R-13 | 95 | 40.5 | 16.3 | 7.1 | 0.18 | 80 |
| 62 | R-14 | 100 | 45.8 | 15.8 | 6.6 | 0.14 | 70 |
| 63 | R-19 | 90 | 50.6 | 12.3 | 6.9 | 0.14 | 70 |
| 64 | R-20 | 95 | 31.2 | 12.5 | 7.5 | 0.14 | 80 |
| 65 | R-21 | 100 | 35.2 | 16.3 | 8.1 | 0.16 | 70 |
| 66 | R-22 | 100 | 36.1 | 15.9 | 7.9 | 0.16 | 70 |
| 67 | R-23 | 100 | 25.4 | 15.2 | 7.5 | 0.18 | 70 |
| Comparative Example 26 | R-24 | 100 | 36.3 | 9.5 | 10.3 | 0.1 | 90 |
| 27 | R-25 | 95 | 25.3 | 10.5 | 9.8 | 0.08 | 90 |
| 28 | R-26 | 110 | 28.3 | 8.3 | 11.5 | 0.1 | 90 |
| 29 | R-27 | 100 | 38.5 | 5.6 | 15.2 | 0.12 | 90 |
| 30 | R-28 | 100 | 35.6 | 7.5 | 9.5 | 0.08 | 90 |
| 31 | R-29 | 110 | 30.5 | 6 | 16.3 | 0.1 | 90 |
| 32 | R-30 | 100 | 45.3 | 10.1 | 13.2 | 0.1 | 90 |
| 33 | R-31 | 100 | 33.3 | 6.6 | 10.7 | 0.08 | 90 |
| 34 | R-32 | 100 | 35.6 | 5.6 | 9.8 | 0.08 | 90 |
| 35 | R-33 | 100 | 33.2 | 4.3 | 10.2 | 0.08 | 90 |
| 36 | R-34 | 105 | 45.6 | 3.2 | 16.3 | 0.07 | 100 |
| 37 | R-35 | 100 | 38.9 | 4.1 | 16.8 | 0.06 | 100 |

As is evident from Table 4, the resist compositions within the scope of the invention have practically acceptable sensitivity. Both EL and DOF have a wide margin. LWR is low as compared with the resists of Comparative Examples. Resolution is also excellent.

[6] ArF Lithography Patterning Test 2

Examples 68 to 73 & Comparative Examples 38 to 40

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A940 having a silicon content of 43 wt % was deposited thereon to a thickness of 35 nm. On this substrate for trilayer process, the resist composition (in Tables 1 and 2) was spin coated, then baked on a hot plate at 100° C. for 60 seconds to form a resist film of 60 nm thick.

Using an ArF excimer laser immersion lithography scanner NSR-S610C (Nikon Corp., NA 1.30, σ0.90/0.72, cross-pole opening 35 deg., cross-pole illumination, azimuthally polarized illumination), exposure was performed through a 6% halftone phase shift mask bearing a contact hole (CH) pattern with a hole size of 55 nm and a pitch of 110 nm (on-wafer size) while varying the dose and focus (dose pitch: 1 mJ/cm², focus pitch: 0.025 µm). After the exposure, the wafer was baked (PEB) at the temperature shown in Table 5 for 60 seconds and puddle developed, in 2.38 wt % TMAH aqueous solution for 30 seconds. The wafer was rinsed with deionized water and spin dried, obtaining a negative pattern. The CH pattern after development was observed under TD-SEM CG4000 (Hitachi Hitechnologies, Ltd.).

Evaluation of Sensitivity

As an index of sensitivity, the optimum dose (Eop, mJ/cm²) which provided a CH pattern with a hole size of 55 nm and a pitch of 110 nm was determined. A smaller dose value indicates a higher sensitivity.

Evaluation of Exposure Latitude (EL)

The exposure dose which provided a CH pattern with a hole size of 55 nm±10% (i.e., 49.5 nm to 60.5 nm) was determined. EL (%) is calculated from the exposure doses according to the following equation:

$$EL(\%)=(|E1-E2|/Eop)\times 100$$

wherein E1 is an exposure dose which provides a CH pattern with a hole size of 49.5 nm and a pitch of 110 nm, E2 is an exposure dose which provides a CH pattern with a hole size of 60.5 nm and a pitch of 110 nm, and Eop is the optimum exposure dose which provides a CH pattern with a hole size of 55 nm and a pitch of 110 nm.

Evaluation of Critical Dimension Uniformity (CDU)

For the CH pattern formed by exposure in the optimum dose (determined in the sensitivity evaluation), the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

The results are shown in Table 5.

TABLE 5

| | | Resist | PEB temp. (° C.) | Eop (mJ/cm²) | EL (%) | CDU 3σ (nm) |
|---|---|---|---|---|---|---|
| Example | 68 | R-01 | 100 | 35.9 | 13.5 | 7.1 |
| | 69 | R-02 | 100 | 33.6 | 11.1 | 6.8 |
| | 70 | R-03 | 120 | 39.6 | 13 | 6.5 |
| | 71 | R-04 | 120 | 36.3 | 13.8 | 6.7 |
| | 72 | R-22 | 100 | 36.8 | 14 | 7 |
| | 73 | R-23 | 120 | 35.8 | 13.7 | 6.9 |
| Comparative | 38 | R-24 | 100 | 34.1 | 7.2 | 10.1 |
| Example | 39 | R-34 | 105 | 37.9 | 6.3 | 11.8 |
| | 40 | R-35 | 100 | 37.8 | 5.9 | 12.1 |

As is evident from Table 5, the resist compositions within the scope of the invention show practically acceptable sensitivity, a wide margin of EL, and excellent CDU.

[7] EB Writing Test

Examples 74 to 79 & Comparative Examples 41 to 44

On a silicon wafer which had been surface treated in HMDS gas phase at 90° C. for 60 seconds, each of the inventive resist compositions or comparative resist compositions in Tables 1 and 2 was spin coated and prebaked on a hot plate at 100° C. for 60 seconds to form a resist film of 60 nm thick. Using an EB lithography system JBX-9000 (JEOL, Ltd.) at an accelerating voltage of 50 kV, a L/S pattern having a space width of 100 nm and a pitch of 200 nm (on-wafer size) was written while varying the dose (dose variation pitch 2 μC/cm²). After the imagewise exposure, the resist film was baked (PEB) at the temperature shown in Table 6 for 60 seconds, puddle developed in 2.38 wt % TMAH aqueous solution for 30 seconds, rinsed with deionized water, and dried, obtaining a negative pattern. The L/S pattern after development was observed under TD-SEM S-9380 (Hitachi Hitechnologies, Ltd.).

Evaluation of Sensitivity

As an index of sensitivity, the optimum dose (Eop, μC/cm²) which provided an L/S pattern with a space width of 100 nm and a pitch of 200 nm was determined. A smaller dose value indicates a higher sensitivity.

Evaluation of Exposure Latitude (EL)

The exposure dose which provided an L/S pattern with a space width of 100 nm±10% (i.e., 90 nm to 110 nm) was determined. EL (%) is calculated from the exposure doses according to the following equation:

$EL(\%) = (|E1 - E2|/Eop) \times 100$ wherein E1 is an exposure dose which provides an L/S pattern with a space width of 90 nm and a pitch of 200 nm, E2 is an exposure dose which provides an L/S pattern with a space width of 110 nm and a pitch of 200 nm, and Eop is the optimum exposure dose which provides an L/S pattern with a space width of 100 nm and a pitch of 200 nm.

Evaluation of Line Width Roughness (LWR)

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Table 6.

TABLE 6

| | | Resist | PEB temp. (° C.) | Eop (μC/cm²) | EL (%) | LWR (nm) |
|---|---|---|---|---|---|---|
| Example | 74 | R-01 | 100 | 41.2 | 13.5 | 4.6 |
| | 75 | R-02 | 100 | 39.6 | 12.3 | 4.5 |
| | 76 | R-03 | 120 | 45.3 | 15.6 | 5.1 |
| | 77 | R-04 | 120 | 40 | 16.3 | 5.5 |
| | 78 | R-22 | 105 | 41.2 | 15.8 | 5.5 |
| | 79 | R-23 | 120 | 42.1 | 15.3 | 5.1 |
| Comparative | 41 | R-24 | 100 | 42.2 | 8.6 | 8.9 |
| Example | 42 | R-25 | 105 | 53.5 | 7.2 | 9.5 |
| | 43 | R-34 | 100 | 55.6 | 6.9 | 10.8 |
| | 44 | R-35 | 105 | 56.8 | 6.3 | 11.4 |

As is evident from Table 6, the resist compositions within the scope of the invention show practically acceptable sensitivity, a wide margin of EL, and low LWR.

It is noted that the invention is not limited to the aforementioned embodiments. While the embodiments are merely exemplary, any embodiments having substantially the same construction as the technical concept set forth in the following claims and exerting equivalent functions and results are believed to be within the spirit, and scope of the invention.

Japanese Patent Application No. 2015-220175 is incorporated herein by reference.

Although, some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer selected from among the following formulae:

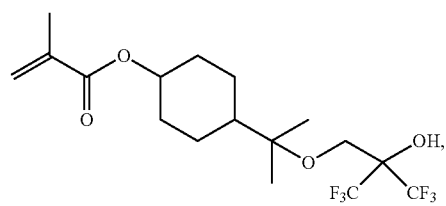

-continued
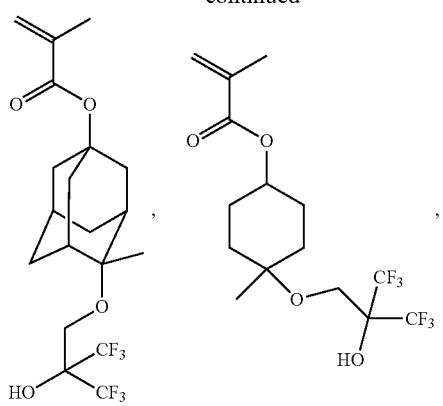
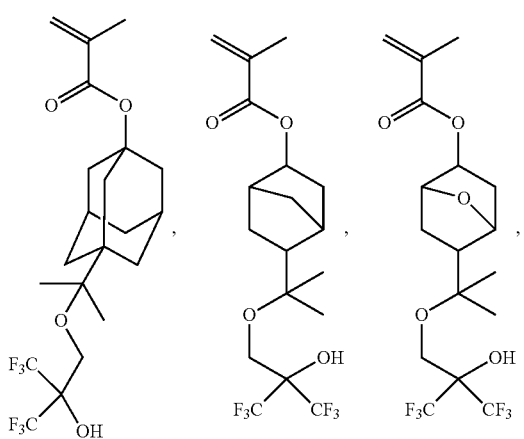
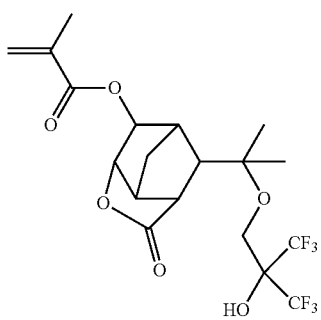
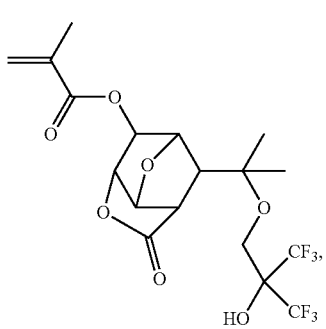
-continued
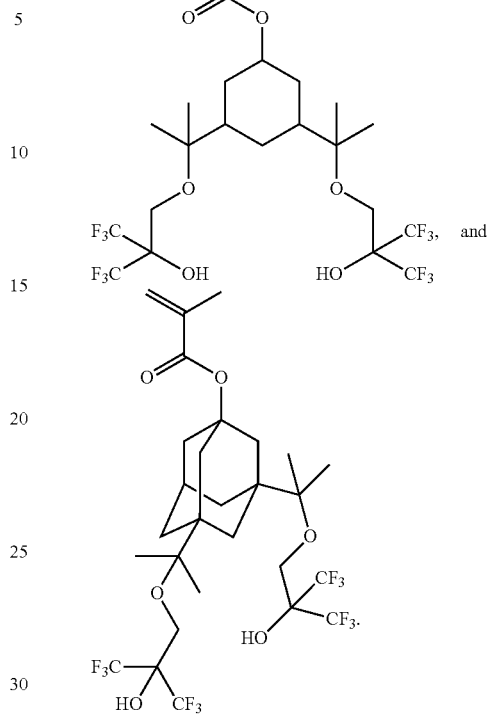
2. A polymer comprising recurring units derived from the monomer of claim 1.
3. The polymer of claim 2, further comprising one or more recurring units selected from recurring units having the formulae (A) to (D):
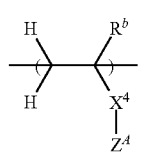 (A)
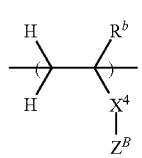 (B)
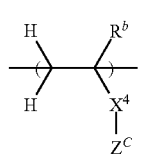 (C)
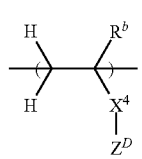 (D)
wherein $R^b$ is hydrogen, methyl or trifluoromethyl, $Z^A$ is a $C_1$-$C_{20}$ fluoroalcohol-containing group, $Z^B$ is a $C_1$-$C_{20}$ phenolic hydroxyl-containing group, $Z^C$ is a $C_1$-$C_{20}$ carboxyl-containing group, $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety, $X^4$ is a single bond, methylene, ethylene, phenylene, fluorinated phenylene, naphthylene, —O—$R^c$—, or —C(=O)—$Z^E$—$R^c$—, $Z^E$ is oxygen or NH, and $R^c$ is a straight, branched or cyclic $C_1$-$C_6$ alkylene group, or a straight, branched or cyclic $C_2$-$C_6$ alkenylene group, phenylene group or naphthylene group, wherein the $R^c$ group may contain a carbonyl, ester, ether or hydroxyl moiety.

4. The polymer of claim 2, further comprising one or more recurring units selected from recurring units having the formulae (3a) to (3d):

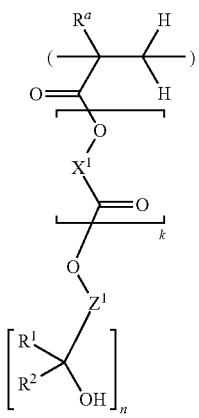

(3a)

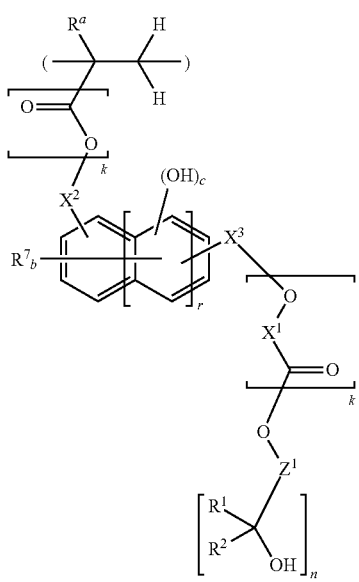

(3b)

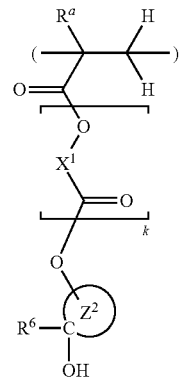

(3c)

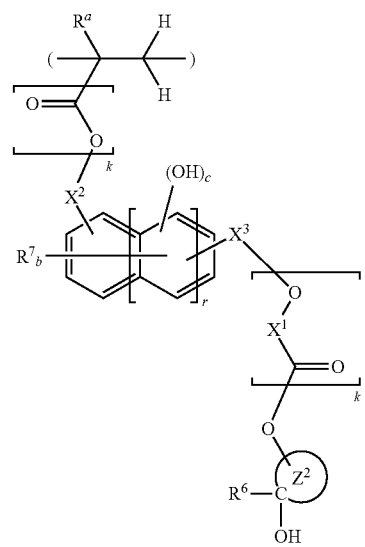

(3d)

wherein $R^a$ is hydrogen, methyl or trifluoromethyl,
$R^1$ and $R^2$ are each independently a straight $C_1$-$C_{10}$ or branched $C_3$-$C_{10}$ or cyclic $C_3$-$C_{10}$ monovalent hydrocarbon group in which any constituent —$CH_2$— moiety may be replaced by —O— or —C(=O)—, a pair of $R^1$ and $R^2$ may bond together to form an alicyclic group with the carbon atom to which they are attached,
$X^1$ is a straight, branched or cyclic $C_1$-$C_{15}$ divalent hydrocarbon group in which any constituent —$CH_2$— moiety may be replaced by —O— or —C(=O)—,
$X^2$ and $X^3$ are each independently a single bond or a straight, branched or cyclic $C_1$-$C_{15}$ divalent hydrocarbon group in which any constituent —$CH_2$— moiety may be replaced by —O— or —C(=O)—,
$Z^1$ is a straight $C_1$-$C_{20}$ or branched $C_3$-$C_{10}$ or cyclic $C_3$-$C_{20}$, (n+1)-valent aliphatic hydrocarbon group in which any constituent —$CH_2$— moiety may be replaced by —O— or —C(=O)—, b is an integer meeting b≤5+2r–c, c is an integer of 1 to 3, k is 0 or 1, n is an integer of 1 to 4, r is an integer of 0 to 2,
$Z^2$ is an atomic group necessary to form a $C_3$-$C_{10}$ alicyclic group with the carbon atom to which it is attached, in which any constituent —$CH_2$— moiety may be replaced by —O— or —C(=O)—,
with the proviso that when the oxygen atom attached to $Z^1$ or $Z^2$ forms a bond with the carbonyl carbon bonded to a polymer main chain or the linker —[O—X$^1$—C(=O)]—, a tertiary ester bond is not formed.

5. The polymer of claim 2, further comprising one or more recurring units selected from recurring units having the formulae (f1) to (f3):

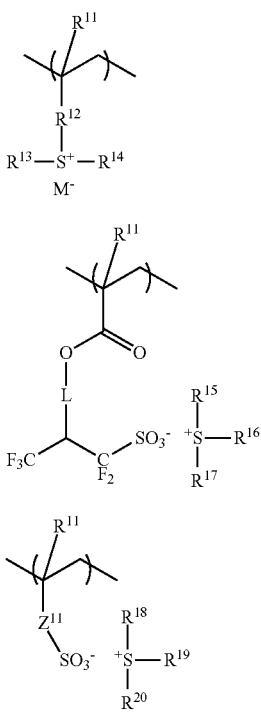

wherein R$^{11}$ is each independently hydrogen or methyl, R$^{12}$ is a single bond, phenylene, —O—R$^{21}$—, or —C(=O)—Z$^{22}$—R$^{21}$—, Z$^{22}$ is oxygen or NH, R$^{21}$ is a straight, branched or cyclic C$_1$-C$_6$ alkylene group, straight, branched or cyclic C$_2$-C$_6$ alkenylene group or phenylene group, and R$^{21}$ may contain a carbonyl (—CO—), ester (—COO—), ether (—O—) or hydroxyl moiety, L is a single bond or —Z$^{33}$—C(=O)—O—, Z$^{33}$ is a straight, branched or cyclic C$_1$-C$_{20}$ divalent hydrocarbon group which may be substituted with a heteroatom, is a single bond, methylene, ethylene, phenylene, fluorinated phenylene, —O—R$^{22}$—, or —C(=O)—Z$^{44}$—R$^{22}$—, Z$^{44}$ is oxygen or NH, R$^{22}$ is a straight, branched or cyclic C$_1$-C$_6$ alkylene group, straight, branched or cyclic C$_2$-C$_6$ alkenylene group or phenylene group, and R$^{22}$ may contain a carbonyl, ester, ether or hydroxyl moiety, R$^{13}$ to R$^{20}$ are each independently a straight, branched or cyclic C$_1$-C$_{20}$ monovalent hydrocarbon group in which at least one hydrogen atom may be substituted by a heteroatom, and M$^-$ is a non-nucleophilic counter ion.

6. A resist composition comprising a base resin, an acid generator, and an organic solvent, the base resin comprising the polymer of claim 2.

7. A pattern forming process comprising the steps of applying the resist composition of claim 6 onto a substrate, baking to form a resist film, exposing the resist film to high-energy radiation to define exposed and unexposed regions, baking, and developing the exposed resist film in a developer to form a pattern.

8. The pattern forming process of claim 7 wherein the developing step uses an alkaline developer in which the unexposed region of resist film is dissolved and the exposed region of resist film is not dissolved, for forming a negative tone pattern.

* * * * *